United States Patent
Lynch et al.

(10) Patent No.: US 12,378,581 B2
(45) Date of Patent: *Aug. 5, 2025

(54) COMPOSITIONS AND METHODS FOR METABOLIC CONTROL OF A BIOFERMENTATION PROCESS WITH SYNTHETIC METABOLIC VALVES

(71) Applicant: Duke University, Durham, NC (US)

(72) Inventors: Michael David Lynch, Durham, NC (US); Zhixia Ye, Raleigh, NC (US)

(73) Assignee: Duke University, Durham, NC (US)

( * ) Notice: Subject to any disclaimer, the term of this patent is extended or adjusted under 35 U.S.C. 154(b) by 6 days.

This patent is subject to a terminal disclaimer.

(21) Appl. No.: 18/317,588

(22) Filed: May 15, 2023

(65) Prior Publication Data

US 2024/0035052 A1 Feb. 1, 2024

Related U.S. Application Data

(63) Continuation of application No. 17/576,290, filed on Jan. 14, 2022, now Pat. No. 11,746,362, which is a continuation of application No. 16/487,542, filed as application No. PCT/US2018/019040 on Feb. 21, 2018, now Pat. No. 11,268,111.

(60) Provisional application No. 62/461,436, filed on Feb. 21, 2017.

(51) Int. Cl.
| | |
|---|---|
| C12P 7/42 | (2006.01) |
| C12N 9/02 | (2006.01) |
| C12N 9/04 | (2006.01) |
| C12N 9/06 | (2006.01) |
| C12N 9/10 | (2006.01) |
| C12N 15/74 | (2006.01) |
| C12P 13/06 | (2006.01) |

(52) U.S. Cl.
CPC ............ *C12P 7/42* (2013.01); *C12N 9/0006* (2013.01); *C12N 9/0008* (2013.01); *C12N 9/001* (2013.01); *C12N 9/0016* (2013.01); *C12N 9/0051* (2013.01); *C12N 9/1025* (2013.01); *C12N 15/746* (2013.01); *C12P 13/06* (2013.01)

(58) Field of Classification Search
None
See application file for complete search history.

(56) References Cited

U.S. PATENT DOCUMENTS

| | | | |
|---|---|---|---|
| 8,916,358 B2 | 12/2014 | Swartz | |
| 10,036,001 B2 | 7/2018 | Swartz | |
| 10,662,426 B2 | 5/2020 | Lynch | |
| 11,193,149 B2 * | 12/2021 | Lynch | C12P 13/06 |
| 11,236,370 B2 * | 2/2022 | Lynch | C12N 15/09 |
| 11,268,111 B2 * | 3/2022 | Lynch | C12N 9/0006 |
| 11,279,956 B2 * | 3/2022 | Lynch | C12N 9/0006 |
| 11,339,413 B2 * | 5/2022 | Lynch | C12N 9/1025 |
| 11,746,362 B2 * | 9/2023 | Lynch | C12N 15/09 435/146 |
| 2011/0125118 A1 | 5/2011 | Lynch | |
| 2011/0244575 A1 | 10/2011 | Lipscomb | |
| 2012/0214170 A1 | 8/2012 | Moore | |
| 2015/0072399 A1 | 3/2015 | Lynch et al. | |

FOREIGN PATENT DOCUMENTS

| | | |
|---|---|---|
| EP | 2842542 A1 | 3/2015 |
| WO | 2012129450 A1 | 9/2012 |
| WO | 2013176772 A1 | 11/2013 |
| WO | 2014160025 A1 | 10/2014 |
| WO | 2015191638 A1 | 12/2015 |
| WO | 2018156646 A1 | 8/2018 |

OTHER PUBLICATIONS

Yuki Soma et al: "Metabolic flux redirection from a central metabolic pathway toward a synthetic pathway using a metabolic toggle switch", Metabolic Engineering, vol. 23, May 1, 2014, pp. 175-184.
Kathleen E. McGinness et al: "Engineering Controllable Protein Degradation", Molecular Cell., vol. 22, No. 5, Jun. 1, 2006, pp. 701-707.
Levchenko Igor et al: "A specificity-enhancing factor for the ClpXP degradation machine", Science, vol. 289, No. 5488, Sep. 29, 2000, pp. 2354-2356.
Lynch et al., "Standarized two-stage bioprocess development using synthetic metabolic valves and dynamic metabolic control", Abstracts of Papers ; ACS National Meeting & Exposition; 249th National Meeting and Exposition of the American-Chemical-Society (ACS), vol. 249, p. BIOT418.
Brockman et al., "Dynamic knockdown of E. coli central metabolism for redirecting fluxes of primary metabolites", Metabolic Engineering, vol. 28., pp. 104-113.
Kim et al., "A genetic strategy to identify targets for the development of drugs that prevent bacterial persistence", Proc. Natl. Acad. Sci. USA (2013); vol. 110, pp. 19095-19100.
Qi et al., "Repurposing CRISPR as an RNA-guided platform for sequence-specific control of gene expression," Cell (2013); vol. 152, pp. 1173-1183.
Chica et al., "Semi-rational approaches to engineering enzyme activity: combining the benefits of directed evolution and rational design" Curr Opin Biotechnol. Aug. 2005; 16(4):378-84. (Year: 2005).

(Continued)

*Primary Examiner* — Christian L Fronda

(74) *Attorney, Agent, or Firm* — Benesch Friedlander Coplan & Aronoff LLP

(57) ABSTRACT

The present disclosure provides compositions and methods for rapid production of chemicals in genetically engineered microorganisms in a large scale. Also provided herein is a high-throughput metabolic engineering platform enabling the rapid optimization of microbial production strains. The platform, which bridges a gap between current in vivo and in vitro bio-production approaches, relies on dynamic minimization of the active metabolic network.

3 Claims, 59 Drawing Sheets

Specification includes a Sequence Listing.

(56) References Cited

OTHER PUBLICATIONS

Singh et al., "Protein Engineering Approaches in the Post-Genomic Era", Curr Protein Pept Sci. 2017, 18, 1-11 (Year: 2017).
Kizer et al., "Application of Functional Genomics to Pathway Optimization for Increased Isoprenoid Production", Appl Environ Microbial. May 2008;74(10):3229-41. (Year: 2008).
Prather et al., "De novo biosynthetic pathways: rational design of microbial chemical factories", Curr Opin Biotechnol. Oct. 2008; 19(5):468-7 4. (Year: 2008).
Rath et al., Efficient programmable gene silencing by Cascade, Nucleic Acids Res. Jan. 9, 2015; 43(1): 237-246. (Year: 2015).
Lynch, "Into new territory: improved microbial synthesis through engineering of the essential metabolic network", Curr Opin Biotechnol. Apr. 2016;38: 106-11. Epub Feb. 10, 2016. (Year: 2016).
Lee et al., "Aerobic production of alanine by *Escherichia coli* aceF ldhA mutants expressing the Bacillus sphaericus alaD gene", Appl Microbial Biotechnol. Jul. 2004;65(1):56-60. (Year: 2004).
Kim et al., "Characterization of the L-alanine exporter AlaE of *Escherichia coli* and its potential role in protecting cells from a toxic-level accumulation of L-alanine and its derivatives" Microbiologyopen. Aug. 2015; 4(4): 632-643. (Year: 2015).
Wang et al., "Improvement of NADPH bioavailability in *Escherichia coli* by replacing NAD(+)-dependent glyceraldehyde-3-phosphate dehydrogenase GapA with NADP (+)-dependent GapB from Bacillus subtilis and addition of NAD kinase", J Ind Microbial Biotechnol. Dec. 2013;40( 12): 1449-60. (Year: 2013).
Vick et al., "*Escherichia coli* enoyl-acyl carrier protein reductase (Fabl) supports efficient operation of a functional reversal of B-oxidation cycle", Appl Environ Microbial. Feb. 2015; 81 (4): 1406-1416. (Year: 2015).

Jan et al., "Metabolic Engineering and Transhydrogenase Effects on NADPH Availability in *Escherichia coli*", Biotechnol Prag. Sep.-Oct. 2013;29(5): 1124-30. (Year: 2013).
Luo et al., "Repurposing endogenous type I CRISPR-Cas systems for programmable gene repression", Nucleic Acids Res. Jan. 9, 2015; 43(1): 674-681. (Year: 2015).
First Action Interview Pilot Program Pre-Interview Communication issued in U.S. Appl. No. 16/487,542 dated Nov. 23, 2020.
Final Office Action Communication issued in U.S. Appl. No. 16/487,542 dated Sep. 22, 2021.
Non-Final Office Action Communication issued in U.S. Appl. No. 16/487,542 dated Mar. 26, 2021.
International Search Report and Written Opinion issued in PCT application No. PCT/US2018/019040 mailing date Jun. 21, 2018.
International Preliminary Report on Patentability issued in PCT application No. PCT/US2018/019040 issue date Jun. 21, 2019.
Gustavsson M. et al: "Prospects of microbial cell factories developed through systems metabolic engineering", Microbial Biotechnology, vol. 9, No. 5, Jul. 20, 2016, pp. 610-617.
Gong Z. et al: "Engineering Robustness of Microbial Cell Factories", Biotechnology Journal, vol. 12, No. 1700014, Sep. 18, 2017, pp. 1-9.
Jiang T. et al: "Recent advances in improving metabolic robustness of microbial cell factories", Current Opinion in Biotechnology, vol. 66, Jul. 16, 2020, pp. 69-77.
Olsson L. et al: "Robustness: linking strain design to viable bioprocesses", Trends in Biotechnology, vol. 40, No. 8, Feb. 1, 2022, pp. 918-931.
Miziorko, H. M. "Enzymes of the mevalonate pathway of isoprenoid biosynthesis." Archives of biochemistry and biophysics 505.2 (2011): 131-143.
Examination Report issued in Australian Patent Application No. 2022224766, dated Mar. 27, 2024.

* cited by examiner

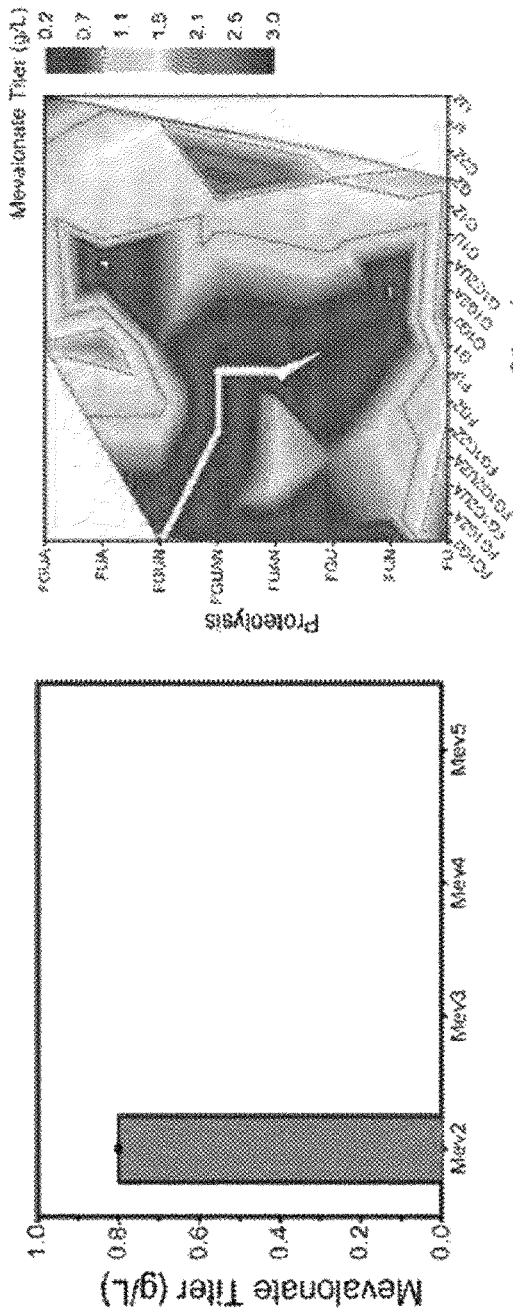
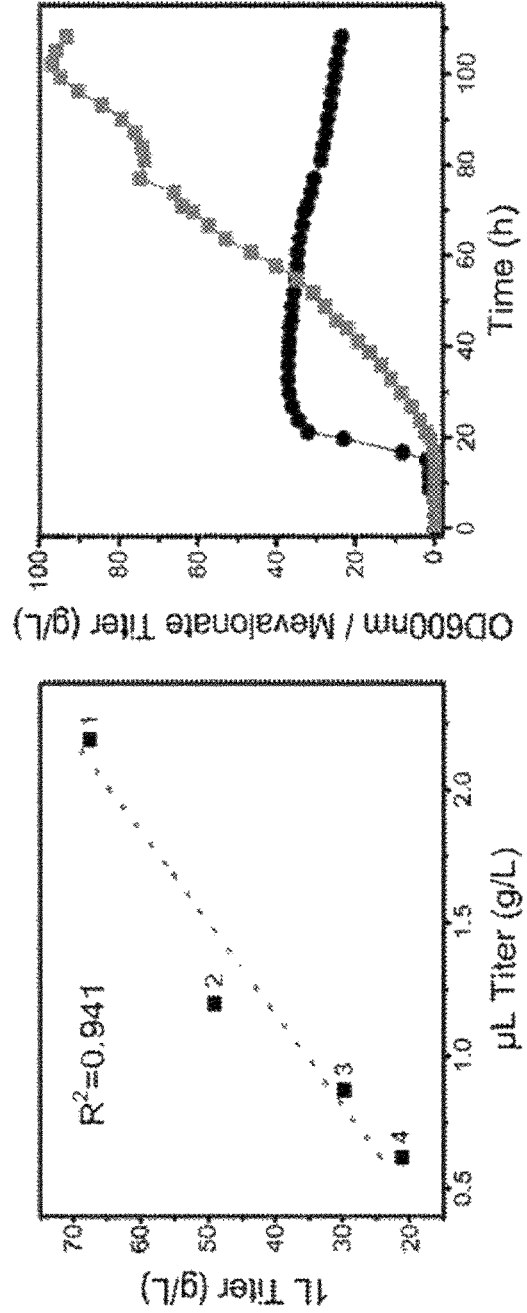
FIGURE 6B
FIGURE 6C
FIGURE 6D
FIGURE 6E

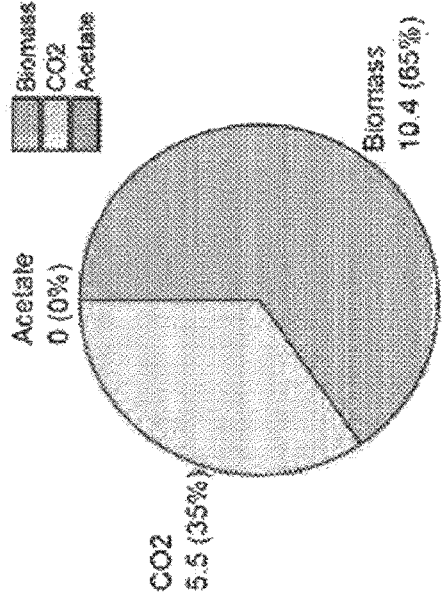
FIGURE 13C
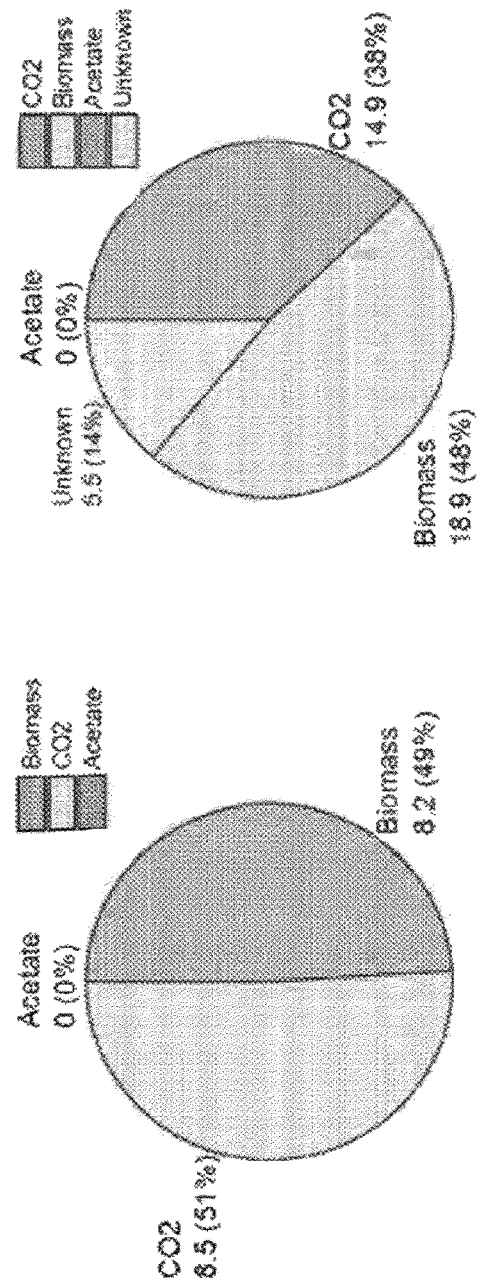
FIGURE 13E
FIGURE 13D

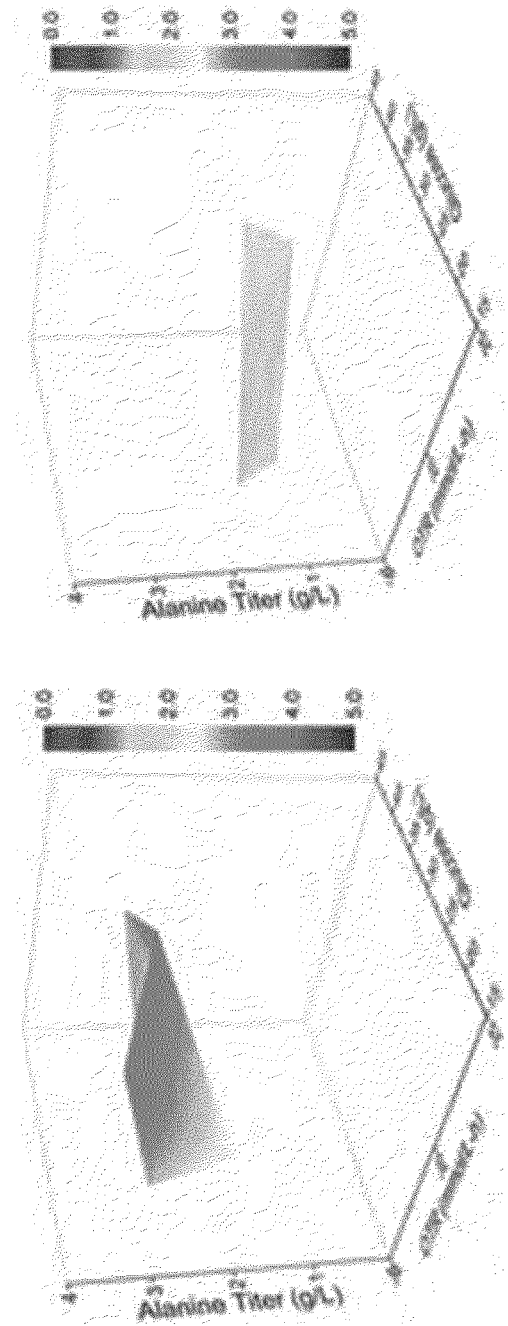
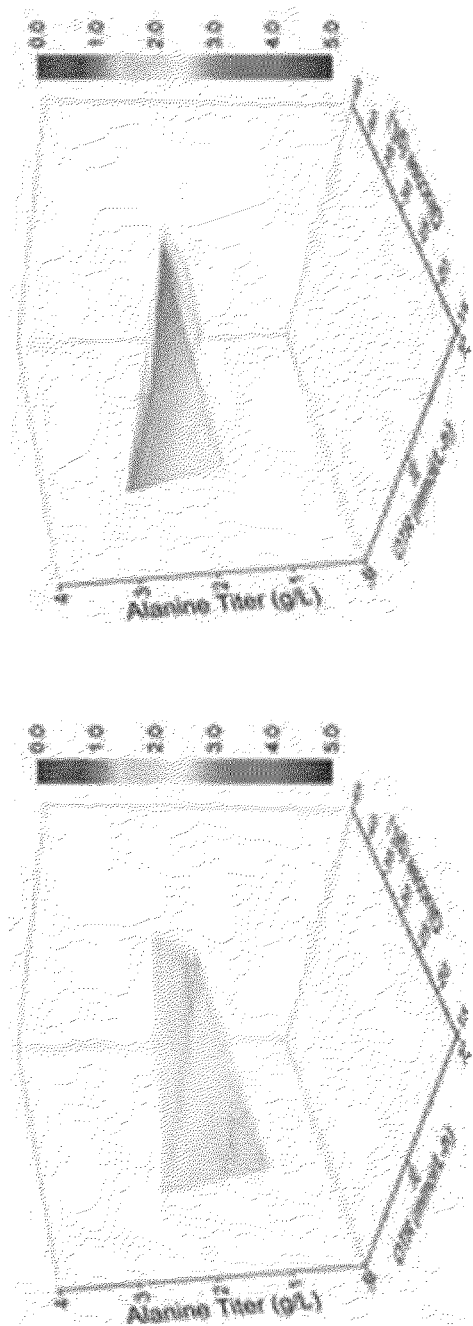
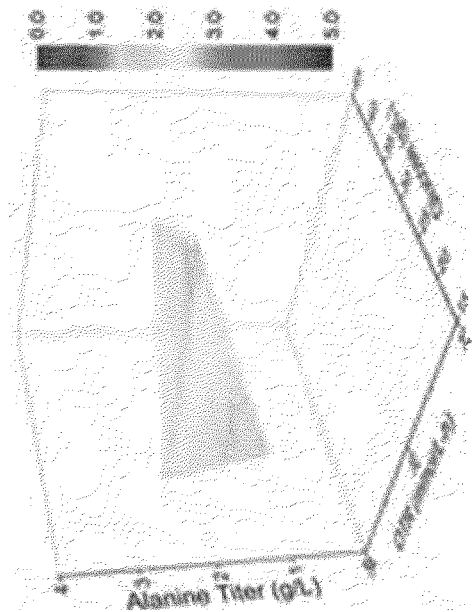
FIGURE 21A
FIGURE 21B
FIGURE 21C
FIGURE 21D

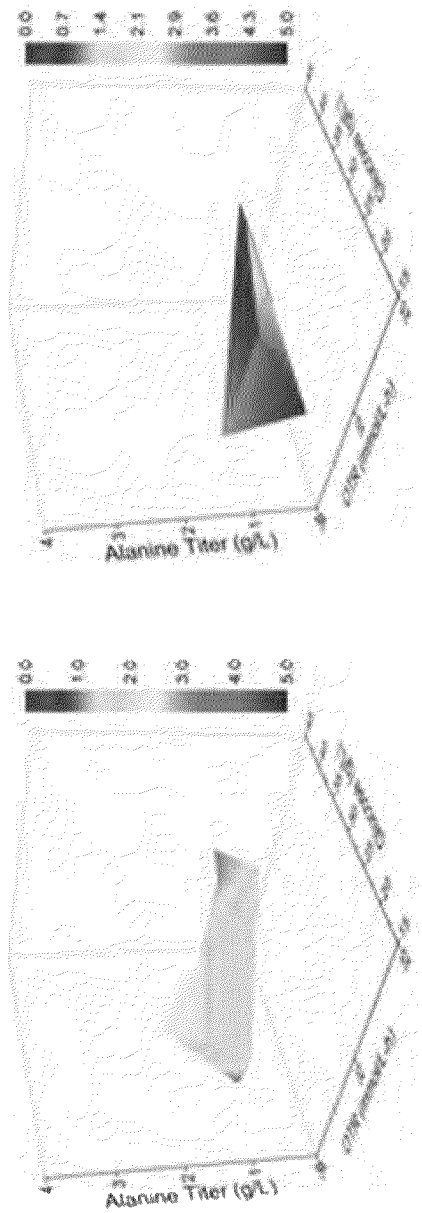
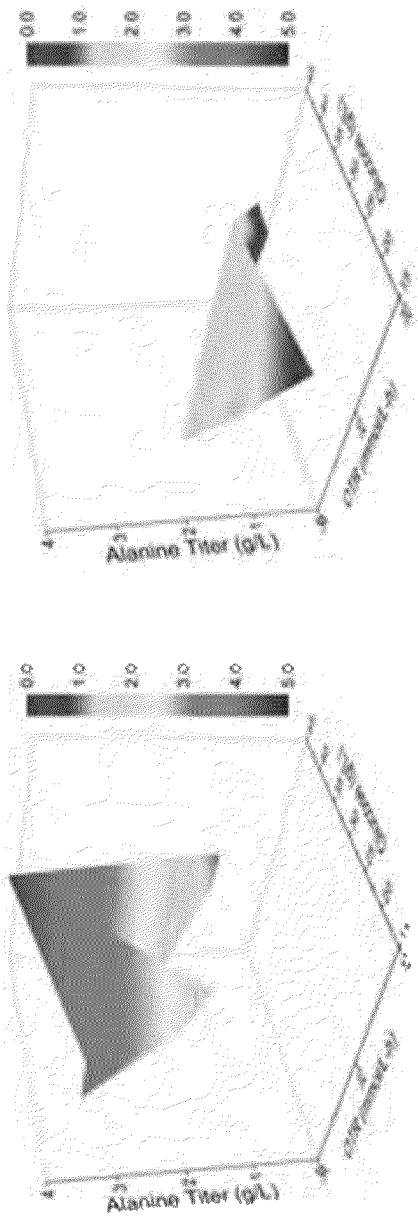
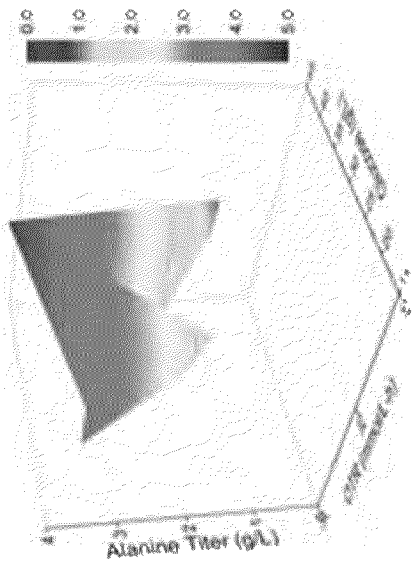
FIGURE 29A
FIGURE 29B
FIGURE 29C
FIGURE 29D

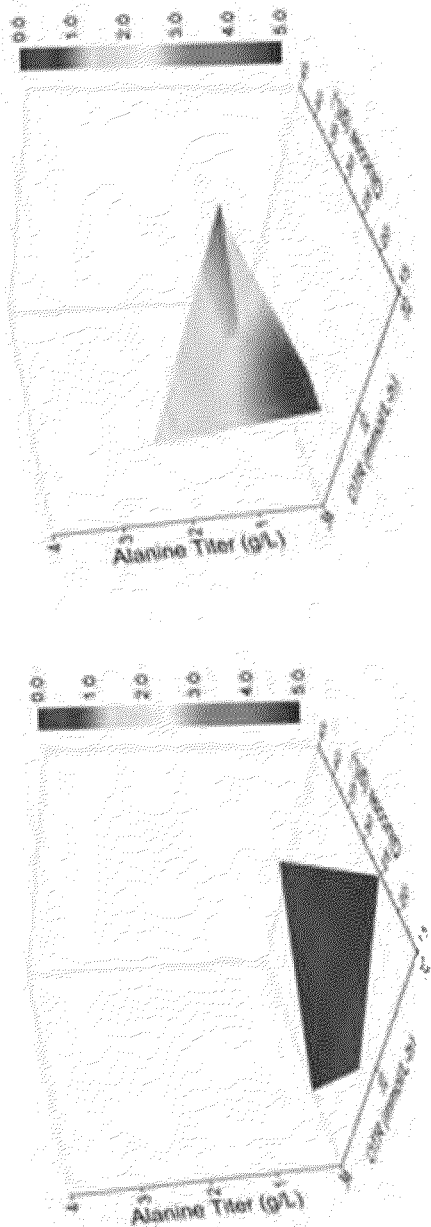
FIGURE 30A
FIGURE 30B
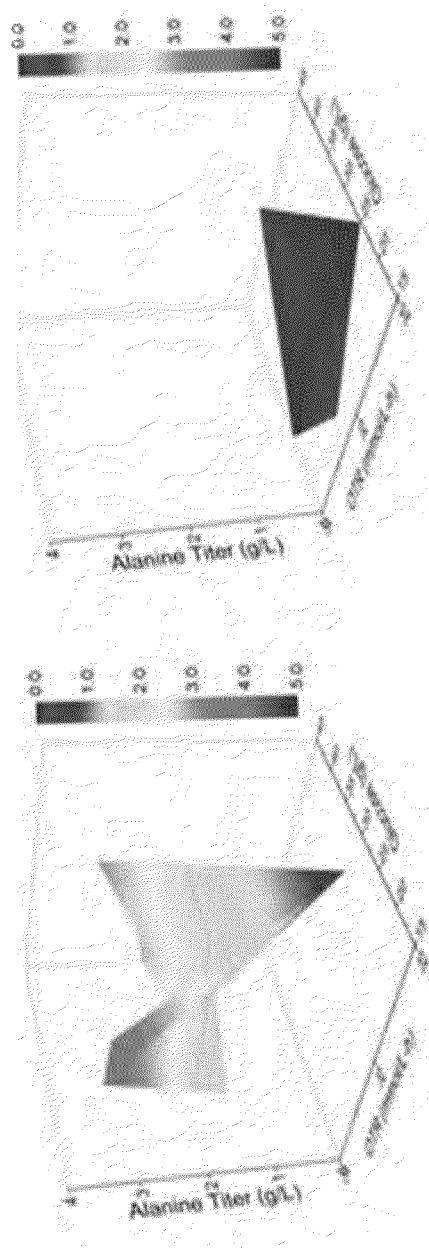
FIGURE 30C
FIGURE 30D

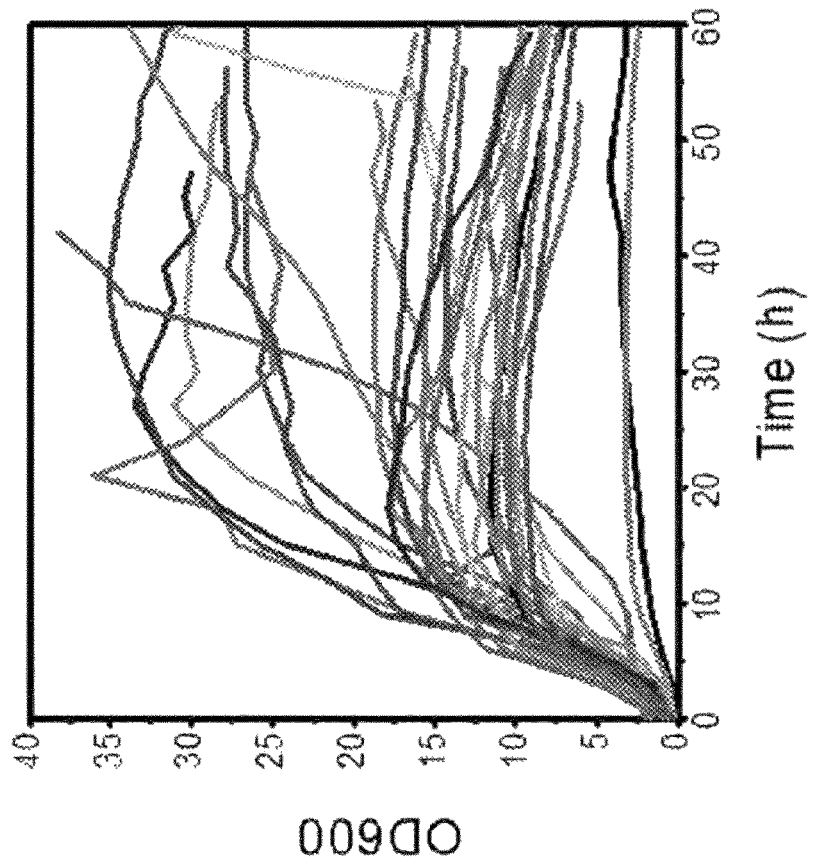
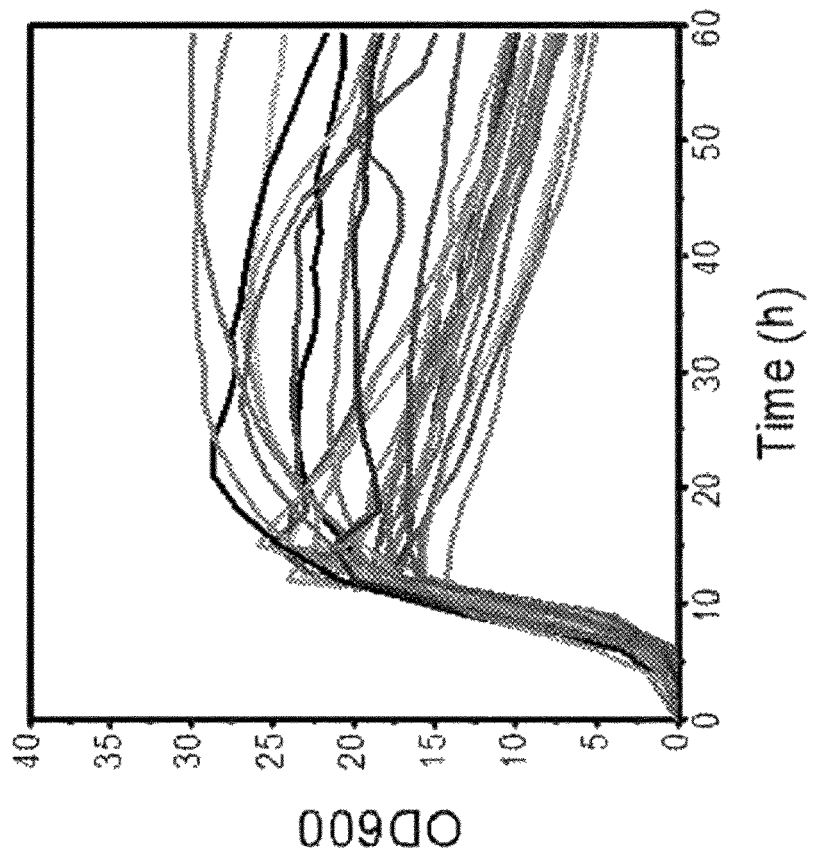
FIGURE 33A
FIGURE 33B

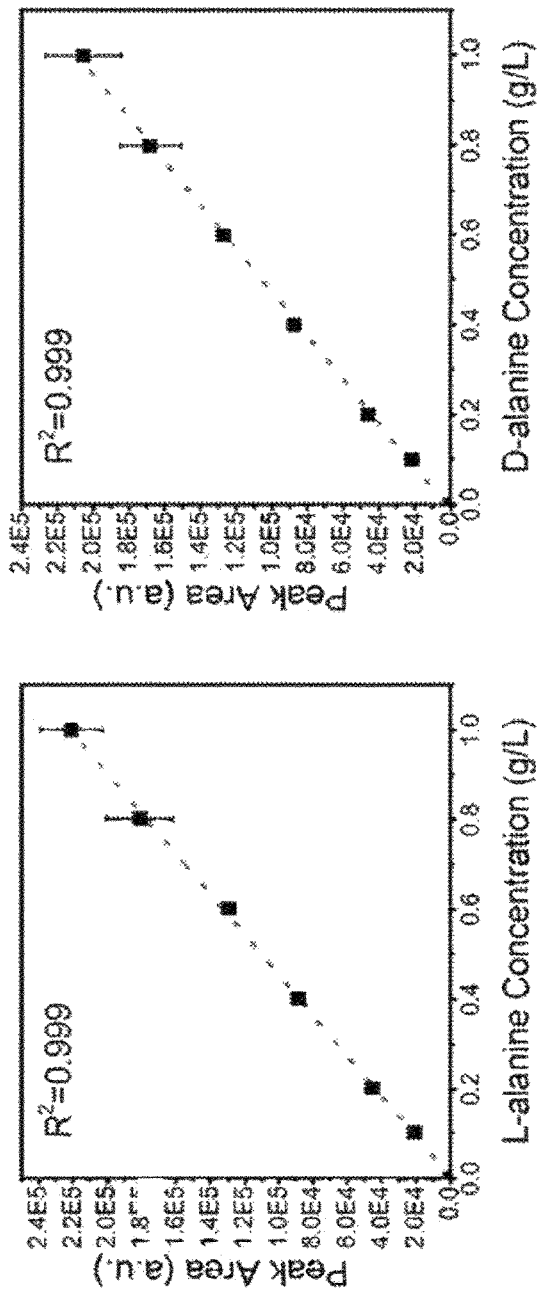
FIGURE 38A
FIGURE 38B
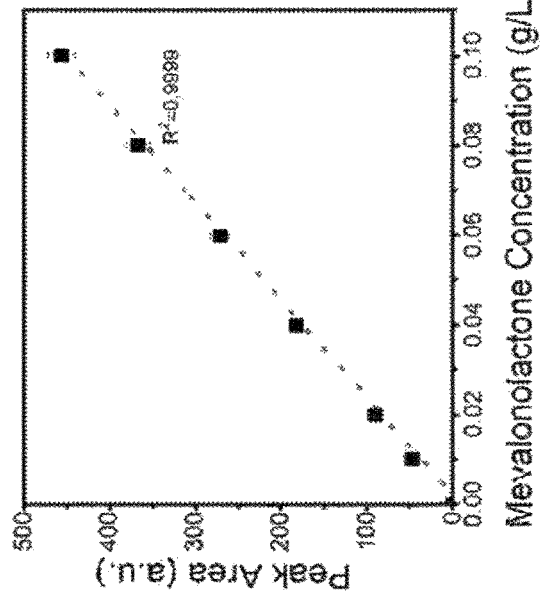
FIGURE 38C
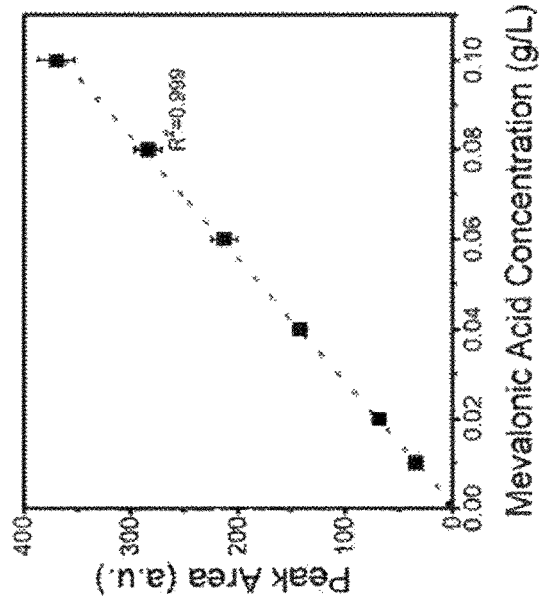
FIGURE 38D

US 12,378,581 B2

SEQUENCE LISTING

```
Sequence total quantity: 204
SEQ ID NO: 1            moltype = DNA  length = 114
FEATURE                 Location/Qualifiers
source                  1..114
                        mol_type = other DNA
                        organism = Escherichia coli
SEQUENCE: 1
tctttctgac accttactat cttacaaatg taacaaaaaa gttattttc tgtaattcga   60
gcatgtcatg ttacccgcg agcataaaac gcgtgtgtag gaggataatc tatg         114
```

```
SEQ ID NO: 2            moltype = DNA  length = 160
FEATURE                 Location/Qualifiers
source                  1..160
                        mol_type = other DNA
                        organism = Escherichia coli
SEQUENCE: 2
gtgcgtaatt gtgctgatct cttatatagc tgctctcatt atctctctac cctgaagtga    60
ctctctcacc tgtaaaaata atatctcaca ggcttaatag tttcttaata caaagcctgt   120
aaaacgtcag gataacttct gtgtaggagg ataatctatg                         160

SEQ ID NO: 3            moltype = DNA  length = 174
FEATURE                 Location/Qualifiers
source                  1..174
                        mol_type = other DNA
                        organism = Escherichia coli
SEQUENCE: 3
cgattacgta aagaagttat tgaagcatcc tcgtcagtaa aaagttaatc ttttcaacag    60
ctgtcataaa gttgtcacgg ccgagactta tagtcgcttt gttttattt tttaatgtat   120
ttgtagtgta ggaggataat ctatggctag caaaggagaa gaacttttca catg         174

SEQ ID NO: 4            moltype = DNA  length = 154
FEATURE                 Location/Qualifiers
source                  1..154
                        mol_type = other DNA
                        organism = Escherichia coli
SEQUENCE: 4
gccacggaaa tcaataacct gaagatatgt gcgacgagct tttcataaat ctgtcataaa    60
tctgacgcat aatgacgtcg cattaatgat cgcaacctat ttattgtgta ggaggataat   120
ctatggctag caaaggagaa gaacttttca catg                               154

SEQ ID NO: 5            moltype = DNA  length = 120
FEATURE                 Location/Qualifiers
source                  1..120
                        mol_type = other DNA
                        organism = Escherichia coli
SEQUENCE: 5
agacagtcaa cgcgcttgat agcctggcga agatcatccg atcttcgcct tacacttttg    60
tttcacattt ctgtgacata ctatcggatg tgcggtaatt gtataggagg ataatctatg   120

SEQ ID NO: 6            moltype = DNA  length = 125
FEATURE                 Location/Qualifiers
source                  1..125
                        mol_type = other DNA
                        organism = Escherichia coli
SEQUENCE: 6
gctatgccgg actgaatgtc caccgtcagt aattttttata cccggcgtaa ctgccgggtt    60
attgcttgtc acaaaaaagt ggtagactca tgcagttaac tcactgtgta ggaggataat   120
ctatg                                                               125

SEQ ID NO: 7            moltype = DNA  length = 206
FEATURE                 Location/Qualifiers
source                  1..206
                        mol_type = other DNA
                        organism = Escherichia coli
SEQUENCE: 7
catccataaa ttttgcataa ttaatgtaaa gaccaggctc gccagtaacg ctaaattcat    60
ttggctgtaa gcgcggtgtc atccgcgtca ggaaaattaa acagttactt taaaaaatga   120
aaacgtaaaa aggttgggtt tcgatgtatt gacgggtaaa ctttgtcgcc cgctaaacat   180
ttgtttgtgt aggaggataa tctatg                                        206

SEQ ID NO: 8            moltype = DNA  length = 184
FEATURE                 Location/Qualifiers
source                  1..184
                        mol_type = other DNA
                        organism = Escherichia coli
SEQUENCE: 8
aatcctgctg aaagcacaca gcttttttca tcactgtcat cactctgtca tctttccagt    60
agaaactaat gtcactgaaa tggtgtttta tagttaaata taagtaaata tattgttgca   120
ataaatgcga gatctgttgt acttattaag tagcagcgga agttcgtgta ggaggataat   180
ctat                                                                184

SEQ ID NO: 9            moltype = DNA  length = 359
FEATURE                 Location/Qualifiers
source                  1..359
                        mol_type = other DNA
                        organism = Escherichia coli
SEQUENCE: 9
ctacagagat gacgtgtaga aaatagttac cgatataaat agttacagct aaacgcctga    60
```

```
aattacatgt cgagggcact atttaaaaca attttgagga tttccttata ttggtggtta   120
gtacgcatgc aattaaaaat gaaattccgc gaccacaagc caaaataaca aacggcaagg   180
agacaaaaat aagcacaaat agccaacacg tcctctgttc actttaaagg gaatcgctga   240
aaaatacgct ctgtttaagg ggattcacct ttctcagaaa gctattccgc ccttttcctg   300
ctgagaaatc gccacattcg gcatgacaac attgtgaaag tgtaggagga taatctatg    359
```

```
SEQ ID NO: 10           moltype = DNA   length = 156
FEATURE                 Location/Qualifiers
source                  1..156
                        mol_type = other DNA
                        organism = Escherichia coli
SEQUENCE: 10
accgaactga agcaggatta caccgtggtg atcgtcaccc acaacatgca gcaggctgcg    60
cgttgttccg accacacggc gtttatgtac ctgggcgaat tgattgagtt cagcaacacg   120
gacgatctgt tcaccagtgt aggaggataa tctatg                             156

SEQ ID NO: 11           moltype = DNA   length = 151
FEATURE                 Location/Qualifiers
source                  1..151
                        mol_type = other DNA
                        organism = Escherichia coli
SEQUENCE: 11
aagactttat ctctctgtca taaaactgtc atattcctta catataactg tcacctgttt    60
gtcctatttt gcttctcgta gccaacaaac aatgctttat gagtgtagga ggataatcta   120
tggctagcaa aggagaagaa cttttcacat g                                  151

SEQ ID NO: 12           moltype = DNA   length = 186
FEATURE                 Location/Qualifiers
source                  1..186
                        mol_type = other DNA
                        organism = Escherichia coli
SEQUENCE: 12
agcatggcgt tttgttgcgc gggatcagca agcctagcgg cagttgttta cgcttttatt    60
acagatttaa taaattacca cattttaaga atattattaa tctgtaatat atctttaaca   120
atctcaggtt aaaaactttc ctgttttcaa cgggactctc ccgctggtgt aggaggataa   180
tctatg                                                              186

SEQ ID NO: 13           moltype = DNA   length = 384
FEATURE                 Location/Qualifiers
misc_feature            1..384
                        note = Description of Artificial Sequence: Synthetic
                         polynucleotide
source                  1..384
                        mol_type = other DNA
                        organism = synthetic construct
SEQUENCE: 13
ccaggcatca aataaaacga aaggctcagt cgaaagactg ggcctttcgt tttatctgtt    60
gtttgtcggt gaacgctctc tactagagtc acactggctc accttcgggt gggcctttct   120
gcgtttatac acagctaaca ccacgtcgtc cctatctgct gccctaggtc tatgagtggt   180
tgctggataa cgtgcgtaat tgtgctgatc tcttatatag ctgctctcat tatctctcta   240
ccctgaagtg actctctcac ctgtaaaaat aatatctcac aggcttaata gtttcttaat   300
acaaagcctg taaaacgtca ggataacttc tatattcagg gagaccacaa cggtttccct   360
ctacaaataa ttttgtttaa cttt                                          384

SEQ ID NO: 14           moltype = DNA   length = 284
FEATURE                 Location/Qualifiers
misc_feature            1..284
                        note = Description of Artificial Sequence: Synthetic
                         polynucleotide
source                  1..284
                        mol_type = other DNA
                        organism = synthetic construct
SEQUENCE: 14
cgcaaaaaac cccgcttcgg cggggttttt tcgcacgtct ccatcgcttg cccaagttgt    60
gaagcacagc taacaccacg tcgtcccctat ctgctgccct aggtctatga gtggttgctg   120
gataacgcca cggaaatcaa taacctgaag atatgtgcga cgagcttttc ataaatctgt   180
cataaatctg acgcataatg acgtcgcatt aatgatcgca acctatttat tatattcagg   240
gagaccacaa cggtttccct ctacaaataa ttttgtttaa cttt                    284

SEQ ID NO: 15           moltype = DNA   length = 365
FEATURE                 Location/Qualifiers
misc_feature            1..365
                        note = Description of Artificial Sequence: Synthetic
                         polynucleotide
source                  1..365
                        mol_type = other DNA
                        organism = synthetic construct
SEQUENCE: 15
cgccgaaaac cccgcttcgg cggggttttg ccgcacgtct ccatcgcttg cccaagttgt    60
```

```
gaagcacagc taacaccacg tcgtccctat ctgctgccct aggtctatga gtggttgctg    120
gataaccatc cataaatttt gcataattaa tgtaaagacc aggctcgcca gtaacgctaa    180
attcatttgg ctgtaagcgc ggtgtcatcc gcgtcaggaa aattaaacag ttactttaaa    240
aaatgaaaac gtaaaaggt tgggtttcga tgtattgacg ggtaaacttt gtcgcccgct     300
aaacatttgt ttatattcag ggagaccaca acggtttccc tctacaaata atttttgttta  360
acttt                                                                365

SEQ ID NO: 16           moltype = DNA   length = 320
FEATURE                 Location/Qualifiers
misc_feature            1..320
                        note = Description of Artificial Sequence: Synthetic
                        polynucleotide
source                  1..320
                        mol_type = other DNA
                        organism = synthetic construct
SEQUENCE: 16
aaaaaaaaac cccgcccctg acagggcggg gttttttttta cgtctccatc gcttgcccaa    60
gttgtgaagc acagctaaca ccacgtcgtc cctatctgct gccctaggtc tatgagtggt   120
tgctggataa caccgaactg aagcaggatt acaccgtggt gatcgtcacc cacaacatgc   180
agcaggctgc gcgttgttcc gaccacacgg cgtttatgta cctgggcgaa ttgattgagt   240
tcagcaacac ggacgatctg ttcaccaata ttcagggaga ccacaacggt ttccctctac   300
aaataatttt gtttaacttt                                                320

SEQ ID NO: 17           moltype = DNA   length = 350
FEATURE                 Location/Qualifiers
misc_feature            1..350
                        note = Description of Artificial Sequence: Synthetic
                        polynucleotide
source                  1..350
                        mol_type = other DNA
                        organism = synthetic construct
SEQUENCE: 17
cgccgcaaac cccgcccctg acagggcggg gtttcgccgc acgtctccat cgcttgccca    60
agttgtgaag cacagctaac accacgtcgt ccctatctgc tgccctaggt ctatgagtgg   120
ttgctggata acaatcctgc tgaaagcaca cagcttttt catcactgtc atcactctgt    180
catctttcca gtagaaacta atgtcactga aatggtgttt tatagttaaa tataagtaaa   240
tatattgttg caataaatgc gagatctgtt gtacttatta agtagcagcg gaagttcata   300
ttcagggaga ccacaacggt ttccctctac aaataatttt gtttaacttt               350

SEQ ID NO: 18           moltype = DNA   length = 208
FEATURE                 Location/Qualifiers
misc_feature            1..208
                        note = Description of Artificial Sequence: Synthetic
                        polynucleotide
source                  1..208
                        mol_type = other DNA
                        organism = synthetic construct
SEQUENCE: 18
cgccgaaaac cccgcttcgg cggggttttg ccgcacgtct ccatcgcttg cccaagttgt    60
gaagcacagc taacaccacg tcgtccctat ctgctgccct aggtctatga gtggttgctg   120
gataacttta cgggcatgca taaggctcgt aggctatatt cagggagacc acaacggttt   180
ccctctacaa ataattttgt ttaacttt                                       208

SEQ ID NO: 19           moltype = DNA   length = 213
FEATURE                 Location/Qualifiers
misc_feature            1..213
                        note = Description of Artificial Sequence: Synthetic
                        polynucleotide
source                  1..213
                        mol_type = other DNA
                        organism = synthetic construct
SEQUENCE: 19
aaaaaaaaac cccgcccctg acagggcggg gttttttttta cgtctccatc gcttgcccaa    60
gttgtgaagc acagctaaca ccacgtcgtc cctatctgct gccctaggtc tatgagtggt   120
tgctggataa ctttacgggc atgcataagg ctcgtaatat atattcaggg agaccacaac   180
ggtttccctc tacaaataat tttgtttaac ttt                                 213

SEQ ID NO: 20           moltype = DNA   length = 214
FEATURE                 Location/Qualifiers
misc_feature            1..214
                        note = Description of Artificial Sequence: Synthetic
                        polynucleotide
source                  1..214
                        mol_type = other DNA
                        organism = synthetic construct
SEQUENCE: 20
cgccgcaaac cccgcccctg acagggcggg gtttcgccgc acgtctccat cgcttgccca    60
agttgtgaag cacagctaac accacgtcgt ccctatctgc tgccctaggt ctatgagtgg   120
ttgctggata actttacggg catgcataag gctcgtatga tatattcagg gagaccacaa   180
```

```
cggtttccct ctacaaataa ttttgtttaa cttt                                214

SEQ ID NO: 21           moltype = DNA   length = 208
FEATURE                 Location/Qualifiers
misc_feature            1..208
                        note = Description of Artificial Sequence: Synthetic
                         polynucleotide
source                  1..208
                        mol_type = other DNA
                        organism = synthetic construct
SEQUENCE: 21
cgcaaaaaac cccgcttcgg cggggttttt tcgcacgtct ccatcgcttg cccaagttgt    60
gaagcacagc taacaccacg tcgtccctat ctgctgccct aggtctatga gtggttgctg   120
gataaccttta cgggcatgca taaggctcgt ataatatatt cagggagacc acaacggttt   180
ccctctacaa ataattttgt ttaactttt                                     208

SEQ ID NO: 22           moltype = DNA   length = 429
FEATURE                 Location/Qualifiers
misc_feature            1..429
                        note = Description of Artificial Sequence: Synthetic
                         polynucleotide
source                  1..429
                        mol_type = other DNA
                        organism = synthetic construct
SEQUENCE: 22
ccaggcatca aataaaacga aaggctcagt cgaaagactg ggcctttcgt tttatctgtt    60
gtttgtcggt gaacgctctc tactagagtc acactggctc accttcgggt gggccttttct  120
gcgtttatac acagctaaca ccacgtcgtc cctatctgct gccctaggtc tatgagtggt   180
tgctggataa cctccttcac agattcccaa tctcttgtta aataacgaaa aagcatcaat   240
taaaacccat gtctttctat attccagcaa tgttttatag gggacatatt gatgaagatg   300
ggtatcacct tagtgaattg ctataagctg ctcttttttg ttcgtgatat actgataaat   360
tgaattttca cacttcatat tcagggagac cacaacggtt tccctctaca ataattttg   420
tttaactttt                                                         429

SEQ ID NO: 23           moltype = DNA   length = 76
FEATURE                 Location/Qualifiers
misc_feature            1..76
                        note = Description of Artificial Sequence: Synthetic primer
source                  1..76
                        mol_type = other DNA
                        organism = synthetic construct
SEQUENCE: 23
taacaataaa aatgaaaatg atttccacga tacagaaaaa agagactgtc atcctaattt    60
ttgttgacac tctatc                                                   76

SEQ ID NO: 24           moltype = DNA   length = 75
FEATURE                 Location/Qualifiers
misc_feature            1..75
                        note = Description of Artificial Sequence: Synthetic primer
source                  1..75
                        mol_type = other DNA
                        organism = synthetic construct
SEQUENCE: 24
tgccactcag gtatgatggg cagaatattg cctctgcccg ccagaaaaag atcaaaggga    60
aaactgtcca tatgc                                                    75

SEQ ID NO: 25           moltype = DNA   length = 19
FEATURE                 Location/Qualifiers
misc_feature            1..19
                        note = Description of Artificial Sequence: Synthetic
                         oligonucleotide
source                  1..19
                        mol_type = other DNA
                        organism = synthetic construct
SEQUENCE: 25
ccgacaggga ttccatctg                                                 19

SEQ ID NO: 26           moltype = DNA   length = 26
FEATURE                 Location/Qualifiers
misc_feature            1..26
                        note = Description of Artificial Sequence: Synthetic
                         oligonucleotide
source                  1..26
                        mol_type = other DNA
                        organism = synthetic construct
SEQUENCE: 26
tatgacgacc attttgtcta cagttc                                         26

SEQ ID NO: 27           moltype = DNA   length = 75
```

```
FEATURE                 Location/Qualifiers
misc_feature            1..75
                        note = Description of Artificial Sequence: Synthetic primer
source                  1..75
                        mol_type = other DNA
                        organism = synthetic construct
SEQUENCE: 27
ggactttttgt acttcctgtt tcgatttagt tggcaattta ggtagcaaac tcctaatttt   60
tgttgacact ctatc                                                     75

SEQ ID NO: 28           moltype = DNA   length = 75
FEATURE                 Location/Qualifiers
misc_feature            1..75
                        note = Description of Artificial Sequence: Synthetic primer
source                  1..75
                        mol_type = other DNA
                        organism = synthetic construct
SEQUENCE: 28
ataaaaacgg cgctaaaaag cgccgttttt tttgacggtg gtaaagccga atcaaaggga   60
aaactgtcca tatgc                                                     75

SEQ ID NO: 29           moltype = DNA   length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 29
cctgactgta ctaacggttg ag                                             22

SEQ ID NO: 30           moltype = DNA   length = 27
FEATURE                 Location/Qualifiers
misc_feature            1..27
                        note = Description of Artificial Sequence: Synthetic
                         oligonucleotide
source                  1..27
                        mol_type = other DNA
                        organism = synthetic construct
SEQUENCE: 30
tgactttttat ggcgttcttt gtttttg                                       27

SEQ ID NO: 31           moltype = DNA   length = 22
FEATURE                 Location/Qualifiers
misc_feature            1..22
                        note = Description of Artificial Sequence: Synthetic primer
source                  1..22
                        mol_type = other DNA
                        organism = synthetic construct
SEQUENCE: 31
ctggtacacg ctgatgaaca cc                                             22

SEQ ID NO: 32           moltype = DNA   length = 21
FEATURE                 Location/Qualifiers
misc_feature            1..21
                        note = Description of Artificial Sequence: Synthetic primer
source                  1..21
                        mol_type = other DNA
                        organism = synthetic construct
SEQUENCE: 32
ctggtcattg ccatttgtgc c                                              21

SEQ ID NO: 33           moltype = DNA   length = 20
FEATURE                 Location/Qualifiers
misc_feature            1..20
                        note = Description of Artificial Sequence: Synthetic primer
source                  1..20
                        mol_type = other DNA
                        organism = synthetic construct
SEQUENCE: 33
gaatcagagc gttccgaccc                                                20

SEQ ID NO: 34           moltype = DNA   length = 20
FEATURE                 Location/Qualifiers
misc_feature            1..20
                        note = Description of Artificial Sequence: Synthetic primer
source                  1..20
                        mol_type = other DNA
```

```
                               organism = synthetic construct
SEQUENCE: 34
gtacgcagtt tgccaacgtg                                              20

SEQ ID NO: 35          moltype = DNA   length = 75
FEATURE                Location/Qualifiers
misc_feature           1..75
                       note = Description of Artificial Sequence: Synthetic primer
source                 1..75
                       mol_type = other DNA
                       organism = synthetic construct
SEQUENCE: 35
aatagcccgc tgatatcatc gataatacta aaaaaacagg gaggctatta tcctaatttt   60
tgttgacact ctatc                                                   75

SEQ ID NO: 36          moltype = DNA   length = 75
FEATURE                Location/Qualifiers
misc_feature           1..75
                       note = Description of Artificial Sequence: Synthetic primer
source                 1..75
                       mol_type = other DNA
                       organism = synthetic construct
SEQUENCE: 36
tacagggatc cagttatcaa taagcaaatt catttgttct ccttcatatg atcaaaggga   60
aaactgtcca tatgc                                                   75

SEQ ID NO: 37          moltype = DNA   length = 27
FEATURE                Location/Qualifiers
misc_feature           1..27
                       note = Description of Artificial Sequence: Synthetic primer
source                 1..27
                       mol_type = other DNA
                       organism = synthetic construct
SEQUENCE: 37
caagacatgt gtatatcact gtaattc                                      27

SEQ ID NO: 38          moltype = DNA   length = 23
FEATURE                Location/Qualifiers
misc_feature           1..23
                       note = Description of Artificial Sequence: Synthetic
                         oligonucleotide
source                 1..23
                       mol_type = other DNA
                       organism = synthetic construct
SEQUENCE: 38
gcgattgcag atttatgatt tgg                                          23

SEQ ID NO: 39          moltype = DNA   length = 19
FEATURE                Location/Qualifiers
misc_feature           1..19
                       note = Description of Artificial Sequence: Synthetic primer
source                 1..19
                       mol_type = other DNA
                       organism = synthetic construct
SEQUENCE: 39
gcaaaatgct ggctcattg                                               19

SEQ ID NO: 40          moltype = DNA   length = 22
FEATURE                Location/Qualifiers
misc_feature           1..22
                       note = Description of Artificial Sequence: Synthetic primer
source                 1..22
                       mol_type = other DNA
                       organism = synthetic construct
SEQUENCE: 40
gaactgaatg gcaaactgac tg                                           22

SEQ ID NO: 41          moltype = DNA   length = 18
FEATURE                Location/Qualifiers
misc_feature           1..18
                       note = Description of Artificial Sequence: Synthetic
                         oligonucleotide
source                 1..18
                       mol_type = other DNA
                       organism = synthetic construct
SEQUENCE: 41
tggggatgat cgaccaca                                                18

SEQ ID NO: 42          moltype = DNA   length = 20
```

-continued

```
FEATURE                 Location/Qualifiers
misc_feature            1..20
                        note = Description of Artificial Sequence: Synthetic primer
source                  1..20
                        mol_type = other DNA
                        organism = synthetic construct
SEQUENCE: 42
tatcatcctg aaagcgatgg                                                         20

SEQ ID NO: 43           moltype = DNA  length = 18
FEATURE                 Location/Qualifiers
misc_feature            1..18
                        note = Description of Artificial Sequence: Synthetic primer
source                  1..18
                        mol_type = other DNA
                        organism = synthetic construct
SEQUENCE: 43
atctcaccgt gtgatcgg                                                           18

SEQ ID NO: 44           moltype = DNA  length = 24
FEATURE                 Location/Qualifiers
misc_feature            1..24
                        note = Description of Artificial Sequence: Synthetic primer
source                  1..24
                        mol_type = other DNA
                        organism = synthetic construct
SEQUENCE: 44
caaaagagat tctgggtatt cact                                                    24

SEQ ID NO: 45           moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 45
ctgctggaaa ccatgcg                                                            17

SEQ ID NO: 46           moltype = DNA  length = 25
FEATURE                 Location/Qualifiers
misc_feature            1..25
                        note = Description of Artificial Sequence: Synthetic
                         oligonucleotide
source                  1..25
                        mol_type = other DNA
                        organism = synthetic construct
SEQUENCE: 46
agagcatgtc gttataggag gtgat                                                   25

SEQ ID NO: 47           moltype = DNA  length = 22
FEATURE                 Location/Qualifiers
misc_feature            1..22
                        note = Description of Artificial Sequence: Synthetic primer
source                  1..22
                        mol_type = other DNA
                        organism = synthetic construct
SEQUENCE: 47
agtactcaac caagtcattc tg                                                      22

SEQ ID NO: 48           moltype = DNA  length = 21
FEATURE                 Location/Qualifiers
misc_feature            1..21
                        note = Description of Artificial Sequence: Synthetic primer
source                  1..21
                        mol_type = other DNA
                        organism = synthetic construct
SEQUENCE: 48
gagcatggtg atcttctcag t                                                       21

SEQ ID NO: 49           moltype = DNA  length = 22
FEATURE                 Location/Qualifiers
misc_feature            1..22
                        note = Description of Artificial Sequence: Synthetic primer
source                  1..22
                        mol_type = other DNA
                        organism = synthetic construct
SEQUENCE: 49
gcgatgaatg tcttactacg ga                                                      22
```

```
SEQ ID NO: 50            moltype = DNA   length = 19
FEATURE                  Location/Qualifiers
misc_feature             1..19
                         note = Description of Artificial Sequence: Synthetic primer
source                   1..19
                         mol_type = other DNA
                         organism = synthetic construct
SEQUENCE: 50
gtcgctgggt aatctgcaa                                                         19

SEQ ID NO: 51            moltype = DNA   length = 23
FEATURE                  Location/Qualifiers
misc_feature             1..23
                         note = Description of Artificial Sequence: Synthetic primer
source                   1..23
                         mol_type = other DNA
                         organism = synthetic construct
SEQUENCE: 51
atcaacgcat atagcgctag cag                                                    23

SEQ ID NO: 52            moltype = DNA   length = 18
FEATURE                  Location/Qualifiers
misc_feature             1..18
                         note = Description of Artificial Sequence: Synthetic primer
source                   1..18
                         mol_type = other DNA
                         organism = synthetic construct
SEQUENCE: 52
actgaagccc agacgatc                                                          18

SEQ ID NO: 53            moltype = DNA   length = 3527
FEATURE                  Location/Qualifiers
misc_feature             1..3527
                         note = Description of Artificial Sequence: Synthetic
                          polynucleotide
source                   1..3527
                         mol_type = other DNA
                         organism = synthetic construct
SEQUENCE: 53
tcctaatttt tgttgacact ctatcattga tagagttatt ttaccactcc ctatcagtga    60
tagagaaaag tgaaatgaat agttcgacaa agatcgcatt ggtaattacg ttactcgatg   120
ccatggggat tggccttatc atgccagtct tgccaacgtt attacgtgaa tttattgctt   180
cggaagatat cgctaaccac tttggcgtat tgcttgcact ttatgcgtta atgcaggtta   240
tctttgctcc ttggcttgga aaaatgtctg accgatttgg tcgcgccca gtgctgttgt   300
tgtcattaat aggcgcatcg ctggattact tattgctggc tttttcaagt gcgctttgga   360
tgctgtattt aggcgtttg cttttcaggga tcacaggagc tactggggct gtcgcggcat   420
cggtcattgc cgataccacc tcagcttctc aacgcgtgaa gtggttcggt tggttagggg   480
caagtttttgg gctggttta atagcggggc ctattattgg tggtttttgca ggagagattt   540
caccgcatag tcccttttt atcgctgcgt tgctaaaatat tgtcactttc cttgtggtta   600
tgttttggtt ccgtgaaacc aaaatacac gtgataatac agataccgaa gtaggggttg   660
agacgcaatc gaattcggta tacatcactt tatttaaaac gatgcccatt ttgttgatta   720
tttattttc agcgcaattg ataggccaaa ttcccgcaac ggtgtgggtg ctatttaccg   780
aaaatcgttt tggatggaat agcatgatgg ttggcttttc attagcgggt cttggtcttt   840
tacactcagt attccaagcc tttgtggcag gaagaatagc cactaaatgg ggcgaaaaaa   900
cggcagtact gctcggattt attgcagata gtagtgcatt tgcctttta gcgtttatat   960
ctgaaggttg gttagttttc cctgttttaa tttattggc tggtggtggg atcgctttac  1020
ctgcattaca gggagtgatg tctatccaaa caaagagtca tcagcaaggt gctttacagg  1080
gattattggt gagccttacc aatgcaaccg tgttattgga cccattactg tttgctgtta  1140
tttataatca ttcactacca atttgggatg gctggatttg gattattggt ttagcgtttt  1200
actgtattat tatcctgcta tcgatgacct tcatgttaac ccctcaagct caggggagta  1260
aacaggagac aagtgcttag ttatttcgtc accaaatgat gttattccgc gaaatataat  1320
gaccctcttg ataacccaag agcatcacat ataacctgccg ttcactatta tttagtgaaa  1380
tgagatatta tgatattttc tgaattgtga ttaaaaaggc aactttatgc ccatgcaaca  1440
gaaactataa aaaatacaga gaatgaaaag aaacagatag attttttagt tctttaggcc  1500
cgtagtctgc aaatccttt atgatttct atcaaacaaa agaggaaaat agaccagttg  1560
caatccaaac gagagtctaa tagaatgagg tcgaaaagta aatcgcgcgg gtttgttact  1620
gataaagcag gcaagaccta aaatgtgtaa agggcaaagt gtatactttg gcgtcacccc  1680
ttacatattt taggtctttt tttattgtgc gtaactaact tgccatctc aaacaggagg  1740
gctggaagaa gcagaccgct aacacagtac ataaaaagg agacatgaac gatgaacatc  1800
aaaaagtttg caaacaagc aacagtatta acctttacta ccgcactgct ggcaggaggc  1860
gcaactcaag cgtttgcgaa agaacgaac caaaagccat ataaggaaac atacggcatt  1920
tcccatatta cacgccatga tatgctgcaa atccctgaac agcaaaaaaa tgaaaaatat  1980
caagttcctg agttcgattc gtcccacaatt aaaaatatct cttctgcaaa aggcctgag   2040
gtttgggaca gctggccatt acaaaacgct gacggcactg tcgcaaacta tcacggctac  2100
cacatcgtct tgcattagc cggagatcct aaaaatgcgg atgacacatc gatttacatg  2160
ttctatcaaa aagtcggcga aacttctatt gacagctgga aaacgctgg ccgcgtcttt  2220
aaagacagcg acaaattcga tgcaaatgat tctatcctaa aagaccaaac acaagaatgg  2280
tcaggttcag ccacatttac atctgacgga aaatccgtt tattctacac tgatttctcc  2340
```

```
ggtaaacatt acggcaaaca aacactgaca actgcacaag ttaacgtatc agcatcagac   2400
agctctttga acatcaacgg tgtagaggat tataaatcaa tctttgacgg tgacggaaaa   2460
acgtatcaaa atgtacagca gttcatcgat gaaggcaact acagctcagg cgacaaccat   2520
acgctgagag atcctcacta cgtagaagat aaaggccaca aatacttagt atttgaagca   2580
aacactggaa ctgaagatgg ctaccaaggc gaagaatctt tatttaacaa agcatactat   2640
ggcaaaagca catcattctt ccgtcaagaa agtcaaaaac ttctgcaaag cgataaaaaa   2700
cgcacggctg agttagcaaa cggcgctctc ggtatgattg agctaaacga tgattacaca   2760
ctgaaaaaag tgatgaaacc gctgattgca tctaacacag taacagatga aattgaacgc   2820
gcgaactgtc ttaaaatgaa cggcaaatgg tacctgttca ctgactcccg cggatcaaaa   2880
atgacgattg acggcattac gtctaacgat atttacatgc ttggttatgt ttctaattct   2940
ttaactggcc catacaagcc gctgaacaaa actggccttg tgttaaaaat ggatcttgat   3000
cctaacgatg taacctttac ttactcacac ttcgctgtac ctcaagcgaa aggaaacaat   3060
gtcgtgatta caagctatat gacaaacaga ggattctacg cagacaaaca atcaacgttt   3120
gcgccaagct tcctgctgaa catcaaaggc aagaaaacat ctgttgtcaa agacagcatc   3180
cttgaacaag gacaattaac agttaacaaa taaaaacgca aaagaaaatg ccgatattga   3240
ctaccggaag cagtgtgacc gtgtgcttct caaatgcctg attcaggctg tctatgtgtg   3300
actgttgagc tgtaacaagt tgtctcaggt gttcaatttc atgttctagt tgctttgttt   3360
tactggtttc acctgttcta ttaggtgtta catgctgttc atctgttaca ttgtcgatct   3420
gttcatggtg aacagcttta aatgcaccaa aaactcgtaa aagctctgat gtatctatct   3480
ttttacacc gttttcatct gtgcatatgg acagttttcc ctttgat                 3527

SEQ ID NO: 54         moltype = DNA   length = 70
FEATURE               Location/Qualifiers
misc_feature          1..70
                      note = Description of Artificial Sequence: Synthetic
                        oligonucleotide
source                1..70
                      mol_type = other DNA
                      organism = synthetic construct
SEQUENCE: 54
aaatgatttc cacgatacag aaaaaagaga ctgtcatggg cagaatattg cctctgcccg   60
ccagaaaaag                                                          70

SEQ ID NO: 55         moltype = DNA   length = 70
FEATURE               Location/Qualifiers
misc_feature          1..70
                      note = Description of Artificial Sequence: Synthetic
                        oligonucleotide
source                1..70
                      mol_type = other DNA
                      organism = synthetic construct
SEQUENCE: 55
ctgtttcgat ttagttggca atttaggtag caaactcggc tttaccaccg tcaaaaaaaa   60
cggcgctttt                                                          70

SEQ ID NO: 56         moltype = DNA   length = 476
FEATURE               Location/Qualifiers
misc_feature          1..476
                      note = Description of Artificial Sequence: Synthetic
                        polynucleotide
source                1..476
                      mol_type = other DNA
                      organism = synthetic construct
SEQUENCE: 56
caagacatgt gtatatcact gtaattcgat atttatgagc agcatcgaaa aatagcccgc   60
tgatatcatc gataatacta aaaaaacagg gaggctatta ccaggcatca aataaaacga   120
aaggctcagt cgaaagactg ggcctttcgt tttatctgtt gtttgtcggt gaacgctctc   180
tactagagtc acactggctc accttcgggt gggcctttct gcgtttatat ctttctgaca   240
ccttactatc ttacaaatgt aacaaaaaag ttattttttct gtaattcgag catgtcatgt   300
taccccgcga gcataaaacg cgtgtgtagg aggataatct ttgacggcta gctcagtcct   360
aggtacagtg ctagccatat gaaggagaac aaatgaattt gcttattgat aactggatcc   420
ctgtacgccc gcgaaacggg gggaaagtcc aaatcataaa tctgcaatcg ctatac       476

SEQ ID NO: 57         moltype = DNA   length = 974
FEATURE               Location/Qualifiers
misc_feature          1..974
                      note = Description of Artificial Sequence: Synthetic
                        polynucleotide
source                1..974
                      mol_type = other DNA
                      organism = synthetic construct
SEQUENCE: 57
caagacatgt gtatatcact gtaattcgat atttatgagc agcatcgaaa aatagcccgc   60
tgatatcatc gataatacta aaaaaacagg gaggctatta ccaggcatca aataaaacga   120
aaggctcagt cgaaagactg ggcctttcgt tttatctgtt gtttgtcggt gaacgctctc   180
tactagagtc acactggctc accttcgggt gggcctttct gcgtttatat ctttctgaca   240
ccttactatc ttacaaatgt aacaaaaaag ttattttttct gtaattcgag catgtcatgt   300
taccccgcga gcataaaacg cgtgtgtagg aggataatct atggatttgt cacagctaac   360
accacgtcgt ccctatctgc tgcgtgcatt ctatgagtgg ttgctggata accagctcac   420
```

```
gccgcacctg gtggtggatg tgacgctccc tggcgtgcag gttcctatgg aatatgcgcg    480
tgacgggcaa atcgtactca acattgcgcc gcgtgctgtc ggcaatctgg aactggcgaa    540
tgatgaggtg cgctttaacg cgcgctttgg tggcattccg cgtcaggttt ctgtgccgct    600
ggctgccgtg ctggctatct acgcccgtga aaatggcgca ggcacgatgt ttgagcctga    660
agctgcctac gatgaagata ccagcatcat gaatgatgaa gaggcatcgg cagacaacga    720
aaccgttatg tcggttattg atggcgacaa gccagatcac gatgatgaca ctcatcctga    780
cgatgaacct ccgcagccac cacgcggtgg tcgaccggca ttacgcgttg tgaagtaatt    840
gacggctagc tcagtcctag gtacagtgct agccatatga aggagaacaa atgaatttgc    900
ttattgataa ctggatccct gtacgcccgc gaaacggggg gaaagtccaa atcataaatc    960
tgcaatcgct atac                                                     974

SEQ ID NO: 58          moltype = DNA  length = 970
FEATURE                Location/Qualifiers
misc_feature           1..970
                       note = Description of Artificial Sequence: Synthetic
                       polynucleotide
source                 1..970
                       mol_type = other DNA
                       organism = synthetic construct
SEQUENCE: 58
ctattgaaga tgtgggtaac tctgcggcat tcctgtgctc cgatctctct gccggtatct     60
ccggtgaagt ggtccacgtt gacggcggtt tcagcattgc tgcaatgaac gaactcgaac    120
tgaaagcggc caacgatgaa actattctg aaaactatgc ggatgcgtct aataggaag    180
ttcctattct ctagaaagta taggaacttc cgaatccatg tgggagttta ttcttgacac    240
agatatttat gatataataa ctgagtaagc ttaacataag gaggaaaaac atatgttacg    300
cagcacgaac gatgttacgc agcagggcag tcgccctaaa acaaagttag gtggctcaag    360
tatgggcatc attcgcacat gtaggctcgg ccctgaccaa gtcaaatcca tgcgggctgc    420
tcttgatctt tcggtcgtg agttcggaga cgtagccacc tactcccaac atcagccgga    480
ctccgattac ctcgggaact tgctccgtag taagacattc atcgcgcttg ctgccttcga    540
ccaagaagcg gttgttggcg ctctcgcggc ttacgtttcg cccaagtttg agcagccgcg    600
tagtgagatc tatatctatg atctcgcagt ctccggcgag caccggaggc agggcattgc    660
caccgcgctc atcaatctcc tcaagcatga ggccaacgcg cttggtgctt atgtgatcta    720
cgtgcaagca gattacggtg acgatcccgc agtggctctc tatacaaagt tgggcatacg    780
ggaagaagtg atgcactttg atatcgaccc aagtaccgcc acctaagaag ttcctattct    840
ctagaaagta taggaacttc cgttctgttg gtaaagatgg gcggcgttct gccgcccgtt    900
atctctgtta tacctttctg atatttgtta tcgccgatcc gtctttctcc ccttcccgcc    960
ttgcgtcagg                                                          970

SEQ ID NO: 59          moltype = DNA  length = 2000
FEATURE                Location/Qualifiers
misc_feature           1..2000
                       note = Description of Artificial Sequence: Synthetic
                       polynucleotide
source                 1..2000
                       mol_type = other DNA
                       organism = synthetic construct
SEQUENCE: 59
tctccaaagc ggccaacgat gaaaactatt ctgaaaacta tgcggatgcg tcttgattga     60
cagctagctc agtcctaggt ataatgctag caactttaaa attaaagagg tatatattaa    120
tgactaagca atataagaat tacgtaaatg gggagtggaa gctttcggag aatgaaaatta    180
agatctatga accagccagt ggggcggaat tgggtgtcagt cccggcaatg tccactgaag    240
aagttgacta tgtctacgcc tcggccaaaa aagcgcagcc agcatggcgc tcgctttcct    300
atattgagcg tgcggcttat ttgcacaaag tcgcagacat cctgatgcgt gacaaggaga    360
aaattggagc ggtattgtcc aaggaagtag cgaaaggcta caaatccgca gtatcggagg    420
tcgtccgcac cgccgagatt attaattatg cggccgaaga agggcttcgc atggagggtg    480
aggtcttgga gggcggcagt tttgaggcgg catccaagaa aaaaatcgct gtcgtccgtc    540
gcgagccggt gggacttgtg cttgctatta gtccgttcaa ttaccccgtg aatctggccg    600
gctccaagat tgcccctgca ctgatcgcgg gcaatgtaat cgcttttaaa ccaccgaccc    660
aaggatcgat tagtggactt cttttagcgg aggcgtttgc ggaggcaggt cttccagccg    720
gcgtattcaa taccatcacg gggcgtggaa gtgaaatcgg ggattacatc gtggagcacc    780
aggcagtaaa tttcatcaac ttcacggggt ccacggggat cggggagcgt atcggtaaga    840
tggctggat gcgtccgatc atgttggaac ttggcggcaa ggatagtgcg attgtgctgg    900
aagacgcaga cttggaattg acagctaaaa acattatcgc tggagccttc gggtatagtg    960
gtcaacgttg cacggcagtt aagcgcgttc ttgttatgga aagtgtcgcg gatgaattgg   1020
tcgagaagat tcgcgagaaa gtgttagctc ttacgattgg aaatccagag gacgatgctg   1080
acatcactcc attgatcgac acgaaatccg cggattacgt cgaggggctg atcaacgacg   1140
cgaacgataa gggagcagcg gctttgaccg agatcaaacg cgaggggaac ctgatctgcc   1200
cgattctttt tgcaaaagtc acaactgaca tgcgcttggc atggaagaa ccctttgcgc   1260
cagtcttgcc tattatccgc gttactagcg tagaggaagc aattgaaatt tccaataaat   1320
ccgaatatgg gttgcaagcg agtatcttta ctaacgattt tccacgtgcc tttggtattg   1380
cggaacagtt agaagtcggg acagttcaca tcaacaacaa gacgcagcgc gggacagata   1440
acttccccctt ttgggagca agaagtctg ggctgaat ccaggggtg aaatactcca   1500
tcgaagccat gacgacggtg aagagcgttg tttttgacat caagtaaaac ataaggagga   1560
aaaacagatg gcgaaactga cctcgcggt tccggttctg acggacgtg atgttggcgg   1620
cgcggttgaa ttttgacgg atcgtctggg cttcagtcgt gattttgtgg aagatgactt   1680
cgcaggcgtg gttcgcgatg acgtcaccct gtttatttcc gcagttcagg atcaagtcgt   1740
gccgacaac acgctggctt gggtgtgggt cgtggcctg gatgaactgt atgcggaatg   1800
gagcgaagtt gtctctacca atttccgtga cgcgagcggt ccggcatga cggaaatcgg   1860
cgaacagccg tggggtcgcg aatttgctct gcgtgacccg gctggcaact gtgtccatct   1920
```

```
cgtggctgaa gaacaagatt gagttgagat gacactgtga tctaaaaaga gcgacttcgg    1980
tcgctctttt ttttacctga                                                2000

SEQ ID NO: 60           moltype = DNA  length = 2000
FEATURE                 Location/Qualifiers
misc_feature            1..2000
                        note = Description of Artificial Sequence: Synthetic
                        polynucleotide
source                  1..2000
                        mol_type = other DNA
                        organism = synthetic construct
SEQUENCE: 60
acgaaaccgg ttactccaac aaagttctgg acctgatcgc tcacatctcc aaatgattga      60
cagctagctc agtcctaggt ataatgctag caactttaaa attaaagagg tatatattaa     120
tgactaagca atataagaat tacgtaaatg gggagtggaa gctttcggag aatgaaatta     180
agatctatga accagccagt ggggcggaat tggggtcagt cccggcaatg tccactgaag     240
aagttgacta tgtctacgcc tcggccaaaa aagcgcagcc agcatggcgc tcgctttcct     300
atattgagcg tgcggcttat ttgcacaaag tcgcagacat cctgatgcgt gacaaggaga     360
aaattggagc ggtattgtcc aaggaagtag cgaaaggcta caaatccgca gtatcggagg     420
tcgtccgcac cgccgagatt attaattatg cggccgaaga agggcttcgc atggagggtg     480
aggtcttgga gggcggcagt tttgaggcgg catccaagaa aaaaatcgct gtcgtccgtc     540
gcgagccggt gggacttgtg cttgctatta gtccgtctca ttaccccgtg aatctggccg     600
gctccaagat tgcccctgca ctgatcgcgg gcaatgtaat cgcttttaaa ccaccgaccc     660
aaggatcgat tagtggactt ctttttagcg aggcgtttgc ggaggcaggt cttccagccg     720
gcgtattcaa taccatcacg gggcgtggaa gtgaaatcgg ggattacatc gtggagcacc     780
aggcagtaaa tttcatcaac ttcacgggtt ccacgggaca cgggagcgt atcggtaaga     840
tggctgggat gcgtccgatc atgttggaac ttggcggcaa ggatagtgcg attgtgctga     900
aagacgcaga cttggaattg acagctaaaa acattatcgc tggagccttc gggtatagtg     960
gtcaacgttg cacggcagtt aagcgcgttc ttgttatgaa aagtgtcgcg gatgaattgg    1020
tcgagaagat tcgcgagaaa gtgttagctc ttacgattgg aaatccagag gacgatgctg    1080
acatcactcc attgatcgac acgaaaatccg cggattacgt cgaggggctg atcaacgacg    1140
cgaacgataa gggagcagcg gctttgaccg agatcaaacg cgaggggaac ctgatctgcc    1200
cgattctttt tgacaaagtc acaactgaca tgcgcttggc atgggaagaa ccttcggcc     1260
cagtcttgcc tattatccgc gttactagcg tagaggaagc aattgaaatt tccaataat      1320
ccgaatatgg gttgcaagcg agtatcttta ctaacgattt tccacgtgcc tttggtattg    1380
cggaacagtt agaagtcggg acagttcaca tcaacaacaa gacgcagcgc gggacagata    1440
acttcccctt tttgggagca aagaagtctg ggctggaat ccaaggggtg aaatactcca     1500
tcgaagccat gacgacggtg aagagcgttg ttttttgacat caagtaaaac ataaggagga   1560
aaaacagatg gcgaaactga cctccgcggt tccggttctg acggcacgtg atgtggcggg    1620
cgcggttgaa ttttgacggg atcgtctggg cttcagtcgt gattttgtgg aagatgactt    1680
cgcaggcgtg gttcgcgatg acgtcaccct gtttatttcc gcagttcagg atcaagtcgt    1740
gccggacaac acgctggctt gggtgtgggt tcgtggcctg gatgaactgt atgcggaatg    1800
gagcgaagtt gtctctacca attccgtga cgcgagcggt ccggccatga cggaaatcgt    1860
cgaacagccg tggggtcgcg aatttgctct gcgtgacccg gctggcaact gtgtccattt    1920
cgtggctgaa gaacaagatt gagttgagat gacactgtga tctaaaaaga gcgacttcgg    1980
tcgctctttt ttttacctga                                                2000

SEQ ID NO: 61           moltype = DNA  length = 907
FEATURE                 Location/Qualifiers
misc_feature            1..907
                        note = Description of Artificial Sequence: Synthetic
                        polynucleotide
source                  1..907
                        mol_type = other DNA
                        organism = synthetic construct
SEQUENCE: 61
tctaccgatt tcaacggcga agtttgcact tccgtgttcg atgctaaagc tggtatcgct     60
ctgaacgaca acttcgtgaa actggtatcc tggtacgaca acgaaaccgg ttactccaac    120
aaagttctgg acctgatcgc tcacatctcc aaagcggcca acgatgaaaa ctattctgaa    180
aactatgcgg atgcgtcttg atcctgacgg atggccttt tgcgttccta caaactcttt    240
ttgtttattt ttctaaatac attcaaatat gtatccgctc atgagacaat aaccctgata    300
aatgcttcaa taatattgaa aaggaagag taatggcgaa actgacctcg gcggttccgg    360
ttctgacggc acgtgatgtg gcgggcgcgg ttgaattttg gacggatcgt ctgggcttca    420
gtcgtgattt tgtggaagat gacttcgcag gcgtggttcg cgatgt accctgttta        480
tttccgcagt tcaggatcaa gtcgtgccgg acaacacgct ggcttgggtg tgggttcgtg    540
gcctggatga actgtatgcg gaatggagcg aagttgtctc taccaatttc cgtgacgcga    600
gcggtccggc catgacggaa atcggcgaac agccgtgggg tcgcgaattt gctctgcgtg    660
acccggctgg caactgtgtc catttcgtgg ctgaagaaca agattgagtt gagatgacac    720
tgtgatctaa aaagagcgac ttcggtcgct ctttttttta cctgattaaaa tgaagttaca    780
ggactcgtc atgattaaga aaattttgtg ccttccggtc atcgaacaaa tctcccctgt    840
cctctcccgt cgtaaactgg atgaactgga cctcattgtg gtcgatcatc cccaggtaaa    900
agcctct                                                              907

SEQ ID NO: 62           moltype = DNA  length = 1421
FEATURE                 Location/Qualifiers
misc_feature            1..1421
                        note = Description of Artificial Sequence: Synthetic
                        polynucleotide
source                  1..1421
```

```
                        mol_type = other DNA
                        organism = synthetic construct
SEQUENCE: 62
gtattccgtc ttccatgttc accgtcattt tcgcaatggc acgtaccgtt ggctggatcg   60
cccactggag cgaaatgcac agtgacggta tgaagattgc ccgtccgcgt cagctgtata  120
caggatatga aaaacgcgac tttaaaagcg atatcaagcg tgcggccaac gatgaaaact  180
attctgaaaa ctatgcggat gcgtcttaat agtcctgacg gatggccttt ttgcgtttct  240
acaaactctt tttgtttatt tttctaaata cattcaaata tgtatccgct catgagacaa  300
taaccctgat aaatgcttca ataattga aaaaggaaga gtatgagtat tcaacatttc    360
cgtgtcgccc ttattccctt ttttgcggca ttttgccttc ctgttttgc tcacccagaa   420
acgctggtga agtaaaagaa tgctgaagat cagttgggtg cacgagtggg ttacatcgaa  480
ctggatctca acagcggtaa gatccttgag agttttcgcc ccgaagaacg ttttccaatg  540
atgagcactt ttaaagttct gctatgtggc gcggtattat cccgtgttga cgccgggcaa  600
gagcaactcg gtcgccgcat acactattct cagaatgact tggttgagta ctcaccagtc  660
acagaaaagc atcttacgga tggcatgaca gtaagagaat tatgcagtgc tgccataacc  720
atgagtgata acactgcggc caacttactt ctgacaacga tcggaggacc gaaggagcta  780
accgcttttt tgcacaacat gggggatcat gtaactcgcc ttgatcgttg gaaccggag   840
ctgaatgaag ccataccaaa cgacgagcgt gacaccacga tgcctacagc aatggcaaca  900
acgttgcgca aactattaac tggcgaacta cttactctag cttcccggca acaattaata  960
gactggatga aggcggataa agttgcagga ccacttctgc gctcggccct tccggctggc 1020
tggtttattg ctgataaatc tggagccggt gagcgtgggt ctcgcggtat cattgcagca 1080
ctggggccag atggtaagcc ctcccgtatc gtagttatct acacgacggg gagtcaggca 1140
actatggatg aacgaaatag acagatcgct gagataggtg cctcactgat taagcattgg 1200
taactgtcag actaatggtt gattgctaag ttgtaaatat tttaacccgc cgttcatatg 1260
gcgggttgat tttatatgc ctaaacacaa aaaattgtaa aataaaatc cattaacaga   1320
cctatataga tatttaaaaa gaatagaaca gctcaaatta tcagcaaccc aatacttca  1380
attaaaaact tcatggtagt cgcatttata accctatgaa a                      1421

SEQ ID NO: 63          moltype = DNA  length = 1078
FEATURE                Location/Qualifiers
misc_feature           1..1078
                        note = Description of Artificial Sequence: Synthetic
                        polynucleotide
source                 1..1078
                        mol_type = other DNA
                        organism = synthetic construct
SEQUENCE: 63
accgtcattt tcgcaatggc acgtaccgtt ggctggatcg cccactggag cgaaatgcac   60
agtgacggta tgaagattgc ccgtccgcgt cagctgtata caggatatga aaaacgcgac  120
tttaaaagcg atatcaagcg tgcggccaac gatgaaaact attctgaaaa ctatgcggat  180
gcgtcttaat cctgacggat ggccttttg cgtttctaca aactcttttt gtttattttt   240
ctaaatacat tcaaatatgt atccgctcat gagacaataa ccctgataaa tgcttcaata  300
atattgaaaa aggaagagta tgactgaata caagcccacg gtacgcttgg cgacgcgcga  360
cgatgttccc cgcgctgttc gtacattagc tgcggccttt gcagattacc cagcgacgcg  420
ccatacggtc gatccggacc gccatatcga gcgtgtcaca gaattgcagg aacttttctt  480
aactcgcgtg ggccttgaca tcggaaaggt ctgggtggct gacgatggcg ctgcagtggc  540
tgtttggaac actccggaga gtgtagaggc tggtgcagtg ttcgccgaaa ttggtcctcg  600
tatggccgaa ttaagtgaaa gtcgtctggc agcccaacaa caaatggaag ggttgcttgc  660
gccccaccgt ccgaaagaac ccgcgtggtt ccttgccacc gttggagtaa gcccagatca  720
ccaggggaag ggtttaggat ctgccgtagt tttaccaggt gtggaggcag cagaacgtgc  780
gggagttccg gccttccttg agacgtcggc ccgcgcaat ttaccgtttt acgaacgtct   840
tggattcacc gttacggcgg acgtggaggt gccggagga ccccgtactt ggtgtatgac   900
tcgtaaaccg ggagcctgat aatgttgat tgctaagttg taaatatttt aacccgccgt   960
tcatatggcg ggttgatttt tatatgccta aacacaaaaa attgtaaaaa taaaatccat 1020
taacagacct atatagatat ttaaaaagaa tagaacagct caaattatca gcaaccca   1078

SEQ ID NO: 64          moltype = DNA  length = 869
FEATURE                Location/Qualifiers
misc_feature           1..869
                        note = Description of Artificial Sequence: Synthetic
                        polynucleotide
source                 1..869
                        mol_type = other DNA
                        organism = synthetic construct
SEQUENCE: 64
gtattccgtc ttccatgttc accgtcattt tcgcaatggc acgtaccgtt ggctggatcg   60
cccactggag cgaaatgcac agtgacggta tgaagattgc ccgtccgcgt cagctgtata  120
caggatatga aaaacgcgac tttaaaagcg atatcaagcg tgcggccaac gatgaaaact  180
attctgaaaa ctatgcggat gcgtcttaat agttgacaat taatcatcgg catagtatat  240
cggcatagta taatacgact cactataggg ggccatcat ggccaagttg accagtgccg   300
ttccggtgct caccgcgcgc gacgtcgccg gagcggtcga gttctggacc gaccggctcg  360
ggttctcccg ggacttcgtg gaggacgact tcgccggtgt ggtccgggac gacgtgaccc  420
tgttcatcag cgcggtccag gaccaggtgg tgccggacaa caccctggcc tgggtgtggg  480
tgcgcggcct ggacgagctg tacgccgagt ggtcggagcg cgtgtccacg aacttccggg  540
acgcctccgg gccggccatg accgagatcg gcgagcagcg gtggggcgg gagttcgccc   600
tgcgcgaccc ggccggcaac tgcgtgcact tgtggcaga ggagcaggac tgaggataag   660
taatggttga ttgctaagtt gtaaatattt taacccgccg ttcatggcg ggttgatttt   720
ttatatgcct aaacacaaaa aattgtaaaa ataaaatcca ttaacagacc tatatagata  780
tttaaaaaga atagaacagc tcaaattatc agcaacccaa tactttcaat taaaaacttc  840
```

```
atggtagtcg catttataac cctatgaaa                                        869

SEQ ID NO: 65           moltype = DNA  length = 1000
FEATURE                 Location/Qualifiers
misc_feature            1..1000
                        note = Description of Artificial Sequence: Synthetic
                        polynucleotide
source                  1..1000
                        mol_type = other DNA
                        organism = synthetic construct
SEQUENCE: 65
gcggcgagct gctgggtgaa atcggcctgg caatcgaaat gggttgtgat gctgaagaca   60
tcgcactgac catccacgcg cacccgactc tgcacgagtc tgtgggcctg gcggcagaag  120
tgttcgaagg tagcattacc gacctgccga acccgaaagc gaagaagaag gcagccaacg  180
atgaaaacta ttctgaaaac tatgcggatg cgtcttaata gcaatccat gtgggagttt   240
attcttgaca cagatattta tgatataata actgagtaag cttaacataa ggaggaaaaa  300
catatgttac gcagcagcaa cgatgttacg cagcagggca gtcgccctaa aacaaagtta  360
ggtggctcaa gtatgggcat cattcgcaca tgtaggctcg gccctgacca agtcaaatcc  420
atgcgggctg ctcttgatct tttcggtcgt gagttcggag acgtagccac ctactcccaa  480
catcagccgg actccgatta cctcgggaac ttgctccgta gtaagacatt catcgcgctt  540
gctgccttcg accaagaagc ggttgttggc gctctcgcgg cttacgttct gcccaagttt  600
gagcagccgc gtagtgagat ctatatctat gatctcgcga tctccggcga gcaccggaag  660
cagggcattg ccaccgcgct catcaatctc ctcaagcatg aggccaacgc gcttggtgct  720
tatgtgatct acgtgcaagc agattacggt gacgatcccg cagtggctct ctatacaaag  780
ttgggcatac gggaagaagt gatgcacttt gatatcgacc caagtaccgc cacctaattt  840
ttcgtttgcc ggaacatccg gcaattaaaa aagcggctaa ccacgccgct ttttttacgt  900
ctgcaattta cctttccagt cttcttgctc cacgttcaga gagacgttcg catactgctg  960
accgttgctc gttattcagc ctgacagtat ggttactgtc                         1000

SEQ ID NO: 66           moltype = DNA  length = 852
FEATURE                 Location/Qualifiers
misc_feature            1..852
                        note = Description of Artificial Sequence: Synthetic
                        polynucleotide
source                  1..852
                        mol_type = other DNA
                        organism = synthetic construct
SEQUENCE: 66
tctgggtatt cactgctttg gcgagcgcgc tgccgaaatt attcatatcg gtcaggcgat   60
tatgaacag aaaggtggcg gcaacactat tgagtacttc gtcaacacca cctttaacta   120
cccgacgatg gcgaagcct atcgggtagc tgcgttaaac ggtttaaacc gcctgtttgc   180
ggccaacgat gaaaactatt ctgaaaacta tgcggatgcg tcttaatagt tgacaattaa   240
tcatcggcat agtatatcgg catagtataa tacgactcac tataggaggg ccatcatgaa   300
gaccttcaac atctctcagc aggatctgga gctggtggag tcgccactg agaagatcac   360
catgctctat gaggacaaca agcaccatgt cggggcggcc atcaggacca agactgggga   420
gatcatctct gctgtccaca ttgaggccta cattggcagg tcactgtct gtgctgaagc   480
cattgccatt gggtctgctg tgagcaacgg gcagaaggac tttgacacca ttgtggctgt   540
caggcacccc tactctgatg aggtggacag atccatcagg gtggtcagcc cctgtggcat   600
gtgcagagag ctcatctctg actatgctcc tgactgcttt gtgctcattg agatgaatgg   660
caagctggtc aaaaccacca ttgaggaact catccccctc aagtacacca ggaactaaag   720
taaaacttta tcgaaatggc catccattct tgcgcggatg gcctctgcca gctgctcata   780
gcggctgcgc agcggtgagc caggacgata aaccaggcca atagtgcggc gtggttccgg   840
cttaatgcac gg                                                       852

SEQ ID NO: 67           moltype = DNA  length = 898
FEATURE                 Location/Qualifiers
misc_feature            1..898
                        note = Description of Artificial Sequence: Synthetic
                        polynucleotide
source                  1..898
                        mol_type = other DNA
                        organism = synthetic construct
SEQUENCE: 67
gaagtggaag aagcctggaa atgggtagac tccattactg aggcgtgggc gatggacaat   60
gatgcgccga aaccgtatca ggccggaacc tggggacccg ttgcctcggt ggcgatgatt  120
acccgtgatg gtcgttcctg gaatgagttt gaggcggcca acgatgaaaa ctattctgaa  180
aactatgcgg atgcgtctta atagttgaca attaatcatc ggcatagtat atcggcatag  240
tataatacga ctcactatag gagggccatc atgaagacct tcaacatctc tcagcaggat  300
ctggagctgg tggaggtcgc cactgagaag atcaccatgc tctatgagga caacaagcac  360
catgtcgggg cggccatcag gaccaagact ggggagatca tctctgctgt ccacattgag  420
gcctacattg gcagggtcac tgtctgtgct gaagccattg ccattgggtc tgctgtgagc  480
aacgggcaga aggactttga caccattgtg gctgtcaggc accctactc tgatgaggtg  540
gacagatcca tcagggtggt cagcccctgt ggcatgtgca gagagctcat ctctgactat  600
gctcctgact gctttgtgct cattgagatg aatggcaagc tggtcaaaac caccattgag  660
gaactcatcc cctcaagta caccaggaac taaagtaata tctgcgctta ccctttatgt  720
ttatttacc ggtaacatga tcttgcgcag attgtagaac aatttttaca ctttcaggcc  780
tcgtgcggat tcacccacga ggcttttttt attacactga ctgaaacgtt tttgcccctat  840
gagctccggt tacaggcgtt tcagtcataa atcctctgaa tgaaacgcgt tgtgaatc   898
```

-continued

```
SEQ ID NO: 68           moltype = DNA   length = 1181
FEATURE                 Location/Qualifiers
misc_feature            1..1181
                        note = Description of Artificial Sequence: Synthetic
                         polynucleotide
source                  1..1181
                        mol_type = other DNA
                        organism = synthetic construct
SEQUENCE: 68
gcgtgcgcac catgacggtg gggaccgtct cgatggatat gctagcggtc gatttaacgc   60
cttgcccgca ggcgggtatt ggtacgccgg ttgagctgtg gggcaaggag atcaaaattg  120
atgatgtcgc cgccgctgcc ggaacggtgg gctatgagtt gatgtgcgcg ctggcgctac  180
gcgtcccggt tgtgacggtg gcggccaacg atgaaaacta ttctgaaaac tatgcggatg  240
cgtcttaatc ctgacggatg gccttttgc gtttctacaa actcttttg tttattttc   300
taaatacatt caaatatgta tccgctcatg agacaataac cctgataaat gcttcaataa  360
tattgaaaaa ggaagagtat gactgaatac aagcccacgg tacgcttggc gacgcgcgac  420
gatgttcccc gcgctgttcg tacattagct gcggcctttg cagattaccc agcgacgcgc  480
catacggtcg atccggaccg ccatatcgag cgtgtcacag aattgcagga acttttctta  540
actcgcgtgg gccttgacat cggaaaggtc tgggtggctg acgatggcgc tgcagtggct  600
gtttggacca ctccggagag tgtagaggct ggtgcagtgt cgccgaaat tggtcctcgt  660
atggccgaat taagtggaag tcgtctggca gcccaacaac aaatgaagg gttgcttgcg  720
ccccaccgtc cgaaagaacc cgcgtggttc cttgccaccg ttggagtgaa cccagatcac  780
caggggaagg gtttaggatc tgccgtagtt ttaccaggtg tggaggcagc agaacgtgcg  840
ggagttccgg cctccttga gacgtcgcg ccgcgcaatt taccgtttta cgaacgtctt   900
ggattcaccg ttacgcgga cgtggaggtg ccggagggac cccgtacttg gtgtatgact   960
cgtaaaccgg gagcctgata acttgttgta agccggatgg aggcaacgt cttctgggtg  1020
caaaaaaatc atccatccgg ctggtcagca actgtagttg ttaatgtgac agagccattg  1080
cccatgatag tgtccattaa aaggatggac actatttccc cggaacctga actcaccgca  1140
caggcgttct acataaaacg cttacgcttc attgttgact c                     1181

SEQ ID NO: 69           moltype = DNA   length = 92
FEATURE                 Location/Qualifiers
misc_feature            1..92
                        note = Description of Artificial Sequence: Synthetic
                         oligonucleotide
source                  1..92
                        mol_type = other DNA
                        organism = synthetic construct
SEQUENCE: 69
tcgagttccc cgcgccagcg gggataaacc gttgattata ataaccgttt atctgttcgt   60
atcgagttcc ccgcgccagc ggggataaac cg                                92

SEQ ID NO: 70           moltype = DNA   length = 59
FEATURE                 Location/Qualifiers
misc_feature            1..59
                        note = Description of Artificial Sequence: Synthetic primer
source                  1..59
                        mol_type = other DNA
                        organism = synthetic construct
SEQUENCE: 70
gtttatctgt tcgtatcgag ttccccgcgc cagcggggat aaaccgaaaa aaaaacccc    59

SEQ ID NO: 71           moltype = DNA   length = 60
FEATURE                 Location/Qualifiers
misc_feature            1..60
                        note = Description of Artificial Sequence: Synthetic primer
source                  1..60
                        mol_type = other DNA
                        organism = synthetic construct
SEQUENCE: 71
ggttattata atcaacggtt tatccccgct ggcgcgggga actcgaggtg gtaccagatc   60

SEQ ID NO: 72           moltype = DNA   length = 92
FEATURE                 Location/Qualifiers
misc_feature            1..92
                        note = Description of Artificial Sequence: Synthetic
                         oligonucleotide
source                  1..92
                        mol_type = other DNA
                        organism = synthetic construct
SEQUENCE: 72
tcgagttccc cgcgccagcg gggataaacc ggttttgta attttacagg caaccttta    60
ttcgagttcc ccgcgccagc ggggataaac cg                                92

SEQ ID NO: 73           moltype = DNA   length = 59
FEATURE                 Location/Qualifiers
misc_feature            1..59
                        note = Description of Artificial Sequence: Synthetic primer
source                  1..59
```

```
                        mol_type = other DNA
                        organism = synthetic construct
SEQUENCE: 73
caggcaacct tttattcgag ttccccgcgc cagcggggat aaaccgaaaa aaaaacccc    59

SEQ ID NO: 74           moltype = DNA   length = 60
FEATURE                 Location/Qualifiers
misc_feature            1..60
                        note = Description of Artificial Sequence: Synthetic primer
source                  1..60
                        mol_type = other DNA
                        organism = synthetic construct
SEQUENCE: 74
taaaattaca aaaaccggtt tatccccgct ggcgcgggga actcgaggtg gtaccagatc   60

SEQ ID NO: 75           moltype = DNA   length = 93
FEATURE                 Location/Qualifiers
misc_feature            1..93
                        note = Description of Artificial Sequence: Synthetic
                         oligonucleotide
source                  1..93
                        mol_type = other DNA
                        organism = synthetic construct
SEQUENCE: 75
tcgagttccc cgcgccagcg gggataaacc gaaaagcata taatgcgtaa aagttatgaa   60
gttcgagttc cccgcgccag cggggataaa ccg                                93

SEQ ID NO: 76           moltype = DNA   length = 62
FEATURE                 Location/Qualifiers
misc_feature            1..62
                        note = Description of Artificial Sequence: Synthetic primer
source                  1..62
                        mol_type = other DNA
                        organism = synthetic construct
SEQUENCE: 76
gcgtaaaagt tatgaagttc gagttccccg cgccagcggg gataaaccga aaaaaaaacc   60
cc                                                                  62

SEQ ID NO: 77           moltype = DNA   length = 59
FEATURE                 Location/Qualifiers
misc_feature            1..59
                        note = Description of Artificial Sequence: Synthetic primer
source                  1..59
                        mol_type = other DNA
                        organism = synthetic construct
SEQUENCE: 77
attatatgct tttcggttta tccccgctgg cgcggggaac tcgaggtggt accagatct    59

SEQ ID NO: 78           moltype = DNA   length = 94
FEATURE                 Location/Qualifiers
misc_feature            1..94
                        note = Description of Artificial Sequence: Synthetic
                         oligonucleotide
source                  1..94
                        mol_type = other DNA
                        organism = synthetic construct
SEQUENCE: 78
tcgagttccc cgcgccagcg gggataaacc gtattgacca attcattcgg gacagttatt   60
agttcgagtt ccccgcgcca gcggggataa accg                               94

SEQ ID NO: 79           moltype = DNA   length = 59
FEATURE                 Location/Qualifiers
misc_feature            1..59
                        note = Description of Artificial Sequence: Synthetic primer
source                  1..59
                        mol_type = other DNA
                        organism = synthetic construct
SEQUENCE: 79
gggacagtta ttagttcgag ttccccgcgc cagcggggat aaaccgaaaa aaaaacccc    59

SEQ ID NO: 80           moltype = DNA   length = 63
FEATURE                 Location/Qualifiers
misc_feature            1..63
                        note = Description of Artificial Sequence: Synthetic primer
source                  1..63
                        mol_type = other DNA
                        organism = synthetic construct
SEQUENCE: 80
gaatgaattg gtcaatacgg tttatccccg ctggcgcggg gaactcgagg tggtaccaga   60
```

```
tct                                                                    63

SEQ ID NO: 81           moltype = DNA   length = 92
FEATURE                 Location/Qualifiers
misc_feature            1..92
                        note = Description of Artificial Sequence: Synthetic
                        oligonucleotide
source                  1..92
                        mol_type = other DNA
                        organism = synthetic construct
SEQUENCE: 81
tcgagttccc cgcgccagcg gggataaacc gagtggttgc tggataactt tacgggcatg   60
ctcgagttcc ccgcgccagc ggggataaac cg                                  92

SEQ ID NO: 82           moltype = DNA   length = 60
FEATURE                 Location/Qualifiers
misc_feature            1..60
                        note = Description of Artificial Sequence: Synthetic primer
source                  1..60
                        mol_type = other DNA
                        organism = synthetic construct
SEQUENCE: 82
aactttacgg gcatgctcga gttccccgcg ccagcgggga taaaccgaaa aaaaaacccc   60

SEQ ID NO: 83           moltype = DNA   length = 60
FEATURE                 Location/Qualifiers
misc_feature            1..60
                        note = Description of Artificial Sequence: Synthetic primer
source                  1..60
                        mol_type = other DNA
                        organism = synthetic construct
SEQUENCE: 83
atccagcaac cactcggttt atccccgctg gcgcggggaa ctcgaggtgg taccagatct   60

SEQ ID NO: 84           moltype = DNA   length = 92
FEATURE                 Location/Qualifiers
misc_feature            1..92
                        note = Description of Artificial Sequence: Synthetic
                        oligonucleotide
source                  1..92
                        mol_type = other DNA
                        organism = synthetic construct
SEQUENCE: 84
tcgagttccc cgcgccagcg gggataaacc gttaccattc tgttgctttt atgtataaga   60
atcgagttcc ccgcgccagc ggggataaac cg                                  92

SEQ ID NO: 85           moltype = DNA   length = 59
FEATURE                 Location/Qualifiers
misc_feature            1..59
                        note = Description of Artificial Sequence: Synthetic primer
source                  1..59
                        mol_type = other DNA
                        organism = synthetic construct
SEQUENCE: 85
ttttatgtat aagaatcgag ttccccgcgc cagcggggat aaaccgaaaa aaaaacccc    59

SEQ ID NO: 86           moltype = DNA   length = 60
FEATURE                 Location/Qualifiers
misc_feature            1..60
                        note = Description of Artificial Sequence: Synthetic primer
source                  1..60
                        mol_type = other DNA
                        organism = synthetic construct
SEQUENCE: 86
gcaacagaat ggtaacggtt tatccccgct ggcgcgggga actcgaggtg gtaccagatc   60

SEQ ID NO: 87           moltype = DNA   length = 92
FEATURE                 Location/Qualifiers
misc_feature            1..92
                        note = Description of Artificial Sequence: Synthetic
                        oligonucleotide
source                  1..92
                        mol_type = other DNA
                        organism = synthetic construct
SEQUENCE: 87
tcgagttccc cgcgccagcg gggataaacc gctcgtaaaa gcagtacagt gcaccgtaag   60
atcgagttcc ccgcgccagc ggggataaac cg                                  92

SEQ ID NO: 88           moltype = DNA   length = 59
```

```
FEATURE                 Location/Qualifiers
misc_feature            1..59
                        note = Description of Artificial Sequence: Synthetic primer
source                  1..59
                        mol_type = other DNA
                        organism = synthetic construct
SEQUENCE: 88
cagtgcaccg taagatcgag ttccccgcgc cagcggggat aaaccgaaaa aaaaacccc    59

SEQ ID NO: 89           moltype = DNA   length = 60
FEATURE                 Location/Qualifiers
misc_feature            1..60
                        note = Description of Artificial Sequence: Synthetic primer
source                  1..60
                        mol_type = other DNA
                        organism = synthetic construct
SEQUENCE: 89
tactgctttt acgagcggtt tatccccgct ggcgcgggga actcgaggtg gtaccagatc    60

SEQ ID NO: 90           moltype = DNA   length = 154
FEATURE                 Location/Qualifiers
misc_feature            1..154
                        note = Description of Artificial Sequence: Synthetic
                         polynucleotide
source                  1..154
                        mol_type = other DNA
                        organism = synthetic construct
SEQUENCE: 90
tcgagttccc cgcgccagcg gggataaacc gttgattata ataaccgttt atctgttcgt    60
atcgagttcc ccgcgccagc ggggataaac cgaaaagcat ataatgcgta aaagttatga   120
agttcgagtt ccccgcgcca gcggggataa accg                               154

SEQ ID NO: 91           moltype = DNA   length = 36
FEATURE                 Location/Qualifiers
misc_feature            1..36
                        note = Description of Artificial Sequence: Synthetic primer
source                  1..36
                        mol_type = other DNA
                        organism = synthetic construct
SEQUENCE: 91
gcgccagcgg ggataaaccg aaaagcatat aatgcg                              36

SEQ ID NO: 92           moltype = DNA   length = 28
FEATURE                 Location/Qualifiers
misc_feature            1..28
                        note = Description of Artificial Sequence: Synthetic primer
source                  1..28
                        mol_type = other DNA
                        organism = synthetic construct
SEQUENCE: 92
cttgcccgcc tgatgaatgc tcatccgg                                       28

SEQ ID NO: 93           moltype = DNA   length = 28
FEATURE                 Location/Qualifiers
misc_feature            1..28
                        note = Description of Artificial Sequence: Synthetic primer
source                  1..28
                        mol_type = other DNA
                        organism = synthetic construct
SEQUENCE: 93
ccggatgagc attcatcagg cgggcaag                                       28

SEQ ID NO: 94           moltype = DNA   length = 59
FEATURE                 Location/Qualifiers
misc_feature            1..59
                        note = Description of Artificial Sequence: Synthetic primer
source                  1..59
                        mol_type = other DNA
                        organism = synthetic construct
SEQUENCE: 94
cggtttatcc ccgctggcgc ggggaactcg atacgaacag ataaacggtt attataatc    59

SEQ ID NO: 95           moltype = DNA   length = 155
FEATURE                 Location/Qualifiers
misc_feature            1..155
                        note = Description of Artificial Sequence: Synthetic
                         polynucleotide
source                  1..155
                        mol_type = other DNA
```

```
                        organism = synthetic construct
SEQUENCE: 95
tcgagttccc cgcgccagcg gggataaacc gttgattata ataaccgttt atctgttcgt    60
atcgagttcc ccgcgccagc ggggataaac cgtattgacc aattcattcg ggacagttat   120
tagttcgagt tccccgcgcc agcggggata aaccg                              155

SEQ ID NO: 96           moltype = DNA   length = 37
FEATURE                 Location/Qualifiers
misc_feature            1..37
                        note = Description of Artificial Sequence: Synthetic primer
source                  1..37
                        mol_type = other DNA
                        organism = synthetic construct
SEQUENCE: 96
gcgccagcgg ggataaaccg tattgaccaa ttcattc                             37

SEQ ID NO: 97           moltype = DNA   length = 28
FEATURE                 Location/Qualifiers
misc_feature            1..28
                        note = Description of Artificial Sequence: Synthetic primer
source                  1..28
                        mol_type = other DNA
                        organism = synthetic construct
SEQUENCE: 97
cttgcccgcc tgatgaatgc tcatccgg                                       28

SEQ ID NO: 98           moltype = DNA   length = 28
FEATURE                 Location/Qualifiers
misc_feature            1..28
                        note = Description of Artificial Sequence: Synthetic primer
source                  1..28
                        mol_type = other DNA
                        organism = synthetic construct
SEQUENCE: 98
ccggatgagc attcatcagg cgggcaag                                       28

SEQ ID NO: 99           moltype = DNA   length = 59
FEATURE                 Location/Qualifiers
misc_feature            1..59
                        note = Description of Artificial Sequence: Synthetic primer
source                  1..59
                        mol_type = other DNA
                        organism = synthetic construct
SEQUENCE: 99
cggtttatcc ccgctggcgc ggggaactcg atacgaacag ataaacggtt attataatc     59

SEQ ID NO: 100          moltype = DNA   length = 153
FEATURE                 Location/Qualifiers
misc_feature            1..153
                        note = Description of Artificial Sequence: Synthetic
                         polynucleotide
source                  1..153
                        mol_type = other DNA
                        organism = synthetic construct
SEQUENCE: 100
tcgagttccc cgcgccagcg gggataaacc gttgattata ataaccgttt atctgttcgt    60
atcgagttcc ccgcgccagc ggggataaac cgttaccatt ctgttgcttt tatgtataag   120
aatcgagttc cccgcgccag cggggataaa ccg                                153

SEQ ID NO: 101          moltype = DNA   length = 34
FEATURE                 Location/Qualifiers
misc_feature            1..34
                        note = Description of Artificial Sequence: Synthetic primer
source                  1..34
                        mol_type = other DNA
                        organism = synthetic construct
SEQUENCE: 101
gcgccagcgg ggataaaccg ttaccattct gttg                                34

SEQ ID NO: 102          moltype = DNA   length = 28
FEATURE                 Location/Qualifiers
misc_feature            1..28
                        note = Description of Artificial Sequence: Synthetic primer
source                  1..28
                        mol_type = other DNA
                        organism = synthetic construct
SEQUENCE: 102
cttgcccgcc tgatgaatgc tcatccgg                                       28
```

```
SEQ ID NO: 103           moltype = DNA  length = 28
FEATURE                  Location/Qualifiers
misc_feature             1..28
                         note = Description of Artificial Sequence: Synthetic primer
source                   1..28
                         mol_type = other DNA
                         organism = synthetic construct
SEQUENCE: 103
ccggatgagc attcatcagg cgggcaag                                          28

SEQ ID NO: 104           moltype = DNA  length = 59
FEATURE                  Location/Qualifiers
misc_feature             1..59
                         note = Description of Artificial Sequence: Synthetic primer
source                   1..59
                         mol_type = other DNA
                         organism = synthetic construct
SEQUENCE: 104
cggtttatcc ccgctggcgc ggggaactcg atacgaacag ataaacggtt attataatc        59

SEQ ID NO: 105           moltype = DNA  length = 153
FEATURE                  Location/Qualifiers
misc_feature             1..153
                         note = Description of Artificial Sequence: Synthetic
                         polynucleotide
source                   1..153
                         mol_type = other DNA
                         organism = synthetic construct
SEQUENCE: 105
tcgagttccc cgcgccagcg gggataaacc gttgattata ataccgtttt atctgttcgt       60
atcgagttcc ccgcgccagc ggggataaac cgctcgtaaa agcagtacag tgcaccgtaa      120
gatcgagttc cccgcgccag cggggataaa ccg                                  153

SEQ ID NO: 106           moltype = DNA  length = 30
FEATURE                  Location/Qualifiers
misc_feature             1..30
                         note = Description of Artificial Sequence: Synthetic primer
source                   1..30
                         mol_type = other DNA
                         organism = synthetic construct
SEQUENCE: 106
gcgccagcgg ggataaaccg ctcgtaaaag                                        30

SEQ ID NO: 107           moltype = DNA  length = 28
FEATURE                  Location/Qualifiers
misc_feature             1..28
                         note = Description of Artificial Sequence: Synthetic primer
source                   1..28
                         mol_type = other DNA
                         organism = synthetic construct
SEQUENCE: 107
cttgcccgcc tgatgaatgc tcatccgg                                          28

SEQ ID NO: 108           moltype = DNA  length = 28
FEATURE                  Location/Qualifiers
misc_feature             1..28
                         note = Description of Artificial Sequence: Synthetic primer
source                   1..28
                         mol_type = other DNA
                         organism = synthetic construct
SEQUENCE: 108
ccggatgagc attcatcagg cgggcaag                                          28

SEQ ID NO: 109           moltype = DNA  length = 59
FEATURE                  Location/Qualifiers
misc_feature             1..59
                         note = Description of Artificial Sequence: Synthetic primer
source                   1..59
                         mol_type = other DNA
                         organism = synthetic construct
SEQUENCE: 109
cggtttatcc ccgctggcgc ggggaactcg atacgaacag ataaacggtt attataatc        59

SEQ ID NO: 110           moltype = DNA  length = 156
FEATURE                  Location/Qualifiers
misc_feature             1..156
                         note = Description of Artificial Sequence: Synthetic
                         polynucleotide
source                   1..156
```

```
                            mol_type = other DNA
                            organism = synthetic construct
SEQUENCE: 110
tcgagttccc cgcgccagcg gggataaacc gaaaagcata taatgcgtaa aagttatgaa    60
gttcgagttc cccgcgccag cggggataaa ccgtattgac caattcattc gggacagtta   120
ttagttcgag ttccccgcgc cagcggggat aaaccg                             156

SEQ ID NO: 111              moltype = DNA   length = 37
FEATURE                     Location/Qualifiers
misc_feature                1..37
                            note = Description of Artificial Sequence: Synthetic primer
source                      1..37
                            mol_type = other DNA
                            organism = synthetic construct
SEQUENCE: 111
gcgccagcgg ggataaaccg tattgaccaa ttcattc                              37

SEQ ID NO: 112              moltype = DNA   length = 28
FEATURE                     Location/Qualifiers
misc_feature                1..28
                            note = Description of Artificial Sequence: Synthetic primer
source                      1..28
                            mol_type = other DNA
                            organism = synthetic construct
SEQUENCE: 112
cttgcccgcc tgatgaatgc tcatccgg                                        28

SEQ ID NO: 113              moltype = DNA   length = 28
FEATURE                     Location/Qualifiers
misc_feature                1..28
                            note = Description of Artificial Sequence: Synthetic primer
source                      1..28
                            mol_type = other DNA
                            organism = synthetic construct
SEQUENCE: 113
ccggatgagc attcatcagg cgggcaag                                        28

SEQ ID NO: 114              moltype = DNA   length = 47
FEATURE                     Location/Qualifiers
misc_feature                1..47
                            note = Description of Artificial Sequence: Synthetic primer
source                      1..47
                            mol_type = other DNA
                            organism = synthetic construct
SEQUENCE: 114
cggtttatcc ccgctggcgc ggggaactcg aacttcataa cttttac                   47

SEQ ID NO: 115              moltype = DNA   length = 154
FEATURE                     Location/Qualifiers
misc_feature                1..154
                            note = Description of Artificial Sequence: Synthetic
                             polynucleotide
source                      1..154
                            mol_type = other DNA
                            organism = synthetic construct
SEQUENCE: 115
tcgagttccc cgcgccagcg gggataaacc gaaaagcata taatgcgtaa aagttatgaa    60
gttcgagttc cccgcgccag cggggataaa ccgttaccat tctgttgctt ttatgtataa   120
gaatcgagtt ccccgcgcca gcggggataa accg                               154

SEQ ID NO: 116              moltype = DNA   length = 34
FEATURE                     Location/Qualifiers
misc_feature                1..34
                            note = Description of Artificial Sequence: Synthetic primer
source                      1..34
                            mol_type = other DNA
                            organism = synthetic construct
SEQUENCE: 116
gcgccagcgg ggataaaccg ttaccattct gttg                                 34

SEQ ID NO: 117              moltype = DNA   length = 28
FEATURE                     Location/Qualifiers
misc_feature                1..28
                            note = Description of Artificial Sequence: Synthetic primer
source                      1..28
                            mol_type = other DNA
                            organism = synthetic construct
SEQUENCE: 117
cttgcccgcc tgatgaatgc tcatccgg                                        28
```

```
SEQ ID NO: 118          moltype = DNA   length = 28
FEATURE                 Location/Qualifiers
misc_feature            1..28
                        note = Description of Artificial Sequence: Synthetic primer
source                  1..28
                        mol_type = other DNA
                        organism = synthetic construct
SEQUENCE: 118
ccggatgagc attcatcagg cgggcaag                                              28

SEQ ID NO: 119          moltype = DNA   length = 47
FEATURE                 Location/Qualifiers
misc_feature            1..47
                        note = Description of Artificial Sequence: Synthetic primer
source                  1..47
                        mol_type = other DNA
                        organism = synthetic construct
SEQUENCE: 119
cggtttatcc ccgctggcgc ggggaactcg aacttcataa cttttac                        47

SEQ ID NO: 120          moltype = DNA   length = 154
FEATURE                 Location/Qualifiers
misc_feature            1..154
                        note = Description of Artificial Sequence: Synthetic
                        polynucleotide
source                  1..154
                        mol_type = other DNA
                        organism = synthetic construct
SEQUENCE: 120
tcgagttccc cgcgccagcg gggataaaacc gaaaagcata taatgcgtaa aagttatgaa    60
gttcgagttc cccgcgccag cggggataaa ccgctcgtaa aagcagtaca gtgcaccgta   120
agatcgagtt ccccgcgcca gcggggataa accg                                154

SEQ ID NO: 121          moltype = DNA   length = 30
FEATURE                 Location/Qualifiers
misc_feature            1..30
                        note = Description of Artificial Sequence: Synthetic primer
source                  1..30
                        mol_type = other DNA
                        organism = synthetic construct
SEQUENCE: 121
gcgccagcgg ggataaaccg ctcgtaaaag                                            30

SEQ ID NO: 122          moltype = DNA   length = 28
FEATURE                 Location/Qualifiers
misc_feature            1..28
                        note = Description of Artificial Sequence: Synthetic primer
source                  1..28
                        mol_type = other DNA
                        organism = synthetic construct
SEQUENCE: 122
cttgcccgcc tgatgaatgc tcatccgg                                              28

SEQ ID NO: 123          moltype = DNA   length = 28
FEATURE                 Location/Qualifiers
misc_feature            1..28
                        note = Description of Artificial Sequence: Synthetic primer
source                  1..28
                        mol_type = other DNA
                        organism = synthetic construct
SEQUENCE: 123
ccggatgagc attcatcagg cgggcaag                                              28

SEQ ID NO: 124          moltype = DNA   length = 47
FEATURE                 Location/Qualifiers
misc_feature            1..47
                        note = Description of Artificial Sequence: Synthetic primer
source                  1..47
                        mol_type = other DNA
                        organism = synthetic construct
SEQUENCE: 124
cggtttatcc ccgctggcgc ggggaactcg aacttcataa cttttac                        47

SEQ ID NO: 125          moltype = DNA   length = 155
FEATURE                 Location/Qualifiers
misc_feature            1..155
                        note = Description of Artificial Sequence: Synthetic
                        polynucleotide
```

```
source                          1..155
                                mol_type = other DNA
                                organism = synthetic construct
SEQUENCE: 125
tcgagttccc cgcgccagcg gggataaacc gtattgacca attcattcgg gacagttatt    60
agttcgagtt ccccgcgcca gcggggataa accgttacca ttctgttgct tttatgtata   120
agaatcgagt tccccgcgcc agcggggata aaccg                              155

SEQ ID NO: 126                  moltype = DNA   length = 34
FEATURE                         Location/Qualifiers
misc_feature                    1..34
                                note = Description of Artificial Sequence: Synthetic primer
source                          1..34
                                mol_type = other DNA
                                organism = synthetic construct
SEQUENCE: 126
gcgccagcgg ggataaaccg ttaccattct gttg                                34

SEQ ID NO: 127                  moltype = DNA   length = 28
FEATURE                         Location/Qualifiers
misc_feature                    1..28
                                note = Description of Artificial Sequence: Synthetic primer
source                          1..28
                                mol_type = other DNA
                                organism = synthetic construct
SEQUENCE: 127
cttgcccgcc tgatgaatgc tcatccgg                                       28

SEQ ID NO: 128                  moltype = DNA   length = 28
FEATURE                         Location/Qualifiers
misc_feature                    1..28
                                note = Description of Artificial Sequence: Synthetic primer
source                          1..28
                                mol_type = other DNA
                                organism = synthetic construct
SEQUENCE: 128
ccggatgagc attcatcagg cgggcaag                                       28

SEQ ID NO: 129                  moltype = DNA   length = 44
FEATURE                         Location/Qualifiers
misc_feature                    1..44
                                note = Description of Artificial Sequence: Synthetic primer
source                          1..44
                                mol_type = other DNA
                                organism = synthetic construct
SEQUENCE: 129
cggtttatcc ccgctggcgc ggggaactcg aactaataac tgtc                     44

SEQ ID NO: 130                  moltype = DNA   length = 155
FEATURE                         Location/Qualifiers
misc_feature                    1..155
                                note = Description of Artificial Sequence: Synthetic
                                 polynucleotide
source                          1..155
                                mol_type = other DNA
                                organism = synthetic construct
SEQUENCE: 130
tcgagttccc cgcgccagcg gggataaacc gtattgacca attcattcgg gacagttatt    60
agttcgagtt ccccgcgcca gcggggataa accgctcgta aaagcagtac agtgcaccgt   120
aagatcgagt tccccgcgcc agcggggata aaccg                              155

SEQ ID NO: 131                  moltype = DNA   length = 30
FEATURE                         Location/Qualifiers
misc_feature                    1..30
                                note = Description of Artificial Sequence: Synthetic primer
source                          1..30
                                mol_type = other DNA
                                organism = synthetic construct
SEQUENCE: 131
gcgccagcgg ggataaaccg ctcgtaaaag                                     30

SEQ ID NO: 132                  moltype = DNA   length = 28
FEATURE                         Location/Qualifiers
misc_feature                    1..28
                                note = Description of Artificial Sequence: Synthetic primer
source                          1..28
                                mol_type = other DNA
                                organism = synthetic construct
SEQUENCE: 132
```
cttgcccgcc tgatgaatgc tcatccgg                                          28

SEQ ID NO: 133         moltype = DNA   length = 28
FEATURE                Location/Qualifiers
misc_feature           1..28
                       note = Description of Artificial Sequence: Synthetic primer
source                 1..28
                       mol_type = other DNA
                       organism = synthetic construct
SEQUENCE: 133
ccggatgagc attcatcagg cgggcaag                                          28

SEQ ID NO: 134         moltype = DNA   length = 44
FEATURE                Location/Qualifiers
misc_feature           1..44
                       note = Description of Artificial Sequence: Synthetic primer
source                 1..44
                       mol_type = other DNA
                       organism = synthetic construct
SEQUENCE: 134
cggtttatcc ccgctggcgc ggggaactcg aactaataac tgtc                        44

SEQ ID NO: 135         moltype = DNA   length = 153
FEATURE                Location/Qualifiers
misc_feature           1..153
                       note = Description of Artificial Sequence: Synthetic
                        polynucleotide
source                 1..153
                       mol_type = other DNA
                       organism = synthetic construct
SEQUENCE: 135
tcgagttccc cgcgccagcg gggataaacc gttaccattc tgttgctttt atgtataaga       60
atcgagttcc ccgcgccagc ggggataaac cgctcgtaaa agcagtacag tgcaccgtaa      120
gatcgagttc cccgcgccag cggggataaa ccg                                   153

SEQ ID NO: 136         moltype = DNA   length = 30
FEATURE                Location/Qualifiers
misc_feature           1..30
                       note = Description of Artificial Sequence: Synthetic primer
source                 1..30
                       mol_type = other DNA
                       organism = synthetic construct
SEQUENCE: 136
gcgccagcgg ggataaaccg ctcgtaaaag                                        30

SEQ ID NO: 137         moltype = DNA   length = 28
FEATURE                Location/Qualifiers
misc_feature           1..28
                       note = Description of Artificial Sequence: Synthetic primer
source                 1..28
                       mol_type = other DNA
                       organism = synthetic construct
SEQUENCE: 137
cttgcccgcc tgatgaatgc tcatccgg                                          28

SEQ ID NO: 138         moltype = DNA   length = 28
FEATURE                Location/Qualifiers
misc_feature           1..28
                       note = Description of Artificial Sequence: Synthetic primer
source                 1..28
                       mol_type = other DNA
                       organism = synthetic construct
SEQUENCE: 138
ccggatgagc attcatcagg cgggcaag                                          28

SEQ ID NO: 139         moltype = DNA   length = 48
FEATURE                Location/Qualifiers
misc_feature           1..48
                       note = Description of Artificial Sequence: Synthetic primer
source                 1..48
                       mol_type = other DNA
                       organism = synthetic construct
SEQUENCE: 139
cggtttatcc ccgctggcgc ggggaactcg attcttatac ataaaagc                    48

SEQ ID NO: 140         moltype = DNA   length = 217
FEATURE                Location/Qualifiers
misc_feature           1..217
                       note = Description of Artificial Sequence: Synthetic

```
                              polynucleotide
source                        1..217
                              mol_type = other DNA
                              organism = synthetic construct
SEQUENCE: 140
tcgagttccc cgcgccagcg gggataaacc gttgattata ataaccgttt atctgttcgt    60
atcgagttcc ccgcgccagc ggggataaac cgaaaagcat ataatgcgta aaagttatga   120
agttcgagtt ccccgcgcca gcggggataa accgtattga ccaattcatt cgggacagtt   180
attagttcga gttccccgcg ccagcgggga taaaccg                            217

SEQ ID NO: 141                moltype = DNA   length = 37
FEATURE                       Location/Qualifiers
misc_feature                  1..37
                              note = Description of Artificial Sequence: Synthetic primer
source                        1..37
                              mol_type = other DNA
                              organism = synthetic construct
SEQUENCE: 141
gcgccagcgg ggataaaccg tattgaccaa ttcattc                              37

SEQ ID NO: 142                moltype = DNA   length = 28
FEATURE                       Location/Qualifiers
misc_feature                  1..28
                              note = Description of Artificial Sequence: Synthetic primer
source                        1..28
                              mol_type = other DNA
                              organism = synthetic construct
SEQUENCE: 142
cttgcccgcc tgatgaatgc tcatccgg                                       28

SEQ ID NO: 143                moltype = DNA   length = 28
FEATURE                       Location/Qualifiers
misc_feature                  1..28
                              note = Description of Artificial Sequence: Synthetic primer
source                        1..28
                              mol_type = other DNA
                              organism = synthetic construct
SEQUENCE: 143
ccggatgagc attcatcagg cgggcaag                                       28

SEQ ID NO: 144                moltype = DNA   length = 47
FEATURE                       Location/Qualifiers
misc_feature                  1..47
                              note = Description of Artificial Sequence: Synthetic primer
source                        1..47
                              mol_type = other DNA
                              organism = synthetic construct
SEQUENCE: 144
cggtttatcc ccgctggcgc ggggaactcg aacttcataa cttttac                  47

SEQ ID NO: 145                moltype = DNA   length = 217
FEATURE                       Location/Qualifiers
misc_feature                  1..217
                              note = Description of Artificial Sequence: Synthetic
                              polynucleotide
source                        1..217
                              mol_type = other DNA
                              organism = synthetic construct
SEQUENCE: 145
tcgagttccc cgcgccagcg gggataaacc gaaaagcata taatgcgtaa aagttatgaa    60
gttcgagttc cccgcgccag cggggataaa ccgtattgac caattcattc gggacagtta   120
ttagttcgag ttccccgcgc cagcgggat aaaccggttt ttgtaatttt acaggcaacc   180
ttttattcga gttccccgcg ccagcgggga taaaccg                            217

SEQ ID NO: 146                moltype = DNA   length = 40
FEATURE                       Location/Qualifiers
misc_feature                  1..40
                              note = Description of Artificial Sequence: Synthetic primer
source                        1..40
                              mol_type = other DNA
                              organism = synthetic construct
SEQUENCE: 146
gcgccagcgg ggataaaccg gtttttgtaa ttttacaggc                          40

SEQ ID NO: 147                moltype = DNA   length = 28
FEATURE                       Location/Qualifiers
misc_feature                  1..28
                              note = Description of Artificial Sequence: Synthetic primer
source                        1..28
```

```
                        mol_type = other DNA
                        organism = synthetic construct
SEQUENCE: 147
cttgcccgcc tgatgaatgc tcatccgg                                          28

SEQ ID NO: 148          moltype = DNA   length = 28
FEATURE                 Location/Qualifiers
misc_feature            1..28
                        note = Description of Artificial Sequence: Synthetic primer
source                  1..28
                        mol_type = other DNA
                        organism = synthetic construct
SEQUENCE: 148
ccggatgagc attcatcagg cgggcaag                                          28

SEQ ID NO: 149          moltype = DNA   length = 44
FEATURE                 Location/Qualifiers
misc_feature            1..44
                        note = Description of Artificial Sequence: Synthetic primer
source                  1..44
                        mol_type = other DNA
                        organism = synthetic construct
SEQUENCE: 149
cggtttatcc ccgctggcgc ggggaactcg aactaataac tgtc                        44

SEQ ID NO: 150          moltype = DNA   length = 217
FEATURE                 Location/Qualifiers
misc_feature            1..217
                        note = Description of Artificial Sequence: Synthetic
                         polynucleotide
source                  1..217
                        mol_type = other DNA
                        organism = synthetic construct
SEQUENCE: 150
tcgagttccc cgcgccagcg gggataaacc gaaaagcata taatgcgtaa aagttatgaa        60
gttcgagttc cccgcgccag cggggataaa ccgtattgac caattcattc gggacagtta      120
ttagttcgag ttccccgcgc cagcggggat aaaccgttac cattctgttg cttttatgta      180
taagaatcga gttccccgcg ccagcgggga taaaccg                               217

SEQ ID NO: 151          moltype = DNA   length = 34
FEATURE                 Location/Qualifiers
misc_feature            1..34
                        note = Description of Artificial Sequence: Synthetic primer
source                  1..34
                        mol_type = other DNA
                        organism = synthetic construct
SEQUENCE: 151
gcgccagcgg ggataaaccg ttaccattct gttg                                   34

SEQ ID NO: 152          moltype = DNA   length = 28
FEATURE                 Location/Qualifiers
misc_feature            1..28
                        note = Description of Artificial Sequence: Synthetic primer
source                  1..28
                        mol_type = other DNA
                        organism = synthetic construct
SEQUENCE: 152
cttgcccgcc tgatgaatgc tcatccgg                                          28

SEQ ID NO: 153          moltype = DNA   length = 28
FEATURE                 Location/Qualifiers
misc_feature            1..28
                        note = Description of Artificial Sequence: Synthetic primer
source                  1..28
                        mol_type = other DNA
                        organism = synthetic construct
SEQUENCE: 153
ccggatgagc attcatcagg cgggcaag                                          28

SEQ ID NO: 154          moltype = DNA   length = 44
FEATURE                 Location/Qualifiers
misc_feature            1..44
                        note = Description of Artificial Sequence: Synthetic primer
source                  1..44
                        mol_type = other DNA
                        organism = synthetic construct
SEQUENCE: 154
cggtttatcc ccgctggcgc ggggaactcg aactaataac tgtc                        44
```

```
SEQ ID NO: 155          moltype = DNA   length = 217
FEATURE                 Location/Qualifiers
misc_feature            1..217
                        note = Description of Artificial Sequence: Synthetic
                        polynucleotide
source                  1..217
                        mol_type = other DNA
                        organism = synthetic construct
SEQUENCE: 155
tcgagttccc cgcgccagcg gggataaacc gaaaagcata taatgcgtaa aagttatgaa    60
gttcgagttc cccgcgccag cggggataaa ccgtattgac caattcattc gggacagtta   120
ttagttcgag ttccccgcgc cagcggggat aaaccgctcg taaaagcagt acagtgcacc   180
gtaagatcga gttccccgcg ccagcgggga taaaccg                            217

SEQ ID NO: 156          moltype = DNA   length = 30
FEATURE                 Location/Qualifiers
misc_feature            1..30
                        note = Description of Artificial Sequence: Synthetic primer
source                  1..30
                        mol_type = other DNA
                        organism = synthetic construct
SEQUENCE: 156
gcgccagcgg ggataaaccg ctcgtaaaag                                    30

SEQ ID NO: 157          moltype = DNA   length = 28
FEATURE                 Location/Qualifiers
misc_feature            1..28
                        note = Description of Artificial Sequence: Synthetic primer
source                  1..28
                        mol_type = other DNA
                        organism = synthetic construct
SEQUENCE: 157
cttgcccgcc tgatgaatgc tcatccgg                                      28

SEQ ID NO: 158          moltype = DNA   length = 28
FEATURE                 Location/Qualifiers
misc_feature            1..28
                        note = Description of Artificial Sequence: Synthetic primer
source                  1..28
                        mol_type = other DNA
                        organism = synthetic construct
SEQUENCE: 158
ccggatgagc attcatcagg cgggcaag                                      28

SEQ ID NO: 159          moltype = DNA   length = 44
FEATURE                 Location/Qualifiers
misc_feature            1..44
                        note = Description of Artificial Sequence: Synthetic primer
source                  1..44
                        mol_type = other DNA
                        organism = synthetic construct
SEQUENCE: 159
cggtttatcc ccgctggcgc ggggaactcg aactaataac tgtc                    44

SEQ ID NO: 160          moltype = DNA   length = 278
FEATURE                 Location/Qualifiers
misc_feature            1..278
                        note = Description of Artificial Sequence: Synthetic
                        polynucleotide
source                  1..278
                        mol_type = other DNA
                        organism = synthetic construct
SEQUENCE: 160
tcgagttccc cgcgccagcg gggataaacc gttgattata ataaccgttt atctgttcgt    60
atcgagttcc ccgcgccagc ggggataaac cgaaaagcat ataatgcgta aagttatga    120
agttcgagtt ccccgcgcca gcggggataa accgtattga ccaattcatt cgggacagtt   180
attagttcga gttccccgcg ccagcgggga taaaccggtt tttgtaattt tacaggcaac   240
cttttattcg agttccccgc gccagcgggg ataaaccg                           278

SEQ ID NO: 161          moltype = DNA   length = 40
FEATURE                 Location/Qualifiers
misc_feature            1..40
                        note = Description of Artificial Sequence: Synthetic primer
source                  1..40
                        mol_type = other DNA
                        organism = synthetic construct
SEQUENCE: 161
gcgccagcgg ggataaaccg gttttttgtaa ttttacaggc                         40
```

| | | |
|---|---|---|
| SEQ ID NO: 162 | moltype = DNA length = 28 | |
| FEATURE | Location/Qualifiers | |
| misc_feature | 1..28 | |
| | note = Description of Artificial Sequence: Synthetic primer | |
| source | 1..28 | |
| | mol_type = other DNA | |
| | organism = synthetic construct | |
| SEQUENCE: 162 | | |
| cttgcccgcc tgatgaatgc tcatccgg | | 28 |

| | | |
|---|---|---|
| SEQ ID NO: 163 | moltype = DNA length = 28 | |
| FEATURE | Location/Qualifiers | |
| misc_feature | 1..28 | |
| | note = Description of Artificial Sequence: Synthetic primer | |
| source | 1..28 | |
| | mol_type = other DNA | |
| | organism = synthetic construct | |
| SEQUENCE: 163 | | |
| ccggatgagc attcatcagg cgggcaag | | 28 |

| | | |
|---|---|---|
| SEQ ID NO: 164 | moltype = DNA length = 44 | |
| FEATURE | Location/Qualifiers | |
| misc_feature | 1..44 | |
| | note = Description of Artificial Sequence: Synthetic primer | |
| source | 1..44 | |
| | mol_type = other DNA | |
| | organism = synthetic construct | |
| SEQUENCE: 164 | | |
| cggtttatcc ccgctggcgc ggggaactcg aactaataac tgtc | | 44 |

| | | |
|---|---|---|
| SEQ ID NO: 165 | moltype = DNA length = 278 | |
| FEATURE | Location/Qualifiers | |
| misc_feature | 1..278 | |
| | note = Description of Artificial Sequence: Synthetic polynucleotide | |
| source | 1..278 | |
| | mol_type = other DNA | |
| | organism = synthetic construct | |
| SEQUENCE: 165 | | |
| tcgagttccc cgcgccagcg gggataaacc gttgattata ataccgtttt atctgttcgt | | 60 |
| atcgagttcc ccgcgccagc ggggataaac cgaaaagcat ataatgcgta aaagttatga | | 120 |
| agttcgagtt ccccgcgcca gcggggataa accgtattga ccaattcatt cgggacagtt | | 180 |
| attagttcga gttccccgcg ccagcgggga taaaccgtta ccattctgtt gcttttatgt | | 240 |
| ataagaatcg agttccccgc gccagcgggg ataaaccg | | 278 |

| | | |
|---|---|---|
| SEQ ID NO: 166 | moltype = DNA length = 37 | |
| FEATURE | Location/Qualifiers | |
| misc_feature | 1..37 | |
| | note = Description of Artificial Sequence: Synthetic primer | |
| source | 1..37 | |
| | mol_type = other DNA | |
| | organism = synthetic construct | |
| SEQUENCE: 166 | | |
| gcgccagcgg ggataaaccg tattgaccaa ttcattc | | 37 |

| | | |
|---|---|---|
| SEQ ID NO: 167 | moltype = DNA length = 28 | |
| FEATURE | Location/Qualifiers | |
| misc_feature | 1..28 | |
| | note = Description of Artificial Sequence: Synthetic primer | |
| source | 1..28 | |
| | mol_type = other DNA | |
| | organism = synthetic construct | |
| SEQUENCE: 167 | | |
| cttgcccgcc tgatgaatgc tcatccgg | | 28 |

| | | |
|---|---|---|
| SEQ ID NO: 168 | moltype = DNA length = 28 | |
| FEATURE | Location/Qualifiers | |
| misc_feature | 1..28 | |
| | note = Description of Artificial Sequence: Synthetic primer | |
| source | 1..28 | |
| | mol_type = other DNA | |
| | organism = synthetic construct | |
| SEQUENCE: 168 | | |
| ccggatgagc attcatcagg cgggcaag | | 28 |

| | | |
|---|---|---|
| SEQ ID NO: 169 | moltype = DNA length = 47 | |
| FEATURE | Location/Qualifiers | |
| misc_feature | 1..47 | |
| | note = Description of Artificial Sequence: Synthetic primer | |

```
source                    1..47
                          mol_type = other DNA
                          organism = synthetic construct
SEQUENCE: 169
cggtttatcc ccgctggcgc ggggaactcg aacttcataa cttttac              47

SEQ ID NO: 170            moltype = DNA  length = 278
FEATURE                   Location/Qualifiers
misc_feature              1..278
                          note = Description of Artificial Sequence: Synthetic
                           polynucleotide
source                    1..278
                          mol_type = other DNA
                          organism = synthetic construct
SEQUENCE: 170
tcgagttccc cgcgccagcg gggataaacc gttgattata ataaccgttt atctgttcgt  60
atcgagttcc ccgcgccagc ggggataaac cgaaaagcat ataatgcgta aaagttatga 120
agttcgagtt ccccgcgcca gcggggataa accgtattga ccaattcatt cgggacagtt 180
attagttcga gttccccgcg ccagcgggga taaaccgctc gtaaaagcag tacagtgcac 240
cgtaagatcg agttccccgc gccagcgggg ataaaccg                         278

SEQ ID NO: 171            moltype = DNA  length = 37
FEATURE                   Location/Qualifiers
misc_feature              1..37
                          note = Description of Artificial Sequence: Synthetic primer
source                    1..37
                          mol_type = other DNA
                          organism = synthetic construct
SEQUENCE: 171
gcgccagcgg ggataaaccg tattgaccaa ttcattc                          37

SEQ ID NO: 172            moltype = DNA  length = 28
FEATURE                   Location/Qualifiers
misc_feature              1..28
                          note = Description of Artificial Sequence: Synthetic primer
source                    1..28
                          mol_type = other DNA
                          organism = synthetic construct
SEQUENCE: 172
cttgcccgcc tgatgaatgc tcatccgg                                    28

SEQ ID NO: 173            moltype = DNA  length = 28
FEATURE                   Location/Qualifiers
misc_feature              1..28
                          note = Description of Artificial Sequence: Synthetic primer
source                    1..28
                          mol_type = other DNA
                          organism = synthetic construct
SEQUENCE: 173
ccggatgagc attcatcagg cgggcaag                                    28

SEQ ID NO: 174            moltype = DNA  length = 47
FEATURE                   Location/Qualifiers
misc_feature              1..47
                          note = Description of Artificial Sequence: Synthetic primer
source                    1..47
                          mol_type = other DNA
                          organism = synthetic construct
SEQUENCE: 174
cggtttatcc ccgctggcgc ggggaactcg aacttcataa cttttac              47

SEQ ID NO: 175            moltype = DNA  length = 278
FEATURE                   Location/Qualifiers
misc_feature              1..278
                          note = Description of Artificial Sequence: Synthetic
                           polynucleotide
source                    1..278
                          mol_type = other DNA
                          organism = synthetic construct
SEQUENCE: 175
tcgagttccc cgcgccagcg gggataaacc gaaaagcata taatgcgtaa aagttatgaa  60
gttcgagttc cccgcgccag cggggataaa ccgtattgac caattcattc gggacagtta 120
ttagttcgag ttccccgcgc cagcgggga taaaccgttac cattctgttg cttttatgta 180
taagaatcga gttccccgcg ccagcgggga taaaccggtt tttgtaattt tacaggcaac 240
cttttattcg agttccccgc gccagcgggg ataaaccg                         278

SEQ ID NO: 176            moltype = DNA  length = 40
FEATURE                   Location/Qualifiers
misc_feature              1..40
```

```
                    note = Description of Artificial Sequence: Synthetic primer
source              1..40
                    mol_type = other DNA
                    organism = synthetic construct
SEQUENCE: 176
gcgccagcgg ggataaaccg gtttttgtaa ttttacaggc                              40

SEQ ID NO: 177      moltype = DNA   length = 28
FEATURE             Location/Qualifiers
misc_feature        1..28
                    note = Description of Artificial Sequence: Synthetic primer
source              1..28
                    mol_type = other DNA
                    organism = synthetic construct
SEQUENCE: 177
cttgcccgcc tgatgaatgc tcatccgg                                          28

SEQ ID NO: 178      moltype = DNA   length = 28
FEATURE             Location/Qualifiers
misc_feature        1..28
                    note = Description of Artificial Sequence: Synthetic primer
source              1..28
                    mol_type = other DNA
                    organism = synthetic construct
SEQUENCE: 178
ccggatgagc attcatcagg cgggcaag                                          28

SEQ ID NO: 179      moltype = DNA   length = 48
FEATURE             Location/Qualifiers
misc_feature        1..48
                    note = Description of Artificial Sequence: Synthetic primer
source              1..48
                    mol_type = other DNA
                    organism = synthetic construct
SEQUENCE: 179
cggtttatcc ccgctggcgc ggggaactcg attcttatac ataaaagc                    48

SEQ ID NO: 180      moltype = DNA   length = 278
FEATURE             Location/Qualifiers
misc_feature        1..278
                    note = Description of Artificial Sequence: Synthetic
                    polynucleotide
source              1..278
                    mol_type = other DNA
                    organism = synthetic construct
SEQUENCE: 180
tcgagttccc cgcgccagcg gggataaacc gaaaagcata taatgcgtaa aagttatgaa       60
gttcgagttc cccgcgccag cggggataaa ccgtattgac caattcattc gggacagtta      120
ttagttcgag ttccccgcgc cagcggggat aaaccgttac cattctgttg cttttatgta      180
taagaatcga gttccccgcg ccagcgggga taaaccgctc gtaaaagcag tacagtgcac      240
cgtaagatcg agttccccgc gccagcgggg ataaaccg                              278

SEQ ID NO: 181      moltype = DNA   length = 30
FEATURE             Location/Qualifiers
misc_feature        1..30
                    note = Description of Artificial Sequence: Synthetic primer
source              1..30
                    mol_type = other DNA
                    organism = synthetic construct
SEQUENCE: 181
gcgccagcgg ggataaaccg ctcgtaaaag                                        30

SEQ ID NO: 182      moltype = DNA   length = 28
FEATURE             Location/Qualifiers
misc_feature        1..28
                    note = Description of Artificial Sequence: Synthetic primer
source              1..28
                    mol_type = other DNA
                    organism = synthetic construct
SEQUENCE: 182
cttgcccgcc tgatgaatgc tcatccgg                                          28

SEQ ID NO: 183      moltype = DNA   length = 28
FEATURE             Location/Qualifiers
misc_feature        1..28
                    note = Description of Artificial Sequence: Synthetic primer
source              1..28
                    mol_type = other DNA
                    organism = synthetic construct
```

```
SEQUENCE: 183
ccggatgagc attcatcagg cgggcaag                                          28

SEQ ID NO: 184          moltype = DNA   length = 48
FEATURE                 Location/Qualifiers
misc_feature            1..48
                        note = Description of Artificial Sequence: Synthetic primer
source                  1..48
                        mol_type = other DNA
                        organism = synthetic construct
SEQUENCE: 184
cggtttatcc ccgctggcgc ggggaactcg attcttatac ataaaagc                    48

SEQ ID NO: 185          moltype = DNA   length = 339
FEATURE                 Location/Qualifiers
misc_feature            1..339
                        note = Description of Artificial Sequence: Synthetic
                         polynucleotide
source                  1..339
                        mol_type = other DNA
                        organism = synthetic construct
SEQUENCE: 185
tcgagttccc cgcgccagcg gggataaacc gttgattata ataccgtttt atctgttcgt       60
atcgagttcc ccgcgccagc ggggataaac cgaaaagcat ataatgcgta aaagttatga      120
agttcgagtt ccccgcgcca gcggggataa accgtattga ccaattcatt cgggacagtt      180
attagttcga gttccccgcg ccagcgggga taaaccgtta ccattctgtt gcttttatgt      240
ataagaatcg agttccccgc gccagcgggg ataaaccggt ttttgtaatt ttacaggcaa      300
ccttttattc gagttccccg cgccagcggg gataaaccg                             339

SEQ ID NO: 186          moltype = DNA   length = 40
FEATURE                 Location/Qualifiers
misc_feature            1..40
                        note = Description of Artificial Sequence: Synthetic primer
source                  1..40
                        mol_type = other DNA
                        organism = synthetic construct
SEQUENCE: 186
gcgccagcgg ggataaaccg gttttttgtaa ttttacaggc                            40

SEQ ID NO: 187          moltype = DNA   length = 28
FEATURE                 Location/Qualifiers
misc_feature            1..28
                        note = Description of Artificial Sequence: Synthetic primer
source                  1..28
                        mol_type = other DNA
                        organism = synthetic construct
SEQUENCE: 187
cttgcccgcc tgatgaatgc tcatccgg                                          28

SEQ ID NO: 188          moltype = DNA   length = 28
FEATURE                 Location/Qualifiers
misc_feature            1..28
                        note = Description of Artificial Sequence: Synthetic primer
source                  1..28
                        mol_type = other DNA
                        organism = synthetic construct
SEQUENCE: 188
ccggatgagc attcatcagg cgggcaag                                          28

SEQ ID NO: 189          moltype = DNA   length = 48
FEATURE                 Location/Qualifiers
misc_feature            1..48
                        note = Description of Artificial Sequence: Synthetic primer
source                  1..48
                        mol_type = other DNA
                        organism = synthetic construct
SEQUENCE: 189
cggtttatcc ccgctggcgc ggggaactcg attcttatac ataaaagc                    48

SEQ ID NO: 190          moltype = DNA   length = 339
FEATURE                 Location/Qualifiers
misc_feature            1..339
                        note = Description of Artificial Sequence: Synthetic
                         polynucleotide
source                  1..339
                        mol_type = other DNA
                        organism = synthetic construct
SEQUENCE: 190
tcgagttccc cgcgccagcg gggataaacc gttgattata ataccgtttt atctgttcgt       60
```

```
atcgagttcc ccgcgccagc ggggataaac cgaaaagcat ataatgcgta aaagttatga    120
agttcgagtt ccccgcgcca gcggggataa accgtattga ccaattcatt cgggacagtt    180
attagttcga gttccccgcg ccagcgggga taaaccgtta ccattctgtt gcttttatgt    240
ataagaatcg agttccccgc gccagcgggg ataaaccgct cgtaaaagca gtacagtgca    300
ccgtaagatc gagttccccg cgccagcggg gataaaccg                           339
```

| | | |
|---|---|---|
| SEQ ID NO: 191 | moltype = DNA  length = 30 | |
| FEATURE | Location/Qualifiers | |
| misc_feature | 1..30 | |
| | note = Description of Artificial Sequence: Synthetic primer | |
| source | 1..30 | |
| | mol_type = other DNA | |
| | organism = synthetic construct | |

```
SEQUENCE: 191
gcgccagcgg ggataaaccg ctcgtaaaag                                      30
```

| | | |
|---|---|---|
| SEQ ID NO: 192 | moltype = DNA  length = 28 | |
| FEATURE | Location/Qualifiers | |
| misc_feature | 1..28 | |
| | note = Description of Artificial Sequence: Synthetic primer | |
| source | 1..28 | |
| | mol_type = other DNA | |
| | organism = synthetic construct | |

```
SEQUENCE: 192
cttgcccgcc tgatgaatgc tcatccgg                                        28
```

| | | |
|---|---|---|
| SEQ ID NO: 193 | moltype = DNA  length = 28 | |
| FEATURE | Location/Qualifiers | |
| misc_feature | 1..28 | |
| | note = Description of Artificial Sequence: Synthetic primer | |
| source | 1..28 | |
| | mol_type = other DNA | |
| | organism = synthetic construct | |

```
SEQUENCE: 193
ccggatgagc attcatcagg cgggcaag                                        28
```

| | | |
|---|---|---|
| SEQ ID NO: 194 | moltype = DNA  length = 48 | |
| FEATURE | Location/Qualifiers | |
| misc_feature | 1..48 | |
| | note = Description of Artificial Sequence: Synthetic primer | |
| source | 1..48 | |
| | mol_type = other DNA | |
| | organism = synthetic construct | |

```
SEQUENCE: 194
cggtttatcc ccgctggcgc ggggaactcg attcttatac ataaaagc                  48
```

| | | |
|---|---|---|
| SEQ ID NO: 195 | moltype = DNA  length = 400 | |
| FEATURE | Location/Qualifiers | |
| misc_feature | 1..400 | |
| | note = Description of Artificial Sequence: Synthetic polynucleotide | |
| source | 1..400 | |
| | mol_type = other DNA | |
| | organism = synthetic construct | |

```
SEQUENCE: 195
tcgagttccc cgcgccagcg gggataaacc gttgattata ataacgtttt atctgttcgt     60
atcgagttcc ccgcgccagc ggggataaac cgaaaagcat ataatgcgta aaagttatga    120
agttcgagtt ccccgcgcca gcggggataa accgtattga ccaattcatt cgggacagtt    180
attagttcga gttccccgcg ccagcgggga taaaccgtta ccattctgtt gcttttatgt    240
ataagaatcg agttccccgc gccagcgggg ataaaccgct cgtaaaagca gtacagtgca    300
ccgtaagatc gagttccccg cgccagcggg gataaaccgg tttttgtaat tttacaggca    360
acctttatt cgagttcccc gcgccagcgg ggataaaccg                           400
```

| | | |
|---|---|---|
| SEQ ID NO: 196 | moltype = DNA  length = 40 | |
| FEATURE | Location/Qualifiers | |
| misc_feature | 1..40 | |
| | note = Description of Artificial Sequence: Synthetic primer | |
| source | 1..40 | |
| | mol_type = other DNA | |
| | organism = synthetic construct | |

```
SEQUENCE: 196
gcgccagcgg ggataaaccg gttttttgtaa ttttacaggc                          40
```

| | | |
|---|---|---|
| SEQ ID NO: 197 | moltype = DNA  length = 28 | |
| FEATURE | Location/Qualifiers | |
| misc_feature | 1..28 | |
| | note = Description of Artificial Sequence: Synthetic primer | |
| source | 1..28 | |
| | mol_type = other DNA | |

```
                        organism = synthetic construct
SEQUENCE: 197
cttgcccgcc tgatgaatgc tcatccgg                                            28

SEQ ID NO: 198          moltype = DNA  length = 28
FEATURE                 Location/Qualifiers
misc_feature            1..28
                        note = Description of Artificial Sequence: Synthetic primer
source                  1..28
                        mol_type = other DNA
                        organism = synthetic construct
SEQUENCE: 198
ccggatgagc attcatcagg cgggcaag                                            28

SEQ ID NO: 199          moltype = DNA  length = 49
FEATURE                 Location/Qualifiers
misc_feature            1..49
                        note = Description of Artificial Sequence: Synthetic primer
source                  1..49
                        mol_type = other DNA
                        organism = synthetic construct
SEQUENCE: 199
cggtttatcc ccgctggcgc ggggaactcg atcttacggt gcactgtac                     49

SEQ ID NO: 200          moltype = DNA  length = 153
FEATURE                 Location/Qualifiers
misc_feature            1..153
                        note = Description of Artificial Sequence: Synthetic
                         polynucleotide
source                  1..153
                        mol_type = other DNA
                        organism = synthetic construct
SEQUENCE: 200
tcgagttccc cgcgccagcg gggataaacc gttaccattc tgttgctttt atgtataaga         60
atcgagttcc ccgcgccagc gggataaaac cgctcgtaaa agcagtacag tgcaccgtaa        120
gatcgagttc cccgcgccag cggggataaa ccg                                    153

SEQ ID NO: 201          moltype = DNA  length = 30
FEATURE                 Location/Qualifiers
misc_feature            1..30
                        note = Description of Artificial Sequence: Synthetic primer
source                  1..30
                        mol_type = other DNA
                        organism = synthetic construct
SEQUENCE: 201
gcgccagcgg ggataaaccg ctcgtaaaag                                          30

SEQ ID NO: 202          moltype = DNA  length = 28
FEATURE                 Location/Qualifiers
misc_feature            1..28
                        note = Description of Artificial Sequence: Synthetic primer
source                  1..28
                        mol_type = other DNA
                        organism = synthetic construct
SEQUENCE: 202
cttgcccgcc tgatgaatgc tcatccgg                                            28

SEQ ID NO: 203          moltype = DNA  length = 28
FEATURE                 Location/Qualifiers
misc_feature            1..28
                        note = Description of Artificial Sequence: Synthetic primer
source                  1..28
                        mol_type = other DNA
                        organism = synthetic construct
SEQUENCE: 203
ccggatgagc attcatcagg cgggcaag                                            28

SEQ ID NO: 204          moltype = DNA  length = 48
FEATURE                 Location/Qualifiers
misc_feature            1..48
                        note = Description of Artificial Sequence: Synthetic primer
source                  1..48
                        mol_type = other DNA
                        organism = synthetic construct
SEQUENCE: 204
cggtttatcc ccgctggcgc ggggaactcg attcttatac ataaaagc                      48
```

COMPOSITIONS AND METHODS FOR METABOLIC CONTROL OF A BIOFERMENTATION PROCESS WITH SYNTHETIC METABOLIC VALVES

CROSS-REFERENCE

This application is a continuation of U.S. application Ser. No. 17/576,290, filed Jan. 14, 2022, which is a continuation of U.S. application Ser. No. 16/487,542, filed Aug. 21, 2019, which is a National Stage Entry of PCT/US 18/19040. filed Feb. 21, 2018 which claims the benefit of U.S. Provisional Application No. 62/461,436, filed Feb. 21, 2017, which application is incorporated herein by reference in its entirety.

STATEMENT AS TO FEDERALLY SPONSORED RESEARCH

This invention was made with Government support under Federal Grant Nos. HR0011-14-C-0075 awarded by DOD/DARPA, 12043956 and N00014-16-1-2558 awarded by NAVY/ONR, and 1445726 awarded by NSF. The Government has certain rights to this invention.

REFERENCE TO A SEQUENCE LISTING

The instant application contains a Sequence Listing which has been filed electronically in ASCII format and is hereby incorporated by reference in its entirety. Said ASCII copy, created on Feb. 21, 2018, is named 52240_702_601_SL.txt and is 81,697 bytes in size.

BACKGROUND OF THE INVENTION

Biotechnology-based fermentation processes have been successfully developed to produce everything from biologics and small molecule therapies to specialty, bulk and commodity chemicals, and even next generation biofuels. These processes have made rapid advancements in recent years due to technology developments in the fields of fermentation science and synthetic biology, as well as metabolic and enzyme engineering. Despite these substantial advances, most successful examples of rational and directed engineering approaches have also greatly relied on numerous and often lengthy cycles of trial and error. The present disclosure provides a strategy that simultaneously reduces the complexity of the problem (as well as the size of the relevant design space), while also minimizing metabolic responses to environmental conditions, increasing robustness and scalability of engineered strains.

SUMMARY OF THE INVENTION

The present disclosure provides, in part, a high-throughput engineering platform that enables the rapid development of microbial production strains.

In one aspect, the present disclosure provides a cell for generating a product, wherein the cell comprises: a heterologous polynucleotide for controlled reduction of expression of an enzyme of a metabolic pathway, wherein the controlled reduction of expression of the enzyme induces a stationary phase of the cell; and a heterologous production polynucleotide for mediating controlled increase in expression of a production enzyme for generation of the product; wherein a rate of production of the product during the stationary phase is reduced less in response to a change of an environmental condition as compared to a cell lacking the enzyme.

In some embodiments, the heterologous polynucleotide reduces flux through the metabolic pathway. In some embodiments, the enzyme is selected from the group consisting of enoyl-ACP/CoA reductase, glucose-6-phosphate dehydrogenase, lipoamide dehydrogenase, citrate synthase, soluble transhydrogenase, and NADH-dependent glyceraldehyde-3-phosphate dehydrogenase. In some embodiments, the production enzyme is selected from the group consisting of NADPH-dependent alanine dehydrogenase, an alanine exporter, and NADPH-dependent glyceraldehyde-3-phosphate dehydrogenase. In some embodiments, the change of an environmental condition comprises increasing or decreasing a concentration of a sugar in a culture medium contacting the cell. In some embodiments, the sugar is glucose. In some embodiments, the change of an environmental condition comprises increasing or decreasing oxygenation of a culture medium contacting the cell. In some embodiments, the product comprises 3-hydroxypropionic acid.

In some embodiments, the product comprises an amino acid. In some aspects, the amino acid comprises alanine. In some aspects, the cell is grown in a culture, and a rate of production of the alanine by the culture is at least 0.5 g/L/hour. In some aspects, the rate of production of the alanine is at least 1.0 g/L/hour. In some aspects, the rate of production of the alanine is at least 1.5 g/L/hour. In some aspects, the rate of production of the alanine is at least 1.6 g/L/hour. In some aspects, the culture produces at least 80 g/L of the alanine. In some aspects, the culture produces at least 100 g/L of the alanine. In some aspects, the culture produces at least 120 g/L of the alanine. In some aspects, the culture produces at least 140 g/L of the alanine. In some aspects, the production polynucleotide encodes an alanine exporter. In some aspects, the alanine exporter is alaE.

In some embodiments, the product comprises mevalonic acid. In some embodiments, the cell is grown in a culture, and a rate of production of the mevalonic acid by the culture is at least 0.5 g/L/hour. In some embodiments, the rate of production of the mevalonic acid is at least 1.0 g/L/hour. In some embodiments, the rate of production of the mevalonic acid is at least 1.2 g/L/hour. In some embodiments, the rate of production of the mevalonic acid is at least 1.25 g/L/hour. In some aspects, the cell is grown in a culture, and the culture produces at least 50 g/L of the mevalonic acid. In some embodiments, the culture produces at least 70 g/L of the mevalonic acid. In some embodiments, the culture produces at least 90 g/L of the mevalonic acid. In some embodiments, the culture produces at least 95 g/L of the mevalonic acid. In some embodiments, the heterologous polynucleotide is selected from the group consisting of: a silencing polynucleotide for repressing transcription of a gene encoding the enzyme; and a degradation polynucleotide for mediating cellular degradation of the enzyme.

In some aspects, the heterologous polynucleotide comprises a silencing polynucleotide, and the silencing polynucleotide comprises a guide RNA (gRNA) comprising a gRNA sequence that recognizes a promoter of a gene encoding the enzyme. In some aspects, the heterologous polynucleotide encodes a CRISPR enzyme, and the CRISPR enzyme specifically binds to the promoter sequence when bound to the gRNA. In some aspects, the CRISPR enzyme is catalytically inactive. In some aspects, the heterologous polynucleotide comprises a degradation polynucleotide, wherein the degradation polynucleotide comprises a sequence encoding a degradation tag, wherein the degradation tag mediates degradation of the enzyme. In some embodiments, expression of the heterologous polynucleotide is regulated by phosphate availability in the cell. In some embodiments, expression of the production polynucleotide is regulated by phosphate availability in the cell. In some embodiments, the cell is an *E. coli* cell.

In another aspect, disclosed herein is a method comprising: culturing independently a plurality of strains of a cell, wherein each strain comprises (i) a heterologous polynucleotide for mediating controlled reduction of expression of an enzyme of a metabolic pathway, wherein the controlled reduction of expression of the enzyme induces a stationary phase of the cell; and (ii) a heterologous production polynucleotide for mediating controlled increase in expression of a production enzyme for generation of the product; wherein each strain of the plurality of strains differs from another strain in a sequence of at least one of the heterologous polynucleotide or the heterologous production polynucleotide; growing the plurality of strains to stationary phase; and selecting a strain of the plurality of strains based on a level of the product produced by the selected strain during the stationary phase.

In some embodiments, the method comprises determining the level of the product. In some embodiments, the method comprises growing the selected strain. In some embodiments, the selected strain is grown in a bioreactor. In some embodiments, a culture medium comprising the selected strain has a volume of at least 500 ml. In some embodiments, the culture medium has a volume of at least 1 L. In some embodiments, the heterologous polynucleotide is selected from the group consisting of: a silencing polynucleotide for repressing transcription of a gene encoding the enzyme; and a degradation polynucleotide for mediating cellular degradation of the enzyme. In some embodiments, a first and second strain of the plurality of strains comprises a silencing polynucleotide. In some embodiments, the silencing polynucleotide comprises a guide RNA (gRNA) comprising a gRNA sequence that recognizes a promoter sequence of a gene encoding the enzyme. In some embodiments, the gRNA sequence differs between the first and second strains. In some embodiments, the first and second strain of the plurality of strains comprise a degradation polynucleotide. In some embodiments, the degradation polynucleotide differs between the first and second strains. In some embodiments, the enzyme is selected from the group consisting of enoyl-ACP/CoA reductase, glucose-6-phosphate dehydrogenase, lipoamide dehydrogenase, citrate synthase, soluble transhydrogenase, and NADH-dependent glyceraldehyde-3-phosphate dehydrogenase. In some embodiments, the production enzyme is selected from the group consisting of NADPH-dependent alanine dehydrogenase, an alanine exporter, and NADPH-dependent glyceraldehyde-3-phosphate dehydrogenase. In some embodiments, the product is selected from the group consisting of mevalonic acid, 3-hydroxypropionic acid, and an amino acid.

In some embodiments, the product is an amino acid and the amino acid is alanine. In some embodiments, the cell of the selected strain a rate of production of the product during the stationary phase is reduced less in response to a change of an environmental condition as compared to a cell lacking the heterologous polynucleotide. In some embodiments, the change of an environmental condition comprises a change in concentration of a sugar of a culture medium contacting the cell. In some embodiments, the change of an environmental condition comprises a change in oxygenation of a culture medium contacting the cell.

In another aspect, disclosed herein is a method of generating a cellular product comprising: culturing a heterologous cell in a culture medium, wherein the heterologous cell comprises: (i) a heterologous polynucleotide for mediating controlled reduction of expression of an enzyme of a metabolic pathway, wherein the controlled reduction of expression of the enzyme induces a stationary phase of the cell; and (ii) a heterologous production polynucleotide for mediating controlled increase in expression of a production enzyme for generation of the product; wherein a rate of production of the product during the stationary phase is reduced less in response to a change of an environmental condition as compared to a cell lacking the enzyme.

In one embodiment, the method further comprises changing the environmental condition. In one embodiment, the environmental condition comprises a concentration of a sugar of the culture medium, and changing the environmental condition comprises increasing or decreasing the concentration. In some embodiments, the sugar is glucose. In some embodiments, the environmental condition comprises an oxygen concentration of the culture medium, and changing the environmental condition comprises increasing or decreasing the oxygen concentration. In some embodiments, the culturing is performed in a bioreactor. In some embodiments, the culture medium has a volume of at least 500 ml. In some embodiments, the culture medium has a volume of at least 1 L. In some embodiments, the product comprises 3-hydroxypropionic acid. In some embodiments, the product comprises an amino acid. In some embodiments, the amino acid comprises alanine. In some embodiments, the rate of production of the alanine is at least 0.5 g/L/hour. In some embodiments, the rate of production of the alanine is at least 1.0 g/L/hour. In some embodiments, the rate of production of the alanine is at least 1.5 g/L/hour. In some embodiments, the rate of production of the alanine is at least 1.6 g/L/hour. In some embodiments, the production polynucleotide encodes an alanine exporter. In some embodiments, the alanine exporter is alaE.

In some embodiments, the product comprises mevalonic acid. In some embodiments, the rate of production of the mevalonic acid is at least 0.5 g/L/hour. In some embodiments, the rate of production of the mevalonic acid is at least 1.0 g/L/hour. In some embodiments, the rate of production of the mevalonic acid is at least 1.2 g/L/hour. In some embodiments, the rate of production of the mevalonic acid is at least 1.25 g/L/hour. In some embodiments, the heterologous polynucleotide is selected from the group consisting of: a silencing polynucleotide for repressing transcription of a gene encoding the enzyme; and a degradation polynucleotide for mediating cellular degradation of the enzyme. In some embodiments, the heterologous polynucleotide comprises a silencing polynucleotide, and the silencing polynucleotide comprises a guide RNA (gRNA) comprising a gRNA sequence that recognizes a promoter sequence of a gene encoding the enzyme. In some embodiments, the heterologous polynucleotide encodes a CRISPR enzyme, wherein the CRISPR enzyme specifically binds to the promoter sequence when bound to the gRNA. In some embodiments, the CRISPR enzyme is catalytically inactive. In some embodiments, the heterologous polynucleotide comprises a degradation polynucleotide, wherein the degradation polynucleotide comprises a sequence encoding a degradation tag, wherein the degradation tag mediates degradation of the enzyme. In some embodiments, the expression of the heterologous polynucleotide is regulated by phosphate availability in the cell. In some embodiments, the expression of the production polynucleotide is regulated by phosphate availability in the cell. In some embodiments, the cell is an *E. coli* cell.

In another aspect, disclosed herein is a cell for production of alanine, wherein the cell comprises: (i) a heterologous polynucleotide for controlled reduction of expression of an enzyme of a metabolic pathway, wherein the enzyme is selected from the group consisting of enoyl-ACP/CoA reductase, glucose-6-phosphate dehydrogenase, lipoamide dehydrogenase (lpd), citrate synthase (gltA), soluble transhydrogenase, and NADH-dependent glyceraldehyde-3-phosphate dehydrogenase; and (ii) an alanine exporter, wherein the alanine exporter is expressed at increased levels as compared to a wildtype cell.

In some embodiments, the alanine exporter is encoded by an alaE gene. In some embodiments, the controlled reduction of expression of the enzyme induces a stationary phase of the cell. In some embodiments, the cell further comprises a heterologous production polynucleotide for controlled increase in expression of a production enzyme for generation of the alanine. In some embodiments, the production enzyme is selected from the group consisting of NADPH-dependent alanine dehydrogenase and NADPH-dependent glyceraldehyde-3-phosphate dehydrogenase. In some embodiments, the heterologous polynucleotide is selected from the group consisting of: a silencing polynucleotide for mediating transcriptional repression of a gene encoding the enzyme; and a degradation polynucleotide for mediating cellular degradation of the enzyme. In some embodiments, the heterologous polynucleotide comprises a silencing polynucleotide, and the silencing polynucleotide comprises a guide RNA (gRNA) comprising a gRNA sequence that recognizes a promoter sequence of a gene encoding the enzyme. In some embodiments, the polynucleotide further encodes a CRISPR enzyme, wherein the CRISPR enzyme specifically binds to the promoter sequence when bound to the gRNA. In some embodiments, the CRISPR enzyme is catalytically inactive. In some embodiments, the heterologous polynucleotide comprises a degradation polynucleotide, wherein the degradation polynucleotide comprises a sequence encoding a degradation tag, wherein the degradation tag mediates degradation of the enzyme. In some embodiments, the polynucleotide is regulated by phosphate availability in the cell. In some embodiments, the production polynucleotide is regulated by phosphate availability in the cell. In some embodiments, the cell is an *E. coli* cell.

In some embodiments, a culture comprises the cell. In some embodiments, a rate of production of the alanine by the culture is at least 0.5 g/L/hour. In some embodiments, a rate of production of the alanine by the culture is at least 1.0 g/L/hour. In some embodiments, a rate of production of the alanine by the culture is at least 1.5 g/L/hour. In some embodiments, a rate of production of the alanine by the culture is at least 1.6 g/L/hour. In some embodiments, the culture produces at least 100 g/L of the alanine. In some embodiments, the culture produces at least 120 g/L of the alanine. In some embodiments, the culture produces at least 140 g/L of the alanine.

In some aspects, disclosed herein is a method of production of alanine comprising growing in a culture medium a cell comprising (i) a heterologous polynucleotide for controlled reduction of expression of a enzyme of a metabolic pathway, wherein the enzyme is selected from the group consisting of enoyl-ACP/CoA reductase, glucose-6-phosphate dehydrogenase, lipoamide dehydrogenase, citrate synthase, soluble transhydrogenase, and NADH-dependent glyceraldehyde-3-phosphate dehydrogenase; and (ii) an alanine exporter, wherein the alanine exporter is expressed at increased levels as compared to a wildtype cell.

In some embodiments, the controlled reduction of expression of the enzyme induces a stationary phase of the cell. In some embodiments, the method further comprises decreasing an oxygenation level or a sugar concentration of the culture medium during the stationary phase, wherein a rate of production of the cellular product is reduced less in response to the decreasing as compared to a cell lacking the heterologous polynucleotide. In some embodiments, the sugar is glucose. In some embodiments, the alanine exporter is encoded by an alaE gene. In some embodiments, the cell further comprises a heterologous production polynucleotide for controlled increase in expression of a production enzyme for generation of the alanine. In some embodiments, the production enzyme is selected from the group consisting of: NADPH-dependent alanine dehydrogenase and NADPH-dependent glyceraldehyde-3-phosphate dehydrogenase. In some embodiments, the heterologous polynucleotide is selected from the group consisting of: a silencing polynucleotide for mediating transcriptional repression of a gene encoding the enzyme; and a degradation polynucleotide for mediating cellular degradation of the enzyme. In some embodiments, the heterologous polynucleotide comprises a silencing polynucleotide, and the silencing polynucleotide comprises a guide RNA (gRNA) comprising a gRNA sequence that recognizes a promoter sequence of a gene encoding the enzyme. In some embodiments, the heterologous polynucleotide encodes a CRISPR enzyme, wherein the CRISPR enzyme specifically binds to the promoter sequence when bound to the gRNA. In some embodiments, the CRISPR enzyme is catalytically inactive. In some embodiments, the heterologous polynucleotide comprises a degradation polynucleotide, wherein the degradation polynucleotide comprises a sequence encoding a degradation tag, wherein the degradation tag mediates degradation of the enzyme.

In some embodiments, the expression of the heterologous polynucleotide is regulated by phosphate availability in the cell. In some embodiments, the production polynucleotide is regulated by phosphate availability in the cell. In some embodiments, the cell is an *E. coli* cell. In some embodiments, a rate of production of the alanine is at least 0.5 g/L/hour. In some embodiments, a rate of production of the alanine is at least 1.0 g/L/hour. In some embodiments, a rate of production of the alanine is at least 1.5 g/L/hour. In some embodiments, a rate of production of the alanine is at least 1.6 g/L/hour.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6A-H depict an example of mevalonate production in E. coli utilizing 2-stage dynamic control.

FIG. 13A-E depict examples of distribution of glucose utilized during the growth phase of starting host strains in 1 L standard minimal medium fermentations.

FIG. 17 depicts micro-fermentation for L-alanine production using different insulated phosphate promoters in DLF_0025 strain.

FIGS. 21A-D depict alanine production in response to different OTR and glucose concentration in micro-fermentation for 4 strains evaluated for robustness.

FIGS. 29A-D depict alanine production in response to different OTR and glucose concentration in micro-fermentation for 4 strains evaluated for robustness.

FIGS. 30A-D depict alanine production in response to different OTR and glucose concentration in micro-fermentation for 4 strains evaluated for robustness.

FIGS. 33A-B depict growth profile for all valve and growth associated strains at 1 L scale evaluated in this paper.

FIGS. 38A-D depict TUV standard curves for L-alanine, D-alanine, mevalonic acid, and mevalonolactone.

DETAILED DESCRIPTION OF THE INVENTION

Definitions

Figure 1A:
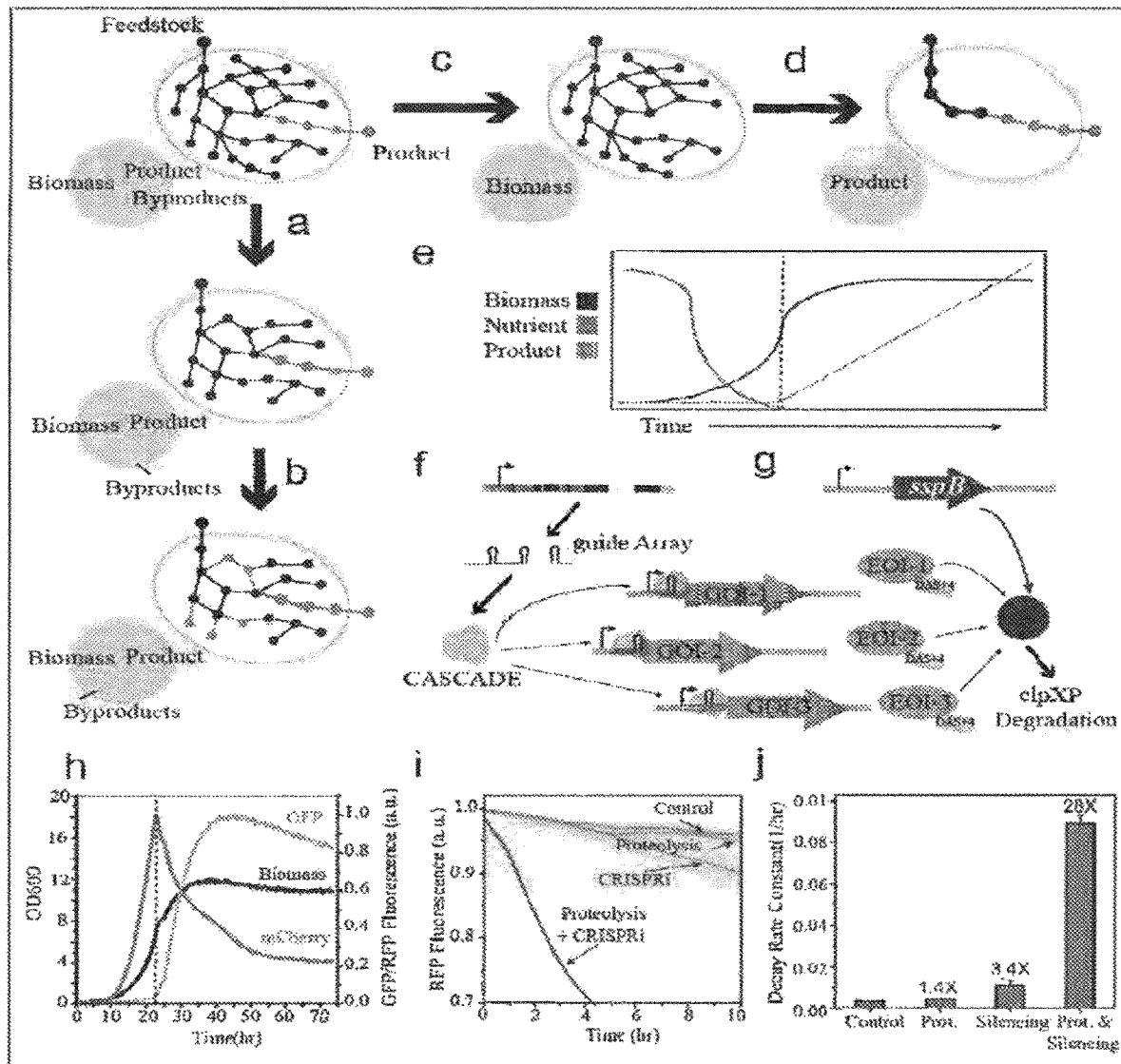
FIG. 1A depicts an overview of dynamic metabolic control in 2-stage fermentations.

As used in the specification and the claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "microorganism" includes a single microorganism as well as a plurality of microorganisms; and the like.

As used herein, "reduced enzymatic activity," "reducing enzymatic activity," and the like is meant to indicate that a microorganism cell's, or an isolated enzyme, exhibits a lower level of activity than that measured in a comparable cell of the same species or its native enzyme. That is, enzymatic conversion of the indicated substrate(s) to indicated product(s) under known standard conditions for that enzyme is at least 10, at least 20, at least 30, at least 40, at least 50, at least 60, at least 70, at least 80, or at least 90 percent less than the enzymatic activity for the same biochemical conversion by a native (non-modified) enzyme under a standard specified condition. This term also can include elimination of that enzymatic activity. A cell having reduced enzymatic activity of an enzyme can be identified using any method known in the art. For example, enzyme activity assays can be used to identify cells having reduced enzyme activity. See, for example, Enzyme Nomenclature, Academic Press, Inc., New York 2007.

The term "heterologous DNA," "heterologous nucleic acid sequence," and the like as used herein refers to a nucleic acid sequence wherein at least one of the following is true: (a) the sequence of nucleic acids foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid, such as a nonnative promoter driving gene expression.

The term "synthetic metabolic valve," and the like as used herein refers to either the use of controlled proteolysis, gene silencing or the combination of both proteolysis and gene silencing to alter metabolic fluxes.

The term "heterologous" is intended to include the term "exogenous" as the latter term is generally used in the art. With reference to the host microorganism's genome prior to the introduction of a heterologous nucleic acid sequence, the nucleic acid sequence that codes for the enzyme is heterologous (whether or not the heterologous nucleic acid sequence is introduced into that genome).

As used herein, the term "gene disruption," or grammatical equivalents thereof (and including "to disrupt enzymatic function," "disruption of enzymatic function," and the like), is intended to mean a genetic modification to a microorganism that renders the encoded gene product as having a reduced polypeptide activity compared with polypeptide activity in or from a microorganism cell not so modified. The genetic modification can be, for example, deletion of the entire gene, deletion or other modification of a regulatory sequence required for transcription or translation, deletion of a portion of the gene which results in a truncated gene product (e.g., enzyme) or by any of various mutation strategies that reduces activity (including reducing activities to no detectable activity level) the encoded gene product. A disruption may broadly include a deletion of all or part of the nucleic acid sequence encoding the enzyme, and also includes, but is not limited to other types of genetic modifications, e.g., introduction of stop codons, frame shift mutations, introduction or removal of portions of the gene, and introduction of a degradation signal, those genetic modifications affecting mRNA transcription levels and/or stability, and altering the promoter or repressor upstream of the gene encoding the enzyme.

Bio-production or fermentation, as used herein, may be aerobic, microaerobic, or anaerobic.

When the genetic modification of a gene product, e.g., an enzyme, is referred to herein, including the claims, it is understood that the genetic modification is of a nucleic acid sequence, such as or including the gene, that normally encodes the stated gene product, e.g., the enzyme.

As used herein, the term "metabolic flux" and the like refers to changes in metabolism that lead to changes in product and/or byproduct formation, including production rates, production titers and production yields from a given substrate.

Species and other phylogenic identifications are according to the classification known to a person skilled in the art of microbiology.

Enzymes are listed here within, with reference to a Universal Protein Resource (Uniprot) identification number, which would be well known to one skilled in the art (Uniprot is maintained by and available through the UniProt Consortium).

Where methods and steps described herein indicate certain events occurring in certain order, those of ordinary skill in the art will recognize that the ordering of certain steps may be modified and that such modifications are in accordance with the variations of the invention.

Additionally, certain steps may be performed concurrently in a parallel process when possible, as well as performed sequentially.

The meaning of abbreviations is as follows: "C" means Celsius or degrees Celsius, as is clear from its usage, DCW means dry cell weight, "s" means second(s), "min" means minute(s), "h," "hr," or "hrs" means hour(s), "psi" means pounds per square inch, "nm" means nanometers, "d" means day(s), "µL" or "μL" or "µl" means microliter(s), "mL" means milliliter(s), "L" means liter(s), "mm" means millimeter(s), "nm" means nanometers, "mM" means millimolar, "µM" or "μM" means micromolar, "M" means molar, "mmol" means millimole(s), "p mol" or "uMol" means micromole(s), "g" means gram(s), "µg" or "μg" means microgram(s) and "ng" means nanogram(s), "PCR" means polymerase chain reaction, "OD" means optical density, "$OD_{600}$" means the optical density measured at a photon wavelength of 600 nm, "kDa" means kilodaltons, "g" means the gravitation constant, "bp" means base pair(s), "kbp" means kilobase pair(s), "w/v" means weight/volume percent, "% v/v" means volume/volume percent, "IPTG" means isopropyl-µ-D-thiogalactopyranoiside, "aTc" means anhydrotetracycline, "RBS" means ribosome binding site, "rpm" means revolutions per minute, "HPLC" means high performance liquid chromatography, and "GC" means gas chromatography.

Overview

Provided herein is a high-throughput metabolic engineering platform enabling the rapid optimization of microbial production strains. The platform, which bridges a gap between current in vivo and in vitro bio-production approaches, relies on dynamic minimization of the active metabolic network. Dynamic metabolic network minimization can be accomplished using combinations of CRISPR interference and controlled proteolysis to reduce the activity of multiple enzymes in essential central metabolism. Minimization can be implemented in the context of standardized 2-stage bio-processes. This approach not only can result in a design space with greatly reduced complexity, but also in increased metabolic fluxes and production rates as well as in strains which are robust to environmental conditions. Robustness can lead to predictable scalability from high-throughput small-scale screens, or "micro-fermentations", to fully instrumented bioreactors. Predictive high-throughput approaches may be critical for metabolic engineering programs to truly take advantage of the rapidly increasing throughput and decreasing costs of synthetic biology. The examples provided herein have not only demonstrated proof of principle for this approach in the common industrial microbe: E. coli, and has validated this approach with the rapid optimization of E. coli strains producing two important industrial chemicals: alanine and mevalonic acid, at commercially meaningful rates, titers (147 g/L and 97 g/L, respectively), and yields.

Also provided herein are systems and methods to rapidly optimize a microorganism for chemical productions in a high-throughput fashion.

Also provided herein are microorganisms that can be used with the disclosed platform and/or methods for chemical productions.

Synthetic metabolic valves (SMVs)

The current disclosure describes the construction of synthetic metabolic valves (SMVs) comprising one or more or a combination of the following: controlled gene silencing and controlled proteolysis. It is appreciated that one well skilled in the art is aware of several methodologies for gene silencing and controlled proteolysis.

The development of platform microbial strains that utilize SMVs can decouple growth from product formation. These strains enable the dynamic control of metabolic pathways, including those that when altered have negative effects on microorganism growth. Dynamic control over metabolism is accomplished via a combination of methodologies including but not limited to transcriptional silencing and controlled enzyme proteolysis. These microbial strains are utilized in a multi-stage bioprocess encompassing as least two stages, the first stage in which microorganisms are grown and metabolism can be optimized for microbial growth and at least one other stage in which growth can be slowed or stopped, and dynamic changes can be made to metabolism to improve production of desired product, such as a chemical or fuel. The transition of growing cultures between stages and the manipulation of metabolic fluxes can be controlled by artificial chemical inducers or preferably by controlling the level of key limiting nutrients. In addition, genetic modifications may be made to provide metabolic pathways for the biosynthesis of one or more chemical or fuel products. Also, genetic modifications may be made to enable the utilization of a variety of carbon feedstocks including but not limited sugars such as glucose, sucrose, xylose, arabinose, mannose, and lactose, oils, carbon dioxide, carbon monoxide, methane, methanol and formaldehyde.

This approach allows for simpler models of metabolic fluxes and physiological demands during a production phase, turning a growing cell into a stationary phase biocatalyst. These synthetic metabolic valves can be used to turn off essential genes and redirect carbon, electrons and energy flux to product formation in a multi-stage fermentation process. One or more of the following enables these synthetic valves: 1) transcriptional gene silencing or repression technologies in combination with 2) inducible enzyme degradation and 3) nutrient limitation to induce a stationary or non-dividing cellular state. SMVs are generalizable to any pathway and microbial host. These synthetic metabolic valves allow for novel rapid metabolic engineering strategies useful for the production of renewable chemicals and fuels and any product that can be produced via whole cell catalysis.

In various cases, one SMV can refer to the manipulation of one gene (or its protein product). The manipulation can be controlled silencing of the gene and/or controlled degradation of its protein product. In certain cases, combination of SMVs can lead to improved production in yields, rate and/or robustness, which includes manipulation of two genes (or their protein products). In some cases, an engineered microorganism comprises at least one SMV. In some cases, an engineered microorganism comprises more than one SMV. In some cases, an engineered microorganism comprises two, three, four, five, six, seven, eight, nine, or ten, or more SMVs.

Method and Systems for Bio-Production

Provided herein are methods or systems for robust large scale production of molecules from biologics and small molecule therapeutics to specialty, bulk and commodity chemicals, and biofuels. The methods or systems provided herein comprise using engineered microorganism which comprises a limited set of metabolic enzymes. In some embodiments, the engineered microorganism comprises at least one metabolic enzyme that has reduced level or activity. In some embodiments, the engineered microorganism comprises two, three, four, five, six, seven, eight, nine, or ten, or more metabolic enzymes that have reduced level or activity. The methods and systems provided herein can reduce metabolic responses to environmental conditions and can be easily transferred from small scale (e.g. mgs) production to large scale (e.g. kgs) production. The methods and systems provided herein can reduce the time and costs associated with transitioning from small scale (e.g. mgs) to large scale (e.g. kgs) production.

Within the scope of the current disclosure are genetically modified microorganism, wherein the microorganism is capable of producing a product derived from any key metabolic intermediate including but not limited to malonyl-CoA, pyruvate, oxaloacetate, erthyrose-4-phosphate, xylulose-5-phosphate, alpha-ketoglutarate and citrate at a specific rate selected from the rates of greater than 0.05 g/gDCW-hr, 0.08 g/gDCW-hr, greater than 0.1 g/gDCW-hr, greater than 0.13 g/gDCW-hr, greater than 0.15 g/gDCW-hr, greater than 0.175 g/gDCW-hr, greater than 0.2 g/gDCW-hr, greater than 0.25 g/gDCW-hr, greater than 0.3 g/gDCW-hr, greater than 0.35 g/gDCW-hr, greater than 0.4 g/gDCW-hr, greater than 0.45 g/gDCW-hr, or greater than 0.5 g/gDCW-hr.

In various embodiments, the invention includes a culture system comprising a carbon source in an aqueous medium and a genetically modified microorganism, wherein said genetically modified organism is present in an amount selected from greater than 0.05 gDCW/L, 0.1 gDCW/L, greater than 1 gDCW/L, greater than 5 gDCW/L, greater than 10 gDCW/L, greater than 15 gDCW/L or greater than 20 gDCW/L, such as when the volume of the aqueous medium is selected from greater than 5 mL, greater than 100 mL, greater than 0.5 L, greater than 1 L, greater than 2 L, greater than 10 L, greater than 250 L, greater than 1000 L, greater than 10,000 L, greater than 50,000 L, greater than 100,000 L or greater than 200,000 L, and such as when the volume of the aqueous medium is greater than 250 L and contained within a steel vessel.

Carbon Sources

Bio-production media, which is used in the present invention with recombinant microorganisms must contain suitable carbon sources or substrates for both growth and production stages. Suitable substrates may include, but are not limited to glucose, sucrose, xylose, mannose, arabinose, oils, carbon dioxide, carbon monoxide, methane, methanol, formaldehyde and glycerol. It is contemplated that all of the above mentioned carbon substrates and mixtures thereof are suitable in the present invention as a carbon source(s).

Microorganisms

Features as described and claimed herein may be provided in a microorganism selected from the listing herein, or another suitable microorganism, that also comprises one or more natural, introduced, or enhanced product bio-production pathways. Thus, in some embodiments the microorganism(s) comprise an endogenous product production pathway (which may, in some such embodiments, be enhanced), whereas in other embodiments the microorganism does not comprise an endogenous product production pathway.

The examples describe specific modifications and evaluations to certain bacterial and fungal microorganisms. The scope of the invention is not meant to be limited to such species, but to be generally applicable to a wide range of suitable microorganisms.

Suitable host cells or host microorganisms for bio-production can be either prokaryotic or eukaryotic. Suitable host cells or host microorganisms can be bacteria such as *Citrobacter, Enterobacter, Clostridium, Klebsiella, Aerobacter, Lactobacillus, Aspergillus, Saccharomyces, Schizosaccharomyces, Zygosaccharomyces, Pichia, Kluyveromyces, Candida, Hansenula, Debaryomyces, Mucor, Torulopsis, Methylobacter, Escherichia, Salmonella, Bacil-*

*lus, Streptomyces*, and *Pseudomonas*. In some embodiments, a host cell or an engineered cell is *E. coli*. In some embodiments, a host cell or an engineered cell is *S. cerevisiae*.

In certain aspects, provided herein is a microorganism genetically modified to comprise: a production pathway comprising at least one enzyme for the biosynthesis of a product, and a combination of multiple synthetic metabolic valves to controllably reduce or eliminate flux through multiple metabolic pathways. In some embodiments, each of the multiple synthetic metabolic valves comprises one or more genes for (i) controlled silencing of gene expression of at least one gene or (ii) the controlled proteolytic inactivation of at least one protein. In some embodiments, a rate of the biosynthesis of the product is increased in a productive stationary phase upon a depletion of a nutrient, wherein the depletion of the nutrient induces the multiple synthetic metabolic valves. In some cases, the controlled silencing of gene expression is accomplished by RNA interference, CRISPR interference or transcriptional repression. In some cases, the controlled proteolytic inactivation is accomplished by protein cleavage by a specific protease or targeted degradation by specific peptide tags. In some cases, the nutrient is phosphate, nitrogen, sulfur, magnesium, or a combination thereof.

In certain aspects, provided herein is a genetically modified microorganism comprising: a production pathway comprising at least one enzyme for the biosynthesis of a product from one of the following metabolites: pyruvate, acetolactate, acetyl-CoA, acetoacetyl-CoA or malonyl-CoA; and a combination of multiple synthetic metabolic valves, wherein each of the multiple synthetic metabolic valves comprises one of a fabI, gltA, lpd, zwf or udhA gene for (i) controlled silencing of gene expression of a corresponding one of said fabI, gltA, lpd, zwf or udhA genes or (ii) controlled proteolytic inactivation of a protein encoded by a corresponding one of said fabI, gltA, lpd, zwf or udhA genes. In some embodiments, a rate of the biosynthesis of the product is increased in a productive stationary phase upon a depletion of a nutrient, wherein the depletion of the nutrient induces the multiple synthetic metabolic valves. In some embodiments, the product is alanine or a derivative thereof. In some embodiments, the product is mevalonate or a derivative thereof. In some embodiments, the product is malonic acid or a derivative thereof. In some embodiments, the nutrient is phosphate, nitrogen, sulfur, magnesium, or a combination thereof.

In certain aspects, provided herein is a genetically modified microorganism comprising: a production pathway to produce alanine from pyruvate; and a combination of multiple synthetic metabolic valves, wherein each of the multiple synthetic metabolic valves comprises one of a fabI, gltA, lpd, zwf or udhA gene for (i) controlled silencing of gene expression of a corresponding one of said fabI, gltA, lpd, zwf or udhA genes or (ii) controlled proteolytic inactivation of a protein encoded by one of said fabI, gltA, lpd, zwf or udhA genes. In some embodiments, a rate of the biosynthesis of alanine is increased in a productive stationary phase upon a depletion of a nutrient, wherein the depletion of the nutrient induces the multiple synthetic metabolic valves. In some embodiments, the nutrient is phosphate, nitrogen, sulfur, magnesium, or a combination thereof.

In some cases, a genetically modified microorganism is a heterologous cell. In some cases, provided herein is a heterologous cell for generating a product. In some cases, a heterologous cell comprises an engineered valve polynucleotide for mediating controlled reduction of expression of a valve enzyme acting in a metabolic pathway. In certain cases, a controlled reduction of expression of a valve enzyme reduces flux through a metabolic pathway, wherein the controlled reduction of expression of the valve enzyme induces a stationary phase of the heterologous cell. In some cases, a heterologous cell further comprises an engineered production polynucleotide for mediating controlled increase in expression of a production enzyme for generation of the product. In some situations, a heterologous cell comprises an engineered valve polynucleotide for mediating controlled reduction of expression of a valve enzyme acting in a metabolic pathway, wherein a rate of production of a product during a stationary phase is reduced less in response to a change of an environmental condition as compared to a cell lacking the controlled reduction of expression of the valve enzyme.

In some cases, provided herein is a heterologous cell for generating a product, wherein said cell comprises: an engineered valve polynucleotide for mediating controlled reduction of expression of a valve enzyme acting in a metabolic pathway, wherein said controlled reduction of expression of said valve enzyme reduces flux through said metabolic pathway, wherein said controlled reduction of expression of said valve enzyme induces a stationary phase of said cell; and an engineered production polynucleotide for mediating controlled increase in expression of a production enzyme for generation of said product; wherein a rate of production of said product during said stationary phase is reduced less in response to a change of an environmental condition as compared to a cell lacking said controlled reduction of expression of said valve enzyme.

In some cases, provided herein is a cell comprising a reduced expression or activity of a valve enzyme, wherein the valve enzyme comprises an enzyme selected from the group consisting of enoyl-ACP/CoA reductase (fabI), glucose-6-phosphate dehydrogenase (zwf), lipoamide dehydrogenase (lpd), citrate synthase (gltA), soluble transhydrogenase (udhA), NADH-dependent glyceraldehyde-3-phosphate dehydrogenase (gapA), and a combination thereof.

In some cases, provided herein is a cell comprising a production enzyme, wherein the production enzyme comprises an enzyme selected from the group consisting of NADPH-dependent alanine dehydrogenase (ald), alanine exporter (alaE), NADPH-dependent glyceraldehyde-3-phosphate dehydrogenase (gapN), and a combination thereof.

Environmental Conditions

Environmental conditions can comprise medium and culture conditions. Environmental factors that may influence production can be temperature, pH, acidity, ethanol, sulfite, and availability of nutrients.

In addition to an appropriate carbon source, such as selected from one of the herein disclosed types, bio-production media may contain suitable minerals, salts, cofactors, buffers and other components, known to those skilled in the art, suitable for the growth of the cultures and promotion of the enzymatic pathway necessary for chemical product bio-production under the present disclosure. Another aspect of the invention regards media and culture conditions that comprise genetically modified microorganisms of the invention and optionally supplements.

Typically cells are grown at a temperature in the range of about 25° C. to about 40° C. in an appropriate medium, as well as up to 70° C. for thermophilic microorganisms. Suitable growth media are well characterized and known in the art.

Suitable pH ranges for the bio-production are between pH 2.0 to pH 10.0, where pH 6.0 to pH 8.0 is a typical pH range for the initial condition. However, the actual culture conditions for a particular embodiment are not meant to be limited by these pH ranges.

Bio-productions may be performed under aerobic, microaerobic or anaerobic conditions with or without agitation.

In some cases, a change of an environmental condition comprises a change in sugar concentration of a culture medium contacting a cell. In some cases, a change in sugar concentration of a culture medium is an increase of sugar concentration. In some other cases, a change in sugar concentration is a decrease of sugar concentration. In some situations, an increase of sugar concentration is from 1% to 2%, from 2% to 3%, from 3% to 4%, from 4% to 5%, from 5% to 10%, from 10% to 15%, from 15% to 20%, from 20% to 30%, from 30% to 40%, from 40% to 50%, from 50% to 60%, from 60% to 70%, from 70% to 80%, from 80% to 90%, or from 90% to 100% more sugar compared with the original sugar concentration in the culture medium. In some situations, a decrease of sugar concentration is from 1% to 2%, from 2% to 3%, from 3% to 4%, from 4% to 5%, from 5% to 10%, from 10% to 15%, from 15% to 20%, from 20% to 30%, from 30% to 40%, from 40% to 50%, from 50% to 60%, from 60% to 70%, from 70% to 80%, from 80% to 90%, or from 90% to 100% less sugar compared with the original sugar concentration in the culture medium.

In some cases, a change of an environmental condition comprises a change in oxygenation of a culture medium contacting a cell. In some cases, a change in oxygenation of a culture medium is an increase of oxygenation. In some other cases, a change in oxygenation of a culture medium is a decrease of oxygenation. In some situations, an increase of oxygenation is the addition of oxygen from 1% to 2%, from 2% to 3%, from 3% to 4%, from 4% to 5%, from 5% to 10%, from 10% to 15%, from 15% to 20%, from 20% to 30%, from 30% to 40%, from 40% to 50%, from 50% to 60%, from 60% to 70%, from 70% to 80%, from 80% to 90%, or from 90% to 100% more than the original amount of oxygen added in a culture medium. In some situations, a decrease of oxygenation is the addition of oxygen from 1% to 2%, from 2% to 3%, from 3% to 4%, from 4% to 5%, from 5% to 10%, from 10% to 15%, from 15% to 20%, from 20% to 30%, from 30% to 40%, from 40% to 50%, from 50% to 60%, from 60% to 70%, from 70% to 80%, from 80% to 90%, or from 90% to 100% less than the original amount of oxygen added in a culture medium.

Bio-production Reactors and Systems

Fermentation systems utilizing methods and/or compositions according to the invention are also within the scope of the invention.

Any of the recombinant microorganisms as described and/or referred to herein may be introduced into an industrial bio-production system where the microorganisms convert a carbon source into a product in a commercially viable operation. The bio-production system includes the introduction of such a recombinant microorganism into a bioreactor vessel, with a carbon source substrate and bio-production media suitable for growing the recombinant microorganism, and maintaining the bio-production system within a suitable temperature range (and dissolved oxygen concentration range if the reaction is aerobic or microaerobic) for a suitable time to obtain a desired conversion of a portion of the substrate molecules to a selected chemical product. Bio-productions may be performed under aerobic, microaerobic, or anaerobic conditions, with or without agitation. Industrial bio-production systems and their operation are well-known to those skilled in the arts of chemical engineering and bioprocess engineering. The amount of a product produced in a bio-production media generally can be determined using a number of methods known in the art, for example, high performance liquid chromatography (HPLC), gas chromatography (GC), or GC/Mass Spectroscopy (MS).

Genetic Modifications, Nucleotide Sequences, and Amino Acid Sequences

Embodiments of the present disclosure may result from introduction of an expression vector into a host microorganism, wherein the expression vector contains a nucleic acid sequence coding for an enzyme that is, or is not, normally found in a host microorganism.

The ability to genetically modify a host cell is essential for the production of any genetically modified (recombinant) microorganism. The mode of gene transfer technology may be by electroporation, conjugation, transduction, or natural transformation. A broad range of host conjugative plasmids and drug resistance markers are available. The cloning vectors are tailored to the host organisms based on the nature of antibiotic resistance markers that can function in that host. Also, as disclosed herein, a genetically modified (recombinant) microorganism may comprise modifications other than via plasmid introduction, including modifications to its genomic DNA.

More generally, nucleic acid constructs can be prepared comprising an isolated polynucleotide encoding a polypeptide having enzyme activity operably linked to one or more (several) control sequences that direct the expression of the coding sequence in a microorganism, such as $E.\ coli$, under conditions compatible with the control sequences. The isolated polynucleotide may be manipulated to provide for expression of the polypeptide.

Manipulation of the polynucleotide's sequence prior to its insertion into a vector may be desirable or necessary depending on the expression vector. The techniques for modifying polynucleotide sequences utilizing recombinant DNA methods are well established in the art.

The control sequence may be an appropriate promoter sequence, a nucleotide sequence that is recognized by a host cell for expression of a polynucleotide encoding a polypeptide of the present disclosure. The promoter sequence may contain transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell. The techniques for modifying and utilizing recombinant DNA promoter sequences are well established in the art.

For various embodiments of the invention the genetic manipulations may be described to include various genetic manipulations, including those directed to change regulation of, and therefore ultimate activity of, an enzyme or enzymatic activity of an enzyme identified in any of the respective pathways. Such genetic modifications may be directed to transcriptional, translational, and post-translational modifications that result in a change of enzyme activity and/or selectivity under selected and/or identified culture conditions and/or to provision of additional nucleic acid sequences such as to increase copy number and/or mutants of an enzyme related to product production. Specific methodologies and approaches to achieve such genetic modification are well known to one skilled in the art.

In various embodiments, to function more efficiently, a microorganism may comprise one or more gene deletions. For example, in *E. coli*, the genes encoding the lactate dehydrogenase (ldhA), phosphate acetyltransferase (pta), pyruvate oxidase (poxB), pyruvateformate lyase (pflB), methylglyoxal synthase (mgsA), acetate kinase (ackA), alcohol dehydrogenase (adhE), the clpXP protease specificity enhancing factor (sspB), the ATPdependent Lon protease (lon), the outer membrane protease (ompT), the arcA transcriptional dual regulator (arcA), and the iclR transcriptional regulator (iclR) may be disrupted, including deleted. Such gene disruptions, including deletions, are not meant to be limiting, and may be implemented in various combinations in various embodiments. Gene deletions may be accomplished by numerous strategies well known in the art, as are methods to incorporate foreign DNA into a host chromosome.

In various embodiments, to function more efficiently, a microorganism may comprise one or more synthetic metabolic valves, composed of enzymes targeted for controlled proteolysis, expression silencing or a combination of both controlled proteolysis and expression silencing. In some embodiments, a microorganism may comprise two, three, four, five, six, seven, eight, nine, or ten, or more synthetic metabolic valves. For example, one enzyme encoded by one gene or a combination of numerous enzymes encoded by numerous genes in *E. coli* may be designed as synthetic metabolic valves to alter metabolism and improve product formation. Representative genes in *E. coli* may include but are not limited to the following: fabI, zwf gltA, ppc, udhA, lpd, sucD, aceA, pfkA, lon, rpoS, tktA or tktB. It is appreciated that it is well known to one skilled in the art how to identify homologues of these genes and or other genes in additional microbial species.

For all nucleic acid and amino acid sequences provided herein, it is appreciated that conservatively modified variants of these sequences are included, and are within the scope of the invention in its various embodiments. Functionally equivalent nucleic acid and amino acid sequences (functional variants), which may include conservatively modified variants as well as more extensively varied sequences, which are well within the skill of the person of ordinary skill in the art, and microorganisms comprising these, also are within the scope of various embodiments of the invention, as are methods and systems comprising such sequences and/or microorganisms.

Accordingly, as described in various sections above, some compositions, methods and systems of the present disclosure comprise providing a genetically modified microorganism that comprises both a production pathway to make a desired product from a central intermediate in combination with synthetic metabolic valves to redistribute flux.

Aspects of the invention also regard provision of multiple genetic modifications to improve microorganism overall effectiveness in converting a selected carbon source into a selected product. Particular combinations are shown, such as in the Examples, to increase specific productivity, volumetric productivity, titer and yield substantially over more basic combinations of genetic modifications. In addition to the above-described genetic modifications, in various embodiments genetic modifications, including synthetic metabolic valves also are provided to increase the pool and availability of the cofactor NADPH and/or NADH which may be consumed in the production of a product.

More generally, and depending on the particular metabolic pathways of a microorganism selected for genetic modification, any subgroup of genetic modifications may be made to decrease cellular production of fermentation product(s) other than the desired fermentation product, selected from the group consisting of acetate, acetoin, acetone, acrylic, malate, fatty acid ethyl esters, isoprenoids, glycerol, ethylene glycol, ethylene, propylene. butylene, isobutylene, ethyl acetate, vinyl acetate, other acetates, 1,4-butanediol, 2,3-butanediol, butanol, isobutanol, sec-butanol, butyrate, isobutyrate, 2-OH-isobutryate, 3-OHbutyrate, ethanol, isopropanol, D-lactate, L-lactate, pyruvate, itaconate, levulinate, glucarate, glutarate, caprolactam, adipic acid, propanol, isopropanol, fusel alcohols, and 1,2-propanediol, 1,3-propanediol, formate, fumaric acid, propionic acid, succinic acid, valeric acid, maleic acid and poly-hydroxybutyrate. Gene deletions may be made as disclosed generally herein, and other approaches may also be used to achieve a desired decreased cellular production of selected fermentation products other than the desired products.

VI.A Gene Silencing

In particular the invention describes the use of controlled gene silencing to help enable the control over metabolic fluxes in controlled multi-stage fermentation processes. There are several methodologies known in the art for controlled gene silencing, including but not limited to mRNA silencing or RNA interference, silencing via transcriptional repressors and CRISPR interference.

In some cases, a valve polynucleotide comprises a polynucleotide selected from the group consisting of: a silencing polynucleotide for repressing transcription of a gene encoding said valve enzyme; a degradation polynucleotide for mediating cellular degradation of said valve enzyme; and a combination thereof.

In some cases, a valve polynucleotide comprises a silencing polynucleotide, and said silencing polynucleotide comprises a guide RNA (gRNA) comprising a gRNA sequence that recognizes a promoter of a gene encoding said valve enzyme.

In some cases, a valve polynucleotide further encodes a CRISPR enzyme, wherein said CRISPR enzyme specifically binds to said promoter sequence when bound to said gRNA. In some cases, a CRISPR enzyme is catalytically inactive.

In some cases, a valve polynucleotide comprises a degradation polynucleotide, wherein said degradation polynucleotide comprises a sequence encoding a degradation tag, wherein said degradation tag mediates degradation of said valve enzyme. In some cases, the expression of a valve polynucleotide is regulated by phosphate availability in a cell. In some cases, the expression of a production polynucleotide is regulated by phosphate availability in a cell. In certain cases, the cell is an *E. coli* cell.

Controlled Proteolysis

In particular the current disclosure describes the use of controlled protein degradation or proteolysis to help enable the control over metabolic fluxes in controlled multi-stage fermentation processes. There are several methodologies known in the art for controlled protein degradation, including but not limited to targeted protein cleavage by a specific protease and controlled targeting of proteins for degradation by specific peptide tags. Systems for the use of the *E. coli* clpXP protease for controlled protein degradation can be used. This methodology relies upon adding a specific C-terminal peptide tag such as a DAS4 (or DAS+4) tag. Proteins with this tag are not degraded by the clpXP protease until the specificity enhancing chaperone sspB is expressed. sspB induces degradation of DAS4 tagged proteins by the clpXP protease. In additional numerous site specific protease systems are well known in the art. Proteins can be engineered to contain a specific target site of a given protease and then cleaved after the controlled expression of the protease. In some embodiments the cleavage can be expected lead to protein inactivation or degradation. For example, an N-terminal sequence can be added to a protein of interest to enable clpS dependent clpAP degradation. In addition, this sequence can further be masked by an additional N-terminal sequence, which can be controllable cleaved such as by a ULP hydrolase. This allows for controlled N-rule degradation dependent on hydrolase expression. It is therefore possible to tag proteins for controlled proteolysis either at the N-terminus or C-terminus.

The preference of using an N-terminal vs. C-terminal tag will largely depend on whether either tag affects protein function prior to the controlled onset of degradation. The invention describes the use of controlled protein degradation or proteolysis to help enable the control over metabolic fluxes in controlled multi-stage fermentation processes, in E. coli. There are several methodologies known in the art for controlled protein degradation in other microbial hosts, including a wide range of gram-negative as well as gram-positive bacteria, yeast and even archaea. In particular, systems for controlled proteolysis can be transferred from a native microbial host and used in a non-native host.

Synthetic Metabolic Valve Control

In particular the current disclosure describes the use of synthetic metabolic valves to control metabolic fluxes in multi-stage fermentation processes. There are numerous methodologies known in the art to induce expression that can be used at the transition between stages in multistage fermentations. These include but are not limited to artificial chemical inducers including: tetracycline, anhydrotetracycline, lactose, IPTG (isopropyl-beta-D-l-thiogalactopyranoside), arabinose, raffinose, tryptophan and numerous others. Systems linking the use of these well known inducers to the control of gene expression silencing and/or controlled proteolysis can be integrated into genetically modified microbial systems to control the transition between growth and production phases in multi-stage fermentation processes.

In addition, it may be desirable to control the transition between growth and production in multi-stage fermentations by the depletion of one or more limiting nutrients that are consumed during growth. Limiting nutrients can include but are not limited to: phosphate, nitrogen, sulfur and magnesium. Natural gene expression systems that respond to these nutrient limitations can be used to operably link the control of gene expression silencing and/or controlled proteolysis to the transition between growth and production phases in multi-stage fermentation processes.

Products

In some embodiments, provided herein is a microorganism or a cell for producing a product. In some cases, the product comprises 3-hydroxypropionic acid. In some cases, the product comprises an amino acid. In some cases, the amino acid comprises alanine. In some cases, the alanine is L-alanine. In some cases, the alanine is D-alanine. In some cases, a rate of production of alanine is at least 0.1 g/L/hr, 0.2 g/L/hr, 0.3 g/L/hr, 0.4 g/L/hr, 0.5 g/L/hr, 0.6 g/L/hr, 0.7 g/L/hr, 0.8 g/L/hr, 0.9 g/L/hr, 1.0 g/L/hr, 1.1 g/L/hr, 1.2 g/L/hr, 1.3 g/L/hr, 1.4 g/L/hr, 1.5 g/L/hr, 1.6 g/L/hr, 1.7 g/L/hr, 1.8 g/L/hr, 1.9 g/L/hr, 2.0 g/L/hr, 2.5 g/L/hr, 3.0 g/L/hr, 3.5 g/L/hr, 4.0 g/L/hr, 4.5 g/L/hr, 5.0 g/L/hr, 5.5 g/L/hr, 6.0 g/L/hr, 7.0 g/L/hr, 8.0 g/L/hr, 9.0 g/L/hr, or at least 10 g/L/hr.

In some cases, the alanine titers after 24 hours can be from 0 to 0.5 g/L, 0.5 g/L to 1 g/L, 1 g/L to 1.5 g/L, 1.5 g/L to 2 g/L, 2 g/L to 2.5 g/L, 2.5 g/L to 3 g/L, 3 g/L to 3.5 g/L, 3.5 g/L to 4 g/L, 4 g/L to 4.5 g/L, 4.5 g/L to 5 g/L, or from 5 g/L to 10 g/L. The dynamic range of alanine production offered by SMVs can be up to a 4-fold increase compared to that offered by solely altering the expression level of the production pathway enzymes (by changing the promoter). In some cases, the dynamic range of alanine production offered by SMVs can be up to a 2-fold, 3-fold, 4-fold, 5-fold, 6-fold, 7-fold, 8-fold, 9-fold, or 10-fold increase compared to that offered by solely altering the expression level of the production pathway enzymes.

In some cases, a production polynucleotide in the microorganism encodes an alanine exporter. In some cases, the alanine exporter is alaE.

In some cases, the product comprises mevalonic acid. In some cases, a rate of production of mevalonic acid is at least 0.1 g/L/hr, 0.2 g/L/hr, 0.3 g/L/hr, 0.4 g/L/hr, 0.5 g/L/hr, 0.6 g/L/hr, 0.7 g/L/hr, 0.8 g/L/hr, 0.9 g/L/hr, 1.0 g/L/hr, 1.1 g/L/hr, 1.2 g/L/hr, 1.3 g/L/hr, 1.4 g/L/hr, 1.5 g/L/hr, 1.6 g/L/hr, 1.7 g/L/hr, 1.8 g/L/hr, 1.9 g/L/hr, 2.0 g/L/hr, 2.5 g/L/hr, 3.0 g/L/hr, 3.5 g/L/hr, 4.0 g/L/hr, 4.5 g/L/hr, 5.0 g/L/hr, 5.5 g/L/hr, 6.0 g/L/hr, 7.0 g/L/hr, 8.0 g/L/hr, 9.0 g/L/hr, or at least 10 g/L/hr.

Methods

Provided herein are methods for producing a product in an engineered microorganism in a large scale. Also provided herein are methods for engineering microorganisms for large-scale production of a product in a high-throughput fashion.

In some cases, provided herein is a method, comprising: culturing a plurality of strains of a cell, wherein each strain of said plurality of strains comprises (i) an engineered valve polynucleotide for mediating controlled reduction of expression of a valve enzyme acting in a metabolic pathway, wherein said controlled reduction of expression of said valve enzyme reduces flux through said metabolic pathway; and (ii) an engineered production polynucleotide for mediating controlled increase in expression of a production enzyme for generation of said product; wherein each strain of said plurality of strains differs from another strain in a sequence of at least one of said engineered valve polynucleotide or said engineered production polynucleotide; measuring a level of said product generated by each of said plurality of strains; and selecting a strain based on said level of said product. In some embodiments, the method further comprises growing said selected strain in a bioreactor. In some embodiments, a culture medium comprising said selected strain has a volume of at least 100 ml, 200 ml, 300 ml, 400 ml, 500 ml, 600 ml, 700 ml, 800 ml, 900 ml, or at least 1000 ml. In some embodiments, a culture medium has a volume of at least 1 L.

In some embodiments, a valve polynucleotide comprises a polynucleotide selected from the group consisting of: a silencing polynucleotide for repressing transcription of a gene encoding said valve enzyme; a degradation polynucleotide for mediating cellular degradation of said valve enzyme; and a combination thereof. In some embodiments, a first and a second strain of said plurality of strains comprise a silencing polynucleotide. In some embodiments, a silencing polynucleotide comprises a guide RNA (gRNA) comprising a gRNA sequence that recognizes a promoter of a gene encoding said valve enzyme. In some embodiments, a gRNA sequence differs between said first and second strains. In some embodiments, a promoter recognized by said gRNA differs between said first and second strains. In some embodiments, a first strain comprises said silencing polynucleotide and said degradation polynucleotide, and a second strain comprises said silencing polynucleotide but does not comprise said degradation polynucleotide. In some embodiments, a level of product is greater in said second strain than said first strain. In some embodiments, a level of product is greater in said first strain than said second strain. In some embodiments, a valve enzyme comprises an enzyme selected from the group consisting of enoyl-ACP/CoA reductase (fabI), glucose-6-phosphate dehydrogenase (zwf), lipoamide dehydrogenase (lpd), citrate synthase (gltA), soluble transhydrogenase (udhA), NADH-dependent glyceraldehyde-3-phosphate dehydrogenase (gapA), and a combination thereof. In some embodiments, a production enzyme comprises an enzyme selected from the group consisting of NADPH-dependent alanine dehydrogenase (ald), alanine exporter (alaE), NADPH-dependent glyceraldehyde-3-phosphate dehydrogenase (gapN), and a combination thereof.

In some embodiments, a product is selected from the group consisting of mevalonic acid, 3-hydroxypropionic acid, an amino acid, and a combination thereof. In some embodiments, the amino acid is alanine. In some embodiments, the alanine is L-alanine. In some embodiments, the alanine is D-alanine.

In some embodiments, a rate of production of the product during said stationary phase is reduced less in response to a change of an environmental condition as compared to a cell lacking said controlled reduction of expression of said valve enzyme.

In some embodiments, a change of an environmental condition comprises a change in a sugar concentration of a culture medium contacting said cell.

In some embodiments, a change of an environmental condition comprises a change in oxygenation of a culture medium contacting said cell.

In some cases, provided herein is a method of generating a cellular product comprising: culturing a heterologous cell in a culture medium, wherein said heterologous cell comprises: (i) an engineered valve polynucleotide for mediating controlled reduction of expression of a valve enzyme acting in a metabolic pathway, wherein said controlled reduction of expression of said valve enzyme reduces flux through said metabolic pathway, wherein said controlled reduction of expression of said valve enzyme induces a stationary phase of said cell; and (ii) an engineered production polynucleotide for mediating controlled increase in expression of a production enzyme for generation of said product; wherein a rate of production of said product during said stationary phase is reduced less in response to a change of an environmental condition as compared to a cell lacking said controlled reduction of expression of said valve enzyme. In some embodiments, the method further comprises changing said environmental condition. In some embodiments, the environmental condition comprises a sugar concentration of said culture medium, and changing said environmental condition comprises increasing or decreasing said sugar concentration. In some cases, said sugar is glucose, sucrose, lactose, maltose, xylose, mannitol, or a combination thereof. In some cases, said sugar is glucose. In some cases, the environmental condition comprises an oxygen concentration of said culture medium, and changing said environmental condition comprises increasing or decreasing said oxygen concentration. In some cases, said culturing is performed in a bioreactor.

In some cases, said culture medium has a volume of at least 100 ml, 200 ml, 300 ml, 400 ml, 500 ml, 600 ml, 700 ml, 800 ml, 900 ml, or at least 1000. In some cases, said culture medium has a volume of at least 1 L. In some case, said product comprises 3-hydroxypropionic acid. In some cases, said product comprises an amino acid. In some cases, said amino acid comprises alanine.

In some cases, a rate of production of said alanine is at least 0.1 g/L/hr, 0.2 g/L/hr, 0.3 g/L/hr, 0.4 g/L/hr, 0.5 g/L/hr, 0.6 g/L/hr, 0.7 g/L/hr, 0.8 g/L/hr, 0.9 g/L/hr, 1.0 g/L/hr, 1.1 g/L/hr, 1.2 g/L/hr, 1.3 g/L/hr, 1.4 g/L/hr, 1.5 g/L/hr, 1.6 g/L/hr, 1.7 g/L/hr, 1.8 g/L/hr, 1.9 g/L/hr, 2.0 g/L/hr, 2.5 g/L/hr, 3.0 g/L/hr, 3.5 g/L/hr, 4.0 g/L/hr, 4.5 g/L/hr, 5.0 g/L/hr, 5.5 g/L/hr, 6.0 g/L/hr, 7.0 g/L/hr, 8.0 g/L/hr, 9.0 g/L/hr, or at least 10 g/L/hr. In some cases, said production polynucleotide encodes an alanine exporter. In some cases, said alanine exporter is alaE. In some cases, said culturing occurs for less than 20 hours, 30 hours, 40 hours, 50 hours, 60 hours, 70 hours, 80 hours, 90 hours, or less than 100 hours. In some cases, said culturing occurs for less than 10 hours, 15 hours, 20 hours, 25 hours, 30 hours, 35 hours, 40 hours, or less than 45 hours. In some cases, said culturing occurs for less than 30 hours.

In some cases, said product comprises mevalonic acid. In some cases, a rate of production of said mevalonic acid is at least 0.1 g/L/hr, 0.2 g/L/hr, 0.3 g/L/hr, 0.4 g/L/hr, 0.5 g/L/hr, 0.6 g/L/hr, 0.7 g/L/hr, 0.8 g/L/hr, 0.9 g/L/hr, 1.0 g/L/hr, 1.1 g/L/hr, 1.2 g/L/hr, 1.3 g/L/hr, 1.4 g/L/hr, 1.5 g/L/hr, 1.6 g/L/hr, 1.7 g/L/hr, 1.8 g/L/hr, 1.9 g/L/hr, 2.0 g/L/hr, 2.5 g/L/hr, 3.0 g/L/hr, 3.5 g/L/hr, 4.0 g/L/hr, 4.5 g/L/hr, 5.0 g/L/hr, 5.5 g/L/hr, 6.0 g/L/hr, 7.0 g/L/hr, 8.0 g/L/hr, 9.0 g/L/hr, or at least 10 g/L/hr. In some cases, said culturing occurs for less than 20 hours, 30 hours, 40 hours, 50 hours, 60 hours, 70 hours, 80 hours, 90 hours, or less than 100 hours. In some cases, said culturing occurs for less than 80 hours.

In some embodiments, a valve polynucleotide comprises a polynucleotide selected from the group consisting of: a silencing polynucleotide for repressing transcription of a gene encoding said valve enzyme; a degradation polynucleotide for mediating cellular degradation of said valve enzyme; and a combination thereof. In some cases, a valve polynucleotide comprises a silencing polynucleotide, and said silencing polynucleotide comprises a guide RNA (gRNA) comprising a gRNA sequence that recognizes a promoter of a gene encoding said valve enzyme. In some cases, a valve polynucleotide further encodes a CRISPR enzyme, wherein said CRISPR enzyme specifically binds to said promoter sequence when bound to said gRNA. In some cases, a CRISPR enzyme is catalytically inactive. In some case, a valve polynucleotide comprises a degradation polynucleotide, wherein said degradation polynucleotide comprises a sequence encoding a degradation tag, wherein said degradation tag mediates degradation of said valve enzyme. In some cases, an expression of said valve polynucleotide is regulated by phosphate. In some cases, an expression of said production polynucleotide is regulated by phosphate. In some cases, said cell is an E. coli cell.

Optimization of Bio-Production

Biotechnology based fermentation processes have been successfully developed to produce everything from biologics and small molecule therapeutics to specialty, bulk and commodity chemicals, and even next generation biofuels[1-3]. These processes have made rapid advancements in recent years due to numerous technology developments[4,5]. It has never been easier to produce new molecules using synthetic biology. Despite these advances, a major challenge remains in taking molecules from proof of concept (POC) to commercially meaningful levels. Strain optimization, or overcoming the "mg" to "kg" hurdle has remained a key barrier to the successful commercialization of bio-processes. After the demonstration of POC, successful bio-process development routinely requires lengthy iterations of both microbial strain and fermentation optimization[6-8] (FIG. 1B). These optimization efforts are often specific to the product or host strain of interest. The throughput of synthetic biology has outpaced that of metabolic engineering, partly due to a lack of broadly useful tools to perform meaningful and standardized optimization of engineered microbial strains in a high-throughput manner[9].

There are numerous challenges in strain optimization and moving past POC levels, not the least of which are the size and complexity of the potential design space. In contrast to simpler gene circuits, amenable to electrical circuit models[10-12], metabolic networks are highly interconnected. Each metabolite and/or enzyme can interact with endless others. This combinatorial complexity results in a huge potential design space, which is intractable to the kinds of systematic experimentation required for the development of standardized design principles (Supplemental Materials, Table 1). The challenges in addressing such a large design space have persisted despite the dramatic advances in, and decreased costs of, reading and writing DNA that have led to new high-throughput DNA assembly and microbial strain construction methods[3-16]. It is not surprising that new synthetic biology technologies involving strain engineering are often demonstrated with easily screened or selected phenotypes[13, 17-19]. Most of these are limited to a focus on optimizing a limited set of pathway specific enzymes.

One approach to overcome the complexity of this challenge is the use of in vitro systems for bio-production, which comprise a limited set of metabolic enzymes. However, these approaches have challenges in replicating key advantages of in vivo systems, including cofactor recycling and energy generation[20, 21]. Another approach to deal with this complexity is to develop faster screening methods for strain evaluation[22]. However, increased throughput alone can never evaluate the full complexity of the potential design space. In addition, results obtained from high-throughput studies often do not translate, even in the same microbe, to a different environment[20, 23, 24]. Small scale screens do not readily translate to larger scale production processes, leading to iterations of process optimization on top of strain optimization (FIG. 1B). This is because metabolism is highly regulated and can respond, sometimes dramatically, to changes in environmental conditions[25 20, 26-28]. A lack of environmental robustness is traditionally one factor making the scale up of fermentation based processes difficult. This issue has led to the development of specialized complex micro-reactor systems for scale down offering only modest improvements in throughput[20, 29-31].

There remains a significant need for broadly applicable, rapid and robust approaches to greatly reduce the time and costs transitioning from "mgs" to "kgs". Ideally, approaches should be amenable to multiple products and production hosts. Provided herein is the development of a generalizable, high-throughput strain optimization approach that enables the use of truly scalable, standardized fermentation processes. This approach, as outlined in FIG. 1B, panel b, involves the dynamic minimization of the active metabolic network[32], which combines the benefits of a smaller design space common to in vitro approaches while maintaining the benefits of in vivo biosynthesis[20]. We can isolate and focus on the minimal metabolic networks required for production. Utilizing combinations of synthetic metabolic valves (SMVs)[32, 33] (FIGS. 2A-D) we can dynamically minimize the metabolic network and redirect metabolic flux in the context of a standardized 2-stage fermentation process[20].

This approach can reduce the complexity of the problem and the size of the relevant design space, greatly speeding up optimization. In various embodiments, it is demonstrated herein that dynamic metabolic network minimization can improve pathway fluxes beyond those achievable with production pathway modifications alone (FIGS. 3A-K and 6A-H). Simultaneously, we demonstrate that dynamic network minimization reduces metabolic responses to environmental conditions, which increases the robustness and scalability of engineered strains (FIGS. 3A-K and 5A-J).

EXAMPLES

2-Stage Synthetic Metabolic Valves in *E. coli*

We first developed improved synthetic metabolic valves (SMVs) in *E. coli* that are capable of the dynamic reduction of protein levels in a 2-stage process. These SMVs can be used to reduce levels of key metabolic enzymes (or reduce enzymatic activities of key metabolic enzymes) and rely on controlled proteolysis or CRISPR-based gene silencing or both proteolysis and silencing in combination (FIGS. 2A-D)[32-35]. Cell growth and dynamic metabolic control can be implemented using phosphate depletion as an environmental trigger. Phosphate can be an ideal candidate as a trigger, as one of the costliest components of minimal media. In addition, stationary phases induced in *E. coli* by phosphate depletion have retained glycolytic uptake as well as increased protein expression[31, 36] Numerous promoter systems responding to phosphate are well characterized in *E. coli* as well as other microbes including *S. cerevisiae*[37]. Phosphate responsive promoter variants were evaluated (Supplemental Materials, Section 1) and subsequently used for 2-stage control.

Figure 2A:
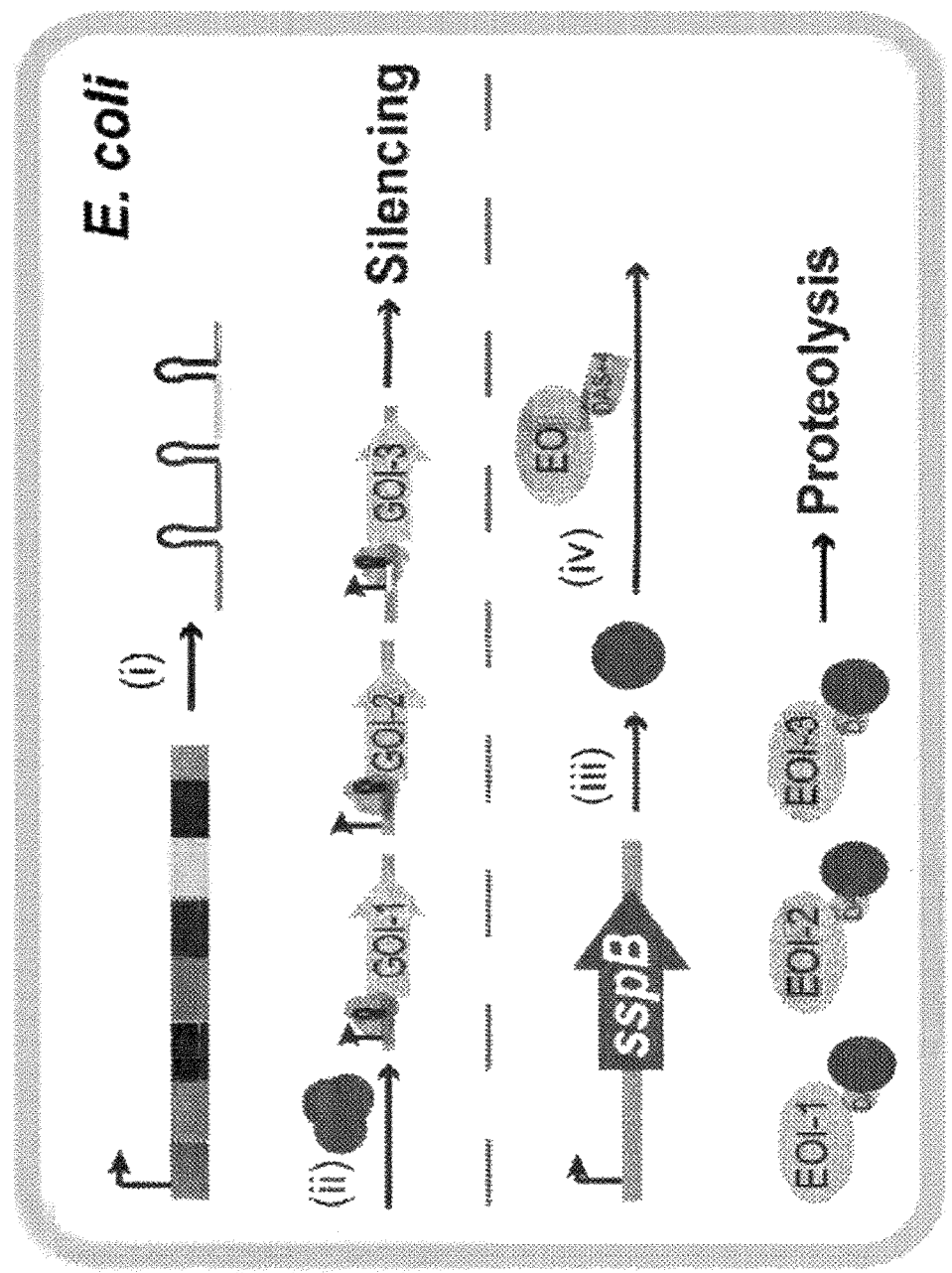
FIGS. 2A-D depict an example of implementation of 2-stage Synthetic Metabolic Valves (SMVs) in E. coli.

SMVs were implemented in *E. coli* using the native Type I-E Cascade CRISPR system for induced gene silencing[34,38], while controlled proteolysis was induced by incorporating C-terminal degron tags on target proteins, both as previously demonstrated[63,33] (FIG. 2A). These systems were introduced into a host strain initially engineered for minimal byproduct formation and high biomass yields and growth rates (*E. coli* strain DLF_0025, Supplemental Materials, Section 3)[24, 27, 28,39]. Using this approach, as FIGS. 2A-D demonstrate, protein levels can be controlled in 2-stage processes, as exemplified by turning "ON" GFPuv and "OFF" mCherry fluorescent proteins with phosphate depletion in minimal medium. The combination of gene silencing with proteolysis results in the largest rates of protein degradation (FIGS. 2C-D). The specific impact of gene silencing and proteolysis on decay rates will likely vary depending on the host, target gene/enzyme, and its specific natural turnover rates and expression levels[40,41].

Metabolic Network Minimization Leads to Improved Fluxes

Figure 3A:
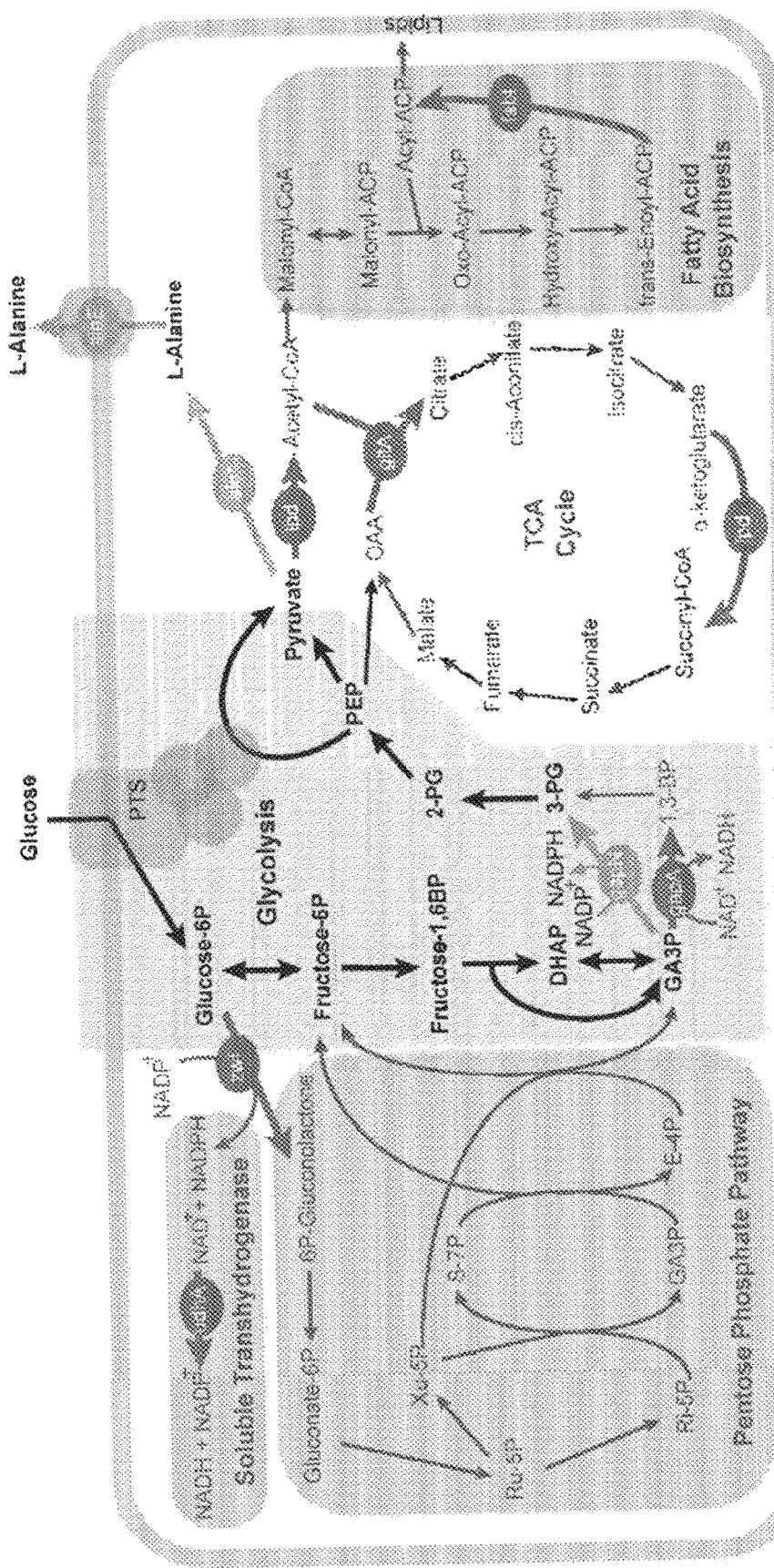
FIGS. 3A-K depict an example of alanine production in E. coli utilizing 2-stage dynamic control.
Figure 3B:
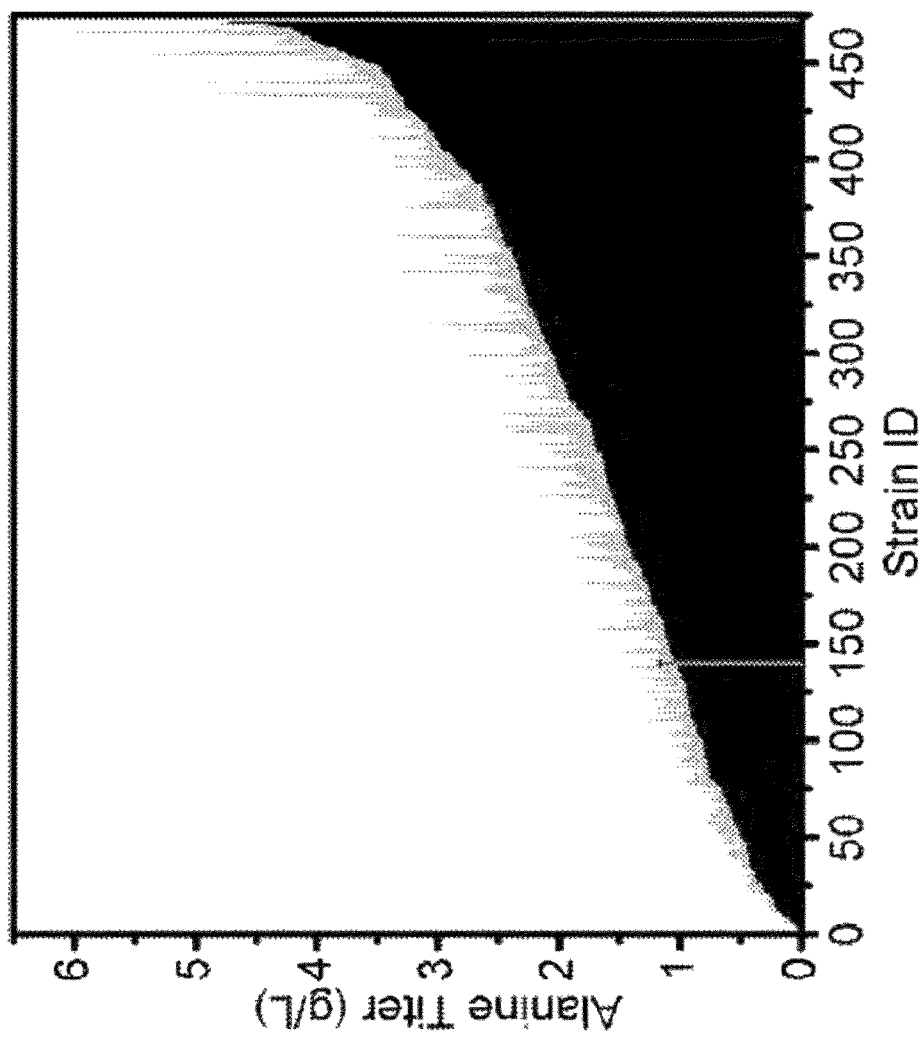
Figure 3C:
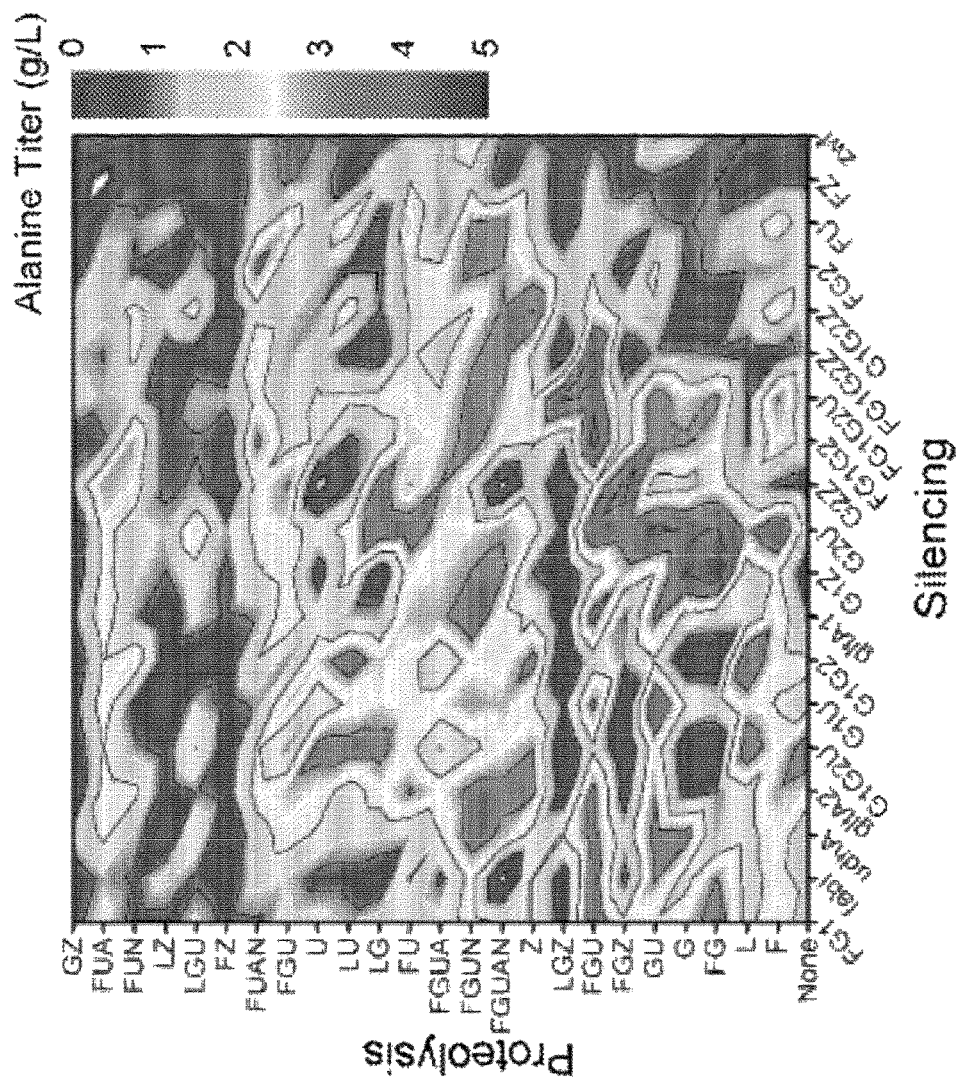
Figure 3D:
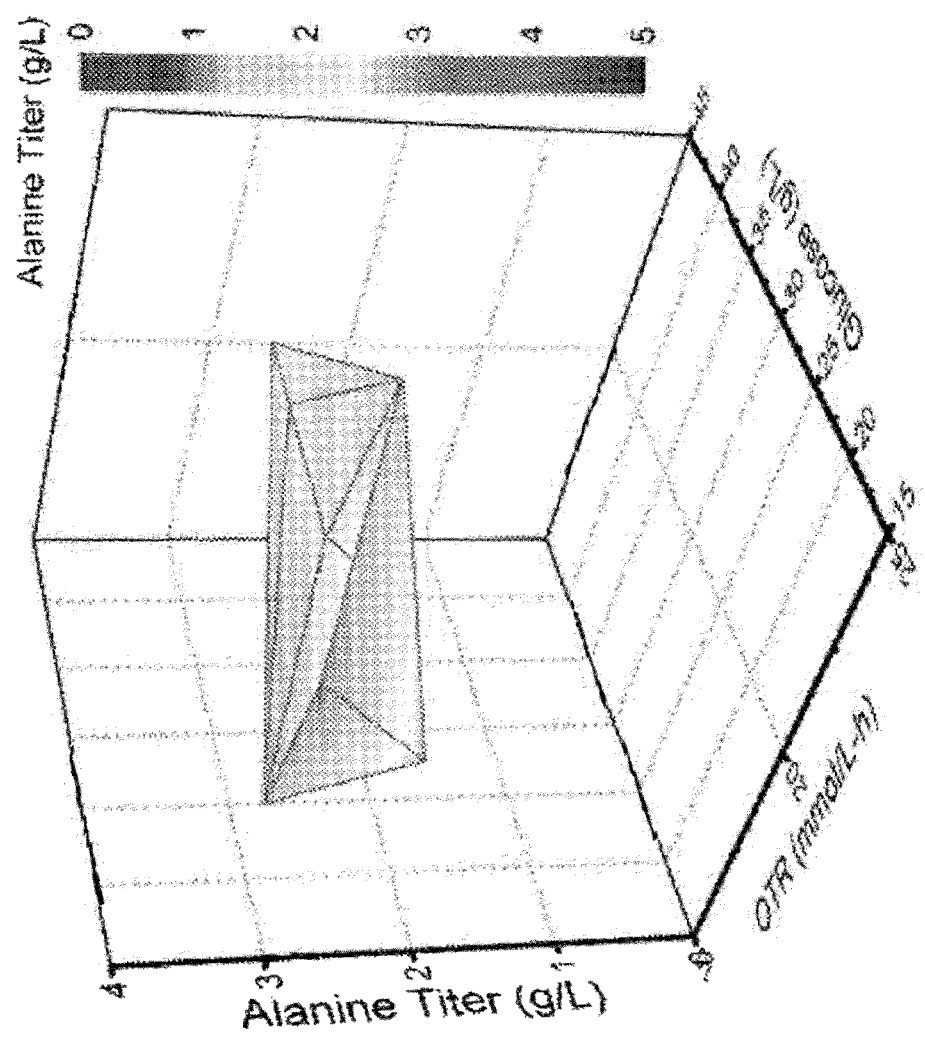

With the successful demonstration of dynamic control of protein levels in a 2-stage process, we turned to investigate the dynamic control of metabolic fluxes in *E. coli* through controlled reduction of key central metabolic enzymes alone and in combination. Reducing fluxes through thermodynamically favored "committed" reactions in the network is expected to lead to increases in network metabolite pools (Supplemental Materials Section 5), and as a result, changes in pathway fluxes. Enzymes in key committed steps in central metabolic pathways were identified and chosen as initial SMV targets and alanine was chosen as an initial test product (FIGS. 3A-K). A set of strains were constructed for alanine production (FIG. 3A), comprising an NADPH-dependent alanine dehydrogenase (ald*)[42]. Variants with multiple combinations of SMVs in central metabolic enzymes were made, with either modifications to induce proteolysis or gene silencing or both in combination. (Supplemental Materials, Section 3). Together the set of strains having SMVs evaluated in 2-stage processes are identified as "Valve" strains. A panel of alanine "Valve" strains (~500 strains in total) were evaluated for alanine production in standardized, 2-stage, 96-well plate based micro-fermentations (Supplemental Materials, Section 7). Alanine titers after 24 hours of production are given in FIGS. 3B-C. Briefly, alanine titers after 24 hours ranged from ~0 g/L to ~4.7 g/L, and as expected, varied significantly with respect to the number and combination of SMVs; most SMV combinations lead to improved performance when compared to the control with no SMVs and the alanine pathway alone. In some cases, the alanine titers after 24 hours can be from 0 to 0.5 g/L, 0.5 g/L to 1 g/L, 1 g/L to 1.5 g/L, 1.5 g/L to 2 g/L, 2 g/L to 2.5 g/L, 2.5 g/L to 3 g/L, 3 g/L to 3.5 g/L, 3.5 g/L to 4 g/L, 4 g/L to 4.5 g/L, 4.5 g/L to 5 g/L, or from 5 g/L to 10 g/L. The dynamic range of alanine production offered by SMVs can be up to a 4-fold increase compared to that offered by solely altering the expression level of the production pathway enzymes (by changing the promoter) (Supplemental Materials, Section 7). In some cases, the dynamic range of alanine production offered by SMVs can be up to a 2-fold, 3-fold, 4-fold, 5-fold, 6-fold, 7-fold, 8-fold, 9-fold, or 10-fold increase compared to that offered by solely altering the expression level of the production pathway enzymes. Importantly, the use of proteolysis or silencing alone and/or in combination had significant impacts on production, indicating that for each enzyme the fine tuning of activity using SMVs is critical. One of the best performing strains from the micro-fermentations was then evaluated in a minimal medium, 2-stage, 1 L fermentation with 10 gdcw/L of biomass (FIG. 3F), which resulted in 80 g/L 100% L-alanine after 48 hours of production with a yield of 0.8 g/g. Further engineering of this strain by overexpressing an alanine exporter (encoded by the E. coli alaE gene[43]) resulted in 147 g/L 100% L-alanine after 27 hours of production with a yield within error of theoretical yield ~1 g/g, (FIG. 3G).

Micro-Fermentation Robustness

A central hypothesis was that by restricting metabolism in the production stage, strain performance could not only be improved, but would be more robust to environmental (process) conditions. Simply put, carbon flow is restricted through a minimized metabolic network, which can no longer adapt via cellular responses to the environment. To test this hypothesis, strains were evaluated under different "micro-fermentation" process conditions. Glucose concentration and oxygen transfer rate (key process variables impacting strain performance in traditional fermentations[26]) were varied (FIG. 3D, Supplemental Materials, Section 8), and alanine production measured. A robustness score (RS) was developed to quantify environmental robustness. Larger RS scores indicate more robust strains. Whereas relative standard deviation (RSD) is one metric for robustness, we wanted to incorporate a stricter measure of robustness which also incorporates the maximal deviation (Max Dev) a strain has under all process conditions (RS, Equation (1)).

$$RS = 100 - \frac{\text{average } (RSD) + \max(Dev)}{2} * 100 \quad \text{Equation (1)}$$

Figure 3E:
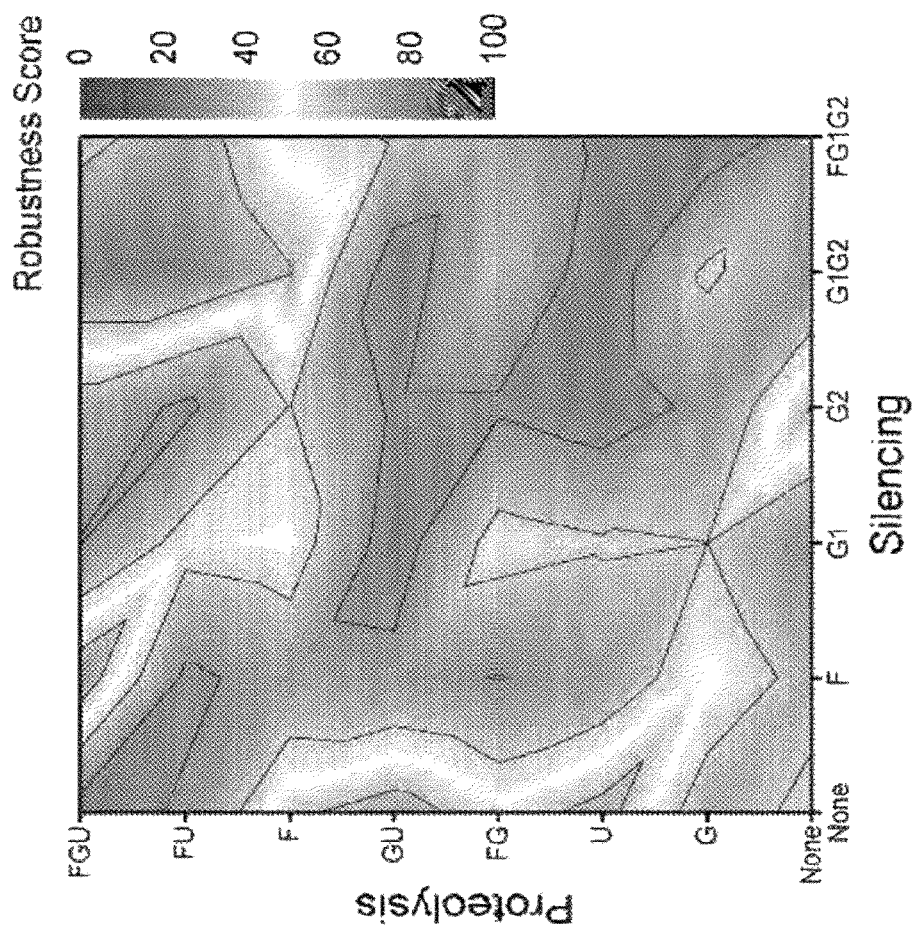
Figure 3G:
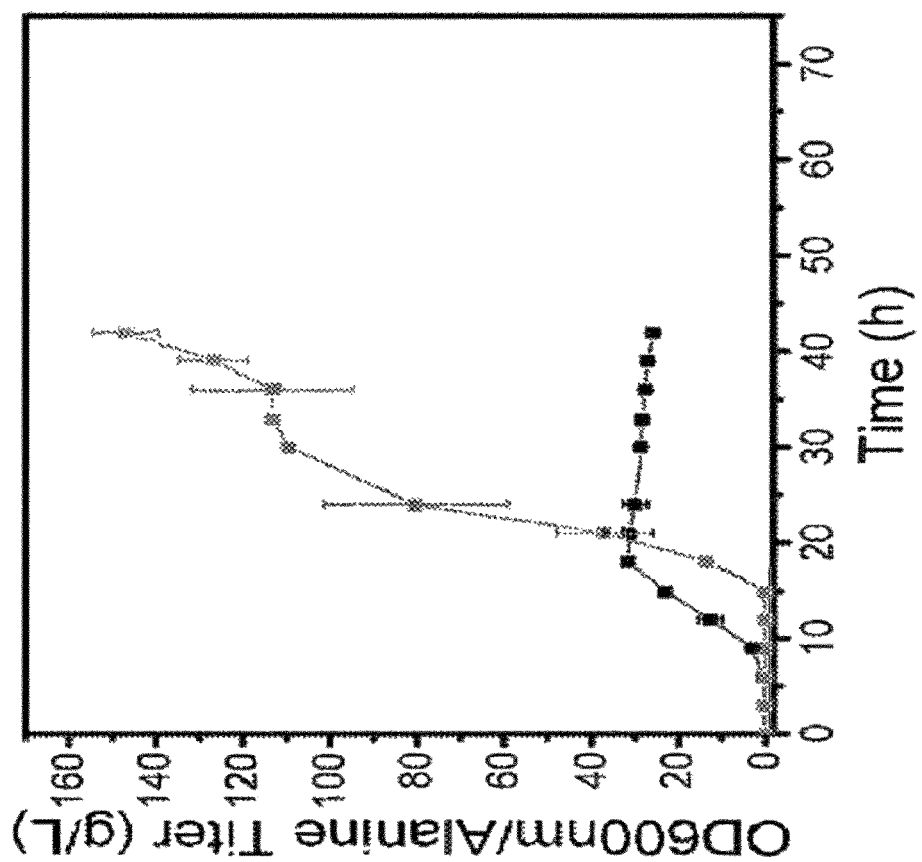

Robustness scores for a subset of 48 alanine "Valve" strains are given in FIG. 3E. Results from these experiments studies are tabulated in Supplemental Materials, Section 8. A $Chi^2$ analysis using a cutoff of RS>0.6 for robustness was used to identify key SMVs which statistically contribute to process robustness. The proteolytic degradation of fabI was a primary contributor to robustness ($Chi^2$=13.85, $P_{value}$<0.001) and as a result, "Valve" strains with proteolytic degradation of fabI were used in further studies. In addition, the "Valve" strains with proteolytic degradation of gltA and/or the combination of the proteolytic degradation of fabI and gltA were found to also be significant contributors of robustness, albeit with a large $P_{value}$.

2-Stage "Valve" Strains Compared to Traditional Growth Associated Strains

To compare the 2-stage approach enabled by SMVs to more traditional growth associated processes, we constructed 5 strains, with constitutively expressed alanine dehydrogenase (ald*), capable of the growth associated production of alanine. These growth associated strains varied in the strength of the promoter used to drive ald* expression[44] (Supplemental Materials, Section 2), yet utilized the same common no-valve control host strain. FIG. 5 illustrates the results of a direct comparison of "Valve" strains in a 2-stage process compared to "Growth Associated (GA)" strains in a traditional fermentation at the microtiter (FIGS. 5A-D) and 1 L (FIGS. 5E-J) scales. In micro-fermentations, 2-stage "Valve" strains outperformed GA strains with respect to titer and process robustness. The most robust GA strain from the micro-fermentation analysis (also with the highest production level) was compared to a robust "Valve" strain in 1 L fermentations with varied process conditions. The "Valve" strains showed consistent performance in all process conditions evaluated (FIG. 5E), consistent with results from micro-fermentations, where the GA strain had significant performance variability dependent on process. We hypothesized that the increased environmental robustness observed in both "micro-" and 1 L scale fermentations for "Valve" strains would lead to predictable scale up, where strains with improved performance in high-throughput micro-fermentations would reliably have improved performance in controlled bioreactors. To evaluate the scalability of the system, "Valve" alanine strains with statistically differentiated performance in micro-fermentations (P-value <0.001) were evaluated in standardized 2-stage 1 L fermentations and compared to all GA strains. Statistically different performances observed in "micro-fermentations" have scaled predictably to 1 L fermentations for 2-stage "Valve" strains. This contrasts with results obtained with GA strains where no correlation between micro-fermentation and 1 L performance was observed (FIGS. 5G-H).

Product Flexibility

Figure 6A:
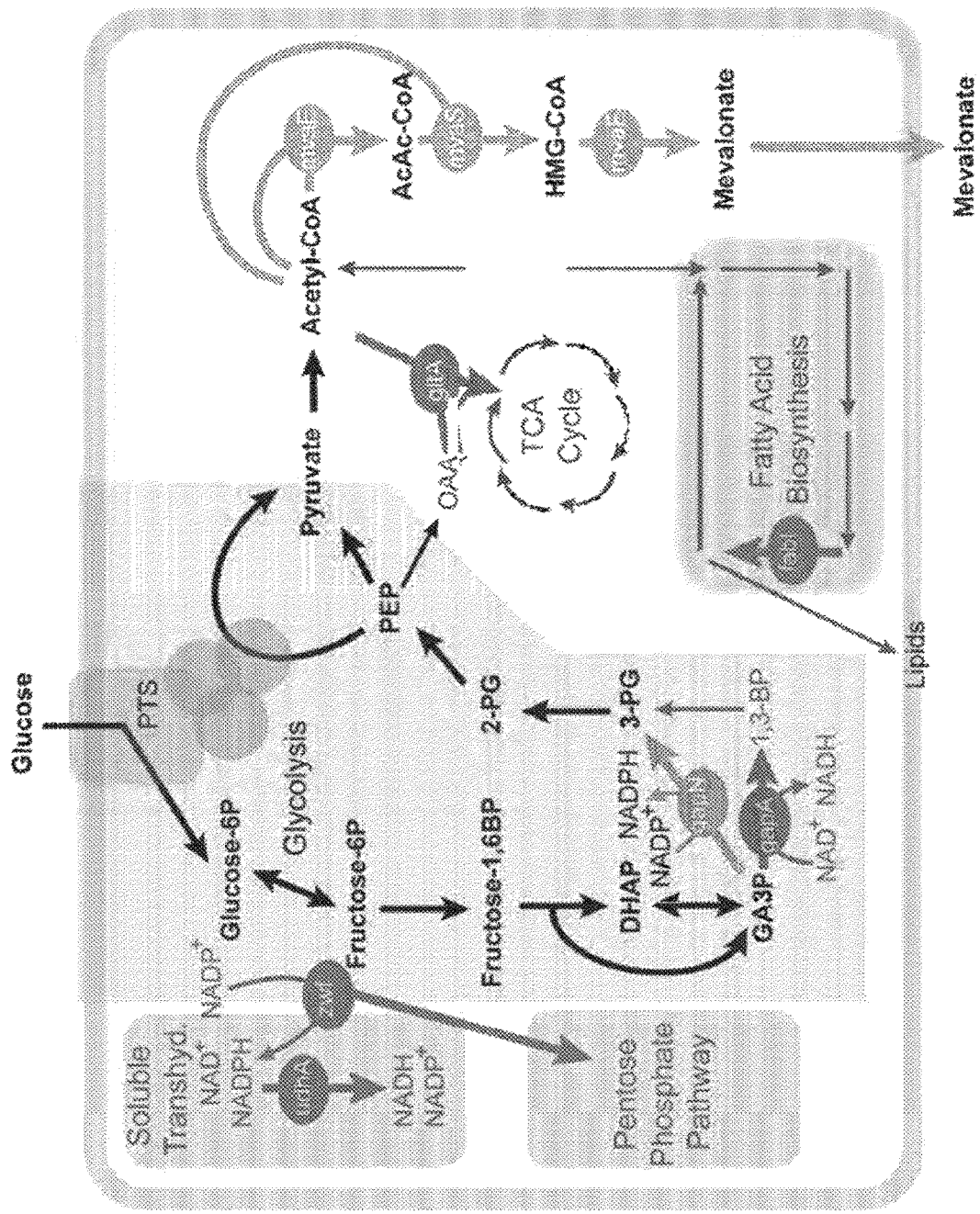

With the successful and predictable scale-up of alanine strains into 1 L fully instrumented fermentations, we moved to validate the technology platform for an additional product: mevalonic acid. To this end, additional dynamic production pathways were constructed for mevalonic acid biosynthesis (FIG. 6A). A set of two-gene production pathway plasmids encoding three enzymatic functions was constructed for mevalonic acid production, consisting of the E. faecalis mvaE and mvaS genes encoding a bifunctional acetyl-CoA acetyltransferase, NADPH dependent HMG-CoA reductase, and HMG-CoA synthase respectively. A mutant mvaS gene, mvaS(A110G) with higher activity was used[45, 46]. Production plasmids were initially evaluated for mevalonate production in the control strain (FIG. 6B). The best producing plasmid was then introduced into a variety of engineered "Valve" strains and evaluated in micro-fermentations (FIG. 6C). A subset of statistically differentiated strains were then evaluated in 1 L fermentations to assess scalability (FIG. 6D), which, as in the case of alanine, was predictive. In some cases, a performing strain produced meaningful titers and yields, 97 g/L in 78 hrs of production with a yield of 0.46 g/g (84% of theoretical yield) (FIG. 6E). Specific productivity for this mevalonate strain is over 4-fold higher than the best previously reported results 4 (Supplemental Materials, Section 9).

Discussion

Historically some of the most successful efforts to metabolically engineer the production of small molecules have leveraged the power of anaerobic metabolism to couple product formation with growth. This has allowed for the classical design and selection of industrial strains to produce many products including ethanol, succinic acid, lactate and isobutanol, which have leveraged the power of evolution and selection to reach optimal metabolic fluxes in engineered networks[48, 49]. While growth associated production is not strictly linked to anaerobic metabolism, growth association greatly limits the number and variety of different molecules that can be made using synthetic biology. A generic, robust and accessible non-growth associated platform would greatly simplify the optimization and scale up of a diverse number of products.

In contrast to most existing 2-stage processes, which have relied on natural metabolic responses to environmental triggers for production improvement, we have taken the next step in actively minimizing the essential metabolic network and redirecting metabolites to products of interest. Many of the targeted essential central metabolic pathways in this work have traditionally been off limits to engineering strategies, as deleting essential enzymes is incompatible with growth and growth associated production in traditional fermentation. The dynamically minimized metabolic network also results in enhanced robustness to environmental variables enabling the faithful translation of high-throughput small-scale studies to larger instrumented fermentations. A current paradigm in the field is to improve the throughput of relevant strain evaluations by developing small-scale, custom-designed micro-reactors for enhanced process control. In contrast, our approach is a move in a new direction involving engineering microbial metabolism to be less sensitive to process changes, simplifying high-throughput experimentation.

Beyond robustness, we have demonstrated that combinatorial modifications to essential enzymes in minimal metabolic networks can lead to significant improvements in production, particularly when compared to altering production pathway expression levels alone. These large variations in performance are due to changes in a limited subset of key central metabolic nodes, likely resulting in altered metabolite levels. Compared to previous approaches to dynamically control enzyme levels, we demonstrate improved potential for fine tuning of protein levels with a combination of gene silencing and proteolysis[50]. As stationary phase cells cannot dilute existing proteins with cell division, this dual approach makes sense. The specific control of the level of any given enzyme will of course also depend on natural turnover mechanisms. At first glance, it may still be surprising that the combination of both gene silencing and proteolysis together does not always result in improved performance, i.e. "more is not always better". Future efforts may be needed to explain these results, which could either be due to a requirement of maintaining minimal fluxes in the larger network or a consequence of changes in the levels of key regulatory metabolites that are not part of the minimal network, yet influence network activity.

While the approach as demonstrated can address many issues common to most bio-production processes, many product specific challenges remain. The toxicity of a product or pathway metabolite may limit titers or production rates. A minimal network that may be optimal at a low titer, may not be optimal at elevated titers. In addition, the engineering of improved enzymes is often a challenge in many "mg" to "kg" projects.

Feasibility of adapting this approach to other microbial hosts is expected. Key requirements for new hosts include a rapid and robust growth phase, the ability to engineer dynamic control over protein levels, and a metabolically active stationary phase. Numerous microbes have well characterized nutrient triggers for productive stationary phase metabolism[36], for example nitrogen limitation in *Ralstonia* species, *Yarrowia* species and others[51 52]. Even when these requirements are not naturally met, they can be engineered into the host such as *S. cerevisiae* or other microbes, with each potential host presenting unique challenges and corresponding solutions.

Future efforts can be aimed at applying this platform for molecules with more complex production pathways. This approach can offer a tractable route for rapid optimization to metabolic engineers and synthetic biologists, who wish to move past POC levels and begin to tackle problems at more industrially relevant rates, titers and yields.

Methods

Reagents and Media

Unless otherwise stated, all materials and reagents were of the highest grade possible and purchased from Sigma (St. Louis, MO). C13 labeled Alanine (2,3-13C2, 99%) (Item #CLM-2734-PK) was purchased from Cambridge Isotope Laboratories, Inc. (Tewksbury, MA). Luria Broth was used for routine strain and plasmid propagation and construction. Working antibiotic concentrations were as follows: ampicillin (100 µg/mL), kanamycin (35 µg/mL), chloramphenicol (35 µg/mL), spectinomycin (100 µg/mL), zeocin (50 µg/mL), gentamicin (10 µg/mL), blasticidin (100 µg/mL), puromycin (150 µg/mL), tetracycline (5 µg/mL). Luria broth with low salt (Lennox formulation) was used to select for zeocin, blasticidin and puromycin resistant clones. In addition, for puromycin selection, phosphate buffer (pH=8.0) was added to LB Lennox to a final concentration of 50 mM. Media formulations including stock solutions are described in Supplemental Materials, Section 7.

*E. coli* Strain Construction

Oligonucleotides and synthetic linear DNA (Gblocks™) used for strain construction and confirmation are all given in Supplemental Materials, Section 3, and they were obtained from Integrated DNA Technologies (IDT, Coralville, IA). Strain BW25113 was obtained from the Yale Genetic Stock Center (CGSC http://cgsc.biology.yale.edu/). Strain BWapldf was a kind gift from George Chen (Tsinghua University)[62]. Chromosomal modifications were made using standard recombineering methodologies[63] either with direct antibiotic cassette integration in the case of C-terminal DAS+4 tags carrying antibiotic resistance cassettes, or through scarless tet-sacB selection and counterselection, strictly following the protocols of Li et al[64]. The recombineering plasmid pSIM5 and the tet-sacB selection/counterselection marker cassette were kind gifts from Donald Court (NCI, https://redrecombineering.ncifcrf.gov/court-lab.html). Briefly, the tet-sacB selection/counterselection cassette was amplified using the appropriate oligos supplying ~50 bp flanking homology sequences using Econotaq (Lucigen Middleton, WI) according to manufacturer's instructions, with an initial 10 minutes denaturation at 94° C., followed by 35 cycles of 94° C., for 15 seconds, 52° C. for 15 seconds, and 72° C. for 5 minutes. Cassettes used for "curing" of the tet-sacB cassette or direct integration (when an antibiotic marker is present) were obtained as gBlocks from IDT. In the case of the sspB gene deletion, the open reading frame deletion replaced with a kanamycin resistance was amplified from the Keio Collection strain, JW3197-1[65], and moved to the appropriate background strain using standard methodologies. The kanamycin resistance cassette was cured using the pCP20 plasmid, leaving an frt scar[63, 65]. Chromosomal modifications were confirmed by PCR amplification and sequencing (Eton Biosciences) using paired oligonucleotides, either flanking the entire region, or in the case of DAS+4 tag insertions an oligo 5' of the insertion and one internal to the resistance cassette.

E. coli Plasmid Construction

Primers used for the design and construction of CAS-CADE guides arrays were listed in Supplemental Materials, Section 6. Gene silencing guide arrays were expressed from a series of pCASCADE plasmids. The pCASCADE-control plasmid was prepared by swapping the pTet promoter in pcrRNA.Tet[73] with an insulated low phosphate induced ugpB promoter 74. Promoter sequences for all genes were obtained from EcoCyc database (https://ecocyc.org/). In order to design CASCADE guide array, CASCADE PAM sites near the −35 or −10 box of the promoter of interest were identified, 30 bp at the 3' end of PAM site was selected as the guide sequence and cloned into pCASCADE plasmid using Q5 site-directed mutagenesis (NEB, MA) following manufacturer's protocol, with the modification that 5% v/v DMSO was added to the Q5 PCR reaction. PCR cycles were as follows: amplification involved an initial denaturation step at 98° C. for 30 second followed by cycling at 98° C. for 10 second, 72° C. for 30 second, and 72° C. for 1.5 min (the extension rate was 30 second/kb) for 25 cycles, then a final extension for 2 min at 72° C. 2 µL of PCR mixture was used for 10 µL KLD reaction, which proceeded under room temperature for 1 hour, after which, 1 µL KLD mixture was used for electroporation.

The pCASCADE guide array plasmids were prepared by sequentially amplifying complementary halves of each smaller guide plasmid by PCR, followed by subsequent DNA assembly. The pCASCADE-control vector was used as template. pCASCADE plasmids with arrays of two or more guides were prepared using Q5 High-Fidelity 2x Master Mix (NEB, MA). PCR cycles were as follows: amplification involved an initial denaturation step at 98° C. for 30 second followed by cycling at 98° C. for 10 second, 66° C. for 30 second, and 72° C. for 45 second (the extension rate was 30 second/kb) for 35 cycles, then a final extension for 2 min at 72° C. PCR product was purified by gel-extraction, 20 µL ultrapure water was used to elute 50 µL PCR reaction purification. 1 µL of each eluted PCR product was used for 10 µL of Gibson Assembly (NEB, MA), which was completed by incubation at 50° C. for 15 min. 1 µL Gibson Assembly mix was used for electroporation.

Production pathways enzymes were expressed from high copy plasmids via low phosphate inducible promoters. Production pathway gene sequences were codon optimized using the Codon Optimization Tool from the IDT website, phosphorylated G-blocks™ were designed and purchased from IDT for each pathway. Plasmids were assembled using NEBuilder® HiFi DNA Assembly Master Mix following manufacturer's protocol (NEB, MA). pSMART-HC-Kan (Lucigen, WI) was used as backbone for all pathway plasmids. All plasmid sequences were confirmed by DNA sequencing (Eton Bioscience, NC) and deposited with Addgene.

E. coli BioLector

Single colonies of each strain were inoculated into 5 mL LB with appropriate antibiotics and cultured at 37° C., 220 rpm for 9 hours or until OD600 reached >2. 500 µL of the culture was inoculated into 10 mL SM10 medium with appropriate antibiotics, and cultured in a square shake flask (CAT #: 25-212, Genesee Scientific, Inc. San Diego, CA) at 37° C., 220 rpm for 16 hours. Cells were pelleted by centrifugation and the culture density was normalized to OD600=5 using FGM3 media. Growth and fluorescence measurements were obtained in a Biolector (m2p labs, Baesweiler, Germany) using a high mass transfer FlowerPlate (CAT #: MTP-48-B, m2p-labs, Germany). 40 µL of the OD normalized culture was inoculated into 760 µL of FGM3 medium with appropriate antibiotics. Biolector settings were as follows: RFP gain=100, GFP gain=20, Biomass gain=20, shaking speed=1300 rpm, temperature=37° C., humidity=85%. Every strain was analyzed in triplicate.

E. coli Micro-Fermentations

Plasmids were transformed into host strains by electroporation using ECM 630 High Throughput Electroporation System (Harvard Apparatus, Inc. Holliston, MA) following manufacturer's protocol or using individual electroporation cuvettes. Glycerol stocks were prepared for each transformation plate by adding equal volume of sterile 20% glycerol, and 3 µL were used to inoculate overnight culture in 150 µL SM10++ medium with appropriate antibiotics. Plates were covered with sandwich covers (Model #CR1596 obtained from EnzyScreen, Haarlam, The Netherlands). These covers ensured minimal evaporative loss during incubation. Unless otherwise stated, 96 well plates were cultured at 37° C., 400 rpm for 16 hours, shaker orbit is 25 mm. This combination of orbit and minimal shaking speed is required to obtain needed mass transfer coefficient and enable adequate culture oxygenation.

After 16 hours of growth, cells were pelleted by centrifugation, excess media was removed and cells were resuspended in 150 µL of FGM3 Wash solution. Subsequently cells were once again pelleted and again excess media was removed, pellet was resuspended in 50 µL FGM3 No Phosphate media containing appropriate antibiotics. 5 µL of the resuspended culture was added to 195 µL of water for OD600 measurement using standard flat bottom 96 well plate. OD600 for production was normalized to OD600=1, using FGM3 No Phosphate media containing appropriate antibiotics, in a total volume of 150 µL using standard 96 well plate. Plates were covered with sandwich covers (Model #CR1596 obtained from EnzyScreen, Haarlam, The Netherlands) and 96 well plate cultures were incubated at 37° C., 400 rpm for 24 hours. After 24 hours of production, all samples from each well were pelleted by centrifugation and the supernatant collected for subsequent analytical measurement. Triplicate micro-fermentations were performed for each strain.

For growth associated alanine micro-fermentations, glycerol stock preparation and 16 hour overnight culture in SM10++ proceeded as described above. After 16 hours of growth in SM10++ medium, 5 µL of overnight culture was inoculated into 150 µL FGM3 with 40 mM phosphate containing appropriate antibiotic. Plates were covered with sandwich covers (Model #CR1596 obtained from Enzy-Screen, Haarlam, The Netherlands) and 96 well plate cultures were incubated at 37° C., 400 rpm for 24 hours. After 24 hours of production, OD600 was recorded, all samples from each well were then pelleted by centrifugation and the supernatant collected for subsequent analytical measurement. Triplicate micro-fermentations were performed for each strain.

Micro-fermentation robustness evaluations were conducted as described in Supplemental Materials, Section 8.

1 L Fermentation Seeds

Single colony from transformation plate was inoculated into 5 mL LB with appropriate antibiotics and cultured at 37° C., 220 rpm for 16 hours. 500 µL of the LB culture was inoculated into 50 mL SM10 media with appropriate antibiotics in square shake flask (CAT #: 25-214, Genesee Scientific, Inc. San Diego, CA), the culture was incubated at 37° C. with a shaking speed of 220 rpm for 24 hours, at which time OD600 is usually between 3 and 10, the culture was harvested by centrifugation at 4000 rpm for 15 min, supernatant was discarded and cell culture was normalized to OD600=10 using SM10 media. For 1 L fermentation seed, 6 mL of normalized OD600=10 culture was added to 1.5 mL of 50% glycerol in cryovials, and stored at −80° C.

1 L Fermentations

An Infors-HT Multifors (Laurel, MD, USA) parallel bioreactor system was used to perform 1 L fermentations, including three gas connection mass flow controllers configured for air, oxygen and nitrogen gases. Vessels used had a total volume of 1400 mL and a working volume of up to 1 L. Online pH and pO2 monitoring and control were accomplished with Hamilton probes. Offgas analysis was accomplished with a multiplexed Blue-in-One BlueSens gas analyzer (BlueSens. Northbrook, IL, USA). Culture densities were continually monitored using Optek 225 mm OD probes, (Optek, Germantown, WI, USA). The system used was running IrisV6.0 command and control software and integrated with a Seg-flow automated sampling system (Flownamics, Rodeo, CA, USA), including FISP cell free sampling probes, a Segmod 4800 and FlowFraction 96 well plate fraction collector.

For the standardized 2-stage process with ~10 gcdw/L biomass, tanks were filled with 800 mL of FGM10 medium, with enough phosphate to target a final *E. coli* biomass concentration ~10 gcdw/L. Antibiotics were added as appropriate. Frozen seed vials were thawed on ice and 7.5 mL of seed culture was used to inoculate the tanks. After inoculation, tanks were controlled at 37° C. and pH 6.8 using 5 M ammonium hydroxide and 1 M hydrochloric acid as titrants. 10 M ammonium hydroxide was used for FIG. 3G fermentation run. The following oxygen control scheme was used to maintain the desired dissolved oxygen set point. First gas flow rate was increased from a minimum of 0.3 L/min of air to 0.8 L/min of air, subsequently, if more aeration was needed, agitation was increased from a minimum of 300 rpm to a maximum of 1000 rpm. Finally, if more oxygen was required to achieve the set point, oxygen supplementation was included using the integrated mass flow controllers. Starting glucose concentration was 25 g/L. A constant concentrated sterile filtered glucose feed (500 g/L) was added to the tanks at specified rate, i.e. 2 g/h, once agitation reached 800 rpm. In cases where feed rate or dissolved oxygen content needed to be varied for robustness study, changes were made after cells entered stationary phase. Fermentation runs were extended for up to ~50 hours after entry into stationary phase and samples automatically withdrawn every 3 hours. Samples were saved for subsequent analytical measurement.

In the case of growth associated fermentation processes, tanks were filled with 800 mL of FGM10 medium with 40 mM phosphate, which was in great excess and ensured phosphate depletion doesn't happen for growth associated fermentation processes. Antibiotics were added as appropriate. Frozen seed vials were thawed on ice and 7.5 mL of seed culture was used to inoculate the tanks. After inoculation, tanks were controlled at 37° C. and pH 6.8 using 5 M ammonium hydroxide and 1 M hydrochloric acid as titrants. The following oxygen control scheme was used to maintain the desired dissolved oxygen set point. First gas flow rate was increased from a minimum of 0.3 L/min of air to 0.8 L/min of air, subsequently, if more aeration was needed, agitation was increased from a minimum of 300 rpm to a maximum of 1000 rpm. Finally, if more oxygen was required to achieve the set point, oxygen supplementation was included using the integrated mass flow controllers. Starting glucose concentration was 25 g/L. A constant concentrated sterile filtered glucose feed (500 g/L) was added to the tanks at specified rate, i.e. 2 g/h, once agitation reached 800 rpm. Feed rate and dissolved oxygen concentration was set to desired values in the beginning, and maintained throughout the fermentation process. Fermentation runs were continued for up to ~50 hours and samples automatically withdrawn every 3 hours. Samples were saved for subsequent analytical analysis.

Analytical Methods

Sample standard curves for all compounds quantified are shown in Supplemental Materials, Section 10.

Glucose and Ethanol Quantification:

A UPLC-RI method was developed for the simultaneous quantification of glucose and ethanol concentrations, using an Acquity H-Class UPLC integrated with a Waters 2414 Refractive Index (RI) detector (Waters Corp., Milford, MA. USA). Chromatographic separation was performed using a Bio-Rad Fast Acid Analysis HPLC Column (100×7.8 mm, 9 µm particle size; CAT #: #1250100, Bio-Rad Laboratories, Inc., Hercules, CA) at 65° C. 5 mM sulfuric acid was used as the eluent. The isocratic elution was as follows: 0-0.1 min, flow rate increased from 0.4 mL/min to 0.42 mL/min, 0.1-12 min flow rate at 0.48 mL/min. Sample injection volume was 10 µL. UPLC method development was carried out using standard aqueous stock solutions of analytes. Peak integration and further analysis was performed using MassLynx v4.1 software. The linear range used for glucose was 1-10 g/L, for ethanol was 1-20 g/L. Samples were diluted as needed to be within the accurate linear range. Dilution was performed using ultrapure water.

Alanine Quantification:

A reverse phase UPLC-MS/MS method was developed for alanine. Chromatographic separation was performed using a Restek Ultra AQ C18 column (150 mm×2.1 i.d., 3 µm; CAT #: 9178362, Restek Corporation, Bellefonte, PA) at 70° C. The following eluents were used: solvent A: $H_2O$, 0.2% formic acid and 0.05% ammonium (v/v); solvent B: MeOH, 0.2% formic acid and 0.05% ammonium (v/v). The gradient elution was as follows: 0-0.1 min isocratic 5% B, flow rate increased from 0.65 mL/min to 0.75 mL/min; 0.1-0.3 min, linear from 5% to 95% B at 0.75 mL/min; 0.3-0.9 min isocratic 95% B at 0.75 mL/min; and 0.9-1.2 min linear from 95% to 5% B at 0.75 mL/min; 1.2-1.3 min isocratic 5% B at 0.75 mL/min. Sample injection volume was 5 µL. UPLC method development was carried out using standard aqueous stock solutions of analyte. Separations were performed using an Acquity H-Class UPLC integrated with a Xevo™ TQD Mass spectrometer (Waters Corp., Milford, MA. USA). MS/MS parameters including MRM transitions were tuned for each analyte and are listed in Table 22. Alanine (2,3-13C2, 99%) was used as internal standard for alanine at a concentration of 5 mg/L. Peak integration and further analysis was performed using Mass-Lynx v4.1 software. The linear range for alanine was 1-100 mg/L. Samples were diluted as needed to be within the accurate linear range. Dilution was performed using ultrapure water, and the final 10-fold dilution was performed using solvent A, with 5 mg/L of C13 alanine (2,3-13C2, 99%).

Mevalonic Acid Quantification:

A reverse phase UPLC-TUV method was developed for the simultaneous quantification of mevalonic acid and mevalonolactone. Chromatographic separation was performed using a Restek Ultra AQ C18 column (150 mm×2.1 i.d., 3 μm; CAT #: 9178362, Restek Corporation, Bellefonte, PA) at 30° C. 20 mM phosphoric acid was used as the eluent. The isocratic elution was as follows: 0-3 min isocratic at 1 mL/min. Sample injection volume was 10 μL. Absorbance was monitored at 210 nm. UPLC method development was carried out using standard aqueous stock solutions of analytes. Separations were performed using an Acquity H-Class UPLC (Waters Corp., Milford, MA. USA). Peak integration and further analysis was performed using MassLynx v4.1 software. The linear range for mevalonic acid and mevalonolactone were 0.01-0.1 g/L. Samples were diluted as needed to be within the accurate linear range. Mevalonic acid diluted in 20 mM phosphoric acid would spontaneously convert to mevalonolactone 8°, thus, quantification of both mevalonic acid and mevalonolactone was necessary for fermentation samples. Mevalonic acid and mevalonolactone standards were prepared fresh each time, and ran immediately on UPLC. Dilution was performed using ultrapure water, and the final 10-fold dilution was performed using 20 mM phosphoric acid.

Alanine Stereoisomer Quantification:

A reverse phase UPLC-TUV method was developed for the simultaneous quantification and differentiation of L-/D-alanine. Chromatographic separation was performed using a Chirex 3126 (D)-penicillamine column (150 ×4.6 mm, 5 μm; Phenomenex Inc., Torrance, CA) at 50° C. 2 mM Copper Sulfate was used as the eluent. The isocratic elution was as follows: 0-10 min at 0.75 mL/min. Sample injection volume was 10 μL. Absorbance was monitored at 254 nm. UPLC method development was carried out using standard aqueous stock solutions of analytes. Separations were performed using an Acquity H-Class UPLC (Waters Corp., Milford, MA. USA). Peak integration and further analysis was performed using MassLynx v4.1 software. The linear range for L-/D-alanine was 0.1-1 g/L. Samples were diluted as needed to be within the accurate linear range. Dilution was performed using ultrapure water.

Supplemental Materials

TABLE 1

Combinatorial complexity of metabolic networks.

| Combination # | Entire E. coli Gene Network | Reduced Central Metabolism Network |
|---|---|---|
| | Number of Experiments | |
| 1 | 4500 | ~45 (Glycolysis, TCA, PPP and ETC genes only) |
| 2 | $1.0 \times 10^6$ | 990 |
| 3 | $1.5 \times 10^{10}$ | 14,190 |
| 4 | $1.7 \times 10^{13}$ | 148,995 |
| 5 | $1.5 \times 10^{16}$ | $1.2 \times 10^6$ |

Section 1: Phosphate Promoters

Figure 7:
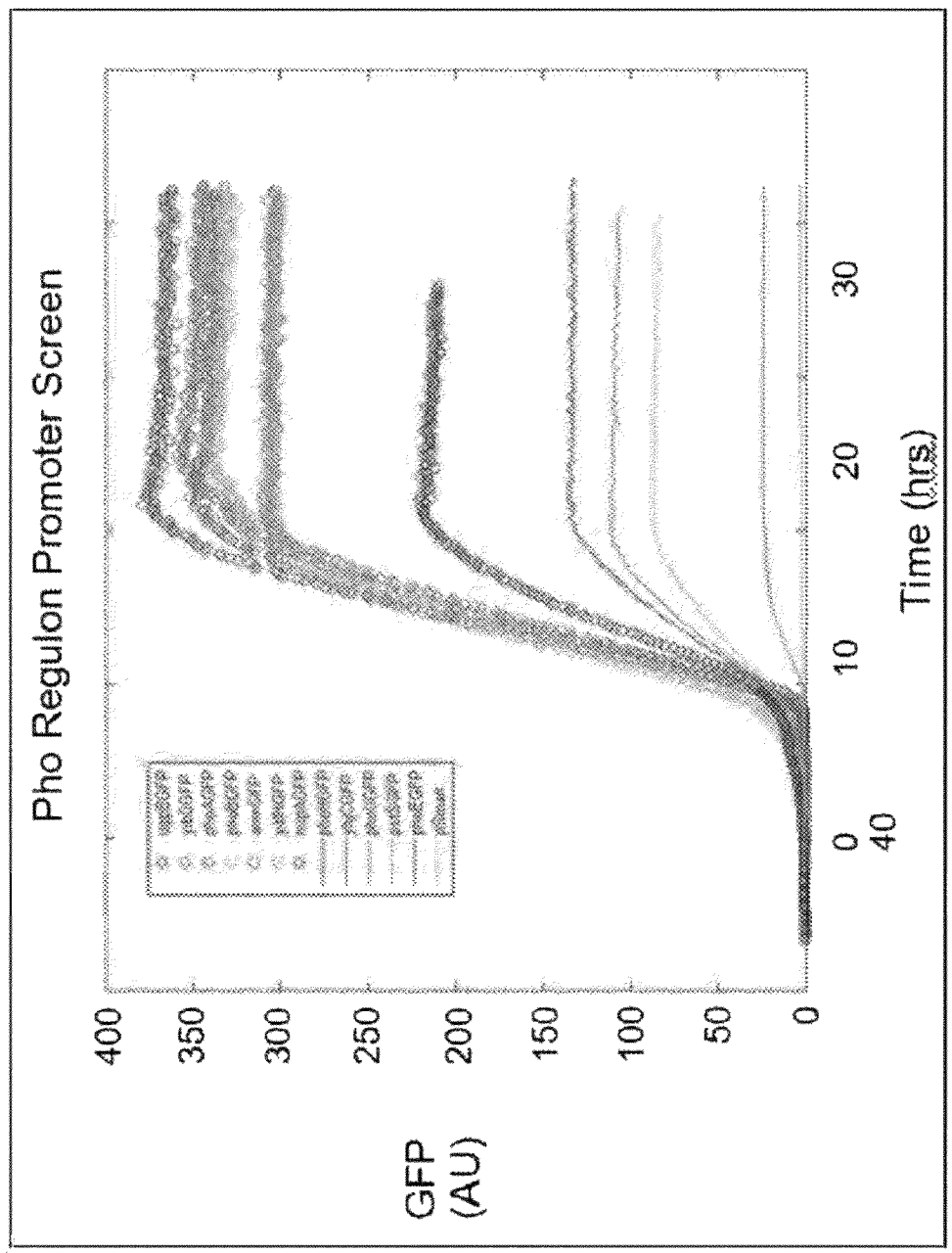
FIG. 7 depicts an example of phosphate depletion promoter characterization.

Phosphate promoter sequences were obtained from the EcoCyc database[81] for PhoB regulated promoters (https://ecocyc.org/, Table 2). We sought to evaluate not only the relative strength of promoters previously characterized to respond to phosphate depletion, but in addition the relative leakiness in phosphate rich conditions. To this aim we constructed a set of fluorescent reporter plasmids. We cloned the ultraviolet excitable GFPuv gene behind a set of 12 phosphate dependent promoters, in the pSMART-HC-Kan (Lucigen, WI) backbone. These reporter strains were evaluated in a 2-stage micro-fermentation protocol in an m2p-labs Biolector™. Results are illustrated in FIG. 7. The ugpB gene promoter was often chosen for high level tightly controlled expression when expression cassettes were chromosomally integrated or for the inducible expression of guide arrays.

Figure 8:
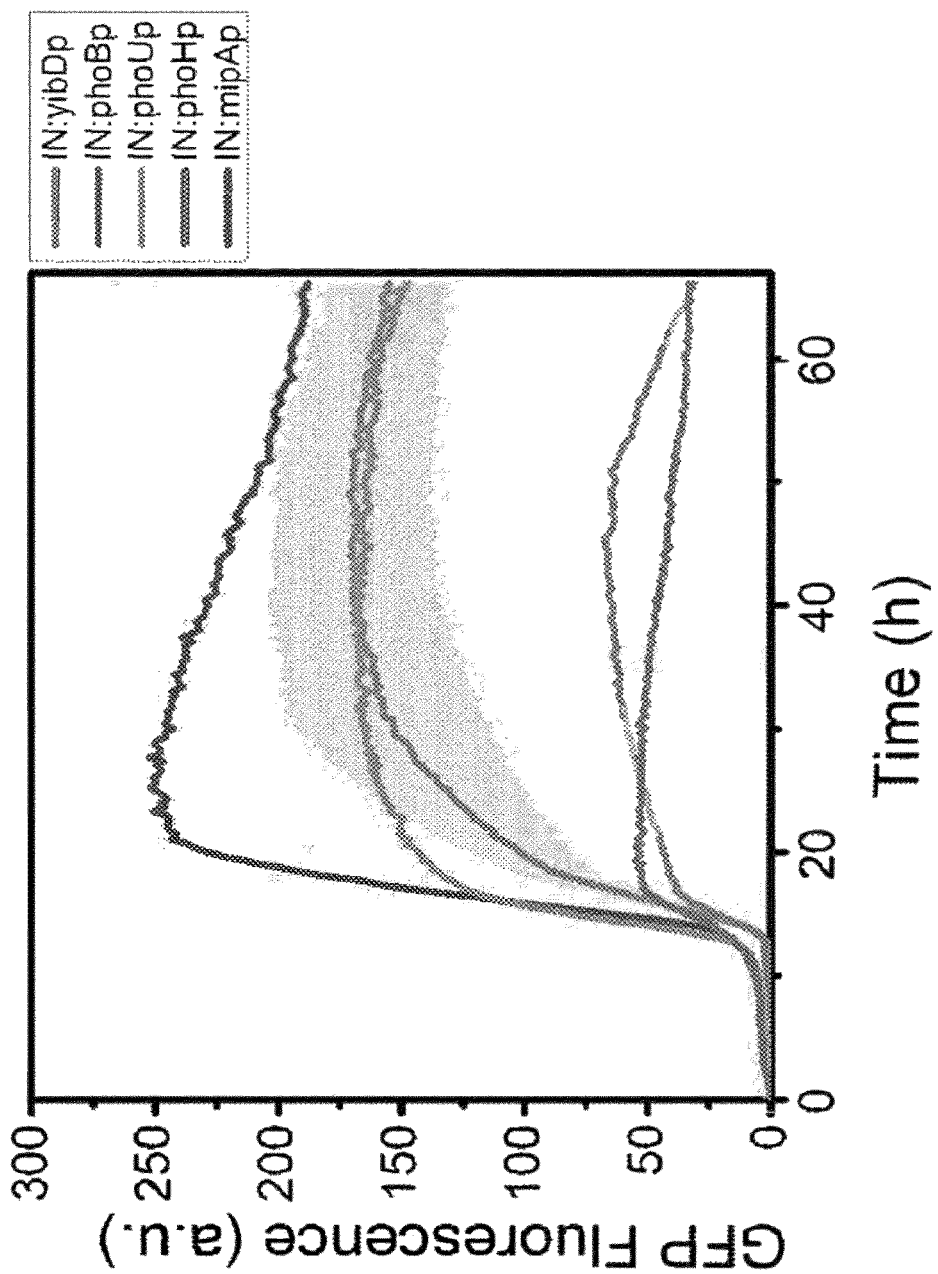
FIG. 8 depicts an example of insulated phosphate depletion promoter characterization.

Insulators[82] were added to both 5' and 3' end of a subset of phosphate promoters (Table 3) to help with consistent performance in different sequence contexts. To reduce read-through transcription, a unique terminator was added to the 5' end of each insulated promoter. Terminator sequences were from http://parts.igem.org/Terminators/Catalog. Insulated phosphate promoters were similarly characterized using GFPuv expression in a m2p-labs Biolector™ (FIG. 8).

TABLE 2

Phosphate inducible promoter sequences evaluated, the ribosomal binding site is underlined, and the start codon of the gene (GFPuv) is shown in green.

| Promoter Name | Sequence | SEQ ID NO |
|---|---|---|
| ugpBp | TCTTTCTGACACCTTACTATCTTACAAATGTAACAAAAAAGTTATTTTTCTGTAATTCGA GCATGTCATGTTACCCCGCGAGCATAAAACGCGTGTGTAGGAGGATAATCTATG | 1 |
| yibDp | GTGCGTAATTGTGCTGATCTCTTATATAGCTGCTCTCATTATCTCTCTACCCTGAAGTGAC TCTCTCACCTGTAAAAATAATATCTCACAGGCTTAATAGTTTCTTAATACAAAGCCTGTA AAACGTCAGGATAACTTCTGTGTAGGAGGATAATCTATG | 2 |
| phoAp | CGATTACGTAAAGAAGTTATTGAAGCATCCTCGTCAGTAAAAAGTTAATCTTTTCAACA GCTGTCATAAAGTTGTCACGGCCGAGACTTATAGTCGCTTTGTTTTTATTTTTTAATGTAT TTGTAGTGTAGGAGGATAATCTATGGCTAGCAAAGGAGAAGAACTTTTCACATG | 3 |
| phoBp | GCCACGGAAATCAATAACCTGAAGATATGTGCGACGAGCTTTTCATAAATCTGTCATAA ATCTGACGCATAATGACGTCGCATTAATGATCGCAACCTATTTATTGTGTAGGAGGATA ATCTATGGCTAGCAAAGGAGAAGAACTTTTCACATG | 4 |
| amnp | AGACAGTCAACGCGCTTGATAGCCTGGCGAAGATCATCCGATCTTCGCCTTACACTTTTG TTTCACATTTCTGTGACATACTATCGGATGTGCGGTAATTGTATAGGAGGATAATCTATG | 5 |

TABLE 2-continued

Phosphate inducible promoter sequences evaluated, the ribosomal binding site is underlined, and the start codon of the gene (GFPuv) is shown in green.

| Promoter Name | Sequence | SEQ ID NO |
|---|---|---|
| ydfHp | GCTATGCCGGACTGAATGTCCACCGTCAGTAATTTTTATACCCGGCGTAACTGCCGGGTT ATTGCTTGTCACAAAAAAGTGGTAGACTCATGCAGTTAACTCACTGTGT<u>AGGAGGA</u>TAA TCTATG | 6 |
| mipAp | CATCCATAAATTTTGCATAATTAATGTAAAGACCAGGCTCGCCAGTAACGCTAAATTCA TTTGGCTGTAAGCGCGGTGTCATCCGCGTCAGGAAAATTAAACAGTTACTTTAAAAAAT GAAAACGTAAAAAGGTTGGGTTTCGATGTATTGACGGGTAAACTTTGTCGCCCGCTAAA CATTTGTTTGTGT<u>AGGAGGA</u>TAATCTATG | 7 |
| phoHp | AATCCTGCTGAAAGCACACAGCTTTTTTCATCACTGTCATCACTCTGTCATCTTTCCAGT AGAAACTAATGTCACTGAAATGGTGTTTTATAGTTAAATATAAGTAAATATATTGTTGCA ATAAATGCGAGATCTGTTGTACTTATTAAGTAGCAGCGGAAGTTCGTGT<u>AGGAGGA</u>TAA TCTAT | 8 |
| yhjCp | CTACAGAGATGACGTGTAGAAAATAGTTACCGATATAAATAGTTACAGCTAAACGCCTG AAATTACATGTCGAGGGCACTATTTAAAACAATTTTGAGGATTTCCTTATATTGGTGGTT AGTACGCATGCAATTAAAAATGAAATTCCGCGACCACAAGCCAAAATAACAAACGGCA AGGAGACAAAAATAAGCACAAATAGCCAACACGTCCTCTGTTCACTTTAAAGGGAATCG CTGAAAAATACGCTCTGTTTAAGGGGATTCACCTTTCTCAGAAAGCTATTCCGCCCTTTT CCTGCTGAGAAATCGCCACATTCGGCATGACAACATTGTGAAAGTG<u>AGGAGGA</u>TAATC TATG | 9 |
| phoUp | ACCGAACTGAAGCAGGATTACACCGTGGTGATCGTCACCCACAACATGCAGCAGGCTGC GCGTTGTTCCGACCACACGGCGTTTATGTACCTGGGCGAATTGATTGAGTTCAGCAACA CGGACGATCTGTTCACCAGTGT<u>AGGAGGA</u>TAATCTATG | 10 |
| pstSp | AAGACTTTATCTCTCTGTCATAAAACTGTCATATTCCTTACATATAACTGTCACCTGTTTG TCCTATTTTGCTTCTCGTAGCCAACAAACAATGCTTTATGAGTGTAGGAGGATAATCTAT GGCTAGCAAAGG<u>AGAAGAA</u>CTTTTCACATG | 11 |
| phoEp | AGCATGGCGTTTTGTTGCGCGGGATCAGCAAGCCTAGCGGCAGTTGTTTACGCTTTTATT ACAGATTTAATAAATTACCACATTTTAAGAATATTATTAATCTGTAATATATCTTTAACA ATCTCAGGTTAAAAACTTTCCTGTTTTCAACGGGACTCTCCCGCTGGTGT<u>AGGAGGA</u>TAA TCTATG | 12 |

TABLE 3

Insulated promoter sequences. Insulator sequences are italicized. -35 and -10 boxes are highlighted in bold and underlined.

| Insulated Promoter | Sequence | SEQ ID NO |
|---|---|---|
| BBa_B0015_IN_yibDp | CCAGGCATCAAATAAAACGAAAGGCTCAGTCGAAAGACTGGGCCTTTCGTT TTATCTGTTGTTTGTCGGTGAACGCTCTCTACTAGAGTCACACTGGCTCACCT TCGGGTGGGCCTTTCTGCGTTTATA*CAGAGCTAACACCACGTCGTCCCTATCTG CTGCCCTAGGTCTATGAGTGGTTGCTGGATAACGTGCGTAATTGTGCTGATCTC* TTATATAGCTGCTCTCATTATCTCTACCCTGAA<u>GTGACT</u>CTCTCACCTGTA AAATAATATCTCACAGGCT<u>TAATA</u>GTTTCTTAATACAAAGCCTGTAAAACG TCAGGATAACTTCTATATT*CAGGGAGACCACAACGGTTTCCCTCTACAAATAATTT TGTTTAACTTT* | 13 |
| BBa_B1002_IN_phoBp | CGCAAAAAACCCCGCTTCGGCGGGGTTTTTTCGCACGTCTCCATCGCTTGCC CAAGTTGTGAAGCACAGCTAACACCACGTCGTCCCTATCTGCTGCCCTAGGTCT *ATGAGTGGTTGCTGGATAACGCCACGGAAATCAATAACCTGAAGATATGTGCG* ACGAGCTT<u>TTCATA</u>AATCTGTCATAAATCTGACG<u>CATAAT</u>GACGTCGCATTA ATGATCGC<u>AACC</u>TATTTATTA*TATTCAGGGAGACCACAACGGTTTCCCTCTACAA ATAATTTTGTTTAACTTT* | 14 |
| BBa_B1004_IN_mipAp | CGCCGAAAACCCCGCTTCGGCGGGGTTTTGCCGCACGTCTCCATCGCTTGCC CAAGTTGTGAAGCACAGCTAACACCACGTCGTCCCTATCTGCTGCCCTAGGTCT *ATGAGTGGTTGCTGGATAACATCCATAAATTTTGCATAATTAATGTAAAGAC* CAGGCTCGCCAGTAACGCTAAATTCATTTGGCTGTAAGCGCGGTGTCATCCG CGTCAGGAAAATTAAACAGTTACTTTAAAAAATGAAAACGTAAAAAGGTTG GGTTTCGATGTATTGACGG<u>GTAAAC</u>TTTGTCGCCCGCTAAACATTTGTTTATA *TTCAGGGAGACCACAACGGTTTCCCTCTACAAATAATTTTGTTTAACTTT* | 15 |
| BBa_B1006_IN_phoUp | AAAAAAAAACCCCGCCCCTGACAGGGCGGGGTTTTTTTACGTCTCCATCGC TTGCCCAAGTTGTGAAGCACAGCTAACACCACGTCGTCCCTATCTGCTGCCCTA *GGTCTATGAGTGGTTGCTGGATAACACCGAACTGAAGCAGGATTACACCGTGG* TGATCGTCACCCACAACATGCAGCAGGCTGCGCGTTGTTCCGACCACA<u>CGG</u> | 16 |

TABLE 3-continued

Insulated promoter sequences. Insulator sequences are italicized. −35 and −10 boxes are highlighted in bold and underlined.

| Insulated Promoter | Sequence | SEQ ID NO |
|---|---|---|
|  | CGTTTATGTACCTGGGCGAATTGATTGAGTTCAGCAACACGGACGATCTGTT *CACCAATATTCAGGGAGACCACAACGGTTTCCCTCTACAAATAATTTTGTTTAACTT T* |  |
| BBa_B1010_IN_phoHp | CGCCGCAAACCCCGCCCCTGACAGGGCGGGGTTTCGCCGCACGTCTCCATCG CTTGCCCAAGTTGTGAAGCACAGCTAACACCACGTCGTCCCTATCTGCTGCCCT AGGTCTATGAGTGGTTGCTGGATAACAATCCTGCTGAAAGCACACAGCTTTTTT CATCACTGTCATCACTCTGTCATCTTTCCAGTAGAAACTAATGTCACTGAAA TGGTGTTTTATAGTTAAATATAAGTAAATATATTGTTGCAATAAATGCGAGA TCTGTTGTACTTATTAAGTAGCAGCGGAAGTTC*ATATTCAGGGAGACCACAAC GGTTTCCCTCTACAAATAATTTTGTTTAACTTT* | 17 |

Section 2: Constitutive Promoters

Figure 9:
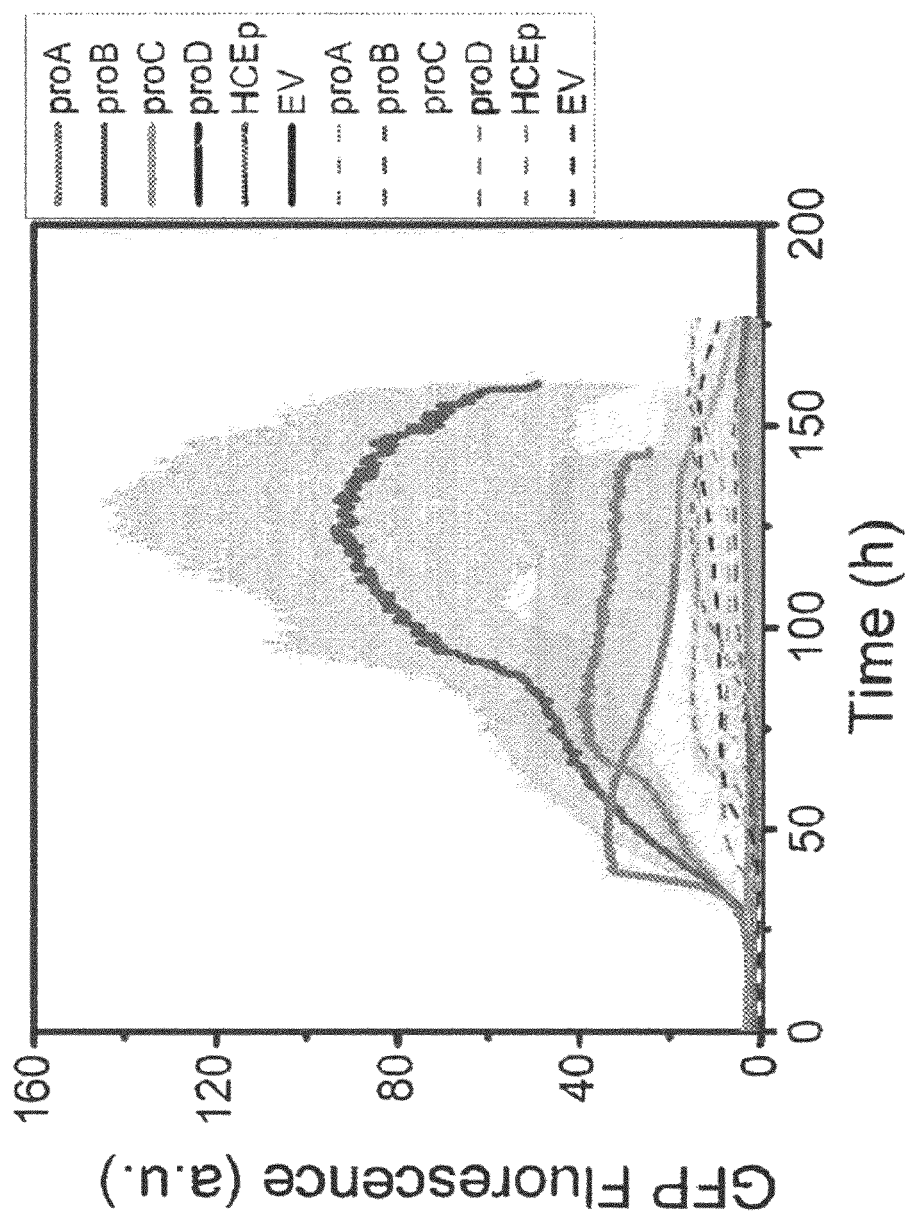
FIG. 9 depicts an example of insulated constitutive promoter characterization.

A set of constitutive insulated promoters of varying strength were used for constitutive expression and taken directly from Davis et al., including the proA, proB, proC, proD promoters[82] and HCEp promoter[83]. Insulator was added to 5' and 3' of HCEp promoter. Similar to insulated phosphate promoters, a unique terminator was added to the 5' end of constitutive promoters. These were used to drive constitutive pathway expression in growth associated production strains as well as to make strain modifications where constitutive heterologous gene expression was appropriate. These promoter sequences are given in Table 4 below and promoter characterized using GFPuv expression (FIG. 9).

TABLE 4

Constitutive promoter sequences.

| Promoter | Sequence | SEQ ID NO |
|---|---|---|
| BBa_B1004_proA | CGCCGAAAACCCCGCTTCGGCGGGGTTTTGCCGCACGTC TCCATCGCTTGCCCAAGTTGTGAAGCACAGCTAACACCA CGTCGTCCCTATCTGCTGCCCTAGGTCTATGAGTGGTTG CTGGATAACTTTACGGGCATGCATAAGGCTCGTAGGCTA TATTCAGGGAGACCACAACGGTTTCCCTCTACAAATAAT TTTGTTTAACTTT | 18 |
| BBa_B1006_proB | AAAAAAAAACCCCGCCCCTGACAGGGCGGGGTTTTTTTT ACGTCTCCATCGCTTGCCCAAGTTGTGAAGCACAGCTAA CACCACGTCGTCCCTATCTGCTGCCCTAGGTCTATGAGT GGTTGCTGGATAACTTTACGGGCATGCATAAGGCTCGTA ATATATATTCAGGGAGACCACAACGGTTTCCCTCTACAA ATAATTTTGTTTAACTTT | 19 |
| BBa_B1010_proC | CGCCGCAAACCCCGCCCCTGACAGGGCGGGGTTTCGCC GCACGTCTCCATCGCTTGCCCAAGTTGTGAAGCACAGCT AACACCACGTCGTCCCTATCTGCTGCCCTAGGTCTATGA GTGGTTGCTGGATAACTTTACGGGCATGCATAAGGCTCG TATGATATATTCAGGGAGACCACAACGGTTTCCCTCTAC AAATAATTTTGTTTAACTTT | 20 |
| BBa_B1002_proD | CGCAAAAAACCCCGCTTCGGCGGGGTTTTTTCGCACGTC TCCATCGCTTGCCCAAGTTGTGAAGCACAGCTAACACCA CGTCGTCCCTATCTGCTGCCCTAGGTCTATGAGTGGTTG CTGGATAACTTTACGGGCATGCATAAGGCTCGTATAATA TATTCAGGGAGACCACAACGGTTTCCCTCTACAAATAAT TTTGTTTAACTTT | 21 |
| BBa_B0015_IN_HCEp | CCAGGCATCAAATAAAACGAAAGGCTCAGTCGAAAGAC TGGGCCTTTCGTTTTATCTGTTGTTTGTCGGTGAACGCTC TCTACTAGAGTCACACTGGCTCACCTTCGGGTGGGCCTT TCTGCGTTTATACACAGCTAACACCACGTCGTCCCTATC TGCTGCCCTAGGTCTATGAGTGGTTGCTGGATAACCTCC TTCACAGATTCCCAATCTCTTGTTAAATAACGAAAAAGC ATCAATTAAAACCCATGTCTTTCTATATTCCAGCAATGT TTTATAGGGACATATTGATGAAGATGGGTATCACCTTA GTGAATTGCTATAAGCTGCTCTTTTTTGTTCGTGATATAC TGATAAATTGAATTTTCACACTTCATATTCAGGGAGACC ACAACGGTTTCCCTCTACAAATAATTTTGTTTAACTTT | 22 |

Section 3: Chromosomally Modified Host Strains

Figure 11:
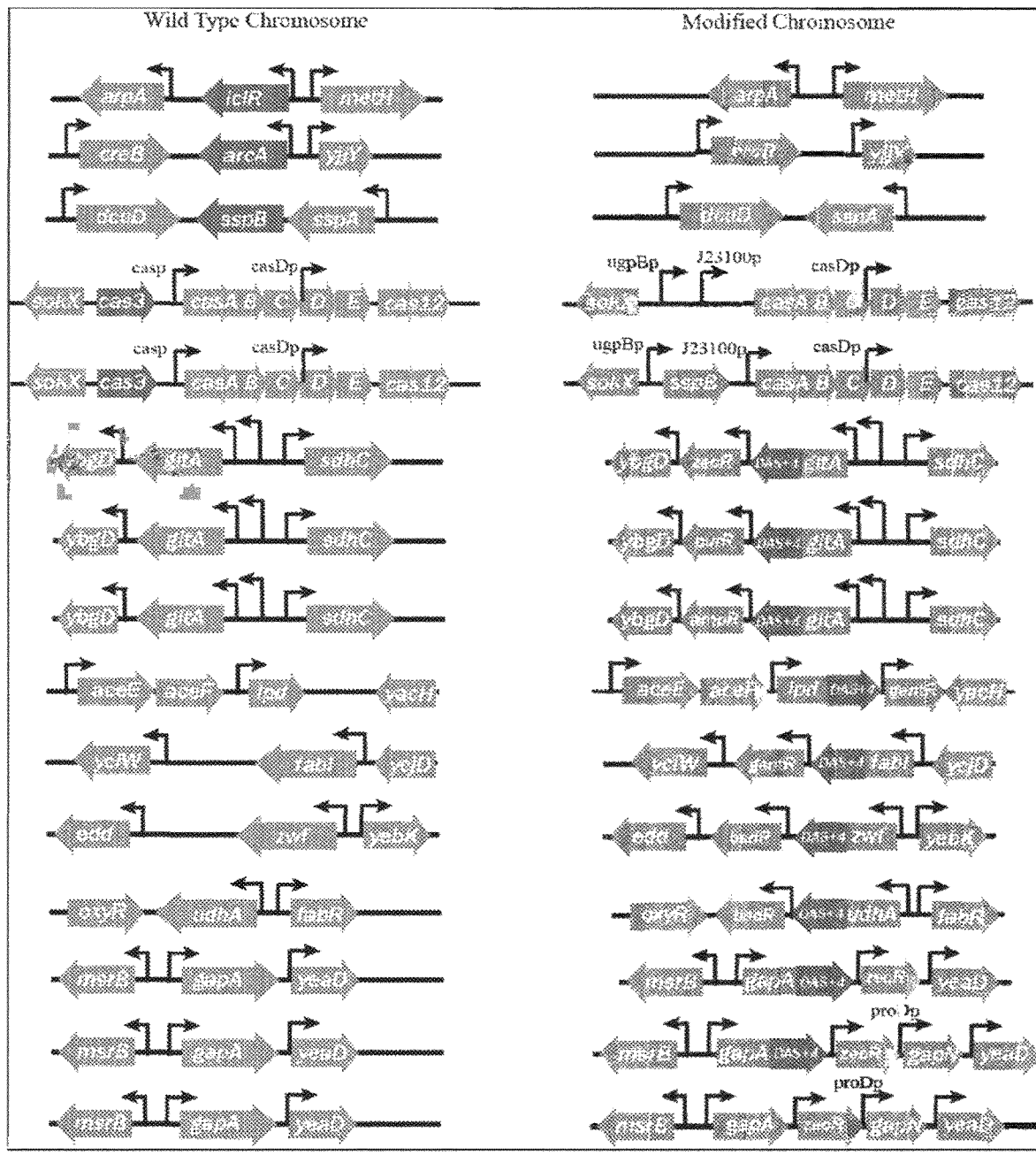
FIG. 11 depicts examples of chromosomal modifications.

FIG. 11 depicts each chromosomal modification. Strains utilized and/or constructed for this study are listed in Table 5. Tables 6 and 7 lists oligonucleotides and synthetic DNA sequences used for strain construction and/or confirmation. FIG. 12 and FIG. 13A-E show growth rates and glucose distribution during growth for control strains in 1 L fermentation.

TABLE 5

List of chromosomally modified strains.

| Strain | Genotype | Source |
|---|---|---|
| BW25113 (wt) | F-, λ-, Δ(araD-araB)567, lacZ4787(del)(::rrnB-3), rph-1, Δ(rhaD-rhaB)568, hsdR514 | CGSC |
| JW3197-1 | BW25113, sspB756(del)::kan | 53 |
| Bwapldf | BW25113, ΔackA-pta, ΔpoxB, ΔpflB, ΔldhA, ΔadhE | 39 |
| DLF_0001 | BWapldf, ΔiclR, ΔarcA | this study |
| DLF_0002 | BWapldf, ΔiclR, ΔarcA, ΔsspB::frt | this study |
| DLF_0025 | DLF_0002, Δcas3::tm-ugpb-sspB-pro-casA(N2S) | this study |
| DLF_0028 | DLF_0025, fabI-DAS + 4-gentR | this study |
| DLF_0031 | DLF_0025, lpd-DAS + 4-gentR | this study |
| DLF_0038 | DLF_0025, fabI-DAS + 4-gentR, udhA-DAS + 4-bsdR | this study |
| DLF_0039 | DLF_0025, fabI-DAS + 4-gentR, gltA-DAS + 4-zeoR | this study |
| DLF_0040 | DLF_0025, fabI-DAS + 4-gentR, zwf-DAS + 4-bsdR | this study |
| DLF_0041 | DLF_0025, lpd-DAS + 4-gentR, gltA-DAS + 4-zeoR | this study |
| DLF_0042 | DLF_0025, lpd-DAS + 4-gentR, udhA-DAS + 4-bsdR | this study |
| DLF_0043 | DLF_0025, gltA-DAS + 4-zeoR | this study |
| DLF_0044 | DLF_0025, gltA-DAS + 4-zeoR, zwf-DAS + 4-bsdR | this study |
| DLF_0045 | DLF_0025, gltA-DAS + 4-zeoR, udhA-DAS + 4-bsdR | this study |
| DLF_0046 | DLF_0025, fabI-DAS + 4-gentR, gltA-DAS + 4-zeoR, zwf-DAS + 4-bsdR | this study |
| DLF_0047 | DLF_0025, fabI-DAS + 4-gentR, gltA-DAS + 4::zeoR, udhA-DAS + 4-bsdR | this study |
| DLF_0048 | DLF_0025, lpd-DAS + 4-gentR, gltA-DAS + 4-zeoR, zwf-DAS + 4-bsdR | this study |
| DLF_0049 | DLF_0025, lpd-DAS + 4-gentR, gltA-DAS + 4-zeoR, udhA-DAS + 4-bsdR | this study |
| DLF_0165 | DLF_0025, lpd-DAS + 4-gentR, zwf-DAS + 4-bsdR | this study |
| DLF_0763 | DLF_0025, udhA-DAS + 4-bsdR | this study |
| DLF_01002 | DLF_0025, zwf-DAS + 4-bsdR | this study |
| DLF_01517 | DLF_0012, Δcas3::pro-casA(N2S) | this study |
| DLF_01530 | DLF_0025, fabI-DAS + 4-gentR, udhA-DAS + 4-bsdR, zeoR-proDp-gapN-zeoR | this study |
| DLF_01531 | DLF_0025, fabI-DAS + 4-gentR, udhA-DAS + 4-bsdR, gltA-DAS + 4-purR | this study |
| DLF_01532 | DLF_0025, fabI-DAS + 4-gentR, udhA-DAS + 4-bsdR, gapA-DAS + 4-zeoR-proDp-gapN | this study |
| DLF_01533 | DLF_0025, fabI-DAS + 4-gentR, udhA-DAS + 4-bsdR, gapA-DAS + 4-zeoR-proDp-gapN, gltA-DAS + 4-purR | this study |
| DLF_01536 | DLF_0025, fabI-DAS + 4-gentR, udhA-DAS + 4-bsdR, zeoR-proDp-gapN, gltA-DAS + 4-purR | this study |
| DLF_01537 | DLF_0025, fabI-DAS + 4-gentR, udhA-DAS + 4-bsdR, gapA-DAS + 4-zeoR | this study |
| DLF_01538 | DLF_0025, fabI-DAS + 4-gentR, gltA-DAS + 4-zeoR, udhA-DAS + 4-bsdR, gapA-DAS + 4-zeoR | this study |

TABLE 6

Oligonucleotides utilized for strain construction.

| Oligo | Sequence | SEQ ID NO |
|---|---|---|
| ilcR_tetA_F | TAACAATAAAAATGAAAATGATTTCCACGATACAGAAA AAAGAGACTGTCATCCTAATTTTTGTTGACACTCTATC | 23 |
| ilcR_sacB_R | TGCCACTCAGGTATGATGGGCAGAATATTGCCTCTGCCC GCCAGAAAAAGATCAAAGGGAAAACTGTCCATATGC | 24 |
| iclR_500up | CCGACAGGGATTCCATCTG | 25 |
| iclR_500dn | TATGACGACCATTTTGTCTACAGTTC | 26 |
| arcA_tetA_F | GGACTTTTGTACTTCCTGTTTCGATTTAGTTGGCAATTTA GGTAGCAAACTCCTAATTTTTGTTGACACTCTATC | 27 |
| arcA_sacB_R | ATAAAAACGGCGCTAAAAAGCGCCGTTTTTTTTGACGGT GGTAAAGCCGAATCAAAGGGAAAACTGTCCATATGC | 28 |
| arcA_500up | CCTGACTGTACTAACGGTTGAG | 29 |

TABLE 6-continued

Oligonucleotides utilized for strain construction.

| Oligo | Sequence | SEQ ID NO |
|---|---|---|
| arcA_500dn | TGACTTTTATGGCGTTCTTTGTTTTTG | 30 |
| sspB_kan_F | CTGGTACACGCTGATGAACACC | 31 |
| sspB_kan_R | CTGGTCATTGCCATTTGTGCC | 32 |
| sspB_conf_F | GAATCAGAGCGTTCCGACCC | 33 |
| sspB_conf_R | GTACGCAGTTTGCCAACGTG | 34 |
| cas3_tetA_F | AATAGCCCGCTGATATCATCGATAATACTAAAAAAACAG GGAGGCTATTATCCTAATTTTTGTTGACACTCTATC | 35 |
| cas3_sacB_R | TACAGGGATCCAGTTATCAATAAGCAAATTCATTTGTTCT CCTTCATATGATCAAAGGGAAAACTGTCCATATGC | 36 |
| cas3_conf_F | CAAGACATGTGTATATCACTGTAATTC | 37 |
| cas3_500dn | GCGATTGCAGATTTATGATTTGG | 38 |
| fabI_conf_F | GCAAAATGCTGGCTCATTG | 39 |
| gapA_conf_F | GAACTGAATGGCAAACTGACTG | 40 |
| gapA_500dn | TGGGGATGATCGACCACA | 41 |
| gltA_conf_F | TATCATCCTGAAAGCGATGG | 42 |
| lpd_conf_F | ATCTCACCGTGTGATCGG | 43 |
| udhA_conf_F | CAAAAGAGATTCTGGGTATTCACT | 44 |
| zwf_conf_F | CTGCTGGAAACCATGCG | 45 |
| zwf_500dn | AGAGCATGTCGTTATAGGAGGTGAT | 46 |
| ampR_intR | AGTACTCAACCAAGTCATTCTG | 47 |
| bsdR_intR | GAGCATGGTGATCTTCTCAGT | 48 |
| gentR_intR | GCGATGAATGTCTTACTACGGA | 49 |
| purR_intR | GTCGCTGGGTAATCTGCAA | 50 |
| tetA_intR | ATCAACGCATATAGCGCTAGCAG | 51 |
| zeoR_intR | ACTGAAGCCCAGACGATC | 52 |

TABLE 7

Synthetic DNA utilized for strain construction.

| | SEQ ID NO |
|---|---|
| tetA-sacB Cassette | |
| TCCTAATTTTTGTTGACACTCTATCATTGATAGAGTTATTTTACCACTCCCTA TCAGTGATAGAGAAAAGTGAAATGAATAGTTCGACAAAGATCGCATTGGTA ATTACGTTACTCGATGCCATGGGATTGGCCTTATCATGCCAGTCTTGCCAA CGTTATTACGTGAATTATTGCTTCGGAAGATATCGCTAACCACTTTGGCGT ATTGCTTGCACTTTATGCGTTAATGCAGGTTATCTTTGCTCCTTGGCTTGGAA AAATGTCTGACCGATTTGGTCGGCGCCCAGTGCTGTTGTTGTCATTAATAGG CGCATCGCTGGATTACTTATTGCTGGCTTTTTCAAGTGCGCTTTGATGCTGT ATTTAGGCCGTTTGCTTTCAGGGATCACAGGAGCTACTGGGGCTGTCGCGGC ATCGGTCATTGCCGATACCACCTCAGCTTCTCAACGCGTGAAGTGGTTCGGT TGGTTAGGGCAAGTTTTGGGCTTGGTTTAATAGCGGGGCCTATTATTGGTG GTTTTGCAGGAGAGATTTCACCGCATAGTCCCTTTTTTATCGCTGCGTTGCTA AATATTGTCACTTTCCTTGTGGTTATGTTTTGGTTCCGTGAAACCAAAAATAC ACGTGATAATACAGATACCGAAGTAGGGGTTGAGACGCAATCGAATTCGGT ATACATCACTTTATTTAAAACGATGCCCATTTTGTTGATTATTTATTTTTCAG CGCAATTGATAGGCCAAATTCCCGCAACGGTGTGGGTGCTATTTACCGAAA ATCGTTTTGGATGGAATAGCATGATGGTTGGCTTTTCATTAGCGGGTCTTGG | 53 |

TABLE 7-continued

Synthetic DNA utilized for strain construction.

| | SEQ ID NO |
|---|---|
| TCTTTTACACTCAGTATTCCAAGCCTTTGTGGCAGGAAGAATAGCCACTAAA<br>TGGGGCGAAAAAACGGCAGTACTGCTCGGATTTATTGCAGATAGTAGTGCA<br>TTTGCCTTTTTAGCGTTTATATCTGAAGGTTGGTTAGTTTTCCCTGTTTTAATT<br>TTATTGGCTGGTGGTGGGATCGCTTTACCTGCATTACAGGGAGTGATGTCTA<br>TCCAAACAAAGAGTCATCAGCAAGGTGCTTTACAGGGATTATTGGTGAGCC<br>TTACCAATGCAACCGGTGTTATTGGCCCATTACTGTTTGCTGTTATTTATAAT<br>CATTCACTACCAATTTGGGATGGCTGGATTTGGATTATTGGTTTAGCGTTTTA<br>CTGTATTATTATCCTGCTATCGATGACCTTCATGTTAACCCCTCAAGCTCAGG<br>GGAGTAAACAGGAGACAAGTGCTTAGTTATTTCGTCACCAAATGATGTTATT<br>CCGCGAAATATAATGACCCTCTTGATAACCCAAGAGCATCACATATACCTGC<br>CGTTCACTATTATTTAGTGAAATGAGATATTATGATATTTTCTGAATTGTGAT<br>TAAAAAGGCAACTTTATGCCCATGCAACAGAAACTATAAAAAATACAGAGA<br>ATGAAAAGAAACAGATAGATTTTTTAGTTCTTTAGGCCCGTAGTCTGCAAAT<br>CCTTTTATGATTTTCTATCAAACAAAAGAGGAAAATAGACCAGTTGCAATCC<br>AAACGAGAGTCTAATAGAATGAGGTCGAAAAGTAAATCGCGCGGGTTTGTT<br>ACTGATAAAGCAGGCAAGACCTAAAATGTGTAAAGGGCAAAGTGTATACTT<br>TGGCGTCACCCCTTACATATTTTAGGTCTTTTTTTATTGTGCGTAACTAACTT<br>GCCATCTTCAAACAGGAGGGCTGGAAGAAGCAGACCGCTAACACAGTACAT<br>AAAAAAGGAGACATGAACGATGAACATCAAAAAGTTTGCAAAACAAGCAA<br>CAGTATTAACCTTTACTACCGCACTGCTGGCAGGAGGCGCAACTCAAGCGTT<br>TGCGAAAGAAACGAACCAAAAGCCATATAAGGAAACATACGGCATTTCCCA<br>TATTACACGCCATGATATGCTGCAAATCCCTGAACAGCAAAAAAATGAAAA<br>ATATCAAGTTCCTGAGTTCGATTCGTCCACAATTAAAAATATCTCTTCTGCA<br>AAAGGCCTGGACGTTTGGGACAGCTGGCCATTACAAAACGCTGACGGCACT<br>GTCGCAAACTATCACGGCTACCACATCGTCTTTGCATTAGCCGGAGATCCTA<br>AAAATGCGGATGACACATCGATTTACATGTTCTATCAAAAAGTCGGCGAAA<br>CTTCTATTGACAGCTGGAAAAACGCTGGCCGCGTCTTTAAAGACAGCGACA<br>AATTCGATGCAAATGATTCTATCCTAAAAGACCAAACACAAGAATGGTCAG<br>GTTCAGCCACATTTACATCTGACGGAAAAATCCGTTTATTCTACACTGATTT<br>CTCCGGTAAACATTACGGCAAACAAACACTGACAACTGCACAAGTTAACGT<br>ATCAGCATCAGACAGCTCTTTGAACATCAACGGTGTAGAGGATTATAAATC<br>AATCTTTGACGGTGACGGAAAAACGTATCAAAATGTACAGCAGTTCATCGA<br>TGAAGGCAACTACAGCTCAGGCGACAACCATACGCTGAGAGATCCTCACTA<br>CGTAGAAGATAAAGGCCACAAATACTTAGTATTTGAAGCAAACACTGGAAC<br>TGAAGATGGCTACCAAGGCGAAGAATCTTTATTTAACAAAGCATACTATGG<br>CAAAAGCACATCATTCTTCCGTCAAGAAAGTCAAAAACTTCTGCAAAGCGA<br>TAAAAAAACGCACGGCTGAGTTAGCAAACGGCGCTCTCGGTATGATTGAGCT<br>AAACGATGATTACACACTGAAAAAAGTGATGAAACCGCTGATTGCATCTAA<br>CACAGTAACAGATGAAATTGAACGCGCGAACGTCTTTAAAATGAACGGCAA<br>ATGGTACCTGTTCACTGACTCCCGCGGATCAAAAATGACGATTGACGGCATT<br>ACGTCTAACGATATTTACATGCTTGGTTATGTTTCTAATTCTTTAACTGGCCC<br>ATACAAGCCGCTGAACAAAACTGGCCTTGTGTTAAAAATGGATCTTGATCCT<br>AACGATGTAACCTTTACTTACTCACACTTCGCTGTACCTCAAGCGAAAGGAA<br>ACAATGTCGTGATTACAAGCTATATGACAAACAGAGGATTCTACGCAGACA<br>AACAATCAACGTTTGCGCCAAGCTTCCTGCTGAACATCAAAGGCAAGAAAA<br>CATCTGTTGTCAAAGACAGCATCCTTGAACAAGGACAATTAACAGTTAACA<br>AATAAAAACGCAAAAGAAAATGCCGATATTGACTACCGGAAGCAGTGTGAC<br>CGTGTGCTTCTCAAATGCCTGATTCAGGCTGTCTATGTGTGACTGTTGAGCT<br>GTAACAAGTTGTCTCAGGTGTTCAATTTCATGTTCTAGTTGCTTTGTTTTACT<br>GGTTTCACCTGTTCTATTAGGTGTTACATGCTGTTCATCTGTTACATTGTCGA<br>TCTGTTCATGGTGAACAGCTTTAAATGCACCAAAAACTCGTAAAGCTCTGA<br>TGTATCTATCTTTTTTACACCGTTTTCATCTGTGCATATGGACAGTTTTCCCTT<br>TGAT | |

ΔiclR-cure

| | |
|---|---|
| AAATGATTTCCACGATACAGAAAAAAGAGACTGTCATGGGCAGAATATTGC<br>CTCTGCCCGCCAGAAAAG | 54 |

ΔarcA-cure

| | |
|---|---|
| CTGTTTCGATTTAGTTGGCAATTTAGGTAGCAAACTCGGCTTTACCACCGTC<br>AAAAAAAACGGCGCTTTT | 55 |

Δcas3-pro-casA

| | |
|---|---|
| CAAGACATGTGTATATCACTGTAATTCGATATTTATGAGCAGCATCGAAAAA<br>TAGCCCGCTGATATCATCGATAATACTAAAAAAACAGGGAGGCTATTACCA<br>GGCATCAAATAAAACGAAAGGCTCAGTCGAAAGACTGGGCCTTTCGTTTTA<br>TCTGTTGTTTGTCGGTGAACGCTCTCTACTAGAGTCACACTGGCTCACCTTCG<br>GGTGGGCCTTTCTGCGTTTATATCTTTCTGACACCTTACTATCTTACAAATGT<br>AACAAAAAGTTATTTTTCTGTAATTCGAGCATGTCATGTTACCCCGCGAGC<br>ATAAAACGCGTGTGTAGGAGGATAATCTTTGACGGCTAGCTCAGTCCTAGGT | 56 |

TABLE 7-continued

Synthetic DNA utilized for strain construction.

| | SEQ ID NO |
|---|---|
| ACAGTGCTAGCCATATGAAGGAGAACAAATGAATTTGCTTATTGATAACTG GATCCCTGTACGCCCGCGAAACGGGGGAAAGTCCAAATCATAAATCTGCA ATCGCTATAC | |

Δcas3::ugBp-sspB-pro-casA

| | |
|---|---|
| CAAGACATGTGTATATCACTGTAATTCGATATTTATGAGCAGCATCGAAAAA TAGCCCGCTGATATCATCGATAATACTAAAAAAACAGGGAGGCTATTACCA GGCATCAAATAAAACGAAAGGCTCAGTCGAAAGACTGGGCCTTTCGTTTTA TCTGTTGTTTGTCGGTGAACGCTCTCTACTAGAGTCACACTGGCTCACCTTCG GGTGGGCCTTTCTGCGTTTATATCTTTCTGACACCTTACTATCTTACAAATGT AACAAAAAAGTTATTTTTCTGTAATTCGAGCATGTCATGTTACCCCGCGAGC ATAAAACGCGTGTGTAGGAGGATAATCTATGGATTTGTCACAGCTAACACC ACGTCGTCCCTATCTGCTGCGTGCATTCTATGAGTGGTTGCTGGATAACCAG CTCACGCCGCACCTGGTGGTGGATGTGACGCTCCCTGGCGTGCAGGTTCCTA TGGAATATGCGCGTGACGGGCAAATCGTACTCAACATTGCGCGCGTGCTGT CGGCAATCTGGAACTGGCGAATGATGAGGTGCGCTTTAACGCGCGCTTTGGT GGCATTCCGCGTCAGGTTTCTGTGCCGCTGGCTGCCGTGCTGGCTATCTACG CCCGTGAAAATGGCGCAGGCACGATGTTTGAGCCTGAAGCTGCCTACGATG AAGATACCAGCATCATGAATGATGAAGAGGCATCGGCAGACAACGAAACC GTTATGTCGGTTATTGATGGCGACAAGCCAGATCACGATGATGACACTCATC CTGACGATGAACCTCCGCAGCCACCACGCGGTGGTCGACCGGCATTACGCG TTGTGAAGTAATTGACGGCTAGCTCAGTCCTAGGTACAGTGCTAGCCATATG AAGGAGAACAAATGAATTTGCTTATTGATAACTGGATCCCTGTACGCCCGCG AAACGGGGGAAAGTCCAAATCATAAATCTGCAATCGCTATAC | 57 | fabI-DAS + 4-gentR

| | |
|---|---|
| CTATTGAAGATGTGGGTAACTCTGCGGCATTCCTGTGCTCCGATCTCTCTGC CGGTATCTCCGGTGAAGTGGTCCACGTTGACGGCGGTTTCAGCATTGCTGCA ATGAACGAACTCGAACTGAAAGCGGCCAACGATGAAAACTATTCTGAAAAC TATGCGGATGCGTCTTAATAGGAAGTTCCTATTCTCTAGAAAGTATAGGAAC TTCCGAATCCATGTGGGAGTTTATTCTTGACACAGATATTTATGATATAATA ACTGAGTAAGCTTAACATAAGGAGGAAAAACATATGTTACGCAGCAGCAAC GATGTTACGCAGCAGGGCAGTCGCCCTAAAACAAAGTTAGGTGGCTCAAGT ATGGGCATCATTCGCACATGTAGGCTCGGCCCTGACCAAGTCAAATCCATGC GGGCTGCTCTTGATCTTTTCGGTCGTGAGTTCGGAGACGTAGCCACCTACTC CCAACATCAGCCGGACTCCGATTACCTCGGGAACTTGCTCCGTAGTAAGACA TTCATCGCGCTTGCTGCCTTCGACCAAGAAGCGGTTGTTGGCGCTCTCGCGG CTTACGTTCTGCCCAAGTTTGAGCAGCCGCGTAGTGAGATCTATATCTATGA TCTCGCAGTCTCCGGCGAGCACCGGAGGCAGGGCATTGCCACCGCGCTCAT CAATCTCCTCAAGCATGAGGCAACGCGCTTGGTGCTTATGTGATCTACGTG CAAGCAGATTACGGTGACGATCCCGCAGTGGCTCTCTATACAAAGTTGGGC ATACGGGAAGAAGTGATGCACTTTGATATCGACCCAAGTACCGCCACCTAA GAAGTTCCTATTCTCTAGAAAGTATAGGAACTTCCGTTCTGTTGGTAAAGAT GGGCGGCGTTCTGCCGCCCGTTATCTCTGTTATACCTTTCTGATATTTGTTAT CGCCGATCCGTCTTTCTCCCCTTCCCGCCTTGCGTCAGG | 58 | gapA-DAS + 4-zeoR-proDp-gapN

| | |
|---|---|
| TCTCCAAAGCGGCCAACGATGAAAACTATTCTGAAAACTATGCGGATGCGT CTTGATTGACAGCTAGCTCAGTCCTAGGTATAATGCTAGCAACTTTAAAATT AAAGAGGTATATATTAATGACTAAGCAATATAAGAATTACGTAAATGGGGA GTGGAAGCTTTCGGAGAATGAAATTAAGATCTATGAACCAGCCAGTGGGGC GGAATTGGGGTCAGTCCCGGCAATGTCCACTGAAGAAGTTGACTATGTCTAC GCCTCGGCCAAAAAAGCGCAGCCAGCATGGCGCTCGCTTTCCTATATTGAGC GTGCGGCTTATTTGCACAAAGTCGCAGACATCCTGATGCGTGACAAGGAGA AAATTGGAGCGGTATTGTCCAAGGAAGTAGCGAAAGGCTACAAATCCGCAG TATCGGAGGTCGTCCGCACCGCCGAGATTATTAATTATGCGGCCGAAGAAG GCTTCGCATGGAGGGTGAGGTCTTGGAGGGCGGCAGTTTTGAGGCGGCAT CCAAGAAAAAAATCGCTGTCGTCCGTCGCGAGCCGGTGGGACTTGTGCTTG CTATTAGTCCGTTCAATTACCCCGTGAATCTGGCCGGCTCCAAGATTGCCCC TGCACTGATCGCGGGCAATGTAATCGCTTTTAAACCACCGACCCAAGGATCG ATTAGTGGACTTCTTTTAGCGGAGGCGTTTGCGGAGGCAGGTCTTCCAGCCG GCGTATTCAATACCATCACGGGGCGTGGAAGTGAAATCGGGGATTACATCG TGGAGCACCAGGCAGTAAATTTCATCAACTTCACGGGTTCCACGGGGATCG GGGAGCGTATCGGTAAGATGGCTGGGATGCGTCCGATCATGTTGGAACTTG GCGGCAAGGATAGTGCGATTGTGCTGGAAGACGCAGACTTGGAATTGACAG CTAAAAACATTATCGCTGGAGCCTTCGGGTATAGTGGTCAACGTTGCACGGC AGTTAAGCGCGTTCTTGTTATGGAAAGTGTCGCGGATGAATTGGTCGAGAA GATTCGCGAGAAAGTGTTAGCTCTTACGATTGGAAATCCAGAGGACGATGC TGACATCACTCCATTGATCGACACGAAATCCGCGGATTACGTCGAGGGGCT GATCAACGACGCGAACGATAAGGGAGCAGCGGCTTTGACCGAGATCAAACG CGAGGGGAACCTGATCTGCCCGATTCTTTTTGACAAAGTCACAACTGACATG CGCTTGGCATGGGAAGAACCCTTCGGCCCAGTCTTGCCTATTATCCGCGTTA | 59 |

TABLE 7-continued

Synthetic DNA utilized for strain construction.

| | SEQ ID NO |
|---|---|
| CTAGCGTAGAGGAAGCAATTGAAATTTCCAATAAATCCGAATATGGGTTGC<br>AAGCGAGTATCTTTACTAACGATTTTCCACGTGCCTTTGGTATTGCGGAACA<br>GTTAGAAGTCGGGACAGTTCACATCAACAACAAGACGCAGCGCGGGACAGA<br>TAACTTCCCCTTTTTGGGAGCAAAGAAGTCTGGGGCTGGAATCCAAGGGGT<br>GAAATACTCCATCGAAGCCATGACGACGGTGAAGAGCGTTGTTTTTGACATC<br>AAGTAAAACATAAGGAGGAAAAACAGATGGCGAAACTGACCTCGGCGGTT<br>CCGGTTCTGACGGCACGTGATGTGGCGGGCGCGGTTGAATTTTGGACGGATC<br>GTCTGGGCTTCAGTCGTGATTTTGTGGAAGATGACTTCGCAGGCGTGGTTCG<br>CGATGACGTCACCCTGTTTATTTCCGCAGTTCAGGATCAAGTCGTGCCGGAC<br>AACACGCTGGCTTGGGTGTGGGTTCGTGGCCTGGATGAACTGTATGCGGAAT<br>GGAGCGAAGTTGTCTCTACCAATTTCCGTGACGCGAGCGGTCCGGCCATGAC<br>GGAAATCGGCGAACAGCCGTGGGGTCGCGAATTTGCTCTGCGTGACCCGGC<br>TGGCAACTGTGTCCATTTCGTGGCTGAAGAACAAGATTGAGTTGAGATGAC<br>ACTGTGATCTAAAAAGAGCGACTTCGGTCGCTCTTTTTTTTACCTGA | | gapA-zeoR-proDp-gapN

| | |
|---|---|
| ACGAAACCGGTTACTCCAACAAAGTTCTGGACCTGATCGCTCACATCTCCAA<br>ATGATTGACAGCTAGCTCAGTCCTAGGTATAATGCTAGCAACTTTAAAATTA<br>AAGAGGTATATATTAATGACTAAGCAATATAAGAATTACGTAAATGGGGAG<br>TGGAAGCTTTCGGAGAATGAAATTAAGATCTATGAACCAGCCAGTGGGGCG<br>GAATTGGGGTCAGTCCCGGCAATGTCCACTGAAGAAGTTGACTATGTCTACG<br>CCTCGGCCAAAAAAGCGCAGCCAGCATGGCGCTCGCTTTCCTATATTGAGCG<br>TGCGGCTTATTTGCACAAAGTCGCAGACATCCTGATGCGTGACAAGGAGAA<br>AATTGGAGCGGTATTGTCCAAGGAAGTAGCGAAAGGCTACAAATCCGCAGT<br>ATCGGAGGTCGTCCGCACCGCCGAGATTATTAATTATGCGGCCGAAGAAGG<br>GCTTCGCATGGAGGGTGAGGTCTTGGAGGGCGGCAGTTTTGAGGCGGCATC<br>CAAGAAAAAAATCGCTGTCGTCCGTCGCGAGCCGGTGGGACTTGTGCTTGCT<br>ATTAGTCCGTTCAATTACCCCGTGAATCTGGCCGGCTCCAAGATTGCCCCTG<br>CACTGATCGCGGGCAATGTAATCGCTTTTAAACCACCGACCCAAGGATCGAT<br>TAGTGGACTTCTTTTAGCGGAGGCGTTTGCGGAGGCAGGTCTTCCAGCCGGC<br>GTATTCAATACCATCACGGGGCGTGGAAGTGAAATCGGGGATTACATCGTG<br>GAGCACCAGGCAGTAAATTTCATCAACTTCACGGGTTCCACGGGGATCGGG<br>GAGCGTATCGGTAAGATGGCTGGGATGCGTCCGATCATGTTGGAACTTGGC<br>GGCAAGGATAGTGCGATTGTGCTGGAAGACGCAGACTTGGAATTGACAGCT<br>AAAAACATTATCGCTGGAGCCTTCGGGTATAGTGGTCAACGTTGCACGGCA<br>GTTAAGCGCGTTCTTGTTATGGAAAGTGTCGCGGATGAATTGGTCGAGAAG<br>ATTCGCGAGAAAGTGTTAGCTCTTACGATTGGAAATCCAGAGGACGATGCT<br>GACATCACTCCATTGATCGACACGAAATCCGCGGATTACGTCGAGGGGCTG<br>ATCAACGACGCGAACGATAAGGGAGCAGCGGCTTTGACCGAGATCAAACGC<br>GAGGGGAACCTGATCTGCCCGATTCTTTTTGACAAAGTCACAACTGACATGC<br>GCTTGGCATGGGAAGAACCCTTCGGCCCAGTCTTGCCTATTATCCGCGTTAC<br>TAGCGTAGAGGAAGCAATTGAAATTTCCAATAAATCCGAATATGGGTTGCA<br>AGCGAGTATCTTTACTAACGATTTTCCACGTGCCTTTGGTATTGCGGAACAG<br>TTAGAAGTCGGGACAGTTCACATCAACAACAAGACGCAGCGCGGGACAGAT<br>AACTTCCCCTTTTTGGGAGCAAAGAAGTCTGGGGCTGGAATCCAAGGGGTG<br>AAATACTCCATCGAAGCCATGACGACGGTGAAGAGCGTTGTTTTTGACATCA<br>AGTAAAACATAAGGAGGAAAAACAGATGGCGAAACTGACCTCGGCGGTTCC<br>GGTTCTGACGGCACGTGATGTGGCGGGCGCGGTTGAATTTTGGACGGATCGT<br>CTGGGCTTCAGTCGTGATTTTGTGGAAGATGACTTCGCAGGCGTGGTTCGCG<br>ATGACGTCACCCTGTTTATTTCCGCAGTTCAGGATCAAGTCGTGCCGGACAA<br>CACGCTGGCTTGGGTGTGGGTTCGTGGCCTGGATGAACTGTATGCGGAATGG<br>AGCGAAGTTGTCTCTACCAATTTCCGTGACGCGAGCGGTCCGGCCATGACGG<br>AAATCGGCGAACAGCCGTGGGGTCGCGAATTTGCTCTGCGTGACCCGGCTG<br>GCAACTGTGTCCATTTCGTGGCTGAAGAACAAGATTGAGTTGAGATGACACT<br>GTGATCTAAAAAGAGCGACTTCGGTCGCTCTTTTTTTTACCTGA | 60 | gapA-DAS + 4-zeoR

| | |
|---|---|
| TCTACCGATTTCAACGGCGAAGTTTGCACTTCCGTGTTCGATGCTAAAGCTG<br>GTATCGCTCTGAACGACAACTTCGTGAAACTGGTATCCTGGTACGACAACGA<br>AACCGGTTACTCCAACAAAGTTCTGGACCTGATCGCTCACATCTCCAAAGCG<br>GCCAACGATGAAAACTATTCTGAAAACTATGCGGATGCGTCTTGATCCTGAC<br>GGATGGCCTTTTTGCGTTTCTACAAACTCTTTTTGTTTATTTTTCTAAATACAT<br>TCAAATATGTATCCGCTCATGAGACAATAACCCTGATAAATGCTTCAATAAT<br>ATTGAAAAGGAAGAGTAATGGCGAAACTGACCTCGGCGGTTCCGGTTCTG<br>ACGGCACGTGATGTGGCGGGCGCGGTTGAATTTTGGACGGATCGTCTGGGC<br>TTCAGTCGTGATTTTGTGGAAGATGACTTCGCAGGCGTGGTTCGCGATGACG<br>TCACCCTGTTTATTTCCGCAGTTCAGGATCAAGTCGTGCCGGACAACACGCT<br>GGCTTGGGTGTGGGTTCGTGGCCTGGATGAACTGTATGCGGAATGGAGCGA<br>AGTTGTCTCTACCAATTTCCGTGACGCGAGCGGTCCGGCCATGACGGAAATC<br>GGCGAACAGCCGTGGGGTCGCGAATTTGCTCTGCGTGACCCGGCTGGCAAC<br>TGTGTCCATTTCGTGGCTGAAGAACAAGATTGAGTTGAGATGACACTGTGAT<br>CTAAAAAGAGCGACTTCGGTCGCTCTTTTTTTACCTGATAAATGAAGTTA<br>AAGGACTGCGTCATGATTAAGAAAATTTTTGCCCTTCCGGTCATCGAACAAA | 61 |

TABLE 7-continued

Synthetic DNA utilized for strain construction.

| | SEQ ID NO |
|---|---|
| TCTCCCCTGTCCTCTCCCGTCGTAAACTGGATGAACTGGACCTCATTGTGGTC GATCATCCCCAGGTAAAAGCCTCT | | gltA-DAS + 4-ampR

| | |
|---|---|
| GTATTCCGTCTTCCATGTTCACCGTCATTTTCGCAATGGCACGTACCGTTGGC TGGATCGCCCACTGGAGCGAAATGCACAGTGACGGTATGAAGATTGCCCGT CCGCGTCAGCTGTATACAGGATATGAAAAACGCGACTTTAAAAGCGATATC AAGCGTGCGGCCAACGATGAAAACTATTCTGAAAACTATGCGGATGCGTCT TAATAGTCCTGACGGATGGCCTTTTTGCGTTTCTACAAACTCTTTTTGTTTAT TTTTCTAAATACATTCAAATATGTATCCGCTCATGAGACAATAACCCTGATA AATGCTTCAATAATATTGAAAAAGGAAGAGTATGAGTATTCAACATTTCCGT GTCGCCCTTATTCCCTTTTTTGCGGCATTTTGCCTTCCTGTTTTTGCTCACCCA GAAACGCTGGTGAAAGTAAAAGATGCTGAAGATCAGTTGGGTGCACGAGTG GGTTACATCGAACTGGATCTCAACAGCGGTAAGATCCTTGAGAGTTTTCGCC CCGAAGAACGTTTTCCAATGATGAGCACTTTTAAAGTTCTGCTATGTGGCGC GGTATTATCCCGTGTTGACGCCGGGCAAGAGCAACTCGGTCGCCGCATACA CTATTCTCAGAATGACTTGGTTGAGTACTCACCAGTCACAGAAAAGCATCTT ACGGATGGCATGACAGTAAGAGAATTATGCAGTGCTGCCATAACCATGAGT GATAACACTGCGGCCAACTTACTTCTGACAACGATCGGAGGACCGAAGGAG CTAACCGCTTTTTTGCACAACATGGGGGATCATGTAACTCGCCTTGATCGTT GGGAACCGGAGCTGAATGAAGCCATACCAAACGACGAGCGTGACACCACG ATGCCTACAGCAATGGCAACAACGTTGCGCAAACTATTAACTGGCGAACTA CTTACTCTAGCTTCCCGGCAACAATTAATAGACTGGATGGAGGCGGATAAA GTTGCAGGACCACTTCTGCGCTCGGCCCTTCCGGCTGGCTGGTTTATTGCTG ATAAATCTGGAGCCGGTGAGCGTGGGTCTCGCGGTATCATTGCAGCACTGG GGCCAGATGGTAAGCCCTCCCGTATCGTAGTTATCTACACGACGGGGAGTC AGGCAACTATGGATGAACGAAATAGACAGATCGCTGAGATAGGTGCCTCAC TGATTAAGCATTGGTAACTGTCAGACTAATGGTTGATTGCTAAGTTGTAAAT ATTTTAACCCGCCGTTCATATGGCGGGTTGATTTTTATATGCCTAAACACAA AAAATTGTAAAAATAAAATCCATTAACAGACCTATATAGATATTTAAAAAG AATAGAACAGCTCAAATTATCAGCAACCCAATACTTTCAATTAAAAACTTCA TGGTAGTCGCATTTATAACCCTATGAAA | 62 | gltA-DAS + 4-purR

| | |
|---|---|
| ACCGTCATTTTCGCAATGGCACGTACCGTTGGCTGGATCGCCCACTGGAGCG AAATGCACAGTGACGGTATGAAGATTGCCCGTCCGCGTCAGCTGTATACAG GATATGAAAAACGCGACTTTAAAAGCGATATCAAGCGTGCGGCCAACGATG AAAACTATTCTGAAAACTATGCGGATGCGTCTTAATCCTGACGGATGGCCTT TTTGCGTTTCTACAAACTCTTTTTGTTTATTTTTCTAAATACATTCAAATATGT ATCCGCTCATGAGACAATAACCCTGATAAATGCTTCAATAATATTGAAAAA GGAAGAGTATGACTGAATACAAGCCCACGGTACGCTTGGCGACGCGCGACG ATGTTCCCCGCGCTGTTCGTACATTAGCTGCGGCCTTTGCAGATTACCCAGC GACGCGCCATACGGTCGATCCGGACCGCCATATCGAGCGTGTCACAGAATT GCAGGAACTTTTCTTAACTCGCGTGGGCCTTGACATCGGAAAGGTCTGGGTG GCTGACGATGGCGCTGCAGTGGCTGTTTGGACCACTCCGGAGAGTGTAGAG GCTGGTGCAGTGTTCGCCGAAATTGGTCCTCGTATGGCCGAATTAAGTGGAA GTCGTCTGGCAGCCCAACAACAAATGGAAGGGTTGCTTGCGCCCCACCGTC CGAAAGAACCCGCGTGGTTCCTTGCCACCGTTGGAGTAAGCCCAGATCACC AGGGGAAGGGTTTAGGATCTGCCGTAGTTTTACCAGGTGTGGAGGCAGCAG AACGTGCGGGAGTTCCGGCCTTCCTTGAGACGTCGGCGCCGCGCAATTTACC GTTTTACGAACGTCTTGGATTCACCGTTACGGCGGACGTGGAGGTGCCGGAG GGACCCCGTACTTGGTGTATGACTCGTAAACCGGGAGCCTGATAATGGTTGA TTGCTAAGTTGTAAATATTTTAACCCGCCGTTCATATGGCGGGTTGATTTTTA TATGCCTAAACACAAAAAATTGTAAAAATAAAATCCATTAACAGACCTATA TAGATATTTAAAAAGAATAGAACAGCTCAAATTATCAGCAACCCA | 63 | gltA-DAS + 4-zeoR

| | |
|---|---|
| GTATTCCGTCTTCCATGTTCACCGTCATTTTCGCAATGGCACGTACCGTTGGC TGGATCGCCCACTGGAGCGAAATGCACAGTGACGGTATGAAGATTGCCCGT CCGCGTCAGCTGTATACAGGATATGAAAAACGCGACTTTAAAAGCGATATC AAGCGTGCGGCCAACGATGAAAACTATTCTGAAAACTATGCGGATGCGTCT TAATAGTTGACAATTAATCATCGGCATAGTATATCGGCATAGTATAATACGA CTCACTATAGGAGGGCCATCATGGCCAAGTTGACCAGTGCCGTTCCGGTGCT CACCGCGCGCGACGTCGCCGGAGCGGTCGAGTTCTGGACCGACCGGCTCGG GTTCTCCCGGGACTTCGTGGAGGACGACTTCGCCGGTGTGGTCCGGGACGAC GTGACCCTGTTCATCAGCGCGGTCCAGGACCAGGTGGTGCCGGACAACACC CTGGCCTGGGTGTGGGTGCGCGGCCTGGACGAGCTGTACGCCGAGTGGTCG GAGGTCGTGTCCACGAACTTCCGGGACGCCTCCGGGCCGGCCATGACCGAG ATCGGCGAGCAGCCGTGGGGGCGGAGTTCGCCCTGCGCGACCCGGCCGGC AACTGCGTGCACTTTGTGGCAGAGGAGCAGGACTGAGGATAAGTAATGGTT GATTGCTAAGTTGTAAATATTTTAACCCGCCGTTCATATGGCGGGTTGATTTT TATATGCCTAAACACAAAAAATTGTAAAAATAAAATCCATTAACAGACCTA | 64 |

TABLE 7-continued

Synthetic DNA utilized for strain construction.

| | SEQ ID NO |
|---|---|
| TATAGATATTTAAAAAGAATAGAACAGCTCAAATTATCAGCAACCCAATAC<br>TTTCAATTAAAAACTTCATGGTAGTCGCATTTATAACCCTATGAAA | | lpd-DAS + 4-gentR

| | |
|---|---|
| GCGGCGAGCTGCTGGGTGAAATCGGCCTGGCAATCGAAATGGGTTGTGATG<br>CTGAAGACATCGCACTGACCATCCACGCGCACCCGACTCTGCACGAGTCTGT<br>GGGCCTGGCGGCAGAAGTGTTCGAAGGTAGCATTACCGACCTGCCGAACCC<br>GAAAGCGAAGAAGAAGGCGGCCAACGATGAAAACTATTCTGAAAACTATG<br>CGGATGCGTCTTAATAGCGAATCCATGTGGGAGTTTATTCTTGACACAGATA<br>TTTATGATATAATAACTGAGTAAGCTTAACATAAGGAGGAAAAACATATGT<br>TACGCAGCAGCAACGATGTTACGCAGCAGGGCAGTCGCCCTAAAACAAAGT<br>TAGGTGGCTCAAGTATGGGCATCATTCGCACATGTAGGCTCGGCCCTGACCA<br>AGTCAAATCCATGCGGGCTGCTCTTGATCTTTTCGGTCGTGAGTTCGGAGAC<br>GTAGCCACCTACTCCCAACATCAGCCGGACTCCGATTACCTCGGGAACTTGC<br>TCCGTAGTAAGACATTCATCGCGCTTGCTGCCTTCGACCAAGAAGCGGTTGT<br>TGGCGCTCTCGCGGCTTACGTTCTGCCCAAGTTTGAGCAGCCGCGTAGTGAG<br>ATCTATATCTATGATCTCGCAGTCTCCGGCGAGCACCGGAGGCAGGGCATTG<br>CCACCGCGCTCATCAATCTCCTCAAGCATGAGGCAACGCGCTTGGTGCTTA<br>TGTGATCTACGTGCAAGCAGATTACGGTGACGATCCCGCAGTGGCTCTCTAT<br>ACAAAGTTGGGCATACGGGAAGAAGTGATGCACTTTGATATCGACCCAAGT<br>ACCGCCACCTAATTTTTCGTTTGCCGGAACATCCGGCAATTAAAAAGCGGC<br>TAACCACGCCGCTTTTTTTACGTCTGCAATTTACCTTTCCAGTCTTCTTGCTC<br>CACGTTCAGAGAGACGTTCGCATACTGCTGACCGTTGCTCGTTATTCAGCCT<br>GACAGTATGGTTACTGTC | 65 | udhA-DAS + 4-bsdR

| | |
|---|---|
| TCTGGGTATTCACTGCTTTGGCGAGCGCGCTGCCGAAATTATTCATATCGGT<br>CAGGCGATTATGGAACAGAAAGGTGGCGGCAACACTATTGAGTACTTCGTC<br>AACACCACCTTTAACTACCCGACGATGGCGGAAGCCTATCGGGTAGCTGCG<br>TTAAACGGTTTAAACCGCCTGTTTGCGGCCAACGATGAAAACTATTCTGAAA<br>ACTATGCGGATGCGTCTTAATAGTTGACAATTAATCATCGGCATAGTATATC<br>GGCATAGTATAATACGACTCACTATAGGAGGGCCATCATGAAGACCTTCAA<br>CATCTCTCAGCAGGATCTGGAGCTGGTGGAGGTCGCCACTGAGAAGATCAC<br>CATGCTCTATGAGGACAACAAGCACCATGTCGGGGCGGCCATCAGGACCAA<br>GACTGGGGAGATCATCTCTGCTGTCCACATTGAGGCCTACATTGGGCAGGGTC<br>ACTGTCTGTGCTGAAGCCATTGCCATTGGGTCTGCTGTGAGCAACGGGCAGA<br>AGGACTTTGACACCATTGTGGCTGTCAGGCACCCCTACTCTGATGAGGTGGA<br>CAGATCCATCAGGGTGGTCAGCCCCTGTGGCATGTGCAGAGAGCTCATCTCT<br>GACTATGCTCCTGACTGCTTTGTGCTCATTGAGATGAATGGCAAGCTGGTCA<br>AAACCACCATTGAGGAACTCATCCCCCTCAAGTACACCAGGAACTAAAGTA<br>AAACTTTATCGAAATGGCCATCCATTCTTGCGCGGATGGCCTCTGCCAGCTG<br>CTCATAGCGGCTGCGCAGCGGTGAGCCAGGACGATAAACCAGGCCAATAGT<br>GCGGCGTGGTTCCGGCTTAATGCACGG | 66 | zwf-DAS + 4-bsdR

| | |
|---|---|
| GAAGTGGAAGAAGCCTGGAAATGGGTAGACTCCATTACTGAGGCGTGGGCG<br>ATGGACAATGATGCGCCGAAACCGTATCAGGCCGGAACCTGGGGACCCGTT<br>GCCTCGGTGGCGATGATTACCCGTGATGGTCGTTCCTGGAATGAGTTTGAGG<br>CGGCCAACGATGAAAACTATTCTGAAAACTATGCGGATGCGTCTTAATAGTT<br>GACAATTAATCATCGGCATAGTATATCGGCATAGTATAATACGACTCACTAT<br>AGGAGGGCCATCATGAAGACCTTCAACATCTCTCAGCAGGATCTGGAGCTG<br>GTGGAGGTCGCCACTGAGAAGATCACCATGCTCTATGAGGACAACAAGCAC<br>CATGTCGGGGCGGCCATCAGGACCAAGACTGGGGAGATCATCTCTGCTGTC<br>CACATTGAGGCCTACATTGGCAGGGTCACTGTCTGTGCTGAAGCCATTGCCA<br>TTGGGTCTGCTGTGAGCAACGGGCAGAAGGACTTTGACACCATTGTGGCTGT<br>CAGGCACCCCTACTCTGATGAGGTGGACAGATCCATCAGGGTGGTCAGCCC<br>CTGTGGCATGTGCAGAGAGCTCATCTCTGACTATGCTCCTGACTGCTTTGTG<br>CTCATTGAGATGAATGGCAAGCTGGTCAAAACCACCATTGAGGAACTCATC<br>CCCCTCAAGTACACCAGGAACTAAAGTAATATCTGCGCTTATCCTTTATGGT<br>TATTTTACCGGTAACATGATCTTGCGCAGATTGTAGAACAATTTTTACACTTT<br>CAGGCCTCGTCGGATTCACCCACGAGGCTTTTTTTATTACACTGACTGAAA<br>CGTTTTTGCCCTATGAGCTCCGGTTACAGGCGTTTCAGTCATAAATCCTCTGA<br>ATGAAACGCGTTGTGAATC | 67 | dadX-DAS + 4-purR

| | |
|---|---|
| GCGTGCGCACCATGACGGTGGGGACCGTCTCGATGGATATGCTAGCGGTCG<br>ATTTAACGCCTTGCCCGCAGGCGGGTATTGGTACGCCGGTTGAGCTGTGGGG<br>CAAGGAGATCAAAATTGATGATGTCGCCGCCGCTGCCGGAACGGTGGGCTA<br>TGAGTTGATGTGCGCGCTGGCGCTACGCGTCCCGGTTGTGACGGTGGCGGCC<br>AACGATGAAAACTATTCTGAAAACTATGCGGATGCGTCTTAATCCTGACGG<br>ATGGCCTTTTTGCGTTTCTACAAACTCTTTTTGTTTATTTTTCTAAATACATTC | 68 |

TABLE 7-continued

Synthetic DNA utilized for strain construction.

SEQ ID NO

```
AAATATGTATCCGCTCATGAGACAATAACCCTGATAAATGCTTCAATAATAT
TGAAAAAGGAAGAGTATGACTGAATACAAGCCCACGGTACGCTTGGCGACG
CGCGACGATGTTCCCCGCGCTGTTCGTACATTAGCTGCGGCCTTTGCAGATT
ACCCAGCGACGCGCCATACGGTCGATCCGGACCGCCATATCGAGCGTGTCA
CAGAATTGCAGGAACTTTTCTTAACTCGCGTGGGCCTTGACATCGGAAAGGT
CTGGGTGGCTGACGATGGCGCTGCAGTGGCTGTTTGGACCACTCCGGAGAG
TGTAGAGGCTGGTGCAGTGTTCGCCGAAATTGGTCCTCGTATGGCCGAATTA
AGTGGAAGTCGTCTGGCAGCCCAACAACAAATGGAAGGGTTGCTTGCGCCC
CACCGTCCGAAAGAACCCGCGTGGTTCCTTGCCACCGTTGGAGTAAGCCCA
GATCACCAGGGGAAGGGTTTAGGATCTGCCGTAGTTTTACCAGGTGTGGAG
GCAGCAGAACGTGCGGGAGTTCCGGCCTTCCTTGAGACGTCGGCGCCGCGC
AATTTACCGTTTTACGAACGTCTTGGATTCACCGTTACGGCCGACGTGGAGG
TGCCGGAGGGACCCCGTACTTGGTGTATGACTCGTAAACCGGGAGCCTGAT
AACTTGTTGTAAGCCGATCGGAGGCAACGTCTTCTGGGTGCAAAAAAATC
ATCCATCCGGCTGGTCAGCAACTGTAGTTGTTAATGTGACAGAGCCATTGCC
CATGATAGTGTCCATTAAAAGGATGGACACTATTTCCCCGGAACCTGAACTC
ACCGCACAGGCGTTCTACATAAAACGCTTACGCTTCATTGTTGACTC
```

Section 4: Dynamic Control Over Protein Levels.

Plasmids expressing fluorescent proteins and silencing guides were transformed into the corresponding hosts strain listed in Table 8. Strains were evaluated in triplicate in an m2p-labs Biolector™, which simultaneously measures fluorescence including GFPuv and mCherry levels, as well as biomass levels.

TABLE 8

Strains used for Dynamic Control over protein levels

| Microbe | Synthetic Metabolic Valves | Plasmid | Host Strain |
|---------|---------------------------|---------|-------------|
| E. coli | RFP-control | pCDF-mcherry1 + pSMART-IN:yibDp-GFPuv | DLF_0002 |
|  | Proteolysis | pCDF-mcherry2 + pSMART-IN:yibDp-GFPuv | DLF_0025 |
|  | Silencing | pCDF-mcherry1 + pCASCADE-proD + pSMART-IN:yibDp-GFPuv | DLF_01517 |

TABLE 8-continued

Strains used for Dynamic Control over protein levels

| Microbe | Synthetic Metabolic Valves | Plasmid | Host Strain |
|---------|---------------------------|---------|-------------|
|  | Proteolysis + Silencing | pCDF-mcherry2 + pCASCADE-proD + pSMART-IN:yibDp-GFPuv | DLF_0025 |

OD600 readings were corrected using the formula below, where OD600 refers to an offline measurement, OD600* refers to Biolector biomass reading, t0 indicates the start point, and tf indicates the final point.

$$OD600_t = (OD600_t^* - OD600_{t0}^*) * \frac{(OD600_{tf} - OD600_{t0})}{(OD600_{tf}^* - OD600_{t0}^*)} + 0.25 \quad \text{Equation S1}$$

Section 5: Metabolic Control
Near Equilibrium Reactions

The impact of Valves on metabolite pools for near equilibrium reactions is illustrated using the G6P node as an example. Abbreviations: Gluc, glucose; G6P, glucose-6-phosphate; F6P, fructose-6-phosphate; 6PGl, 6-phosphate-gluconolactone.

G6P Node without Valves

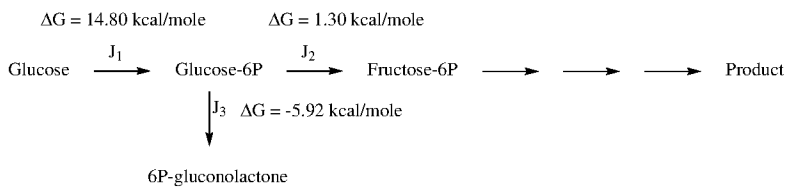

Steady State Mass balance $J_1 = J_2 + J_3$  Equation S2

Net Flux $= J_i = e^{\frac{-dG}{RT}} - 1$  Equation S3

$e^{\frac{-dG1}{RT}} - 1 = e^{\frac{-dG2}{RT}} - 1 + e^{\frac{-dG3}{RT}} - 1$  Equation S4

$e^{\frac{-dG1}{RT}} = e^{\frac{-dG2}{RT}} + e^{\frac{-dG3}{RT}} - 1$  Equation S5

$Keq1 = Keq2 + Keq3 - 1$  Equation S6

$Keq1 + 1 = Keq2 + Keq3$  Equation S7

$\frac{[G6P]}{[Gluc]} + 1 = \frac{[F6P]}{[G6P]} + \frac{[6PGl]}{[G6P]}$  Equation S8

$\frac{[G6P]}{[Gluc]} + 1 = \frac{[F6P] + [6PGl]}{[G6P]}$  Equation S9

$\frac{[G6P]^2}{[Gluc]} + [G6P] = [F6P] + [6PGl]$  Equation S10

$[F6P] = \frac{[G6P]^2}{[Gluc]} + [G6P] - [6PGl]$  Equation S11

G6P Node with Valves

When zwf valve is in effect, $J_3 \approx 0$.

$\Delta G = 14.80$ kcal/mole   $\Delta G = 1.30$ kcal/mole

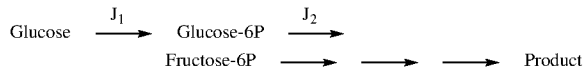

Glucose $\xrightarrow{J_1}$ Glucose-6P $\xrightarrow{J_2}$ Fructose-6P $\longrightarrow$ $\longrightarrow$ $\longrightarrow$ Product Steady State Mass balance $J_1 = J_2$  Equation S12

Net Flux $= J_i = e^{\frac{-dG}{RT}} - 1$  Equation S13

$e^{\frac{-dG1}{RT}} - 1 = e^{\frac{-dG2}{RT}} - 1$  Equation S14

$Keq1 = Keq2$  Equation S15

$\frac{[G6P]}{[Gluc]} = \frac{[F6P]}{[G6P]}$  Equation S16

$[F6P] = \frac{[G6P]^2}{[Gluc]}$  Equation S17

Impact of Valves $[F6P] \text{ network} = \frac{[G6P]^2}{[Gluc]} + [G6P] - [6PGl]$  Equation S11

$[F6P] \text{ valve} = \frac{[G6P]^2}{[Gluc]}$  Equation S17

Since close to equilibrium $[6PGl] > [G6P]$ $[F6P] \text{ valve} >= [F6P] \text{ network}$ The removal of thermodynamically favored reactions near equilibrium from the network will result in increased metabolite pools.

Section 6: Gene Silencing Arrays & Pathway Expression Constructs

The design and construction of CASCADE guides and guide arrays is illustrated below in FIG. 14 and FIG. 15A-B. The pCASCADE-control plasmid was prepared by swapping the pTet promoter in pcrRNA.Tet[88] with an insulated low phosphate induced ugpB promoter[82]. Two promoters were responsible for regulating gltA gene, and sgRNA was designed for both promoters, resulting in guide gltA1 (G1) and gltA2 (G2).[89] Four promoters were responsible for regulating gapA gene, and sgRNA was designed for the first promoter, since during exponential phase of growth, gapA mRNAs were mainly initiated at the highly efficient gapA P1 promoter and remained high during stationary phase compared to the other three gapA promoters.[90] Multiple promoters upstream of lpd gene were involved in lpd regulation (https://ecocyc.org/gene?orgid=ECOLI&id=EG10543 #tab=showAll), thus design of unique and effective sgRNA for lpd only was not possible. Promoter sequences for fabI, udhA and zwf were obtained from EcoCyc database (https://ecocyc.org/). To design CASCADE guide array, CASCADE PAM sites near the −35 or −10 box of the promoter of interest were identified, 30 bp at the 3' end of PAM site was selected as the guide sequence and cloned into pCASCADE plasmid using Q5 site-directed mutagenesis (NEB, MA) following manufacturer's protocol, with the modification that 5% v/v DMSO was added to the Q5 PCR reaction. The pCASCADE-control vector was used as template. pCASCADE plasmids with arrays of two or more guides were prepared as illustrated in FIG. 15A-B. The pCASCADE guide array plasmid was prepared by sequentially amplifying complementary halves of each smaller guide plasmid by PCR, followed by subsequent DNA assembly. Table 9 lists sgRNA guide sequences and primers used to construct them. All pCASCADE silencing plasmids are listed in Table 10 below and are available at Addgene.

TABLE 9

List of sgRNA guide sequences and primers used to construct them. Spacers are italicized.

| sgRNA/Primer Name | Sequence | SEQ ID NO | Template |
|---|---|---|---|
| fabI | TCGAGTTCCCCGCGCCAGCGGG GATAAACCGTTGATTATAATAA CCGTTTATCTGTTCGTATCGAG TTCCCCGCGCCAGCGGGGATAA ACCG | 69 | |
| fabI-FOR | GTTTATCTGTTCGTATCGAGTT CCCCGCGCCAGCGGGGATAAAC CGAAAAAAAAACCCC | 70 | pCASCADE control |
| fabI-REV | GGTTATTATAATCAACGGTTTA TCCCCGCTGGCGCGGGGAACT CGAGGTGGTACCAGATC | 71 | |

TABLE 9-continued

List of sgRNA guide sequences and primers used to construct them. Spacers are italicized.

| sgRNA/Primer Name | Sequence | SEQ ID NO | Template |
|---|---|---|---|
| gapAP1 | *TCGAGTTCCCCGCGCCAGCGGG GATAAACCGGTTTTTGTAATTTT* ACAGGCAACCTTTTATT*CGAGT TCCCCGCGCCAGCGGGGATAAA CCG* | 72 | |
| gapAP1-FOR | CAGGCAACCTTTTATT*CGAGTT CCCCGCGCCAGCGGGGATAAAC CGAAAAAAAAACCCC* | 73 | pCASCADE control |
| gapAP1-REV | TAAAATTACAAAAACCGGTTT ATCCCCGCTGGCGCGGGGAAC TCGAGGTGGTACCAGATC | 74 | |
| gltA1 | *TCGAGTTCCCCGCGCCAGCGGG GATAAACCGAAAAGCATATAAT GCGTAAAAGTTATGAAGTTCG AGTTCCCCGCGCCAGCGGGGAT AAACCG* | 75 | |
| gltA1-FOR | GCGTAAAAGTTATGAAGTT*CG AGTTCCCCGCGCCAGCGGGGAT AAACCGAAAAAAAAACCCC* | 76 | pCASCADE control |
| gltA1-REV | ATTATATGCTTTTCGGTTTATC CCCGCTGGCGCGGGGAACTCG AGGTGGTACCAGATCT | 77 | |
| gltA2 | *TCGAGTTCCCCGCGCCAGCGGG GATAAACCGTATTGACCAATTC ATTCGGGACAGTTATTAGTTCG AGTTCCCCGCGCCAGCGGGGAT AAACCG* | 78 | |
| gltA2-FOR | GGGACAGTTATTAGTT*CGAGTT CCCCGCGCCAGCGGGGATAAAC CGAAAAAAAAACCCC* | 79 | pCASCADE control |
| gltA2-REV | GAATGAATTGGTCAATACGGT TTATCCCCGCTGGCGCGGGA ACTCGAGGTGGTACCAGATCT | 80 | |
| proD | *TCGAGTTCCCCGCGCCAGCGGG GATAAACCGAGTGGTTGCTGGA TAACTTTACGGGCATGCTCGAG TTCCCCGCGCCAGCGGGGATAA ACCG* | 81 | |
| proD-FOR | AACTTTACGGGCATGC*TCGAGT TCCCCGCGCCAGCGGGGATAAA CCGAAAAAAAAACCCC* | 82 | pCASCADE control |
| proD-REV | ATCCAGCAACCACTCGGTTTAT CCCCGCTGGCGCGGGGAACTC GAGGTGGTACCAGATCT | 83 | |
| udhA | *TCGAGTTCCCCGCGCCAGCGGG GATAAACCGTTACCATTCTGTT GCTTTTATGTATAAGAATCGAG TTCCCCGCGCCAGCGGGGATAA ACCG* | 84 | |
| udhA-FOR | TTTTATGTATAAGAA*TCGAGTT CCCCGCGCCAGCGGGGATAAAC CGAAAAAAAAACCCC* | 85 | pCASCADE control |
| udhA-REV | GCAACAGAATGGTAACGGTTT ATCCCCGCTGGCGCGGGGAAC TCGAGGTGGTACCAGATC | 86 | |
| zwf | *TCGAGTTCCCCGCGCCAGCGGG GATAAACCGCTCGTAAAAGCAG TACAGTGCACCGTAAGATCGA GTTCCCCGCGCCAGCGGGGATA AACCG* | 87 | |
| zwf-FOR | CAGTGCACCGTAAGATCGAGTT*CCCCGCGCCAGCGGGGATAAAC CGAAAAAAAAACCCC* | 88 | pCASCADE control |

TABLE 9-continued

List of sgRNA guide sequences and primers used to construct them. Spacers are italicized.

| sgRNA/Primer Name | Sequence | SEQ ID NO | Template |
|---|---|---|---|
| zwf-REV | TACTGCTTTTACGAGCGGTTTA TCCCCGCTGGCGCGGGGAACT CGAGGTGGTACCAGATC | 89 | |
| FG1 | *TCGAGTTCCCCGCGCCAGCGGG GATAAACCGTTGATTATAATAA CCGTTTATCTGTTCGTAT*CGAG TT*CCCCGCGCCAGCGGGGATAA ACC*GAAAAGCATATAATGCGT AAAAGTTATGAAGT*TCGAGTTC CCCGCGCCAGCGGGGATAAACC G* | 90 | |
| gltA1-FOR | GCGCCAGCGGGGATAAACCGA AAAGCATATAATGCG | 91 | pCASCADE-gltA1 |
| pCASCADE-REV | CTTGCCCGCCTGATGAATGCTC ATCCGG | 92 | |
| pCASCADE-FOR | CCGGATGAGCATTCATCAGGC GGGCAAG | 93 | pCASCADE-fabI |
| fabI-REV | CGGTTTATCCCCGCTGGCGCG GGGAACTCGATACGAACAGAT AAACGGTTATTATAATC | 94 | |
| FG2 | *TCGAGTTCCCCGCGCCAGCGGG GATAAACCGTTGATTATAATAA CCGTTTATCTGTTCGTAT*CGAG TT*CCCCGCGCCAGCGGGGATAA ACC*GTATTGACCAATTCATTCG GGACAGTTATTAGT*TCGAGTTC CCCGCGCCAGCGGGGATAAACC G* | 95 | |
| gltA2-FOR | GCGCCAGCGGGGATAAACCGT ATTGACCAATTCATTC | 96 | pCASCADE-gltA2 |
| pCASCADE-REV | CTTGCCCGCCTGATGAATGCTC ATCCGG | 97 | |
| pCASCADE-FOR | CCGGATGAGCATTCATCAGGC GGGCAAG | 98 | pCASCADE-fabI |
| fabI-REV | CGGTTTATCCCCGCTGGCGCG GGGAACTCGATACGAACAGAT AAACGGTTATTATAATC | 99 | |
| FU | *TCGAGTTCCCCGCGCCAGCGGG GATAAACCGTTGATTATAATAA CCGTTTATCTGTTCGTAT*CGAG TT*CCCCGCGCCAGCGGGGATAA ACC*GTTACCATTCTGTTGCTTT TATGTATAAGAA*TCGAGTTCCC CGCGCCAGCGGGGATAAACCG* | 100 | |
| udhA-FOR | GCGCCAGCGGGGATAAACCGT TACCATTCTGTTG | 101 | pCASCADE-udhA |
| pCASCADE-REV | CTTGCCCGCCTGATGAATGCTC ATCCGG | 102 | |
| pCASCADE-FOR | CCGGATGAGCATTCATCAGGC GGGCAAG | 103 | pCASCADE-fabI |
| fabI-REV | CGGTTTATCCCCGCTGGCGCG GGGAACTCGATACGAACAGAT AAACGGTTATTATAATC | 104 | |
| FZ | *TCGAGTTCCCCGCGCCAGCGGG GATAAACCGTTGATTATAATAA CCGTTTATCTGTTCGTAT*CGAG TT*CCCCGCGCCAGCGGGGATAA ACC*GCTCGTAAAAGCAGTACA GTGCACCGTAAGAT*CGAGTTCC CCGCGCCAGCGGGGATAAACCG* | 105 | |
| zwf-FOR | GCGCCAGCGGGGATAAACCGC TCGTAAAAG | 106 | pCASCADE-zwf |
| pCASCADE-REV | CTTGCCCGCCTGATGAATGCTC ATCCGG | 107 | |

TABLE 9-continued

List of sgRNA guide sequences and primers used to construct them. Spacers are italicized.

| sgRNA/Primer Name | Sequence | SEQ ID NO | Template |
|---|---|---|---|
| pCASCADE-FOR | CCGGATGAGCATTCATCAGGCGGGCAAG | 108 | pCASCADE-fabI |
| fabI-REV | CGGTTTATCCCCGCTGGCGCGGGGAACTCGATACGAACAGATAAACGGTTATTATAATC | 109 | |
| G1G2 | *TCGAGTTCCCCGCGCCAGCGGGGATAAACCGAAAAGCATATAATGCGTAAAAGTTATGAAGTTCGAGTTCCCCGCGCCAGCGGGGATAAACCGTATTGACCAATTCATTCGGGACAGTTATTAGTTCGAGTTCCCCGCGCCAGCGGGGATAAACCG* | 110 | |
| gltA2-FOR | GCGCCAGCGGGGATAAACCGT*ATTGACCAATTCATTC* | 111 | pCASCADE-gltA2 |
| pCASCADE-REV | CTTGCCCGCCTGATGAATGCTCATCCGG | 112 | |
| pCASCADE-FOR | CCGGATGAGCATTCATCAGGCGGGCAAG | 113 | pCASCADE-gltA1 |
| gltA1-REV | CGGTTTATCCCCGCTGGCGCGGGGAACTCGAACTTCATAACTTTTAC | 114 | |
| G1U | *TCGAGTTCCCCGCGCCAGCGGGGATAAACCGAAAAGCATATAATGCGTAAAAGTTATGAAGTTCGAGTTCCCCGCGCCAGCGGGGATAAACCGTTACCATTCTGTTGCTTTTATGTATAAGAATCGAGTTCCCCGCGCCAGCGGGGATAAACCG* | 115 | |
| udhA-FOR | GCGCCAGCGGGGATAAACCGT*TACCATTCTGTTG* | 116 | pCASCADE-udhA |
| pCASCADE-REV | CTTGCCCGCCTGATGAATGCTCATCCGG | 117 | |
| pCASCADE-FOR | CCGGATGAGCATTCATCAGGCGGGCAAG | 118 | pCASCADE-gltA1 |
| gltA1-REV | CGGTTTATCCCCGCTGGCGCGGGGAACTCGAACTTCATAACTTTTAC | 119 | |
| G1Z | *TCGAGTTCCCCGCGCCAGCGGGGATAAACCGAAAAGCATATAATGCGTAAAAGTTATGAAGTTCGAGTTCCCCGCGCCAGCGGGGATAAACCGCTCGTAAAAGCAGTACAGTGCACCGTAAGATCGAGTTCCCCGCGCCAGCGGGGATAAACCG* | 120 | |
| zwf-FOR | GCGCCAGCGGGGATAAACCGC*TCGTAAAAG* | 121 | pCASCADE-zwf |
| pCASCADE-REV | CTTGCCCGCCTGATGAATGCTCATCCGG | 122 | |
| pCASCADE-FOR | CCGGATGAGCATTCATCAGGCGGGCAAG | 123 | pCASCADE-gltA1 |
| gltA1-REV | CGGTTTATCCCCGCTGGCGCGGGGAACTCGAACTTCATAACTTTTAC | 124 | |
| G2U | *TCGAGTTCCCCGCGCCAGCGGGGATAAACCGTATTGACCAATTCATTCGGGACAGTTATTAGTTCGAGTTCCCCGCGCCAGCGGGGATAAACCGTTACCATTCTGTTGCTTTTATGTATAAGAATCGAGTTCCCCGCGCCAGCGGGGATAAACCG* | 125 | |

TABLE 9-continued

List of sgRNA guide sequences and primers used to construct them. Spacers are italicized.

| sgRNA/Primer Name | Sequence | SEQ ID NO | Template |
| --- | --- | --- | --- |
| udhA-FOR | GCGCCAGCGGGGATAAACCGT TACCATTCTGTTG | 126 | pCASCADE-udhA |
| pCASCADE-REV | CTTGCCCGCCTGATGAATGCTC ATCCGG | 127 | |
| pCASCADE-FOR | CCGGATGAGCATTCATCAGGC GGGCAAG | 128 | pCASCADE-gltA2 |
| gltA2-REV | CGGTTTATCCCCGCTGGCGCG GGGAACTCGAACTAATAACTG TC | 129 | |
| G2Z | *TCGAGTTCCCCGCGCCAGCGGG GATAAACCGTATTGACCAATTCA TTCGGGACAGTTATTAGTTCGA GTTCCCCGCGCCAGCGGGGATA AACCGCTCGTAAAAGCAGTAC AGTGCACCGTAAGATCGAGTTC CCCGCGCCAGCGGGGATAAACC G* | 130 | |
| zwf-FOR | GCGCCAGCGGGGATAAACCGC TCGTAAAAG | 131 | pCASCADE-zwf |
| pCASCADE-REV | CTTGCCCGCCTGATGAATGCTC ATCCGG | 132 | |
| pCASCADE-FOR | CCGGATGAGCATTCATCAGGC GGGCAAG | 133 | pCASCADE-gltA2 |
| gltA2-REV | CGGTTTATCCCCGCTGGCGCG GGGAACTCGAACTAATAACTG TC | 134 | |
| UZ | *TCGAGTTCCCCGCGCCAGCGGG GATAAACCGTTACCATTCTGTT GCTTTTATGTATAAGAATCGAG TTCCCCGCGCCAGCGGGGATAA ACCGCTCGTAAAAGCAGTACA GTGCACCGTAAGATCGAGTTCC CCGCGCCAGCGGGGATAAACCG* | 135 | |
| zwf-FOR | GCGCCAGCGGGGATAAACCGC TCGTAAAAG | 136 | pCASCADE-zwf |
| pCASCADE-REV | CTTGCCCGCCTGATGAATGCTC ATCCGG | 137 | |
| pCASCADE-FOR | CCGGATGAGCATTCATCAGGC GGGCAAG | 138 | pCASCADE-udhA |
| udhA-REV | CGGTTTATCCCCGCTGGCGCG GGGAACTCGATTCTTATACAT AAAAGC | 139 | |
| FG1G2 | *TCGAGTTCCCCGCGCCAGCGGG GATAAACCGTTGATTATAATAA CCGTTTATCTGTTCGTATCGAG TTCCCCGCGCCAGCGGGGATAA ACCGAAAAGCATATAATGCGT AAAAGTTATGAAGTTCGAGTTC CCGCGCCAGCGGGGATAAACC GTATTGACCAATTCATTCGGG ACAGTTATTAGTTCGAGTTCCC CGCGCCAGCGGGGATAAACCG* | 140 | |
| gltA2-FOR | GCGCCAGCGGGGATAAACCGT ATTGACCAATTCATTC | 141 | pCASCADE-gltA2 |
| pCASCADE-REV | CTTGCCCGCCTGATGAATGCTC ATCCGG | 142 | |
| pCASCADE-FOR | CCGGATGAGCATTCATCAGGC GGGCAAG | 143 | pCASCADE-FG1 |
| gltA1-REV | CGGTTTATCCCCGCTGGCGCG GGGAACTCGAACTTCATAACT TTTAC | 144 | |
| G1G2A | *TCGAGTTCCCCGCGCCAGCGGG GATAAACCGAAAAGCATATAAT* | 145 | |

TABLE 9-continued

List of sgRNA guide sequences and primers used to construct them. Spacers are italicized.

| sgRNA/Primer Name | Sequence | SEQ ID NO | Template |
|---|---|---|---|
| | GCGTAAAAGTTATGAAGT*TCG* *AGTTCCCCGCGCCAGCGGGGAT* *AAACCGTATTGACCAATTCATT* *CGGGACAGTTATTAGT*TCGAGT *TCCCCGCGCCAGCGGGGATAAA* *CCGGTTTTTGTAATTTTACAGG* *CAACCTTTTATT*TCGAGTTCCCC *GCGCCAGCGGGGATAAACCG* | | |
| gapAP1-FOR | GCGCCAGCGGGGATAAACCGG TTTTTGTAATTTTACAGGC | 146 | pCASCADE-gapAP1 |
| pCASCADE-REV | CTTGCCCGCCTGATGAATGCTC ATCCGG | 147 | |
| pCASCADE-FOR | CCGGATGAGCATTCATCAGGC GGGCAAG | 148 | pCASCADE-G1G2 |
| gltA2-REV | CGGTTTATCCCCGCTGGCGCG GGGAACTCGAACTAATAACTG TC | 149 | |
| G1G2U | *TCGAGTTCCCCGCGCCAGCGGG* *GATAAACCGAAAAGCATATAAT* GCGTAAAAGTTATGAAGT*TCG* *AGTTCCCCGCGCCAGCGGGGAT* *AAACCGTATTGACCAATTCATT* *CGGGACAGTTATTAGT*TCGAGT *TCCCCGCGCCAGCGGGGATAAA* *CCGTTACCATTCTGTTGCTTTT* *ATGTATAAGAA*TCGAGTTCCCC *GCGCCAGCGGGGATAAACCG* | 150 | |
| udhA-FOR | GCGCCAGCGGGGATAAACCGT TACCATTCTGTTG | 151 | pCASCADE-udhA |
| pCASCADE-REV | CTTGCCCGCCTGATGAATGCTC ATCCGG | 152 | |
| pCASCADE-FOR | CCGGATGAGCATTCATCAGGC GGGCAAG | 153 | pCASCADE-G1G2 |
| gltA2-REV | CGGTTTATCCCCGCTGGCGCG GGGAACTCGAACTAATAACTG TC | 154 | |
| G1G2Z | *TCGAGTTCCCCGCGCCAGCGGG* *GATAAACCGAAAAGCATATAAT* GCGTAAAAGTTATGAAGT*TCG* *AGTTCCCCGCGCCAGCGGGGAT* *AAACCGTATTGACCAATTCATT* *CGGGACAGTTATTAGT*TCGAGT *TCCCCGCGCCAGCGGGGATAAA* *CCGCTCGTAAAAGCAGTACAG* *TGCACCGTAAGA*TCGAGTTCCC *CGCGCCAGCGGGGATAAACCG* | 155 | |
| zwf-FOR | GCGCCAGCGGGGATAAACCGC TCGTAAAAG | 156 | pCASCADE-zwf |
| pCASCADE-REV | CTTGCCCGCCTGATGAATGCTC ATCCGG | 157 | |
| pCASCADE-FOR | CCGGATGAGCATTCATCAGGC GGGCAAG | 158 | pCASCADE-G1G2 |
| gltA2-REV | CGGTTTATCCCCGCTGGCGCG GGGAACTCGAACTAATAACTG TC | 159 | |
| FG1G2A | *TCGAGTTCCCCGCGCCAGCGGG* *GATAAACCGTGATTATAATAA* *CCGTTTATCTGTTCGTATCGAG* *TTCCCCGCGCCAGCGGGGATAA* *ACCGAAAAGCATATAATGCGT* AAAAGTTATGAAGT*TCGAGTTC* *CCCGCGCCAGCGGGGATAAACC* *GTATTGACCAATTCATTCGGG* ACAGTTATTAGT*TCGAGTTCCC* *CGCGCCAGCGGGGATAAACCGG* TTTTTGTAATTTTACAGGCAAC | 160 | |

TABLE 9-continued

List of sgRNA guide sequences and primers used to construct them. Spacers are italicized.

| sgRNA/Primer Name | Sequence | SEQ ID NO | Template |
|---|---|---|---|
| | CTTTTAT*TCGAGTTCCCCGCGC CAGCGGGGATAAACCG* | | |
| gapAP1-FOR | GCGCCAGCGGGGATAAACCGG TTTTTGTAATTTTACAGGC | 161 | pCASCADE-gapAP1 |
| pCASCADE-REV | CTTGCCCGCCTGATGAATGCTC ATCCGG | 162 | |
| pCASCADE-FOR | CCGGATGAGCATTCATCAGGC GGGCAAG | 163 | pCASCADE-FG1G2 |
| gltA2-REV | CGGTTTATCCCCGCTGGCGCG GGGAACTCGAACTAATAACTG TC | 164 | |
| FG1G2U | *TCGAGTTCCCCGCGCCAGCGGG GATAAACCGTTGATTATAATAA CCGTTTATCTGTTCGTATCGAG TTCCCCGCGCCAGCGGGGATAA ACCGAAAAGCATATAATGCGT AAAAGTTATGAAGTTCGAGTTC CCCGCGCCAGCGGGGATAAACC GTATTGACCAATTCATTCGGG ACAGTTATTAGTTCGAGTTCCC CGCGCCAGCGGGGATAAACCGT TACCATTCTGTTGCTTTTATGT ATAAGAATCGAGTTCCCCGCGC CAGCGGGGATAAACCG* | 165 | |
| gltA2-FOR | GCGCCAGCGGGGATAAACCGT *ATTGACCAATTCATTC* | 166 | pCASCADE-udhA |
| pCASCADE-REV | CTTGCCCGCCTGATGAATGCTC ATCCGG | 167 | |
| pCASCADE-FOR | CCGGATGAGCATTCATCAGGC GGGCAAG | 168 | pCASCADE-FG1G2 |
| gltA1-REV | CGGTTTATCCCCGCTGGCGCG GGGAACTCGAACTTATAACT TTTAC | 169 | |
| FG1G2Z | *TCGAGTTCCCCGCGCCAGCGGG GATAAACCGTTGATTATAATAA CCGTTTATCTGTTCGTATCGAG TTCCCCGCGCCAGCGGGGATAA ACCGAAAAGCATATAATGCGT AAAAGTTATGAAGTTCGAGTTC CCCGCGCCAGCGGGGATAAACC GTATTGACCAATTCATTCGGG ACAGTTATTAGTTCGAGTTCCC CGCGCCAGCGGGGATAAACCGC TCGTAAAAGCAGTACAGTGCA CCGTAAGATCGAGTTCCCCGCG CCAGCGGGGATAAACCG* | 170 | |
| gltA2-FOR | GCGCCAGCGGGGATAAACCGT *ATTGACCAATTCATTC* | 171 | pCASCADE-zwf |
| pCASCADE-REV | CTTGCCCGCCTGATGAATGCTC ATCCGG | 172 | |
| pCASCADE-FOR | CCGGATGAGCATTCATCAGGC GGGCAAG | 173 | pCASCADE-FG1G2 |
| gltA1-REV | CGGTTTATCCCCGCTGGCGCG GGGAACTCGAACTTATAACT TTTAC | 174 | |
| G1G2UA | *TCGAGTTCCCCGCGCCAGCGGG GATAAACCGAAAAGCATATAAT GCGTAAAAGTTATGAAGTTCG AGTTCCCCGCGCCAGCGGGGAT AAACCGTATTGACCAATTCATT CGGGACAGTTATTAGTTCGAGT TCCCCGCGCCAGCGGGGATAAA CCGTTACCATTCTGTTGCTTTT ATGTATAAGAATCGAGTTCCCC GCGCCAGCGGGGATAAACCGGT TTTTGTAATTTTACAGGCAAC* | 175 | |

TABLE 9-continued

List of sgRNA guide sequences and primers used to construct them. Spacers are italicized.

| sgRNA/Primer Name | Sequence | SEQ ID NO | Template |
|---|---|---|---|
| | CTTTTAT*TCGAGTTCCCCGCGC CAGCGGGGATAAACCG* | | |
| gapAP1-FOR | GCGCCAGCGGGGATAAACCGG TTTTTGTAATTTTACAGGC | 176 | pCASCADE-gapAP1 |
| pCASCADE-REV | CTTGCCCGCCTGATGAATGCTC ATCCGG | 177 | |
| pCASCADE-FOR | CCGGATGAGCATTCATCAGGC GGGCAAG | 178 | pCASCADE-G1G2U |
| udhA-REV | CGGTTTATCCCCGCTGGCGCG GGGAACTCGATTCTTATACAT AAAAGC | 179 | |
| G1G2UZ | *TCGAGTTCCCCGCGCCAGCGGG GATAAACCGAAAAGCATATAAT GCGTAAAAGTTATGAAGTTCG AGTTCCCCGCGCCAGCGGGGAT AAACCGTATTGACCAATTCATT CGGGACAGTTATTAGTTCGAGT TCCCCGCGCCAGCGGGGATAAA CCGTTACCATTCTGTTGCTTTT ATGTATAAGAATCGAGTTCCCC GCGCCAGCGGGGATAAACCGCT CGTAAAAGCAGTACAGTGCAC CGTAAGATCGAGTTCCCCGCGC CAGCGGGGATAAACCG* | 180 | |
| zwf-FOR | GCGCCAGCGGGGATAAACCGC TCGTAAAAG | 181 | pCASCADE-zwf |
| pCASCADE-REV | CTTGCCCGCCTGATGAATGCTC ATCCGG | 182 | |
| pCASCADE-FOR | CCGGATGAGCATTCATCAGGC GGGCAAG | 183 | pCASCADE-G1G2U |
| udhA-REV | CGGTTTATCCCCGCTGGCGCG GGGAACTCGATTCTTATACAT AAAAGC | 184 | |
| FG1G2UA | *TCGAGTTCCCCGCGCCAGCGGG GATAAACCGTTGATTATAATAA CCGTTTATCTGTTCGTATCGAG TTCCCCGCGCCAGCGGGGATAA ACCGAAAAGCATATAATGCGT AAAAGTTATGAAGTTCGAGTTC CCCGCGCCAGCGGGGATAAACC GTATTGACCAATTCATTCGGG ACAGTTATTAGTTCGAGTTCCC CGCGCCAGCGGGGATAAACCGT TACCATTCTGTTGCTTTTATGT ATAAGAATCGAGTTCCCCGCGC CAGCGGGGATAAACCGGTTTTT GTAATTTTACAGGCAACCTTT TATTCGAGTTCCCCGCGCCAGC GGGGATAAACCG* | 185 | |
| gapAP1-FOR | GCGCCAGCGGGGATAAACCGG TTTTTGTAATTTTACAGGC | 186 | pCASCADE-gapAP1 |
| pCASCADE-REV | CTTGCCCGCCTGATGAATGCTC ATCCGG | 187 | |
| pCASCADE-FOR | CCGGATGAGCATTCATCAGGC GGGCAAG | 188 | pCASCADE-FG1G2U |
| udhA-REV | CGGTTTATCCCCGCTGGCGCG GGGAACTCGATTCTTATACAT AAAAGC | 189 | |
| FG1G2UZ | *TCGAGTTCCCCGCGCCAGCGGG GATAAACCGTTGATTATAATAA CCGTTTATCTGTTCGTATCGAG TTCCCCGCGCCAGCGGGGATAA ACCGAAAAGCATATAATGCGT AAAAGTTATGAAGTTCGAGTTC CCCGCGCCAGCGGGGATAAACC GTATTGACCAATTCATTCGGG* | 190 | |

TABLE 9-continued

List of sgRNA guide sequences and primers used to construct them. Spacers are italicized.

| sgRNA/Primer Name | Sequence | SEQ ID NO | Template |
|---|---|---|---|
| | *ACAGTTATTAGTTCGAGTTCCC CGCGCCAGCGGGGATAAACCGT* TACCATTCTGTTGCTTTTATGT ATAAGAA*TCGAGTTCCCCGCGC CAGCGGGGATAAACCGCTCGTA* AAAGCAGTACAGTGCACCGTA AGA*TCGAGTTCCCCGCGCCAGC GGGGATAAACCG* | | |
| zwf-FOR | GCGCCAGCGGGGATAAACCGC TCGTAAAAG | 191 | pCASCADE-zwf |
| pCASCADE-REV | CTTGCCCGCCTGATGAATGCTC ATCCGG | 192 | |
| pCASCADE-FOR | CCGGATGAGCATTCATCAGGC GGGCAAG | 193 | pCASCADE-FG1G2U |
| udhA-REV | CGGTTTATCCCCGCTGGCGCG GGAACTCGATTCTTATACAT AAAAGC | 194 | |
| FG1G2UZA | *TCGAGTTCCCCGCGCCAGCGGG GATAAACCGT*TGATTATAATAA CCGTTTATCTGTTCGTATCGAG *TTCCCCGCGCCAGCGGGGATAA ACCG*AAAAGCATATAATGCGT AAAAGTTATGAAGT*TCGAGTTC CCCGCGCCAGCGGGGATAAACC GT*ATTGACCAATTCATTCGGG ACAGTTATTAGT*TCGAGTTCCC CGCGCCAGCGGGGATAAACCGT* TACCATTCTGTTGCTTTTATGT ATAAGAA*TCGAGTTCCCCGCGC CAGCGGGGATAAACCGCTCGTA* AAAGCAGTACAGTGCACCGTA AGA*TCGAGTTCCCCGCGCCAGC GGGGATAAACCG*GTTTTGTAA TTTTACAGGCAACCTTTTAT*TC GAGTTCCCCGCGCCAGCGGGGA TAAACCG* | 195 | |
| gapAP1-FOR | GCGCCAGCGGGGATAAACCGG TTTTTGTAATTTTACAGGC | 196 | pCASCADE-gapAP1 |
| pCASCADE-REV | CTTGCCCGCCTGATGAATGCTC ATCCGG | 197 | |
| pCASCADE-FOR | CCGGATGAGCATTCATCAGGC GGGCAAG | 198 | pCASCADE-FG1G2UZ |
| zwf-REV | CGGTTTATCCCCGCTGGCGCG GGAACTCGATCTTACGGTGC ACTGTAC | 199 | |
| UZ | *TCGAGTTCCCCGCGCCAGCGGG GATAAACCGT*TACCATTCTGTT GCTTTTATGTATAAGAA*TCGAG TTCCCCGCGCCAGCGGGGATAA ACCG*CTCGTAAAAGCAGTACA GTGCACCGTAAGA*TCGAGTTCC CCGCGCCAGCGGGGATAAACCG* | 200 | |
| zwf-FOR | GCGCCAGCGGGGATAAACCGC TCGTAAAAG | 201 | pCASCADE-zwf |
| pCASCADE-REV | CTTGCCCGCCTGATGAATGCTC ATCCGG | 202 | |
| pCASCADE-FOR | CCGGATGAGCATTCATCAGGC GGGCAAG | 203 | pCASCADE-udhA |
| udhA-REV | CGGTTTATCCCCGCTGGCGCG GGAACTCGATTCTTATACAT AAAAGC | 204 | |

TABLE 10

List of plasmids used in this study.

Plasmid Utilized in this Study

| Plasmid | Purpose | Source |
|---|---|---|
| pSIM5 | Recombineering and Strain Construction | Court Lab[54] |
| pCP20 | FRT kanamycin cassette curing | Court Lab[54] |
| pSMART-HC-Kan | Backbone Vector | Lucigen |
| pcrRNA.Tet | pCASCADE-control backbone | Beisel Lab[34] |

Plasmid Constructed in this Study

| Plasmid | Plasmid Name | Addgene ID |
|---|---|---|
| pSMART-Ala2 | pSMART-HCKan-IN:yibDp-ald* | 71326 |
| pSMART-Ala3 | pSMART-HCKan-IN:phoBp-ald* | 71327 |
| pSMART-Ala4 | pSMART-HCKan-IN:phoHp-ald* | 71328 |
| pSMART-Ala5 | pSMART-HCKan-IN:mipAp-ald* | 71329 |
| pSMART-Ala11 | pSMART-HCKan-proA-ald* | 87172 |
| pSMART-Ala12 | pSMART-HCKan-proC-ald* | 87173 |
| pSMART-Ala13 | pSMART-HCKan-proD-ald* | 87174 |
| pSMART-Ala14 | pSMART-HCKan-proB-ald* | 101079 |
| pSMART-Ala15 | pSMART-HCKan-HCEp-ald* | 101080 |
| pSMART-Mev2 | pSMART-IN:yibDp1-mvaE-IN:phoBp2-mvaS(A110G) | 66642 |
| pSMART-Mev3 | pSMART-IN:yibDp1-mvaE-IN:mipAp2-mvaS(A110G) | 102761 |
| pSMART-Mev4 | pSMART-IN:yibDp1-mvaE-IN:phoHp2-mvaS(A110G) | 102762 |
| pSMART-Mev5 | pSMART-IN:mipAp1-mvaE-IN:yibD2-mvaS(A110G) | 102763 |
| pSMART-3HP | pSMART-3HP-NADPH-rhtA | 87143 |
| pCDF-mcherry1 | pCDF-proD-mcherry | 87144 |
| pCDF-mcherry2 | pCDF-proD-mcherry-DAS4 | 87145 |
| pSMART-GFPuv | pSMART-IN:yibDp-GFPuv | 65822 |
| pSMART-GFPuv2 | pSMART-IN:phoBp-GFPuv | 71517 |
| pSMART-GFPuv3 | pSMART-IN:phoUp-GFPuv | 71518 |
| pSMART-GFPuv4 | pSMART-IN:phoHp-GFPuv | 71519 |
| pSMART-GFPuv5 | pSMART-IN:mipAp-GFPuv | 71520 |
| pCASCADE-control | pCASCADE | 65821 |
| pCASCADE-proD | pCASCADE-proD | 65820 |
| pCASCADE-gapAP1 | pCASCADE-gapAP1 | 87146 |
| pCASCADE-fabI | pCASCADE-fabI | 66635 |
| pCASCADE-FG1 | pCASCADE-fabI-gltA1 | 71340 |
| pCASCADE-FG1G2 | pCASCADE-fabI-gltA1-gltA2 | 71342 |
| pCASCADE-FG1G2A | pCASCADE-fabI-gltAl-gltA2-gapA | 87147 |
| pCASCADE-FG1G2U | pCASCADE-fabI-gltA1-gltA2-udhA | 66637 |
| pCASCADE-FG1G2UA | pCASCADE-fabI-gltA1-gltA2-udhA-gapA | 87154 |
| pCASCADE-FG1G2UZ | pCASCADE-fabI-gltA1-gltA2-udhA-zwf | 87148 |
| pCASCADE-FG1G2UZA | pCASCADE-fabI-gltA1-gltA2-udhA-zwf-gapA | 87149 |
| pCASCADE-FG1G2Z | pCASCADE-fabI-gltA1-gltA2-zwf | 66638 |
| pCASCADE-FG2 | pCASCADE-fabI-gltA2 | 71341 |
| pCASCADE-FU | pCASCADE-fabI-udhA | 66636 |
| pCASCADE-FZ | pCASCADE-fabI-zwf | 71335 |
| pCASCADE-G1G2 | pCASCADE-gltA1-gltA2 | 71348 |
| pCASCADE-G1G2A | pCASCADE-gltA1-gltA2-gapA | 87150 |
| pCASCADE-G1G2U | pCASCADE-gltA1-gltA2-udhA | 71343 |
| pCASCADE-GIG2UA | pCASCADE-gltA1-gltA2-udhA-gapA | 87151 |
| pCASCADE-G1G2UZ | pCASCADE-gltA1-gltA2-udhA-zwf | 87152 |
| pCASCADE-G1G2Z | pCASCADE-gltA1-gltA2-zwf | 71347 |
| pCASCADE-G1U | pCASCADE-gltAl-udhA | 71339 |
| pCASCADE-G1Z | pCASCADE-gltA1-zwf | 71337 |
| pCASCADE-G2U | pCASCADE-gltA2-udhA | 65819 |
| pCASCADE-G2Z | pCASCADE-gltA2-zwf | 71338 |
| pCASCADE-gltA1 | pCASCADE-gltA1 | 71334 |
| pCASCADE-gltA2 | pCASCADE-gltA2 | 65817 |
| pCASCADE-udhA | pCASCADE-udhA | 65818 |
| pCASCADE-UZ | pCASCADE-udhA-zwf | 87153 |
| pCASCADE-zwf | pCASCADE-zwf | 65825 |

Section 7: 2-Stage Micro-Fermentations

*E. coli* Media Stock Solutions

10× concentrated Ammonium-Citrate 30 salts (1 L), mix 30 g of $(NH_4)_2SO_4$ and 1.5 g citric acid in water with stirring, adjust pH to 7.5 with 10 M NaOH. Autoclave and store at room temperature (RT).

10× concentrated Ammonium-Citrate 90 salts (1 L), mix 90 g of $(NH_4)_2SO_4$ and 2.5 g citric acid in water with stirring, adjust pH to 7.5 with 10 M NaOH. Autoclave and store at RT.

1 M Potassium 3-(N-morpholino) propanesulfonic Acid (MOPS), adjust to pH 7.4 with 5000 KOH. Filter sterilize (0.2 m) and store at RT.

0.5 M potassium phosphate buffer, pH 6.8, mix 248.5 mL of 1.0 M $K_2HPO_4$ and 251.5 mL of 1.0 M $KH_2PO4$ and adjust to a final volume of 1000 mL with ultrapure water. Filter sterilize (0.2 m) and store at RT.

2 M $MgSO_4$ and 10 mM $CaSO_4$ solutions. Filter sterilize (0.2 μm) and store at RT.

50 g/L solution of thiamine-HCl. Filter sterilize (0.2 m) and store at 4° C.
500 g/L solution of glucose, dissolve by stirring with heat. Cool, filter sterilize (0.2 μm), and store at RT.
100 g/L yeast extract, autoclave, and store at RT.
100 g/L casamino acid, autoclave, and store at RT.
500× Trace Metal Stock: Prepare a solution of micronutrients in 1000 mL of water containing 10 mL of concentrated $H_2SO_4$·0.6 g $CoSO_4$·$7H_2O$, 5.0 g $CuSO_4$·$5H_2O$, 0.6 g $ZnSO_4$·$7H_2O$, 0.2 g $Na_2MoO_4$·$2H_2O$, 0.1 g $H_3BO_3$, and 0.3 g $MnSO_4$·$H_2O$. Filter sterilize (0.2 μm) and store at RT in the dark.
Prepare a fresh solution of 40 mM ferric sulfate heptahydrate in water, filter sterilize (0.2 μm) before preparing media each time.

Media Components

Prepare the final working medium by aseptically mixing stock solutions based on the following tables in the order written to minimize precipitation, then filter sterilize (with a 0.2 μm filter).

TABLE 11

Seed Media, pH 6.8:

| Ingredient | Unit | SM10 | SM10++ |
|---|---|---|---|
| $(NH_4)_2SO_4$ | g/L | 9 | 9 |
| Citric Acid | g/L | 0.25 | 0.25 |
| Potassium Phosphate | mM | 5 | 5 |
| $CoSO_4$•$7H_2O$ | g/L | 0.0048 | 0.0048 |
| $CuSO_4$•$5H_2O$ | g/L | 0.04 | 0.04 |
| $ZnSO_4$•$7H_2O$ | g/L | 0.0048 | 0.0048 |
| $Na_2MoO_4$•$2H_2O$ | g/L | 0.0016 | 0.0016 |
| $H_3BO_3$ | g/L | 0.0008 | 0.0008 |
| $MnSO_4$•$H_2O$ | g/L | 0.0024 | 0.0024 |
| $FeSO_4$•$7H_2O$ | g/L | 0.044 | 0.044 |
| $MgSO_4$ | mM | 2.5 | 2.5 |
| $CaSO_4$ | mM | 0.06 | 0.06 |
| Glucose | g/L | 45 | 45 |
| MOPS | mM | 200 | 200 |
| Thiamine-HCl | g/L | 0.01 | 0.01 |
| Yeast Extract | g/L | 1 | 2.5 |
| Casamino Acids | g/L | 0 | 2.5 |

TABLE 12

Production/Wash Media, pH 6.8:

| Ingredient | Unit | FGM3 | FGM3 No Phosphate | FGM3 Wash | FGM3 + 40 mM phosphate | FGM10 |
|---|---|---|---|---|---|---|
| $(NH_4)_2SO_4$ | g/L | 3 | 3 | 3 | 3 | 9 |
| Citric Acid | g/L | 0.15 | 0.15 | 0.15 | 0.15 | 0.25 |
| Potassium Phosphate | mM | 1.8 | 0 | 0 | 40 | 5 |
| $CoSO_4$•$7H_2O$ | g/L | 0.0024 | 0.0024 | 0 | 0.0024 | 0.0048 |
| $CuSO_4$•$5H_2O$ | g/L | 0.02 | 0.02 | 0.00 | 0.02 | 0.04 |
| $ZnSO_4$•$7H_2O$ | g/L | 0.0024 | 0.0024 | 0 | 0.0024 | 0.0048 |
| $Na_2MoO_4$•$2H_2O$ | g/L | 0.0008 | 0.0008 | 0 | 0.0008 | 0.0016 |
| $H_3BO_3$ | g/L | 0.0004 | 0.0004 | 0 | 0.0004 | 0.0008 |
| $MnSO_4$•$H_2O$ | g/L | 0.0012 | 0.0012 | 0 | 0.0012 | 0.0024 |
| $FeSO_4$•$7H_2O$ | g/L | 0.022 | 0.022 | 0 | 0.022 | 0.044 |
| $MgSO_4$ | mM | 2 | 2 | 0 | 2 | 2.5 |
| $CaSO_4$ | mM | 0.05 | 0.05 | 0 | 0.05 | 0.06 |
| Glucose | g/L | 45 | 25 | 0 | 45 | 25 |
| MOPS | mM | 200 | 200 | 0 | 200 | 0 |
| Thiamine-HCl | g/L | 0.01 | 0.01 | 0 | 0.01 | 0.01 |

Micro-Fermentations

Figure 16A:
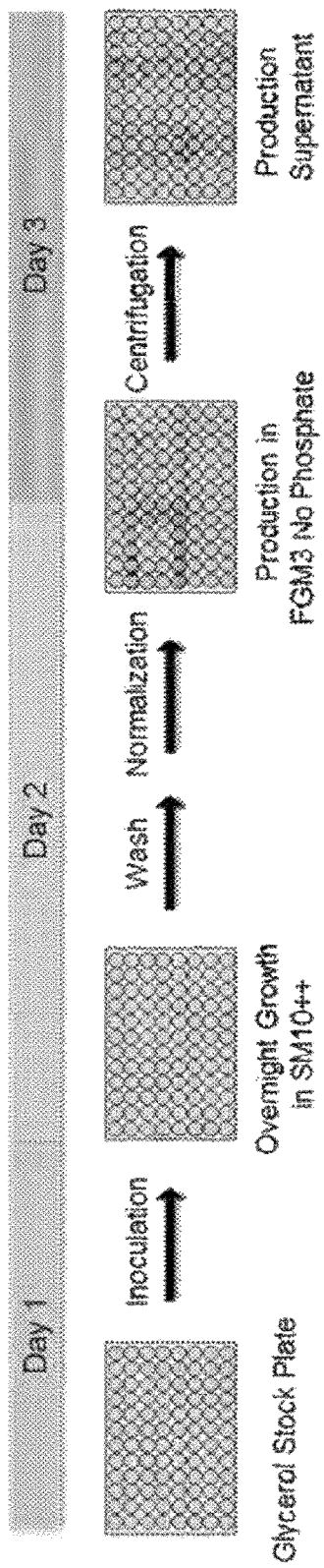
FIGS. 16A-C depict an overview of micro-fermentation process.
Figure 16C:
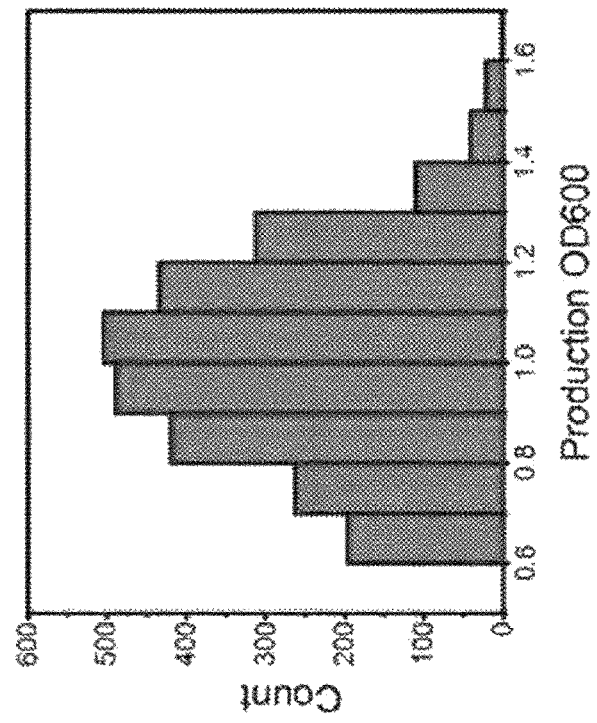
Figure 16B:
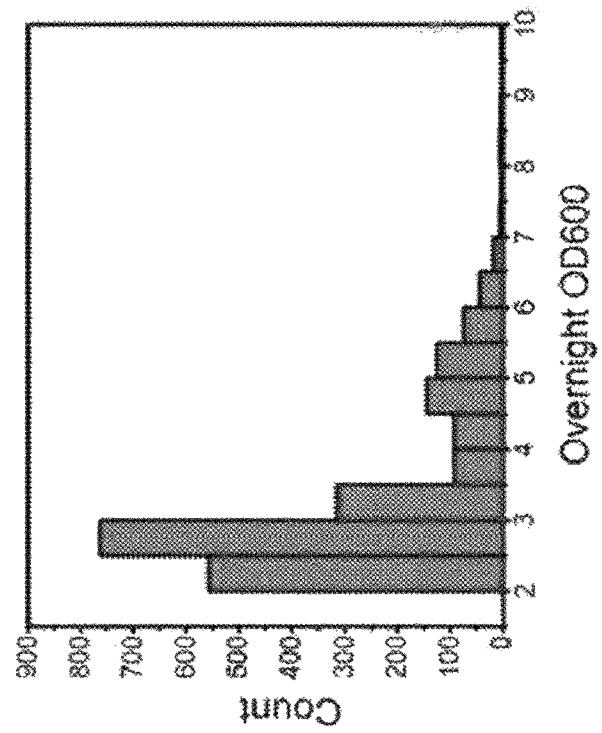
Figure 7:
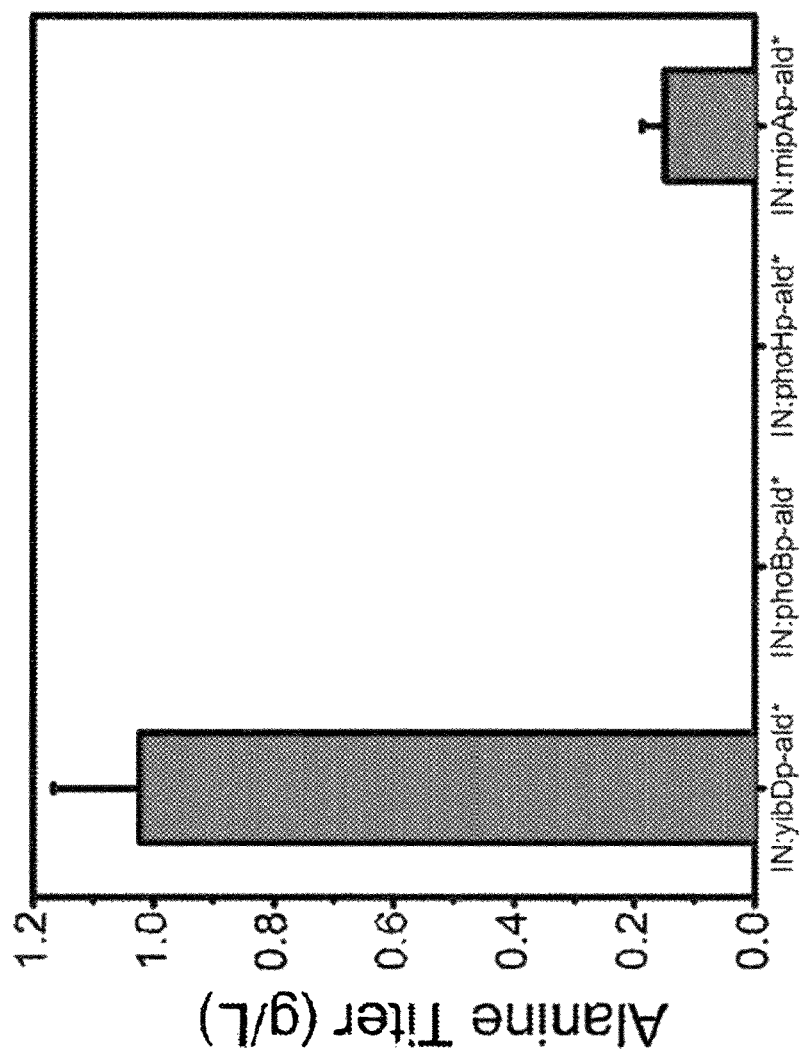

An overview of the micro-fermentation protocol is illustrated in FIG. 16A-C. Strains were evaluated for production in 96 well plate micro-fermentations, wherein cells were initially grown to mid-log phase, harvested, washed, resuspended and normalized in a phosphate free production medium to an OD600=1, for a 24 hour production stage. The success of the micro-fermentations required: (1) syncing strains up by harvesting all strains in exponential phase; (2) the use of low biomass levels, so that batch sugar could be kept low while enabling significant potential product accumulation; and (3) a method to supply adequate mixing and aeration, while minimizing evaporative losses. To address the final requirement, commercially available microplate sandwich covers and clamps from EnzyScreen™ was used, which greatly reduce evaporative losses while enabling high levels of mixing and aeration in standard 25 mm orbit shakers operating at 400 rpm[92-93]. Micro-fermentation results for alanine production with different insulated phosphate promoters are shown in FIG. 17. Micro-fermentation results for strains evaluated with gapA and gapN gene alterations are given in FIG. 18.

Section 8: Micro-Fermentations Robustness Evaluation

During micro-fermentation oxygen robustness studies, production culture volume was varied to achieve desired oxygen transfer rate (OTR) values as previously reported (http://www.enzyscreen.com/oxygen_transfer_rates.htm)[92-93], and as listed below in Table 14. Batch glucose levels during the production stage were altered to assess robustness to glucose. Strains utilized in the robustness experiments at the micro-fermentation scale are listed in Table 15. Results from the micro-fermentation robustness studies are given in FIGS. 19A-D, FIGS. 20A-D, FIGS. 21A-D, FIGS. 22A-D, FIGS. 23A-D, FIGS. 24A-D, FIGS. 25A-D, FIGS. 26A-D, FIGS. 27A-D, FIGS. 28A-D, FIGS. 29A-D, FIGS. 30A-D, FIGS. 31A-D, and FIG. 32.

TABLE 14

Culture conditions for different OTR values.
25 mm orbit shaker

| Max OTR (mmol/L-hr) | Shaking Speed (rpm) | Fill Volume (μL) |
|---|---|---|
| 25 | 400 | 100 |
| 20 | 400 | 150 |
| 15 | 400 | 200 |

TABLE 15

List of strains used for micro-fermentation robustness evaluations and their RS scores.

| Strain # | Silencing | Proteolysis | Plasmid | RS |
|---|---|---|---|---|
| 1 | gltA1 | FU | pSMART-Ala2 | 89.6 |
| 2 | gltA1 | F | pSMART-Ala2 | 89.5 |
| 3 | gltA1 | GU | pSMART-Ala2 | 89.4 |
| 4 | FG1G2 | None | pSMART-Ala2 | 89.3 |
| 5 | G1G2 | GU | pSMART-Ala2 | 88.8 |
| 6 | FG1G2 | G | pSMART-Ala2 | 88.2 |
| 7 | G1G2 | F | pSMART-Ala2 | 83.4 |
| 8 | gltA2 | FGU | pSMART-Ala2 | 83.4 |
| 9 | gltA1 | FGU | pSMART-Ala2 | 83.1 |
| 10 | G1G2 | FGU | pSMART-Ala2 | 82.3 |
| 11 | gltA2 | U | pSMART-Ala2 | 82.2 |
| 12 | gltA2 | F | pSMART-Ala2 | 80.6 |
| 13 | FG1G2 | FG | pSMART-Ala2 | 80.5 |
| 14 | None | G | pSMART-Ala2 | 79.9 |
| 15 | gltA2 | GU | pSMART-Ala2 | 77.9 |
| 16 | fabI | FGU | pSMART-Ala2 | 75.7 |
| 17 | None | FG | pSMART-Ala2 | 75.4 |
| 18 | G1G2 | FU | pSMART-Ala2 | 75.3 |
| 19 | None | FGU | pSMART-Ala2 | 73.4 |
| 20 | None | FU | pSMART-Ala2 | 73.3 |
| 21 | gltA1 | U | pSMART-Ala2 | 72.9 |
| 22 | fabI | FG | pSMART-Ala2 | 69.1 |
| 23 | FG1G2 | FU | pSMART-Ala2 | 67.6 |
| 24 | gltA2 | FU | pSMART-Ala2 | 67.5 |
| 25 | None | F | pSMART-Ala2 | 65.6 |
| 26 | gltA2 | FG | pSMART-Ala2 | 62.1 |
| 27 | FG1G2 | F | pSMART-Ala2 | 61.1 |
| 28 | fabI | GU | pSMART-Ala2 | 59.9 |
| 29 | fabI | F | pSMART-Ala2 | 59.6 |
| 30 | gltA1 | FG | pSMART-Ala2 | 58.1 |
| 31 | gltA1 | None | pSMART-Ala2 | 57.1 |
| 32 | None | None | pSMART-Ala2 | 55.5 |
| 33 | G1G2 | None | pSMART-Ala2 | 54.1 |
| 34 | fabI | U | pSMART-Ala2 | 53.9 |
| 35 | gltA2 | G | pSMART-Ala2 | 52.8 |
| 36 | fabI | None | pSMART-Ala2 | 50.3 |
| 37 | fabI | FU | pSMART-Ala2 | 48.4 |
| 38 | gltA2 | None | pSMART-Ala2 | 47.8 |
| 39 | FG1G2 | FGU | pSMART-Ala2 | 44.6 |
| 40 | None | GU | pSMART-Ala2 | 42.9 |
| 41 | None | U | pSMART-Ala2 | 39.3 |
| 42 | fabI | G | pSMART-Ala2 | 39.2 |
| 43 | gltA1 | G | pSMART-Ala2 | 34.7 |
| 44 | G1G2 | FG | pSMART-Ala2 | 32.8 |
| 45 | FG1G2 | U | pSMART-Ala2 | 29.4 |
| 46 | FG1G2 | GU | pSMART-Ala2 | 24.3 |
| 47 | G1G2 | G | pSMART-Ala2 | 24.1 |
| 48 | G1G2 | U | pSMART-Ala2 | -25.3 |
| 49 | None | None | pSMART-Ala13 | 55.7 |
| 50 | None | None | pSMART-Ala12 | -31.5 |
| 51 | None | None | pSMART-Ala15 | -103.2 |
| 52 | None | None | pSMART-Ala11 | -114.1 |
| 53 | None | None | pSMART-Ala14 | -441.5 |

Section 9: Standardized 2-Stage Fermentations

A standardized phosphate limited 2-stage fermentation protocol was utilized for evaluation of all valve strains. This protocol yields highly reproducible growth stage results, with minimal strain to strain variability even with strains making different products. More significant variability was observed during the production stage as a result of differing feed rates and base utilization by different strains. FIG. 33A gives the growth curves for all valve strains with a 10 g·cdw/L biomass level in 1 L fermentations performed in this study. This consistency is contrasted to the more variable growth of growth associated production strains, given in FIG. 33B.

TABLE 16

Strains used for mevalonic acid scalability.

| Strain # | Silencing | Proteolysis | Plasmid |
|---|---|---|---|
| 1 | FG1G2 | FU | pSMART-Mev2 |
| 2 | G2Z | FGUA | pSMART-Mev2 |
| 3 | FG1G2A | FUN | pSMART-Mev2 |
| 4 | UZ | FGUA | pSMART-Mev2 |

Section 10: Analytical Methods

TABLE 17

UPLC-MS/MS parameters

| Analyte | Retention Time (min) | ESI Mode | MRM Transition(s) | Cone Voltage | Collision Energy |
|---|---|---|---|---|---|
| Alanine | 0.5 | + | 89.95→44.08 | 15 | 9 |
| C13-Alanine | 0.5 | + | 91.95→46.08 | 15 | 9 |

DETAILED DESCRIPTION OF FIGURES

Figure 1B:
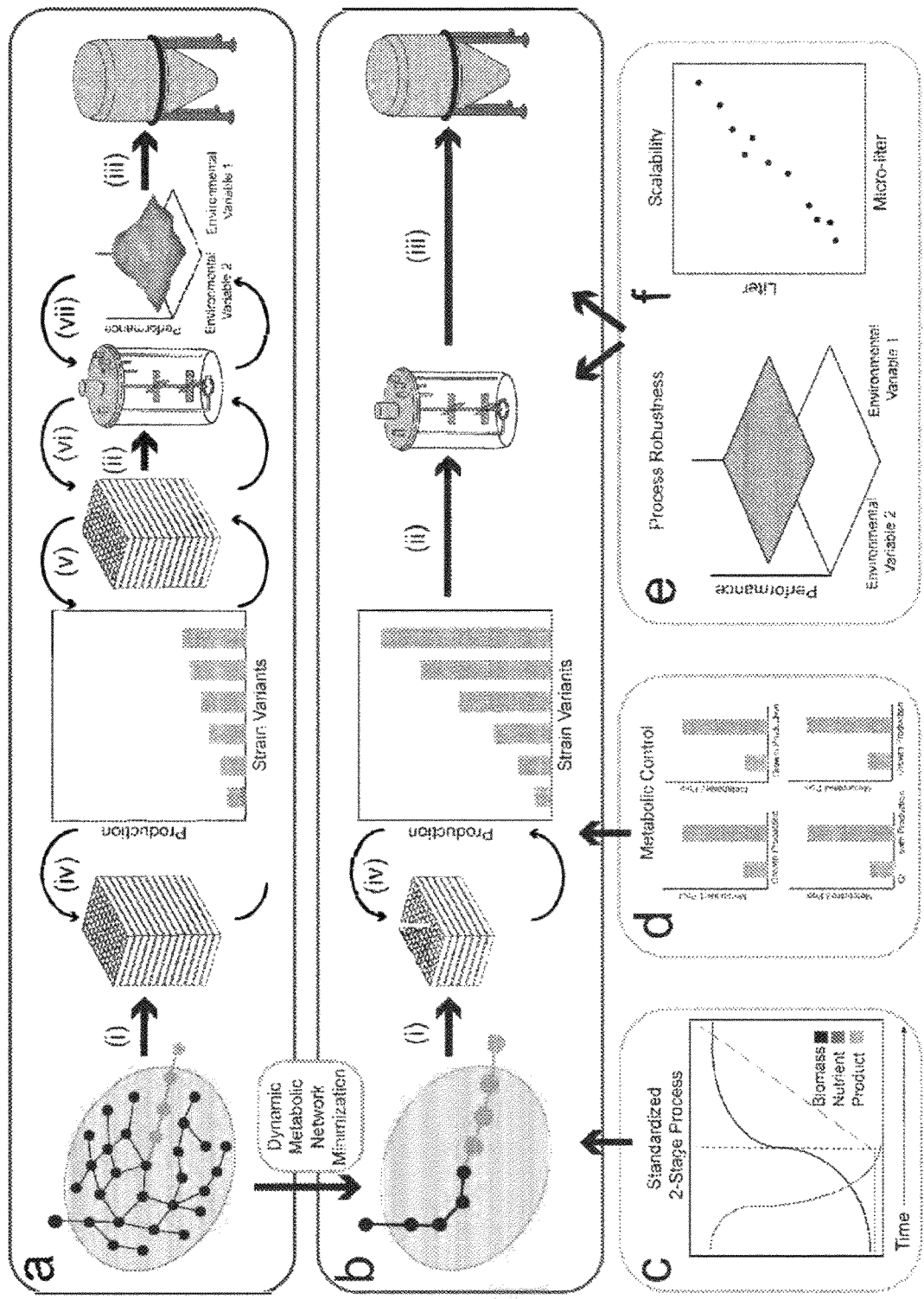
FIG. 1B depicts strain and bioprocess optimization.

FIG. 1A: An Overview of Dynamic Metabolic Control in 2-Stage Fermentations. Metabolic engineering involves optimizing a metabolic pathway to a desired product to the existing metabolic network of a host, converting feedstocks to a desired product. Filled circles indicate metabolites and lines indicate enzymatic reactions. Traditional optimization in metabolic engineering, often involves three key steps (a) the deletion of competing non-essential metabolic pathways including those leading to undesired byproducts and the overexpression of enzymes in the pathway converting feedstock molecules to the product (indicated by thicker lines) and potentially (b) attenuating enzymes in essential metabolism (indicated by orange lines) to further increase production. This process is iterated to optimize the yield to the desired product (pie charts). By contrast, dynamic metabolic network minimization can be used to fully unlock the potential of commonly used 2-stage fermentation processes (c-d). In the first stage of these processes (c) biomass growth and yield are optimized, while in the second stage (d) product formation is optimized, which is well suited for a 2-stage process (e) in which biomass levels accumulate and consume a limiting nutrient (in this case inorganic phosphate), which when depleted triggers entry into a productive stationary phase. Synthetic metabolic valves utilizing CRISPRi based gene silencing and/or controlled proteolysis can be used (f and g) to greatly reduce the pertinent metabolic network upon the transition to the production stage, (f) and array of silencing guides can be induced, processed by the CASCADE complex into individual guides and used to silencing target multiple genes of interest (GOI). (g) If C-terminal DAD+4 tags are added to enzymes of interest (EOI) through chromosomal modification, they can be inducibly degraded by the clpXP protease in the present of and inducible sspB chaperone. (h) Dynamic control over protein levels in *E. coli* using 2 stage dynamic control with inducible proteolysis and CRISPRi silencing. As cells grow phosphate is depleted, and cells "turn off mCherry and "turn on" GFPuv. Shaded areas represent one standard deviation from the mean, n=3. (i) Relative impact of proteolysis and gene silencing alone and in combination on mCherry degradation, with (j) decays rates.

FIG. 1B: Strain and Bioprocess Optimization. (a) Conventional approaches for strain and process optimization in metabolic engineering often involves deletion of competing non-essential metabolic pathways and overexpression of pathway enzymes (Filled circles: metabolites; lines: enzymatic reactions. green indicated a production pathway). (a-i) Strain variants are evaluated at screening scale (microtiter plates, shake flasks, etc), (a-ii) the best strains are assessed in larger scale instrumented bioreactors. Numerous design-build-test cycles (a-vi-vii) are used to iteratively optimize both the production strain and process, including the often-critical optimization of environmental (process) variables (a-vii). (a-iii) The best performing strains and associated optimized process conditions are scaled to industrially relevant levels. (b) Rapid strain and bioprocess optimization using 2-stage dynamic metabolic control. The metabolic network in the cell is dynamically minimized to only the steps essential for product formation. This is accomplished in a standardized 2-stage bioprocess (c), where a biomass accumulating growth stage is followed by a production stage, with only a minimal metabolic network. The limitation of a macronutrient can be used to "switch" cellular metabolism from growth to production. The approach results in a smaller subset of potential strain variants for screening (b-i). Metabolic network minimization helps increase relevant metabolite levels (d) and thus production levels, it also enhances process robustness (e), and as a result process and strain scalability (f). The best producers identified from screening are predictably and rapidly scaled to (b-ii) larger instrumented bioreactors, and (b-iii) subsequently to industrially relevant levels. If needed, limited design-build-test cycles (b-iv) are incorporated to guide improvements. Product independent, standardized protocols are followed for strain evaluation at all scales, eliminating the need for intensive process optimization.

Figure 2B:
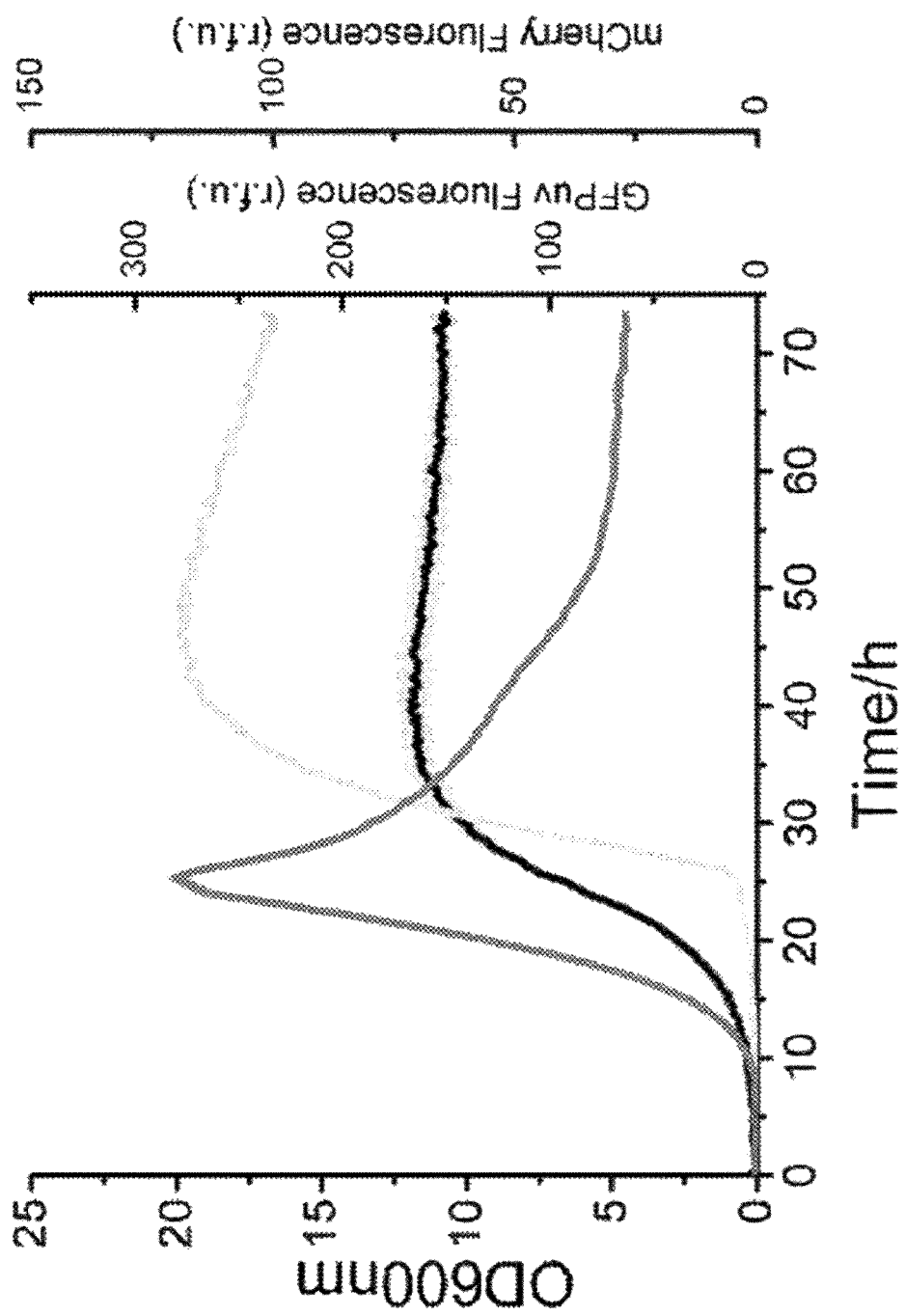
Figure 2C:
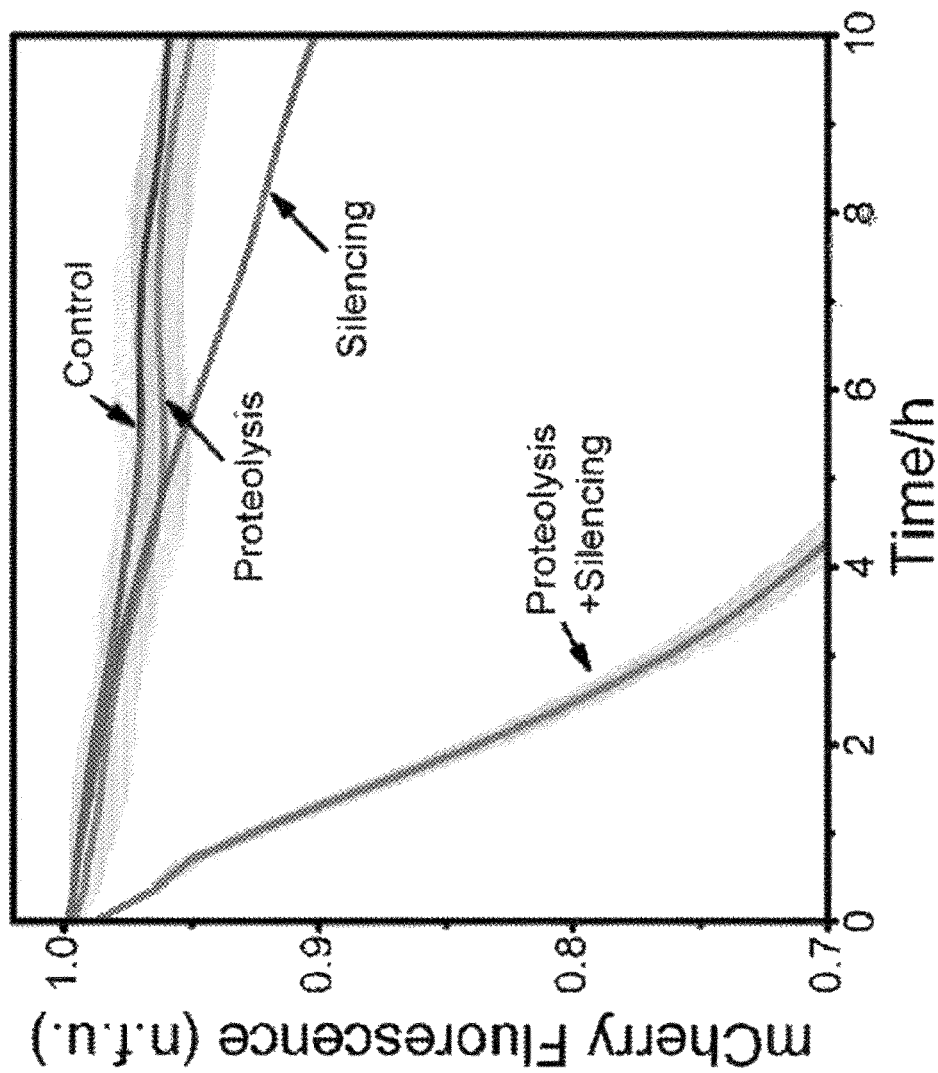
Figure 2D:
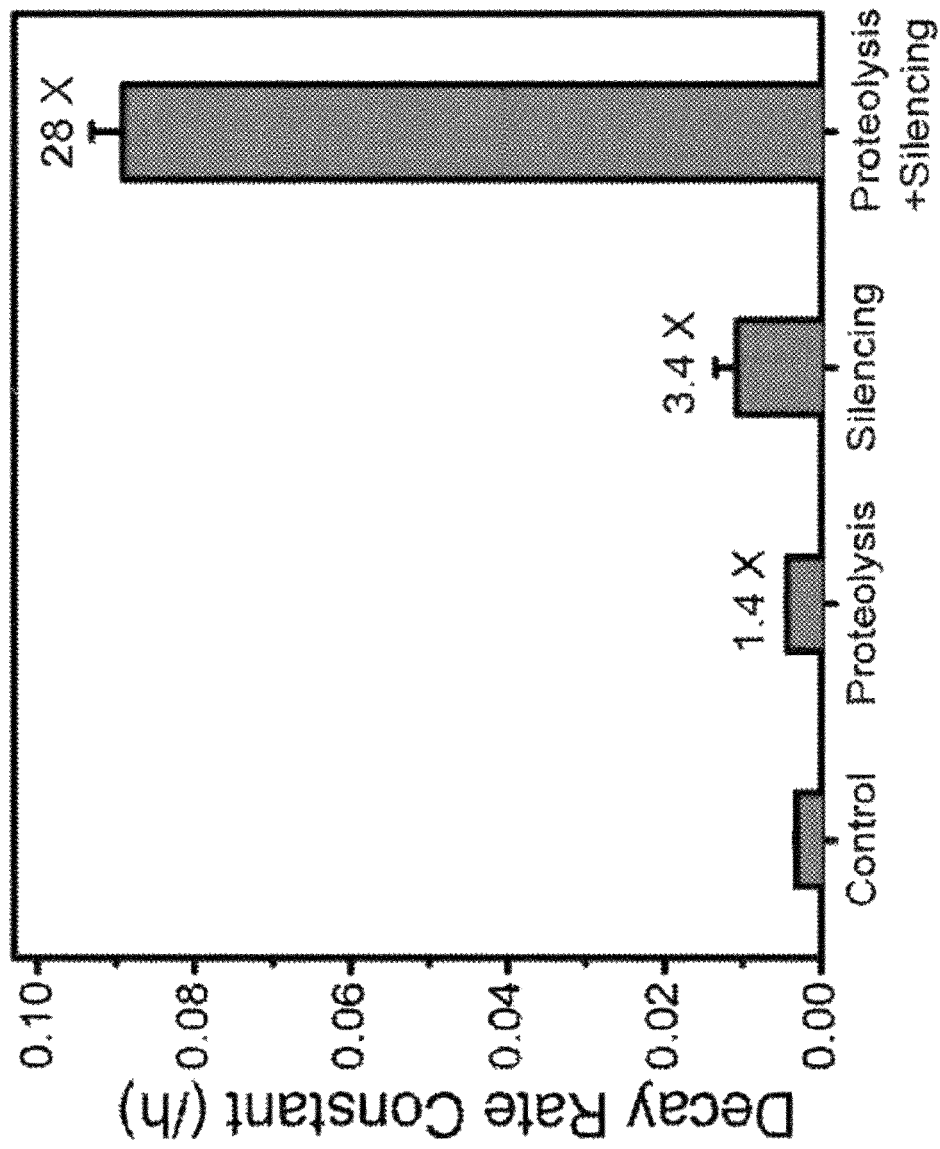

FIGS. 2A-D: Implementation of 2-stage Synthetic Metabolic Valves (SMVs) in *E. coli*. FIG. 2A depicts SMVs utilizing CRISPRi based gene silencing and/or controlled proteolysis were constructed. (Top) Silencing: An array of inducible silencing guide RNAs (i) can be used to silence expression of multiple genes of interest (GOI) when the native *E. coli* CRISPR/Cascade machinery is expressed, which can process guide arrays into individual guides (ii). (Bottom) Proteolysis: When C-terminal DAS+4 tags are added to enzymes of interest (EOI) (through chromosomal modification), they can be degraded by the clpXP protease (iv) upon the controlled induction of the sspB chaperone (iii). FIG. 2B depicts dynamic control over protein levels in *E. coli* using inducible proteolysis and CRISPRi silencing. As cells grow phosphate is depleted, cells "turn OFF" mCherry and "turn ON" GFPuv. Shaded areas represent one standard deviation from the mean, r.f.u, relative fluorescence units. FIG. 2C depicts relative impact of proteolysis and gene silencing alone and in combination on mCherry degradation, n.f.u. normalized fluorescence units (normalized to maximal fluorescence). FIG. 2D depicts relative impact of proteolysis and gene silencing alone and in combination on observed mCherry fluorescence decays rates (per hour).

Figure 3F:
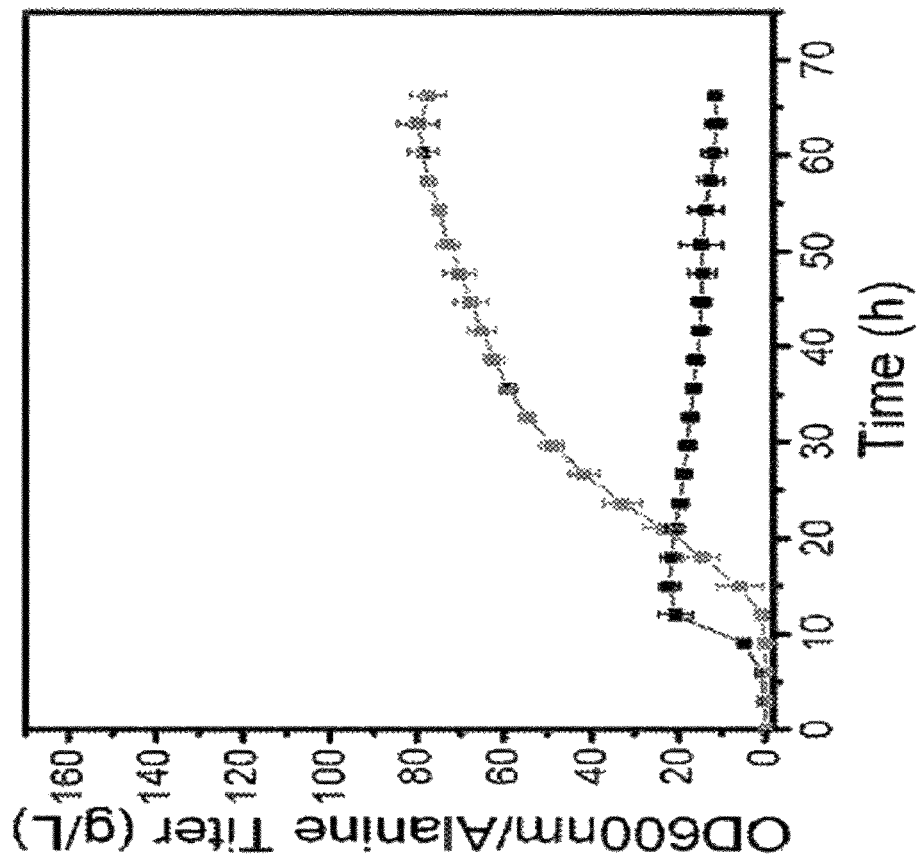
Figure 3H:
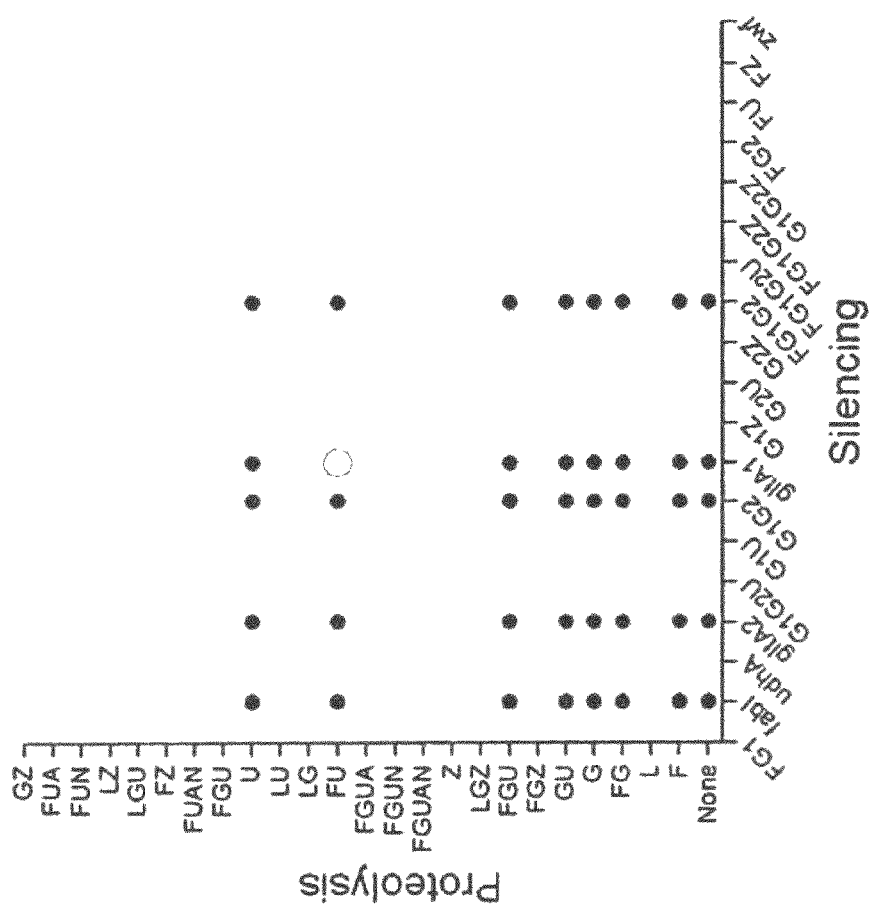
Figure 3I:
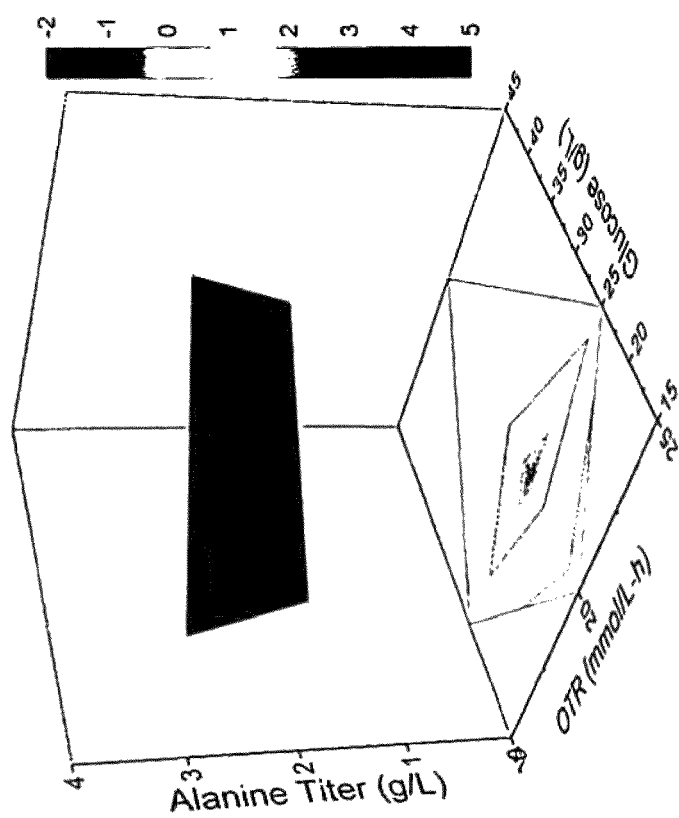
Figure 3K:
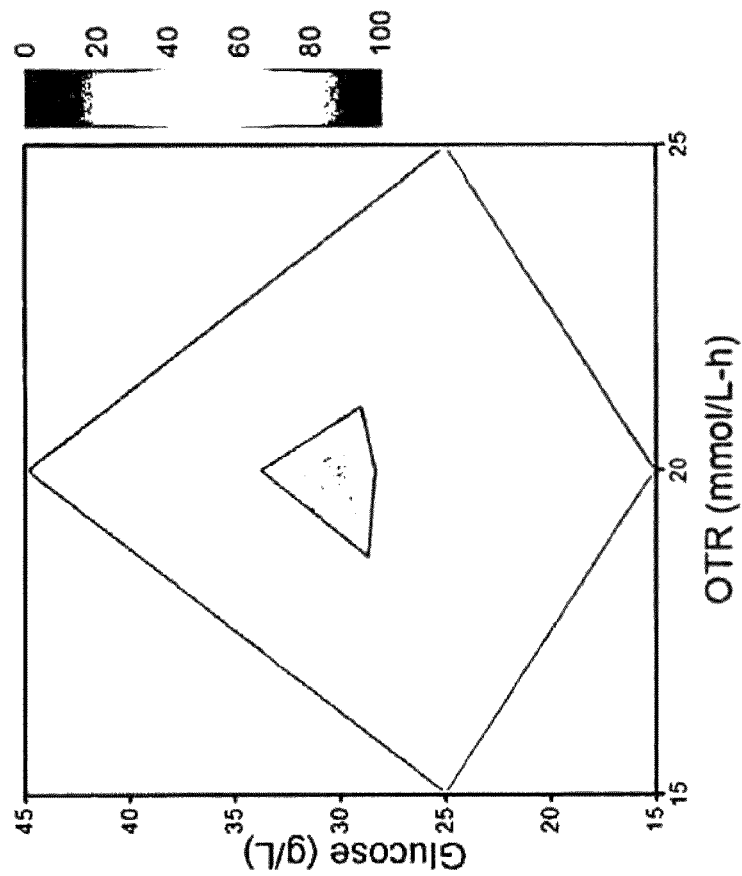
Figure 3J:
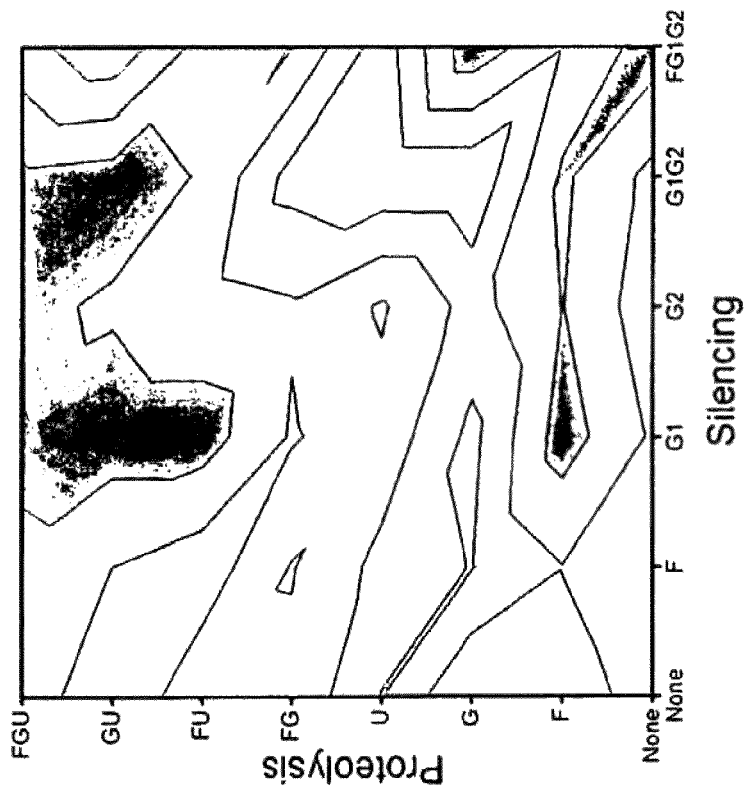

FIGS. 3A-K: Alanine Production in *E. coli* utilizing 2-stage Dynamic Control. FIG. 3A depicts strain variant design. Primary pathways in central metabolism are shown including: Glycolysis, the Pentose Phosphate Pathway, the Citric Acid Cycle (TCA), Fatty Acid Biosynthesis, and the Soluble Transhydrogenase. Key valve candidate enzymes/genes that are "turned OFF" to reduce flux through central metabolism can include: glucose-6-phosphate dehydrogenase (zwf-"Z"), lipoamide dehydrogenase (lpd-"L"), citrate synthase (gltA-"G"), enoyl-ACP reductase (fabI-"F"), and the soluble transhydrogenase (udhA-"U"). Importantly, dynamic elimination of fabI has been previously demonstrated to increase intracellular malonyl-CoA pools as well as malonyl-CoA flux[55]. Enzymes that are dynamically "turned ON" can include the metabolic pathways to produce the products of interest, in this case alanine. Specific pathway enzymes include an NADPH-dependent alanine dehydrogenase (ald*) and an alanine exporter (alaE). Additionally, as the alanine production pathway utilizes NADPH as a cofactor, the NADPH-dependent glyceraldehyde-3-phosphate dehydrogenase encoded by the gapN gene[56] from *S. mutans* was turned on alone and in combination with turning off the native gapA-"A" gene (NADH dependent glyceraldehyde dehydrogenase). Abbreviation: PTS-glucose phosphotransferase transport system, P—phosphate, BP-bisphosphate, OAA—oxaloacetate, DHAP—dihydroxyacetone phosphate, GA3P—glyceraldehyde-3-phosphate, 1,3-BPG—1,3 bisphosphoglycerate, 3-PG—3-phosphoglycerate, 2-PG—2-phosphoglycerate, PEP-phosphoenolpyruvate, MSA—malonate semialdehyde, ACP—acyl carrier protein, Ru—ribulose, Xu—xylulose, E—erthryose, Ri—ribose, S—sedoheptulose. Strains were engineered with SMVs for the dynamic control of all combinations of valve genes/enzymes, either through gene silencing alone, proteolysis alone, or the combination of both. These strains were evaluated for alanine production in standardized micro-fermentations. FIG. 3B depicts rank order plot for average alanine titer (black) of all valve strains examined in 2-stage micro-fermentation, grey area represents standard deviation. Alanine production in the control strain was colored in red. FIG. 3C depicts average alanine titer in 2-stage production in response to different proteolysis and silencing combinations, from 0 g/L (purple) to 5 g/L (red). FIG. 3D depicts average alanine titer in response to different oxygen transfer rates (OTR) and glucose concentrations evaluated for a single "Valve" alanine strain (Silencing of gltA1 ("G1"), Proteolysis of fabI and udhA ("FU")). The results of this surface were used to calculate a strain-specific robustness score (RS) (refer to text), this strain has the highest RS score. FIG. 3E depicts a heat map of the robustness score for a subset of 48 "Valve" strains evaluated across multiple process conditions. FIG. 3F depicts scale up of one of the best producing strain from micro-fermentations (Silencing of fabI-gltA1-gltA2 ("FG1G2"), Proteolysis of fabI, gltA and udhA ("FGU")) to 1 L bioreactors results in a titer of 80 g/L after 48 hrs of production, with a yield of 0.8 g/g. FIG. 3G depicts overexpression of the alaE alanine exporter in this strain (Panel f) results in significantly improved production, reaching 147 g/L in 27 hrs of production, with a yield of ~1 g/g. (Refer to Supplemental Materials, Section 3 for additional details). FIG. 3H depicts strains selected for robustness evaluation in micro-fermentations. FIG. 3I depicts robustness and titer for the most robust "Valve" alanine strain (Silencing_gltA1, Proteolysis_FU). Bottom surface shows heat map for the alanine titer normalized to the median of all process conditions assessed, upper surface shows alanine tiler under all process conditions, the same color scale (alanine titer in g/L) was used for both panels. FIG. 3J depicts RS3 scores for the selected strains. FIG. 3K depicts process reproducibility heat map for all conditions evaluated, the same grayscale was used for FIG. 3J and FIG. 3K.

Figure 4A:
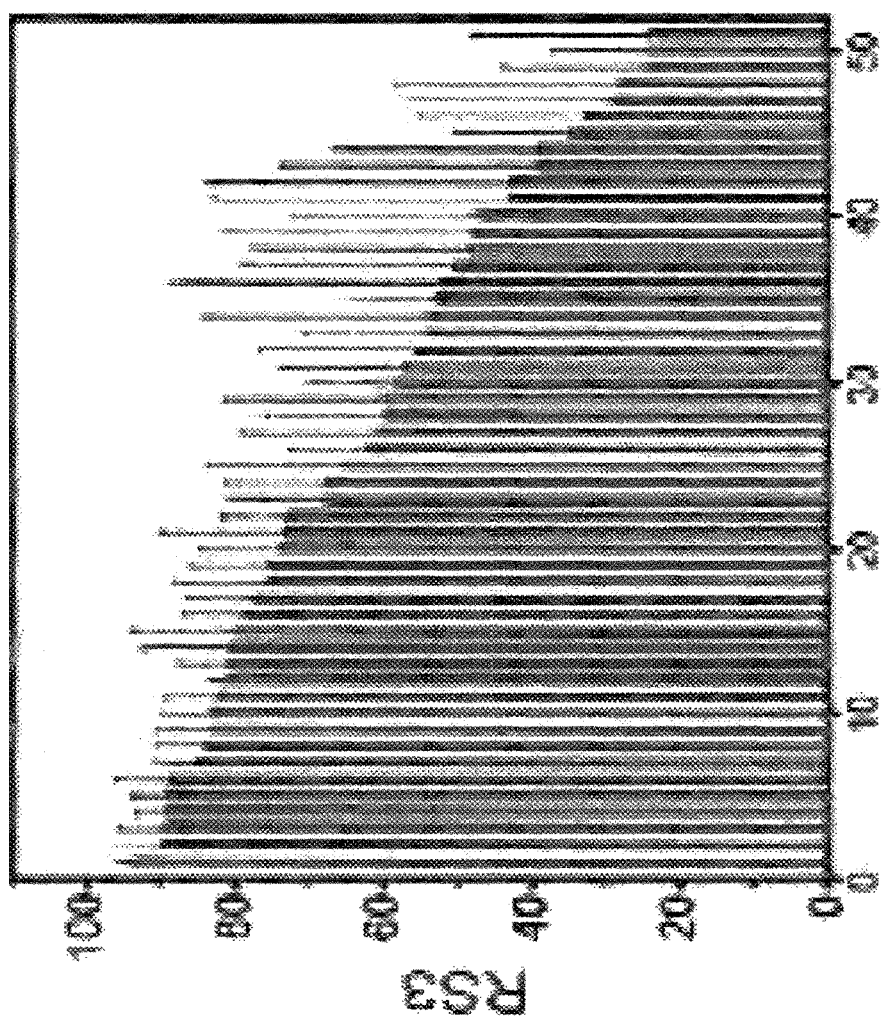
FIGS. 4A-F depict example robustness comparison between 2-stage and growth associated approaches.
Figure 4C:
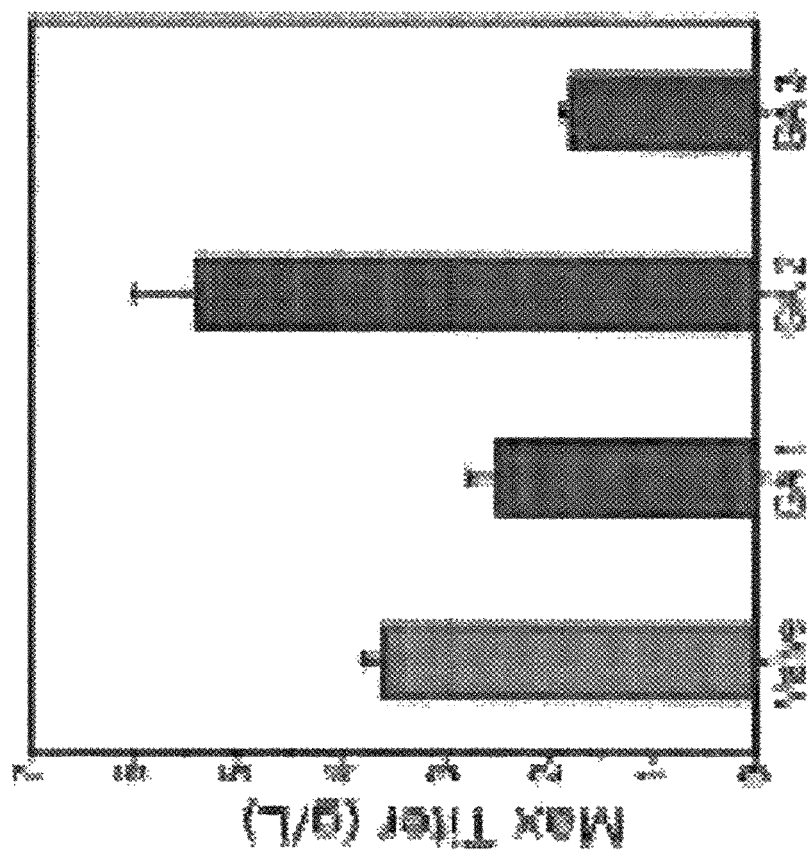
Figure 4B:
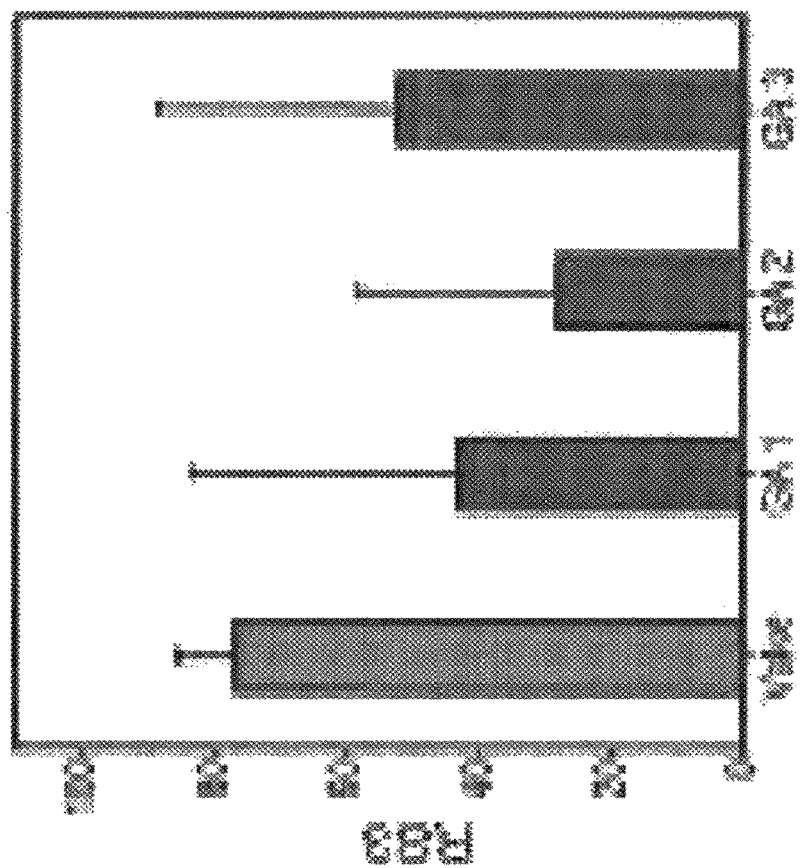
Figure 4D:
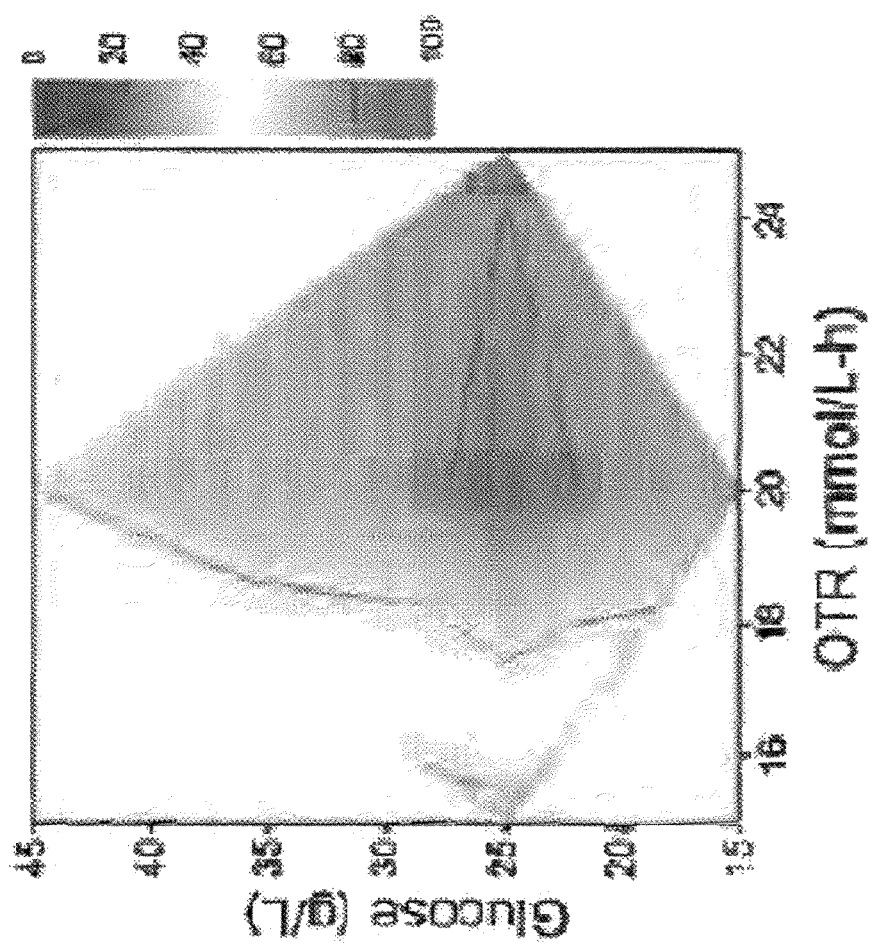
Figure 4E:
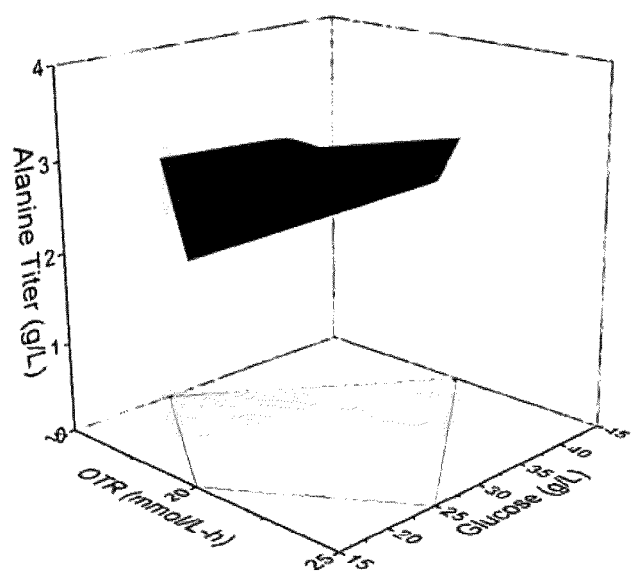
Figure 4F:
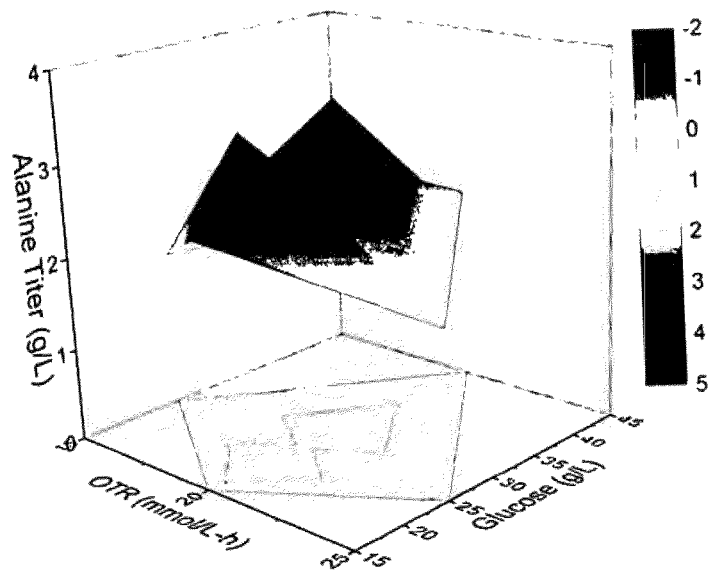

FIGS. 4A-F: Robustness Comparison Between 2-Stage and Growth Associated Approaches. FIG. 4A depicts rank order of the RS3 scores for all alanine strains evaluated, red bars indicate valve alanine strains, and blue bars indicate growth associated (GA) alanine strains. FIG. 4B depicts average RS3 score for "Valve" alanine strains with proteolysis "F" valve, and growth associated alanine strains. FIG. 4C depicts max titer plot for a representative "Valve" alanine (Proteolysis_FGU, Silencing_gltA1), and growth associated alanine strains in micro-fermentation of all conditions evaluated. FIG. 4D depicts process reproducibility for growth associated alanine strains under all conditions evaluated. FIG. 4E depicts robustness and titer for a representative robust "Valve" alanine (Proteolysis_FGU, Silencing_gltA1). FIG. 4F depicts robustness and titer for the GA2 strain. Bottom surface, heat map for the alanine titer normalized to the median of all process conditions assessed, upper surface, alanine titer under all process conditions, the same color scale (alanine titer in g/L) was used for both panels.

Figure 5A:
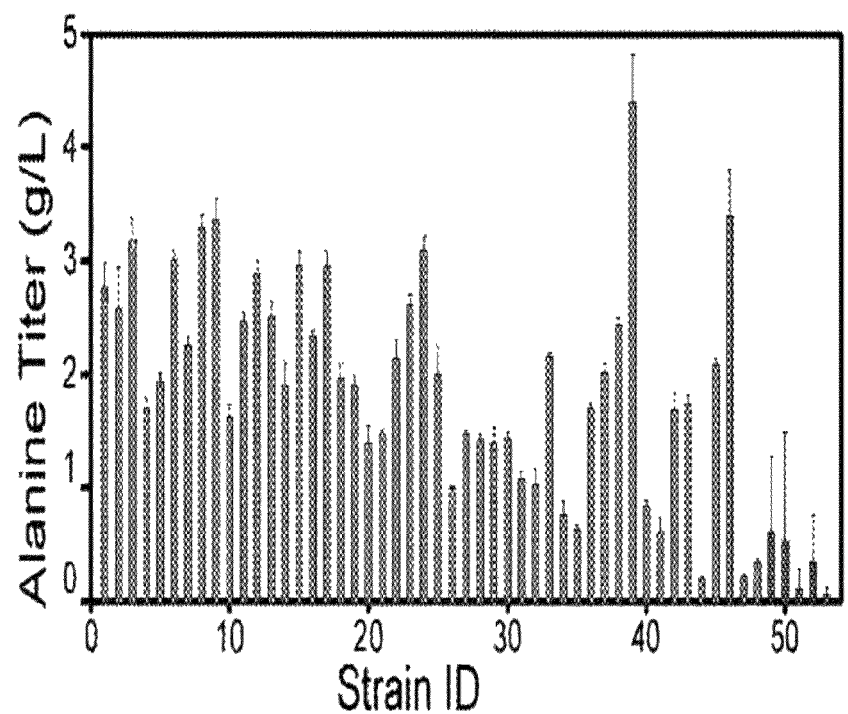
FIGS. 5A-J depict example comparisons of "Valve" and growth associated alanine production in micro-fermentations and 1 L fermentation.
Figure 5B:
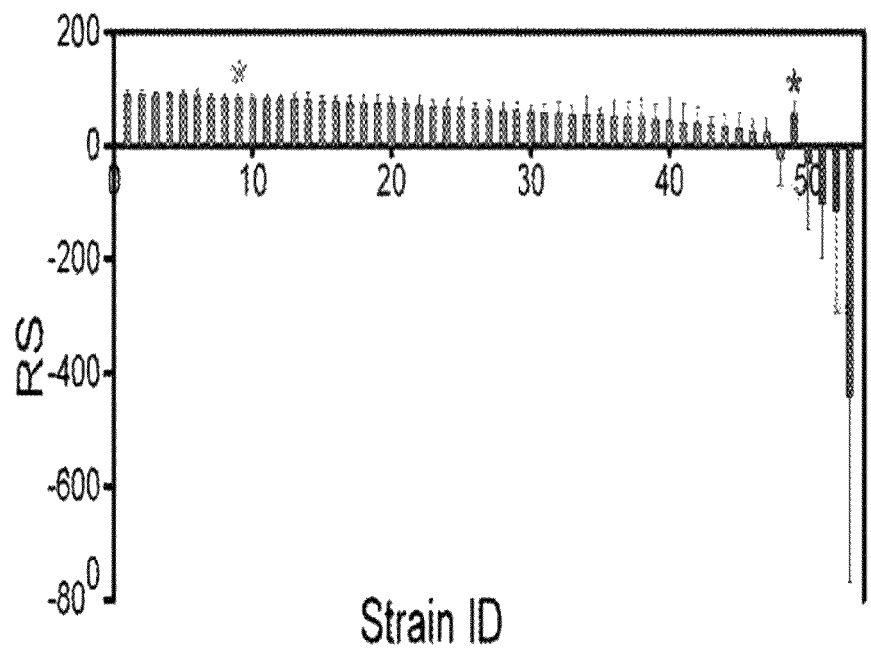
Figure 5D:
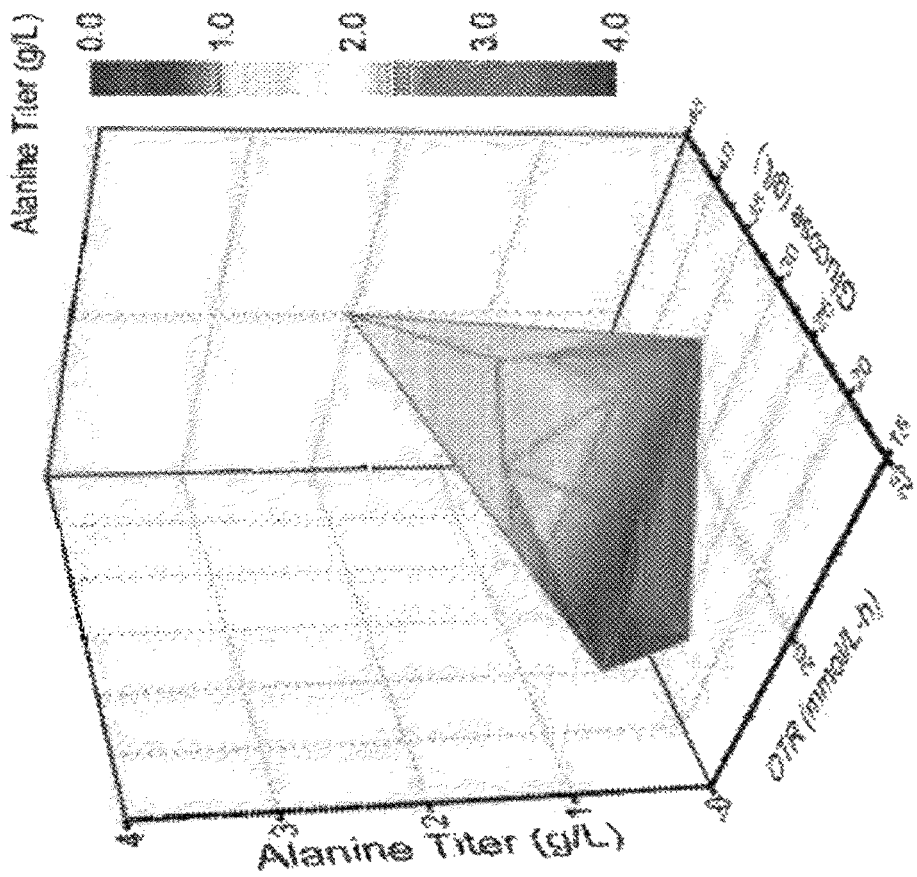
Figure 5C:
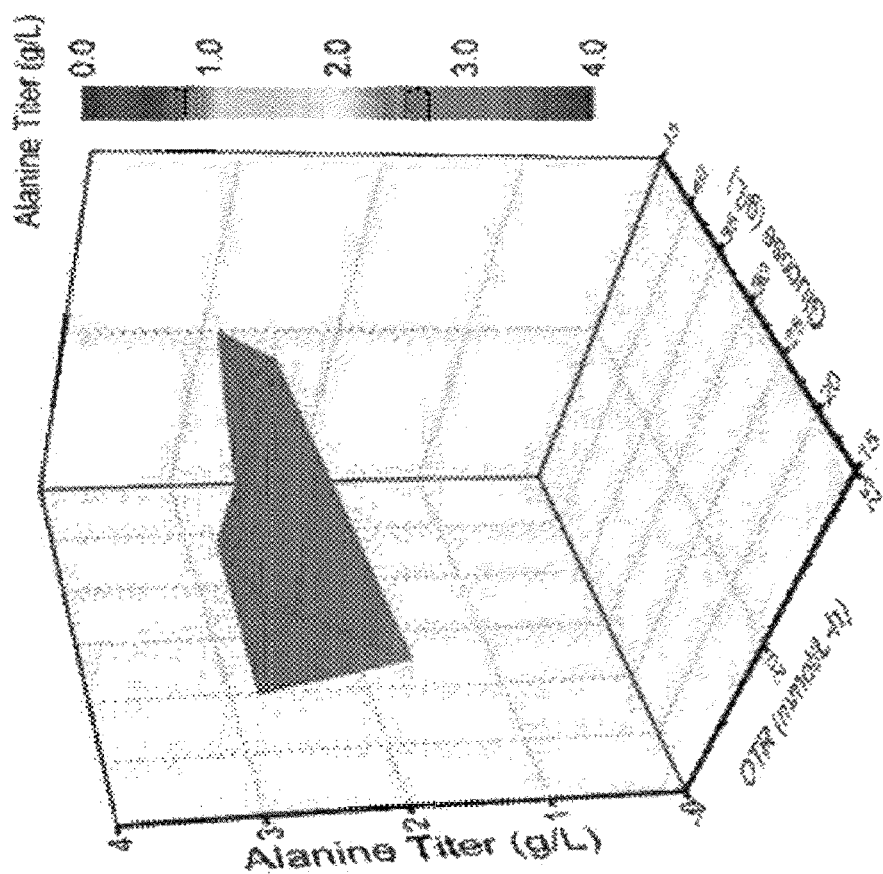
Figures 5E, 5F:
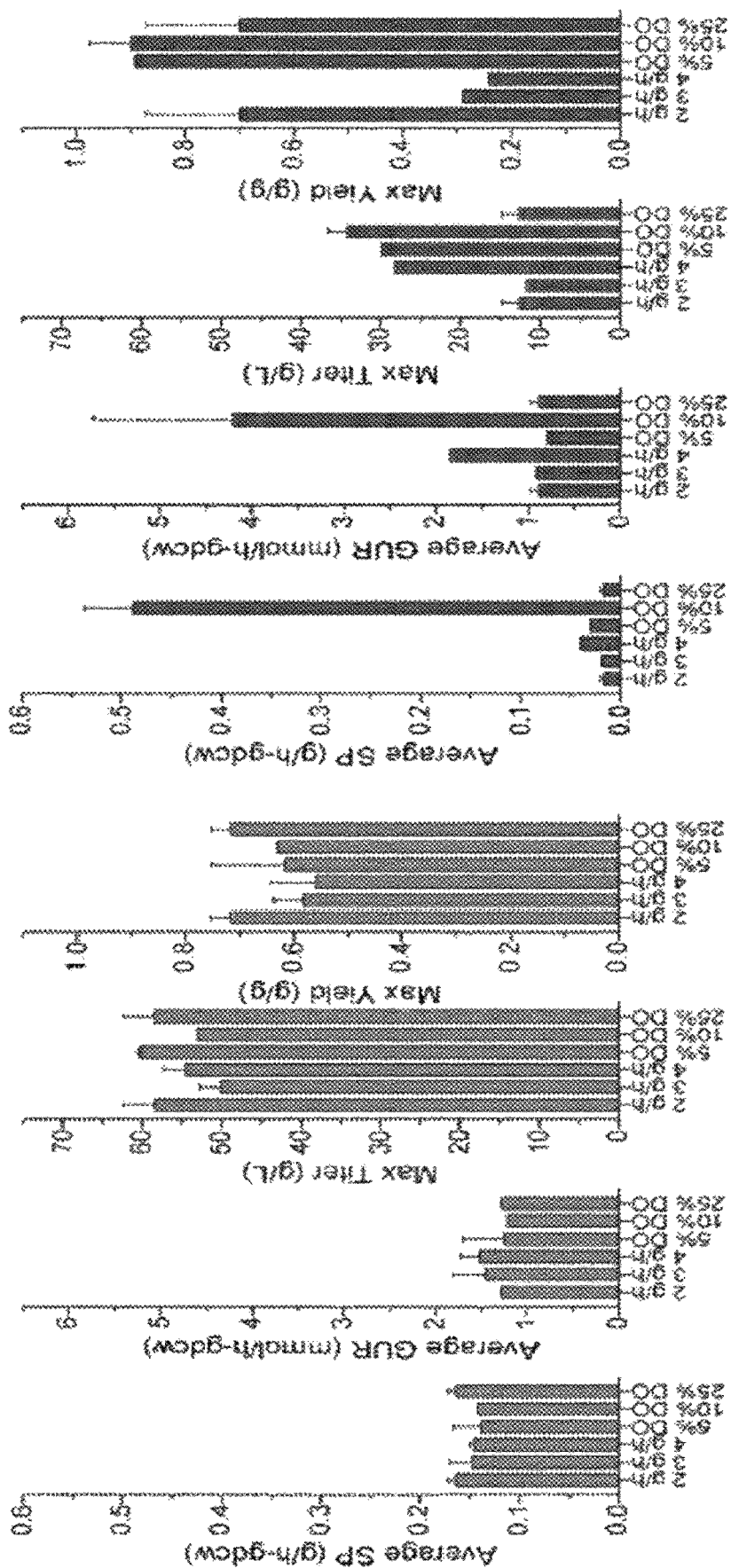
Figure 5G:
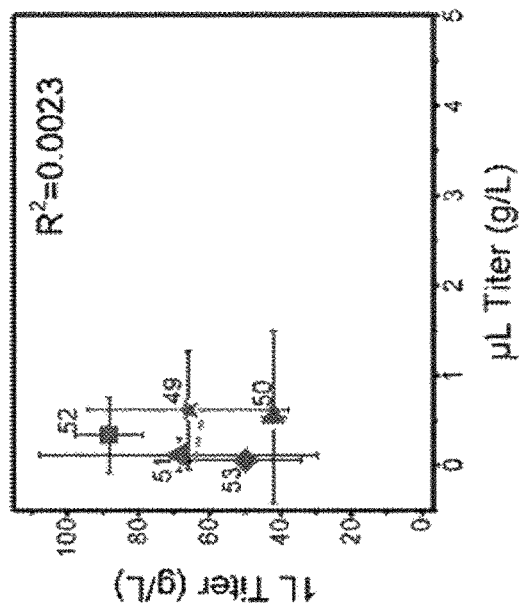
Figure 5H:
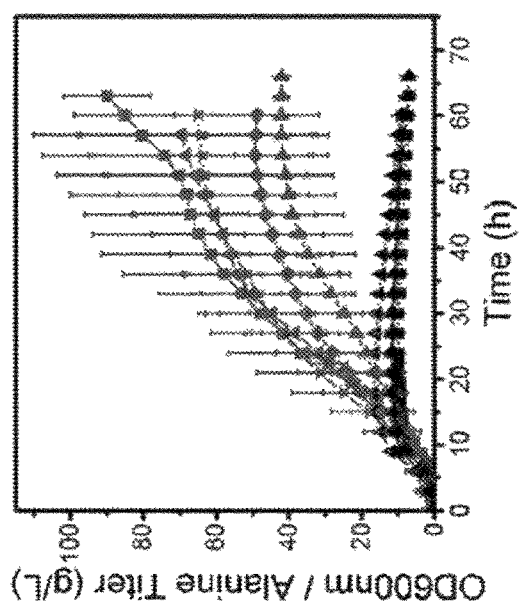
Figure 5I:
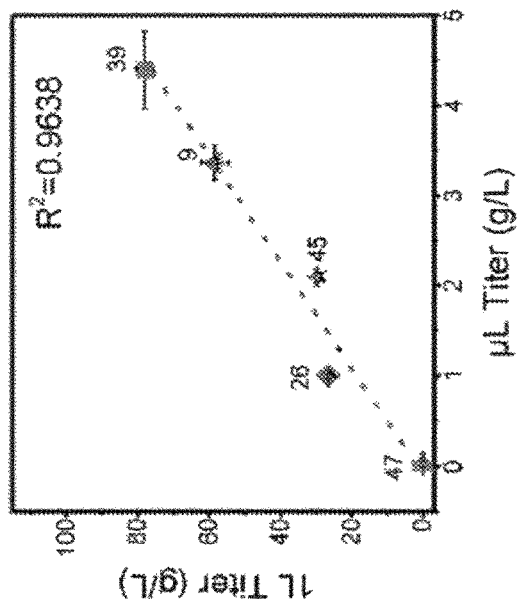
Figure 5J:
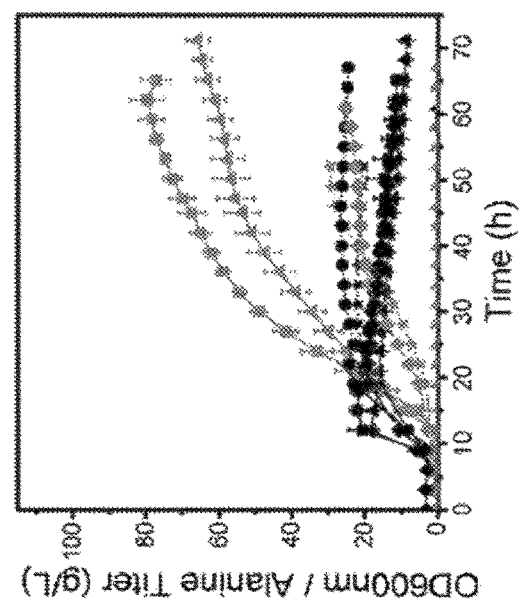

FIGS. 5A-J: Comparisons of "Valve" and growth associated alanine production in micro-fermentations (FIGS. 5A-D) and 1 L fermentation (FIGS. 5E-J). Average alanine titer (FIG. 5A) and robustness score (FIG. 5B) for all strains used for robustness analysis. Average alanine titer in response to different OTR and glucose concentrations for selected "Valve" (FIG. 5C) and growth associated (FIG. 5D) alanine strains. Strains marked by asterisk in (FIG. 5B) were used for this analysis. These two strains were selected for 1 L performance comparison. FIG. 5E and FIG. 5F depicts 1 L performance metrics evaluated, including average specific productivity (SP, g/gdcw-h), average glucose uptake rate (GUR, g/gcdw-h), max titer (g/L), and max yield (g/g). FIG. 5G and FIG. 5H depicts µL to 1 L scalability. 1 L data was standardized to the maximal titer within 50 hours of production. Adequate feed was used for growth associated strains to avoid glucose depletion. FIG. 5I and FIG. 5J depicts 1 L production profiles for all strains used in scalability plot FIG. 5G and FIG. 5H respectively, darker symbols represent growth curves, lighter symbols represent production curves, shape of symbols encode the same strains in FIG. 5G or FIG. 5H.

Figure 6F:
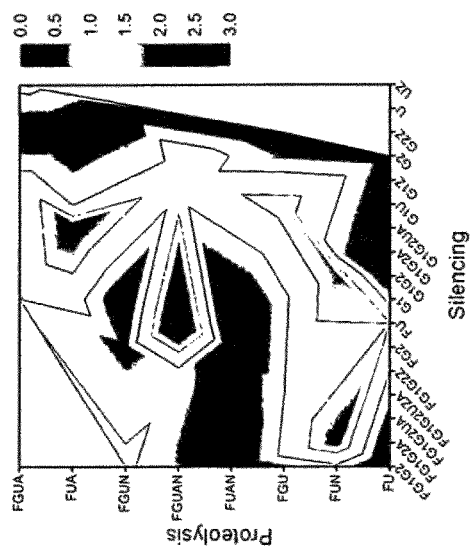
Figure 6H:
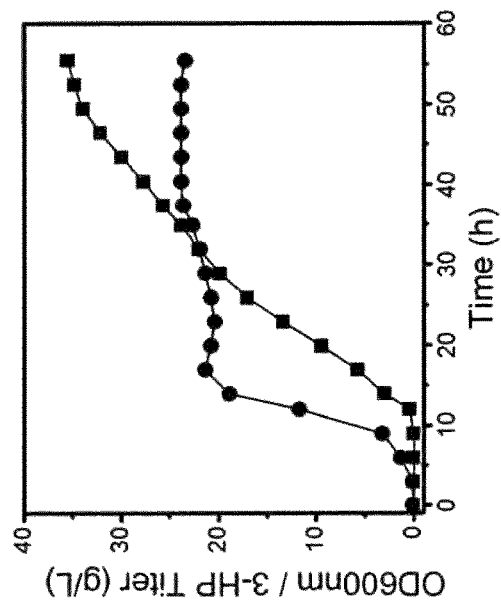
Figure 6G:
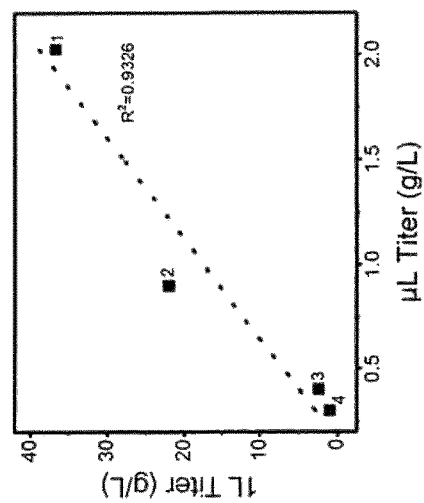

FIG. 6A-E: Mevalonate Production in *E. coli* utilizing 2-stage Dynamic Control. FIG. 6A depicts Metabolic Pathways and SMVs for mevalonate production. FIG. 6B depicts mevalonate production using several production pathway plasmid variants with varied promoter combinations in the control strain. FIG. 6C depicts micro-fermentation results for a subset of "Valve" strains producing mevalonate, using the best production pathway from FIG. 6B, along with combinations of proteolytic and silencing SMVs. FIG. 6D depicts µL to 1 L scalability for a subset of mevalonate strains evaluated at the 1 L scale. n=3 for µL data and n=1 for 1 L data. The maximal titer within 50 hours of production time was used for the correlation. FIG. 6E depicts production of the best mevalonate strain from FIG. 6D (Silencing of fabI-gltA1-gltA2 ("FG1G2"), Proteolysis of fabI and udhA ("FU")) in 1 L bioreactors. A titer of 97 g/L was observed in 78 hrs of production. Yields during the production stage reached 0.46 g/g (84% of theoretical yield). (Refer to Supplemental Materials, Section 9 for additional details). FIG. 6F depicts micro-fermentation results for a subset of strains producing 3-HP. FIG. 6G depicts µL to 1 L scalability for a subset of 3-HP strains evaluated at the 1 L scale (Supplemental Materials Tables S21 and S22). FIG. 6H depicts production performance for the best 3-HP strains in the 1 L systems, squares, 3-HP/mevalonic acid titer; circles, OD600. Yields during the production stage reached for the 0.46 g/g for mevalonic acid and 0.63 g/g for 3-HP in the highest producers.

FIG. 7: Phosphate depletion promoter characterization. A set of GFP reporter vectors were constructed to assess the expression level of 12 previously identified phosphate regulated promoters. Strains were evaluated continuously for GFP expression in the Biolector™ using a standardized protocol wherein in minimal medium limited for phosphate is used. After Biomass levels reach a peak (not shown for clarity), GFP expression begins. Importantly the current set of promoters enables a large range of expression levels.

FIG. 8: Insulated phosphate depletion promoter characterization. A set of GFP reporter vectors were constructed to assess the expression level of five insulated phosphate regulated promoters in FGM3 media. Strains were evaluated continuously for GFP expression in the Biolector™ using a standardized protocol wherein in minimal medium limited for phosphate is used. After Biomass levels reach a peak (not shown for clarity), GFP expression begins. Importantly the current set of promoters enables a large range of expression levels.

FIG. 9: Insulated constitutive promoter characterization. A set of GFP reporter vectors were constructed to assess the expression level of five insulated constitutive promoters in FGM3 with 40 mM phosphate media. Shaded area represents standard deviations, n=3. Strains were evaluated continuously for GFP expression in the Biolector™. GFP expression was observed only for promoters proA, proB and proD.

Figure 10:
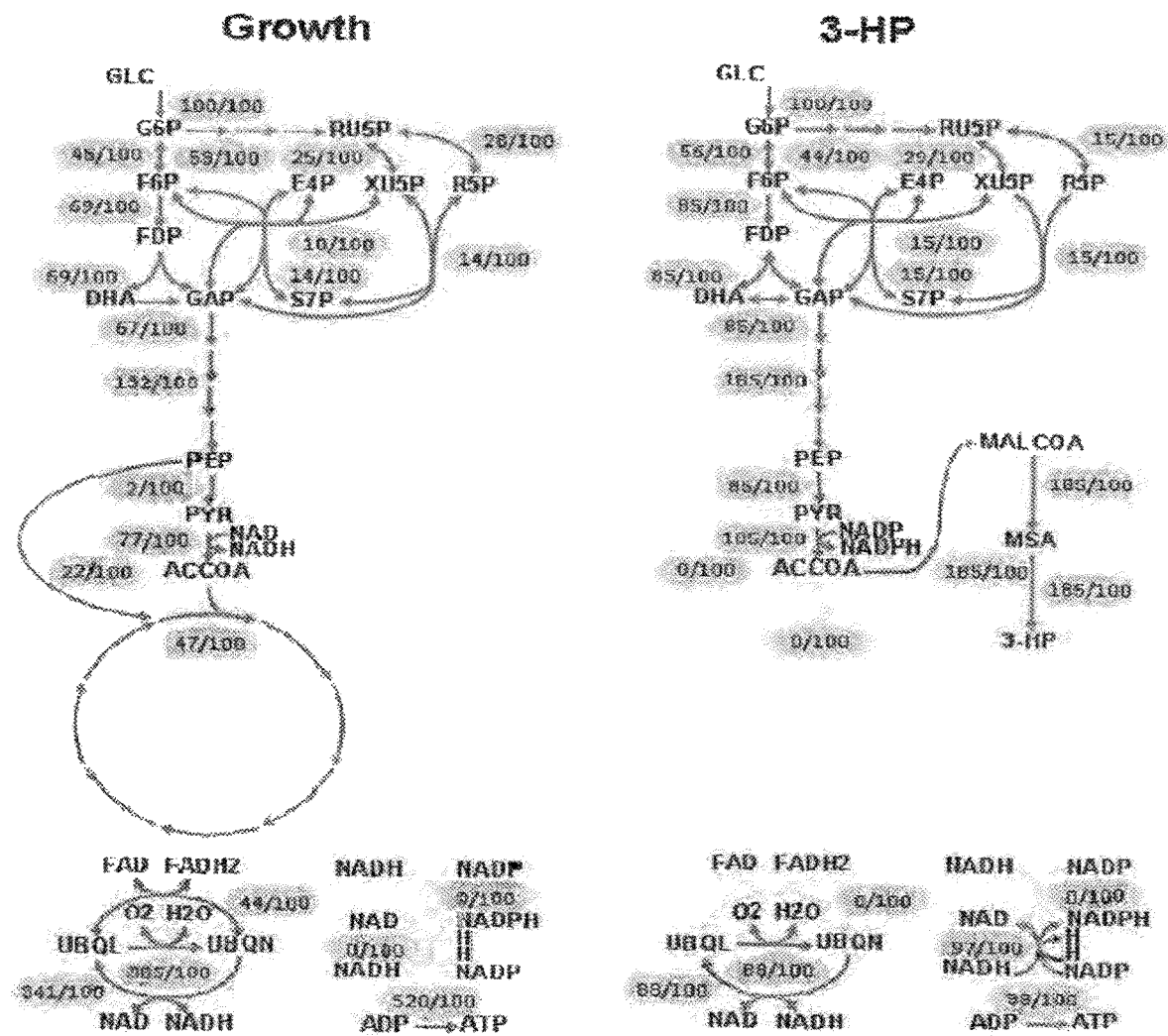
FIG. 10 depicts an example of metabolic modeling results for optimal 3-HP flux in two stage fermentations.

FIG. 10: Metabolic modeling results for optimal 3-HP flux in two stage fermentations. LEFT: Optimized fluxes during the growth stage where biomass production was used as the objective function. RIGHT: Optimized fluxes during the 3-HP production stage where 3-HP production was used as the objective function (biomass production was set to 0). Fluxes are listed as relative ratios or moles of flux through a given reaction per 100 moles of glucose utilized.

FIG. 11: Chromosomal modifications.

Figure 12:
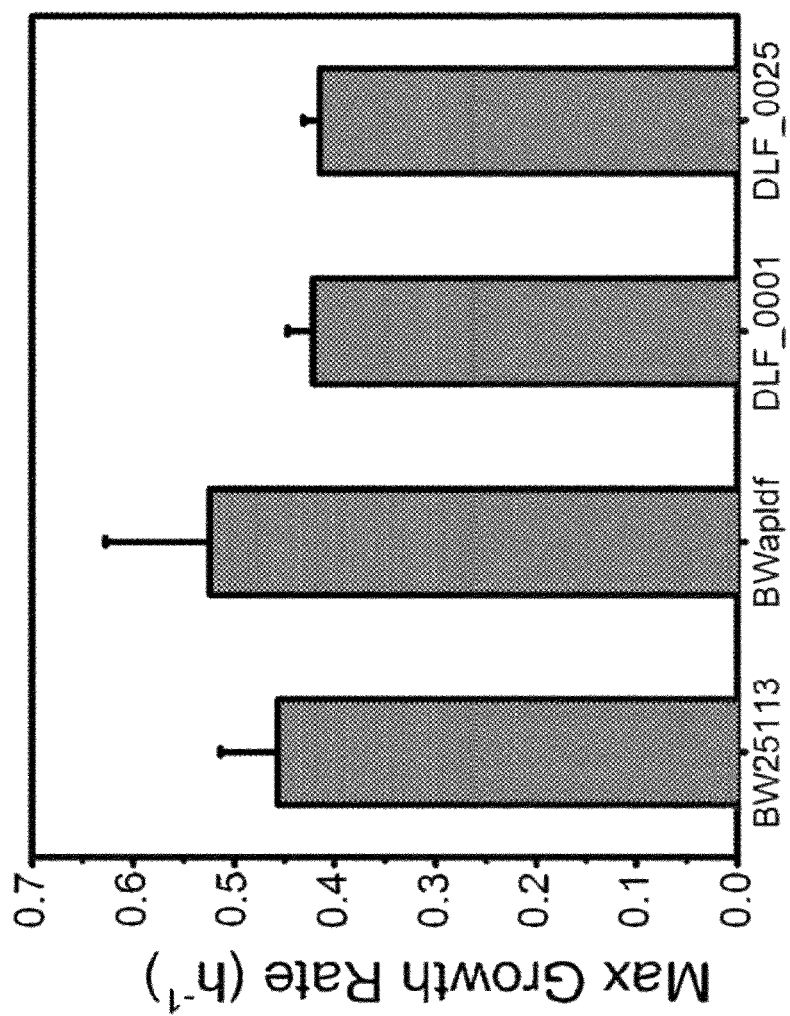
FIG. 12 depicts an example of average maximal growth rates of starting host strains in 1 L FGM10 minimal medium fermentations, n=2.

FIG. 12: Average maximal growth rates of starting host strains in 1 L FGM10 minimal medium fermentations, n=2.

Figure 13B:
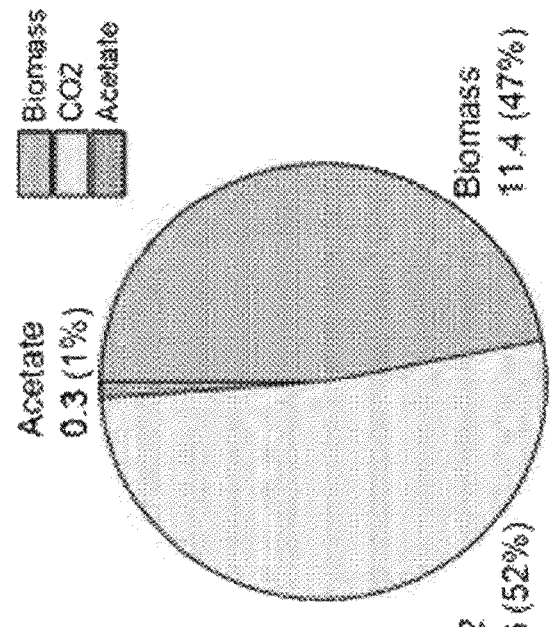
Figure 13A:
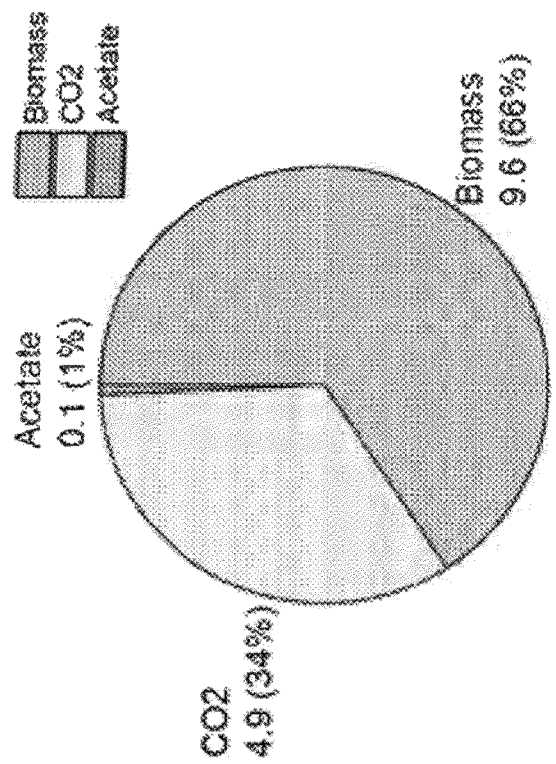

FIG. 13A-E: Distribution of glucose utilized during the growth phase of starting host strains in 1 L standard minimal medium fermentations. Mid exponential and final growth period results are given for DLF_0025 as "production" begins in mid-late exponential phase. Results are averages of duplicate fermentations. FIG. 13A, BW25113; FIG. 13B, BWapldf; FIG. 13C, DLF_0001; FIG. 13D, DLF_0025 at mid-exponential; FIG. 13E, DLF_0025 at end of growth phase. Unit was gram glucose.

Figure 14:
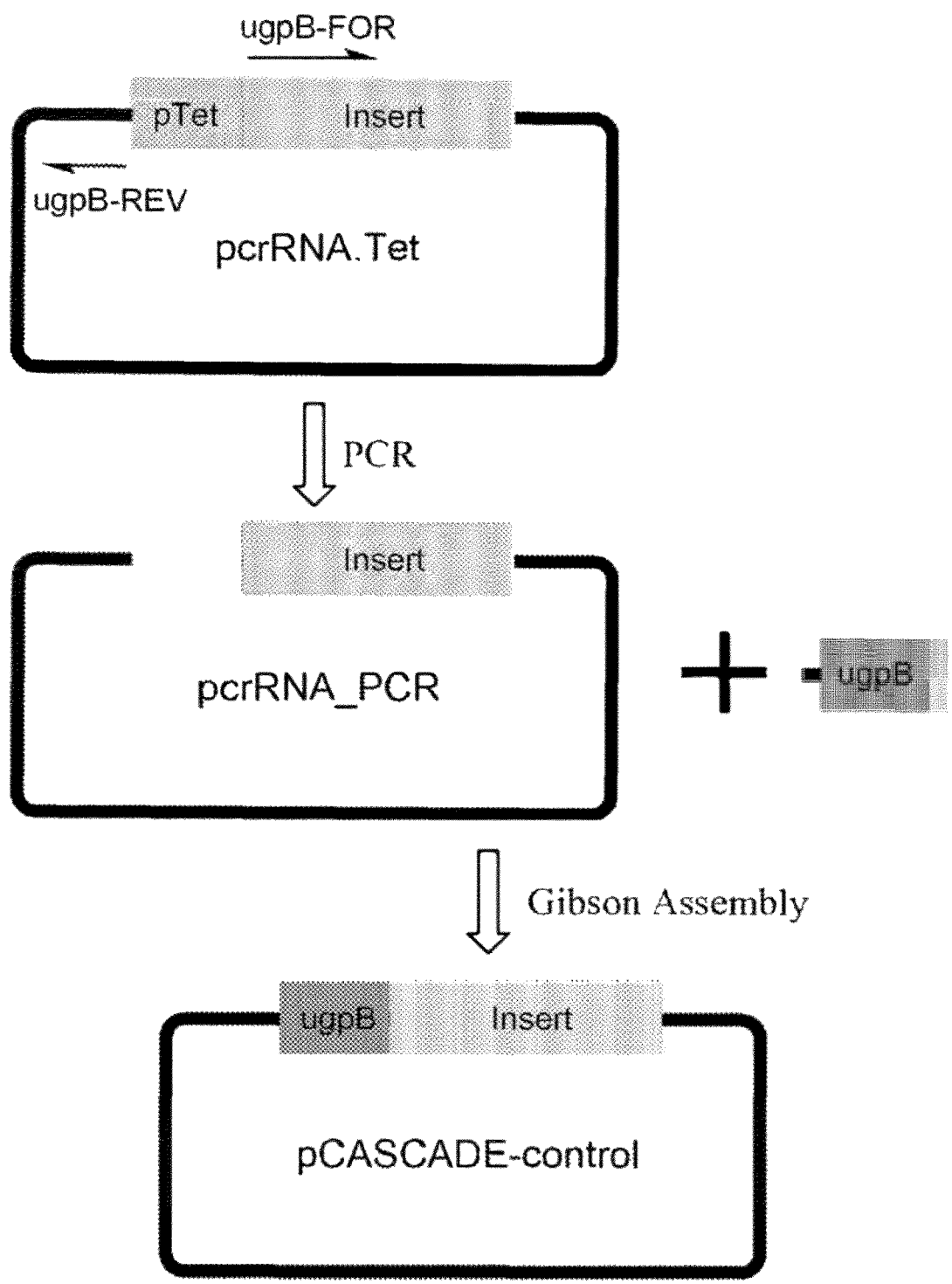
FIG. 14 depicts pCASCADE-control plasmid construction scheme.
Figure 15A:
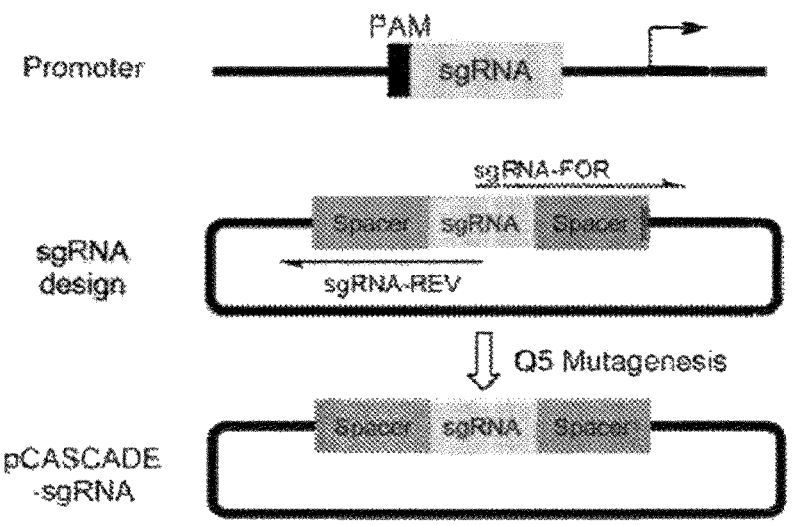
FIGS. 15A-B depict pCASCADE construction scheme.
Figure 15B:
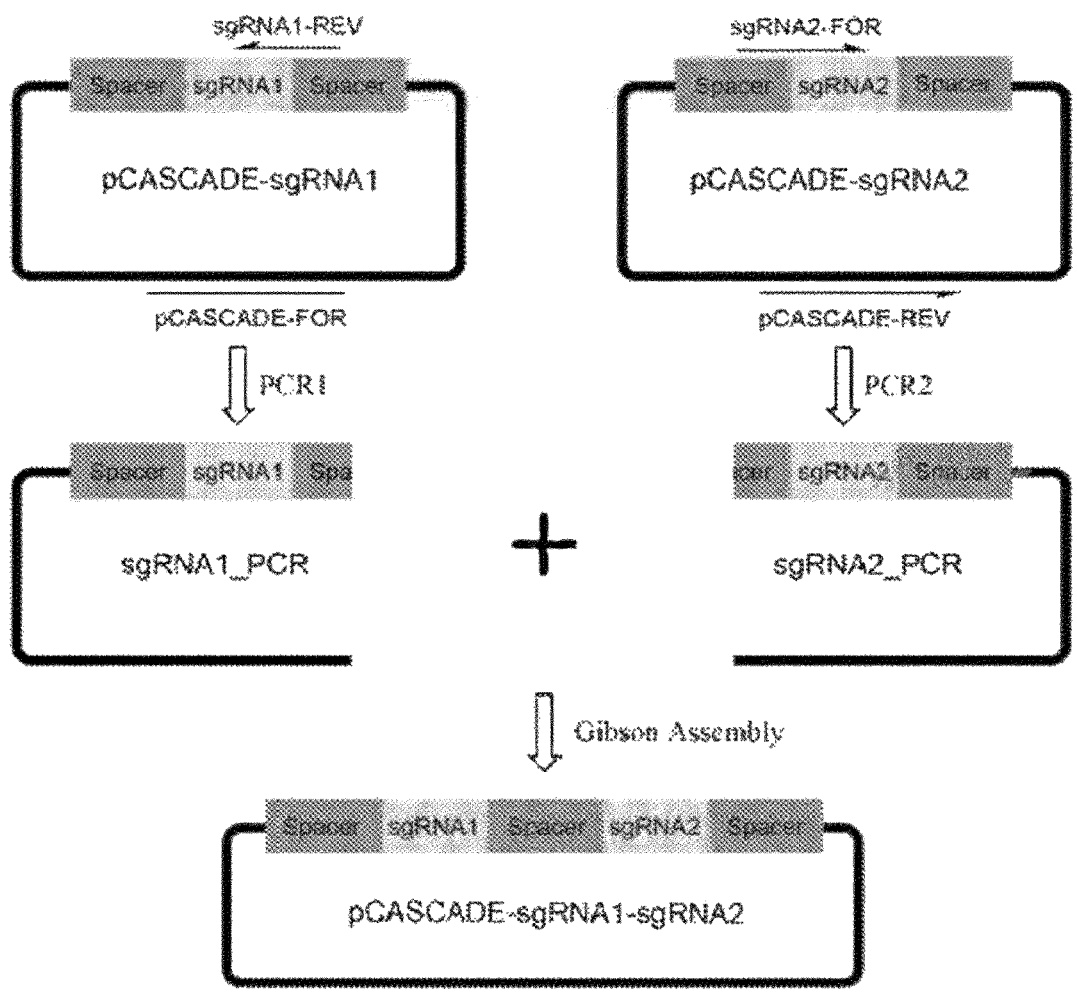

FIG. 14: pCASCADE-control plasmid construction scheme.

FIG. 15A-B: pCASCADE construction scheme. FIG. 15A, single sgRNA cloning; FIG. 15B, double sgRNA.

FIG. 16A-C: Micro-fermentation process overview. (A) An overview of the high throughput micro-fermentation protocol. Freezer stocks (alternatively colonies may be used) are used to inoculate into SM10++ in 96 well plates. Cultures are grown overnight for 16 hours, harvested by centrifugation, washed with no-phosphate medium and resuspended in no-phosphate medium at target biomass levels. (OD600 nm=1.0). EnzyScreen™ covers and clamps are used to reduce evaporation and enable high oxygen transfer rates. The protocol is implemented with a Tecan Evo liquid handler. (B) Representative overnight growth in a 96 well plates culture, distribution of OD600 for overnight culture was plotted. (C) Representative OD600 distribution after normalization using Tecan Evo liquid handler.

FIG. 17: Micro-fermentation for L-alanine production using different insulated phosphate promoters in DLF_0025 strain.

Figure 18:
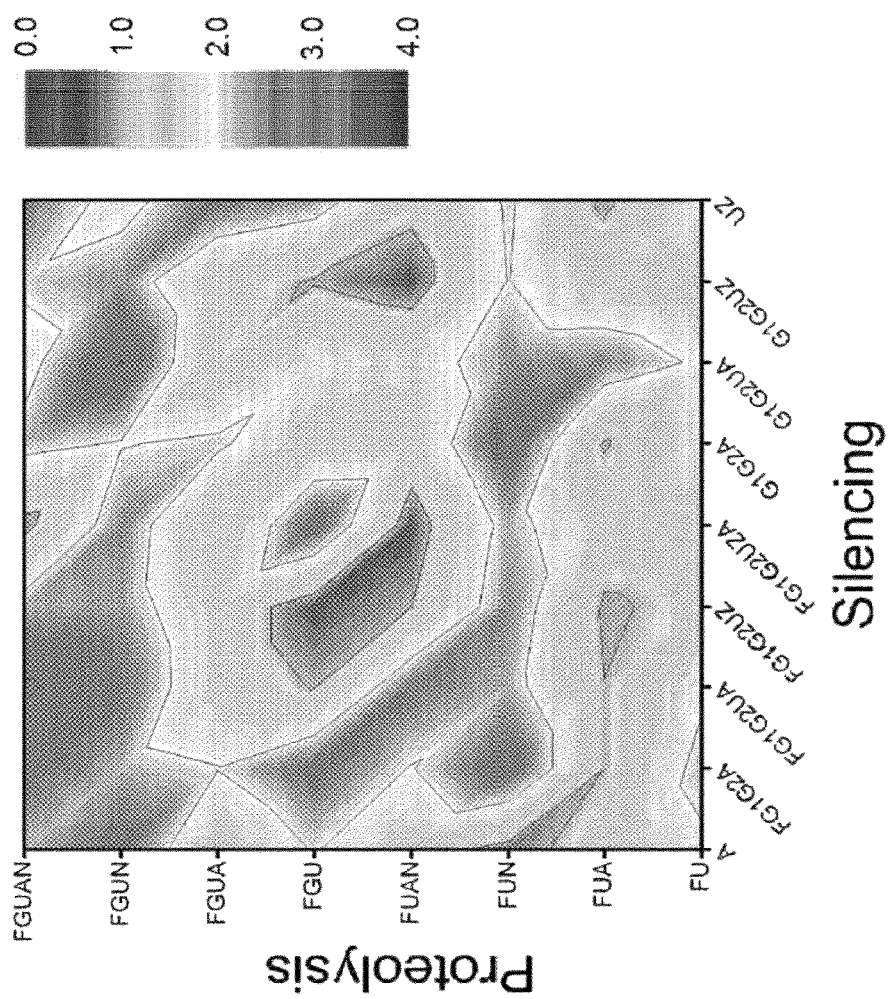
FIG. 18 depicts Heatmap for L-alanine production by gapN/gapA strains.
Figure 19A:
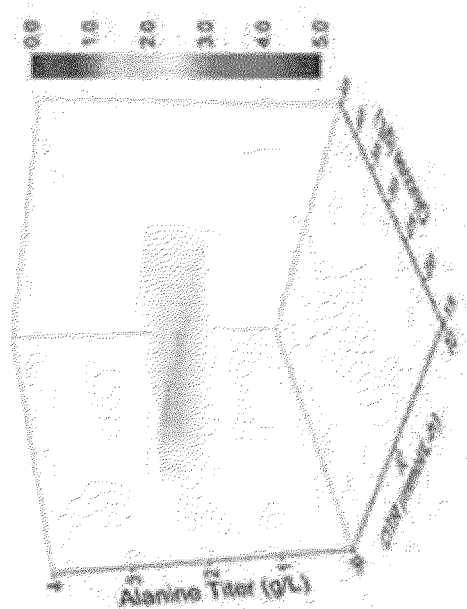
FIGS. 19A-D depict alanine production in response to different OTR and glucose concentration in micro-fermentation for 4 strains evaluated for robustness.
Figure 19B:
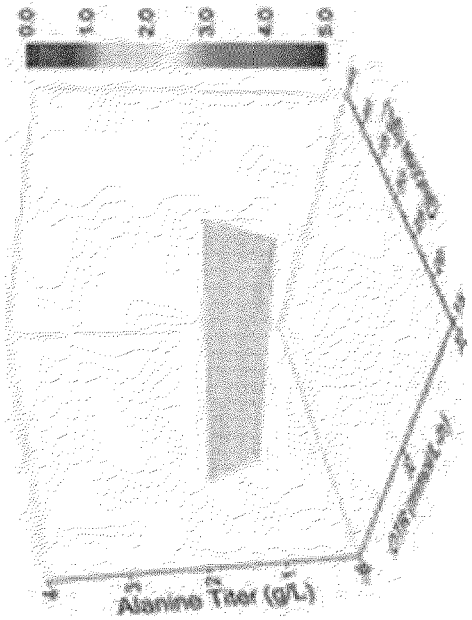
Figure 19C:
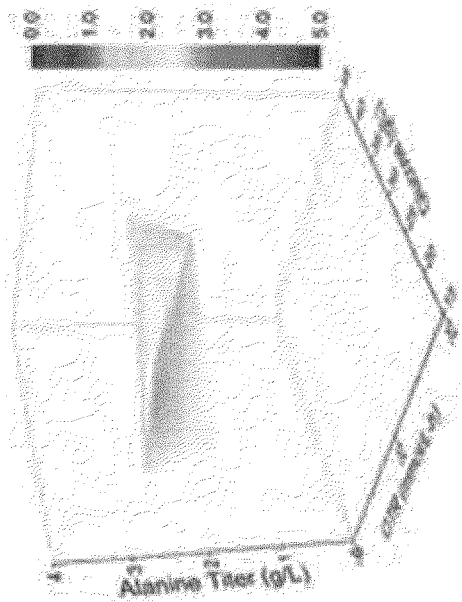
Figure 19D:
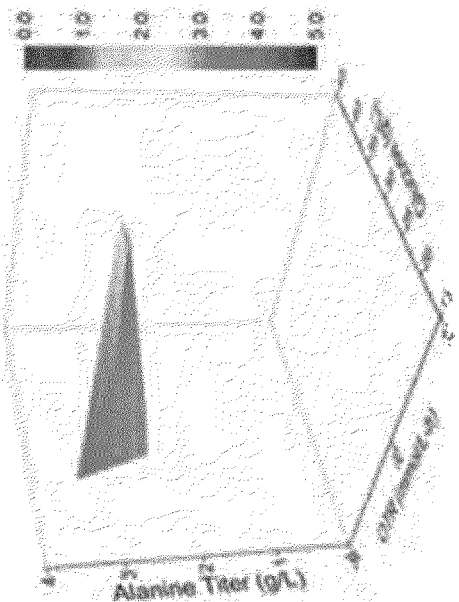
Figure 20A:
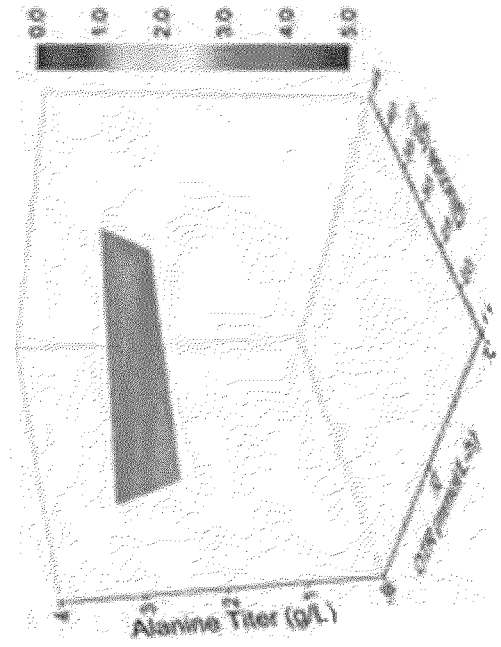
FIGS. 20A-D depict alanine production in response to different OTR and glucose concentration in micro-fermentation for 4 strains evaluated for robustness.
Figure 20B:
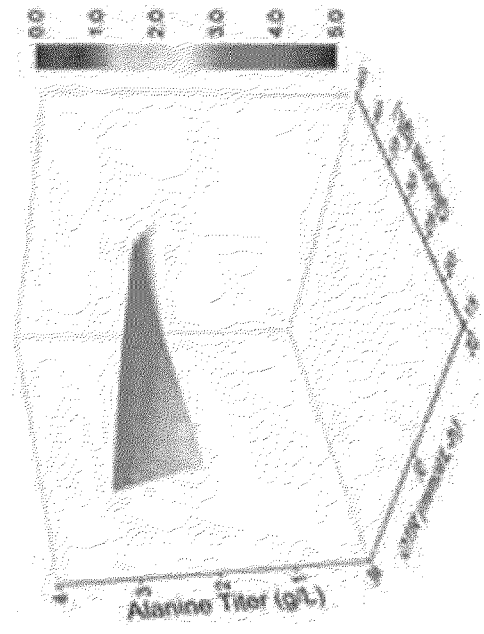
Figure 20C:
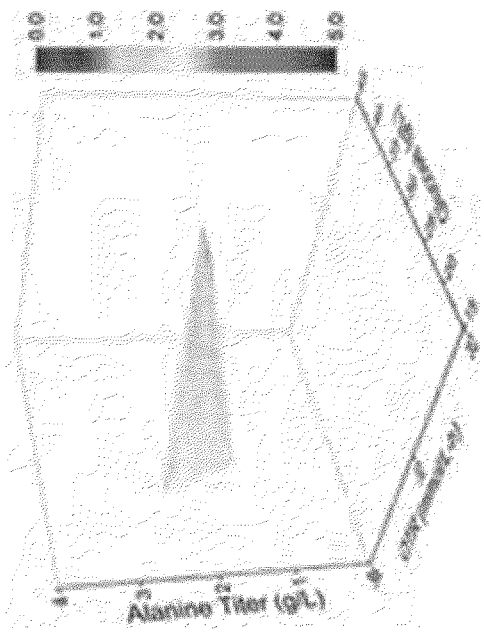
Figure 20D:
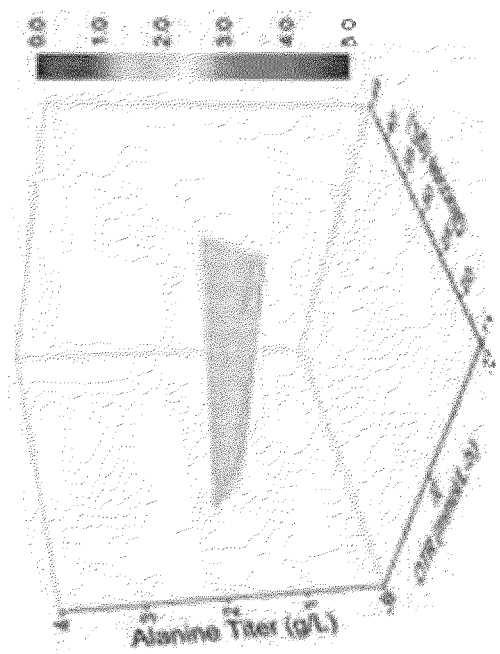
Figure 22B:
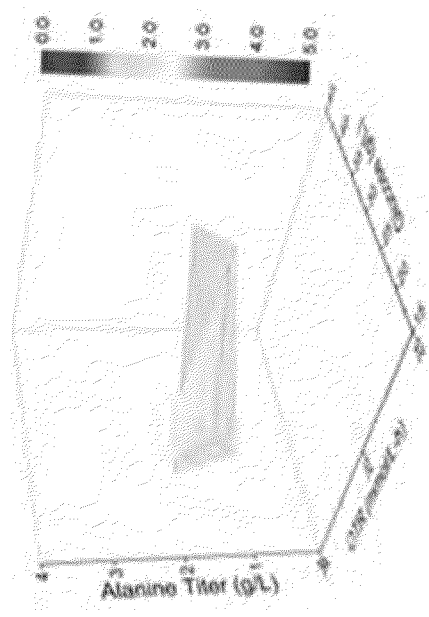
FIGS. 22A-D depict alanine production in response to different OTR and glucose concentration in micro-fermentation for 4 strains evaluated for robustness.
Figure 22D:
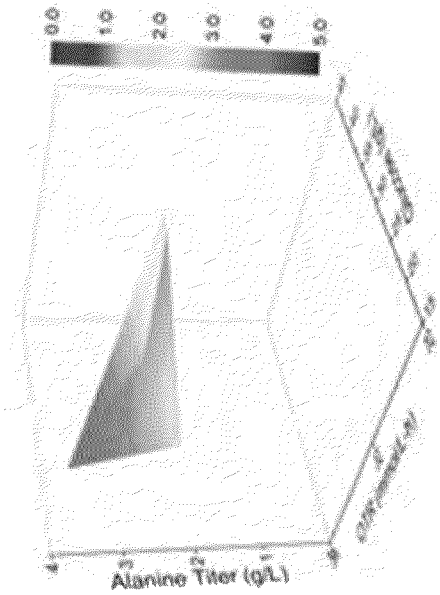
Figure 22A:
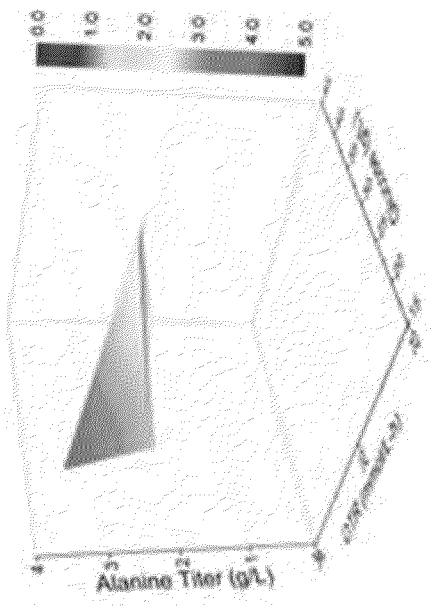
Figure 22C:
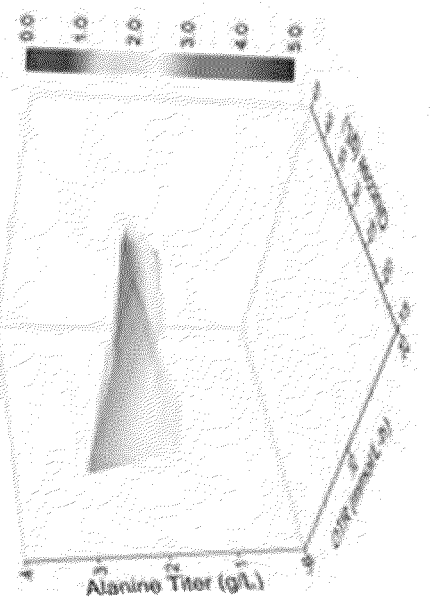
Figure 23A:
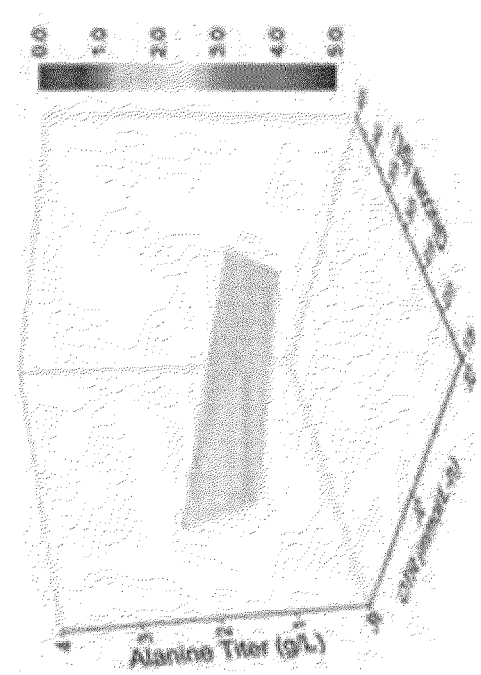
FIGS. 23A-D depict alanine production in response to different OTR and glucose concentration in micro-fermentation for 4 strains evaluated for robustness.
Figure 23B:
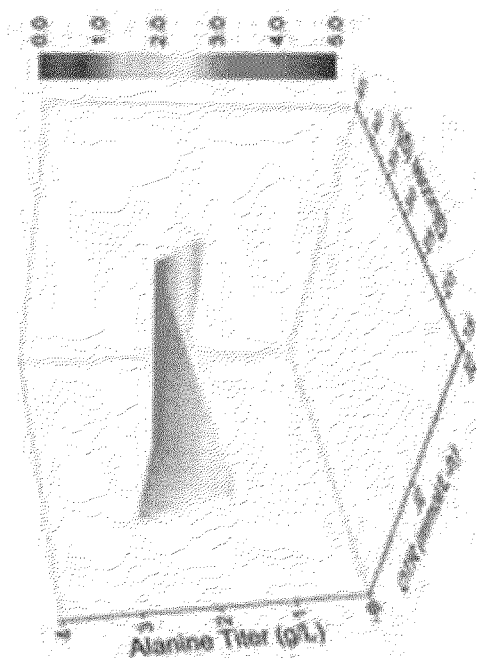
Figure 23C:
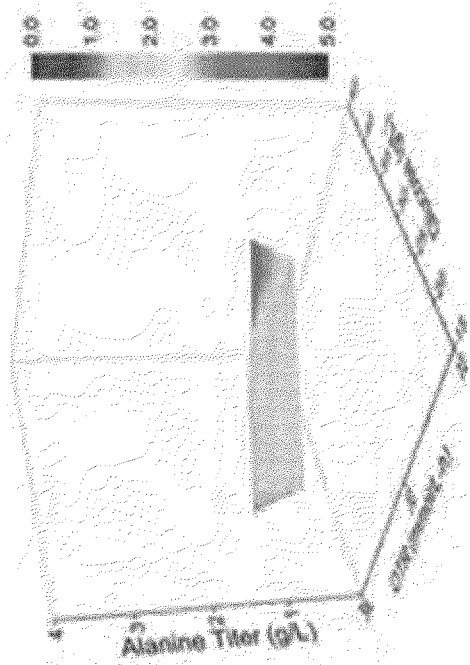
Figure 23D:
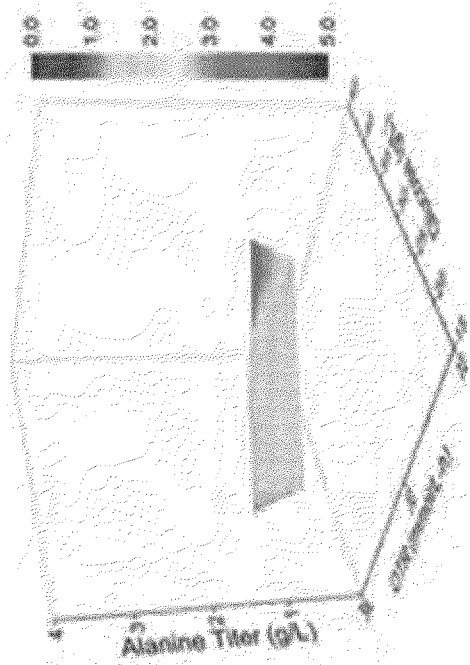
Figure 24A:
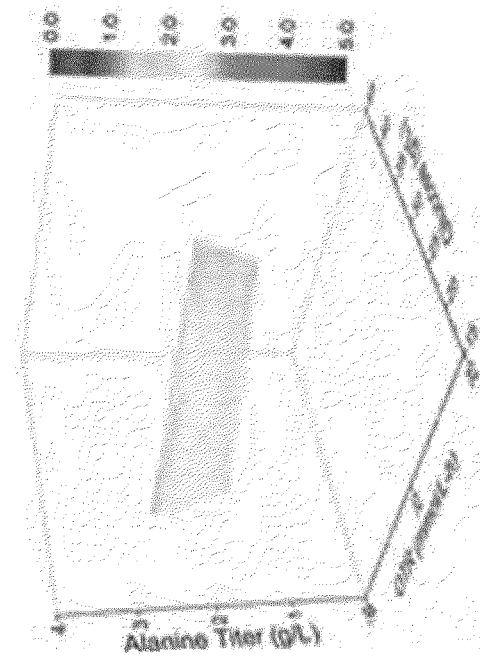
FIGS. 24A-D depict alanine production in response to different OTR and glucose concentration in micro-fermentation for 4 strains evaluated for robustness.
Figure 24B:
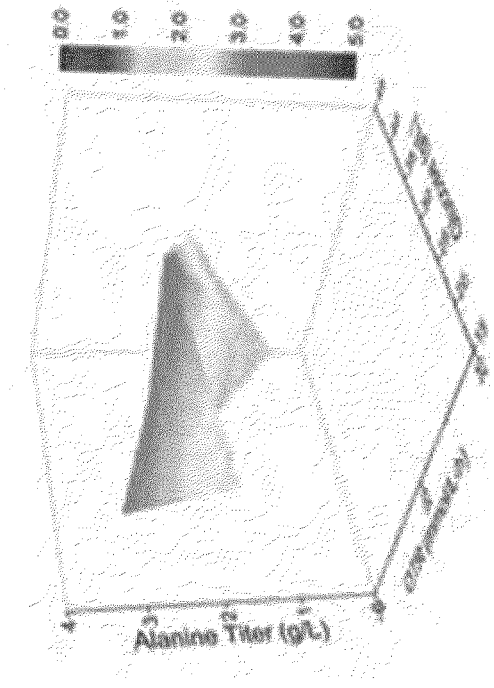
Figure 24C:
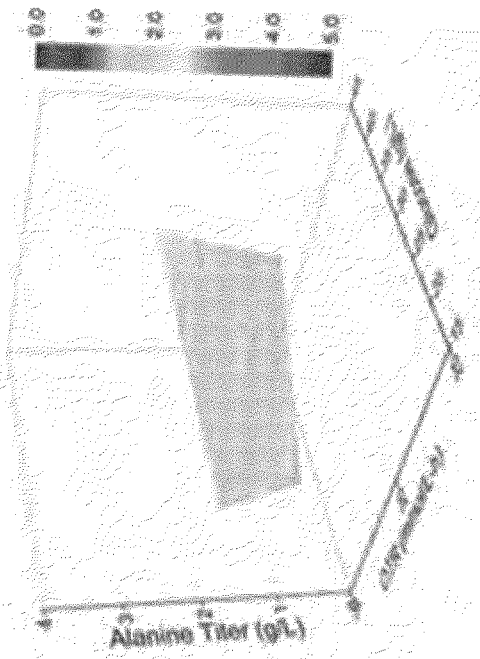
Figure 24D:
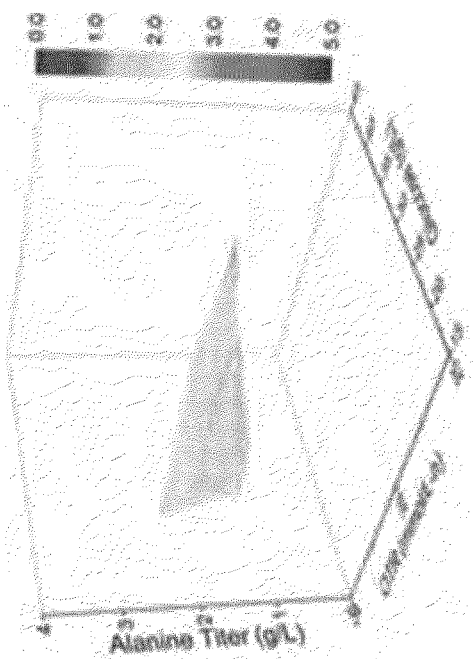
Figure 25A:
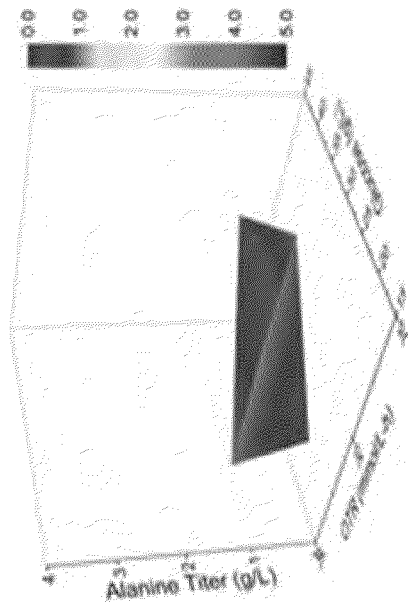
FIGS. 25A-D depict alanine production in response to different OTR and glucose concentration in micro-fermentation for 4 strains evaluated for robustness.
Figure 25B:
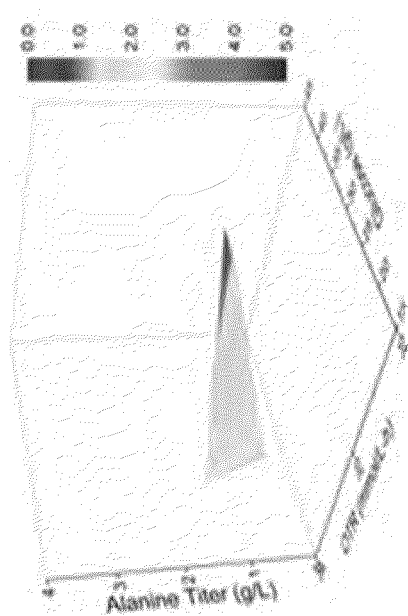
Figure 25C:
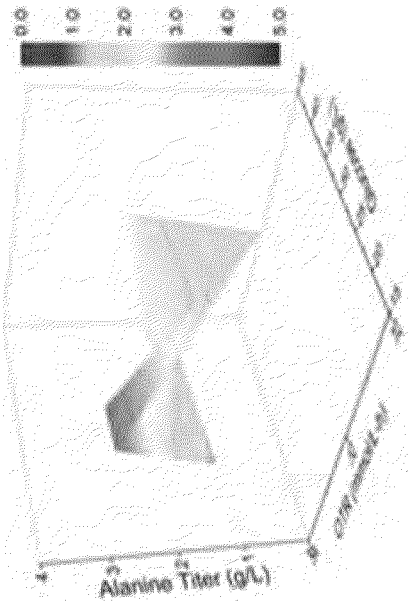
Figure 25D:
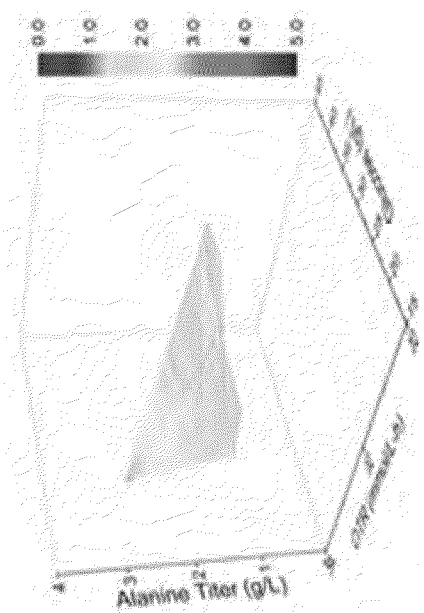
Figure 26A:
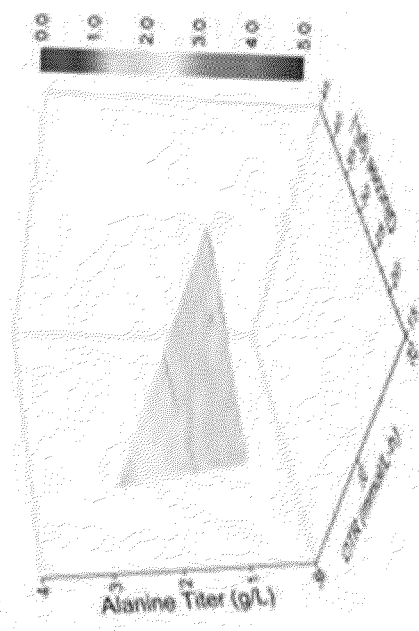
FIGS. 26A-D depict alanine production in response to different OTR and glucose concentration in micro-fermentation for 4 strains evaluated for robustness.
Figure 26B:
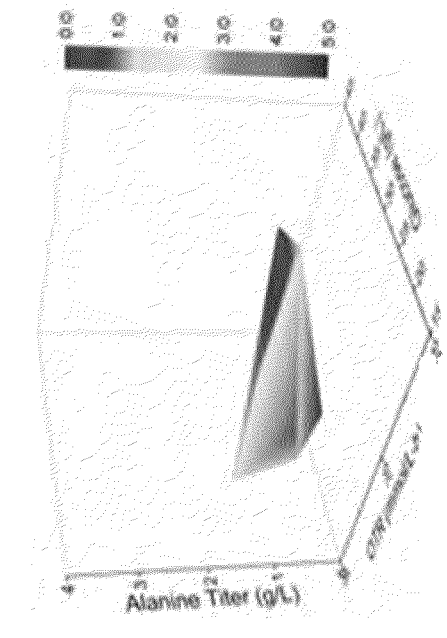
Figure 26C:
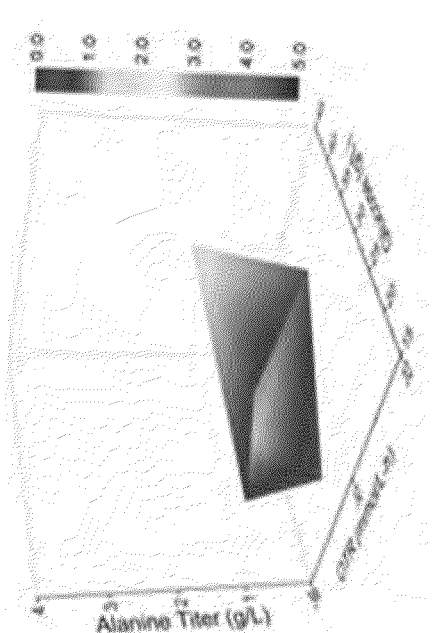
Figure 26D:
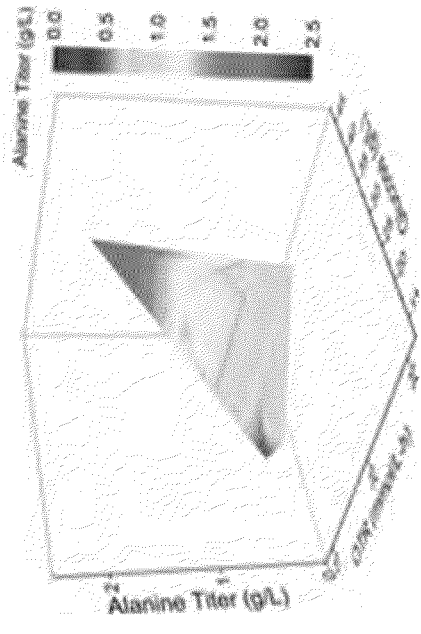
Figure 27A:
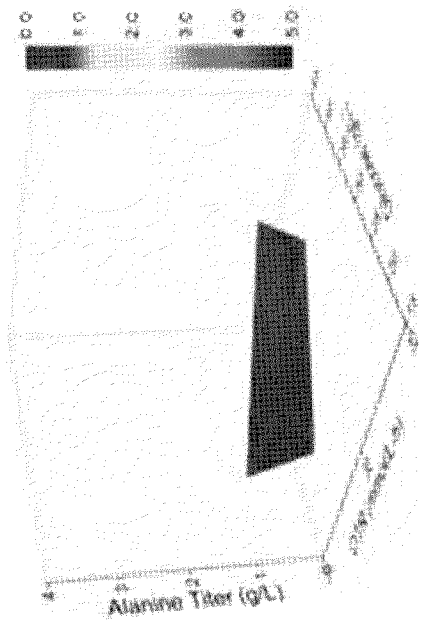
FIGS. 27A-D depict alanine production in response to different OTR and glucose concentration in micro-fermentation for 4 strains evaluated for robustness.
Figure 27B:
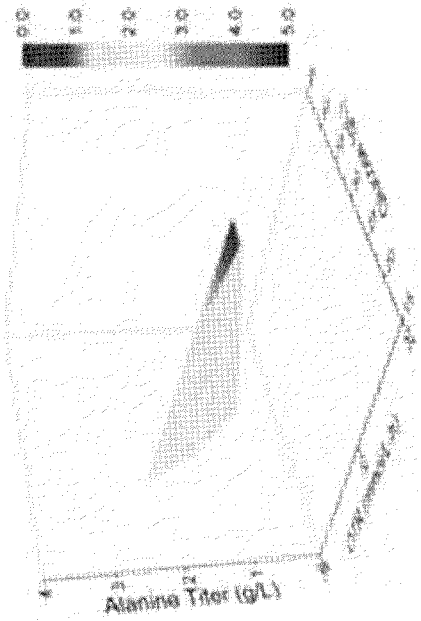
Figure 27C:
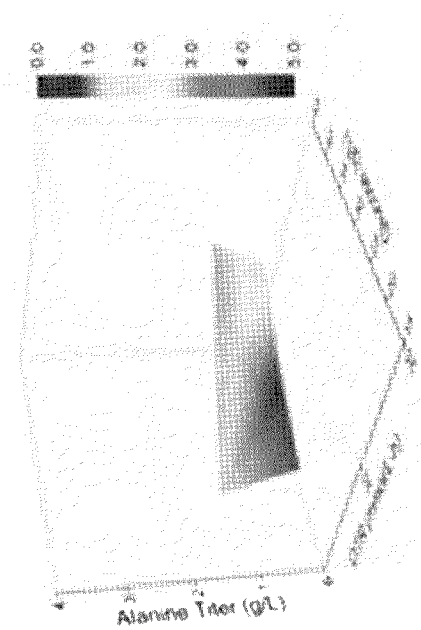
Figure 27D:
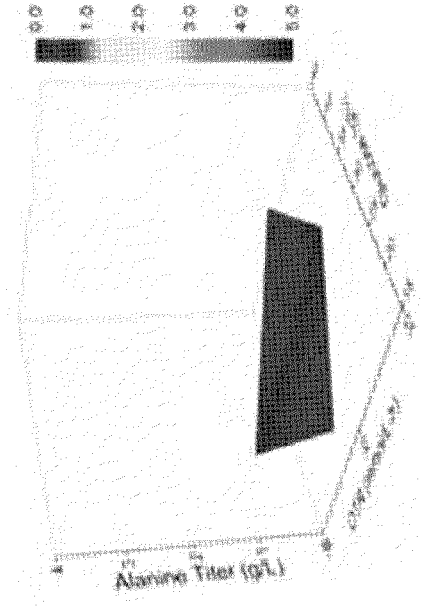
Figure 28A:
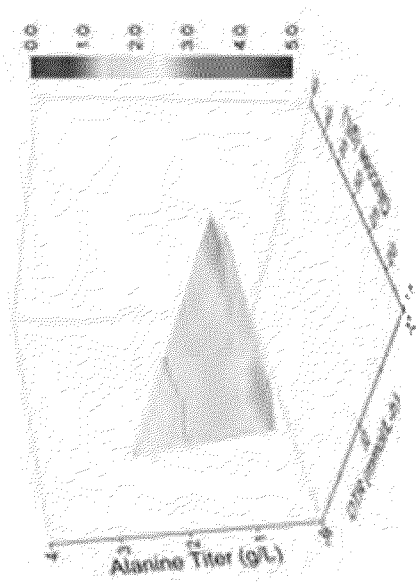
FIGS. 28A-D depict alanine production in response to different OTR and glucose concentration in micro-fermentation for 4 strains evaluated for robustness.
Figure 28B:
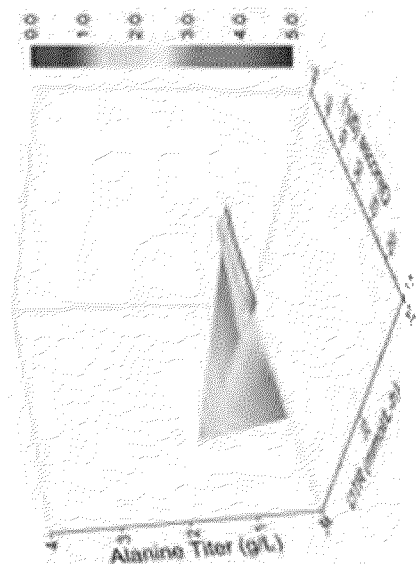
Figure 28C:
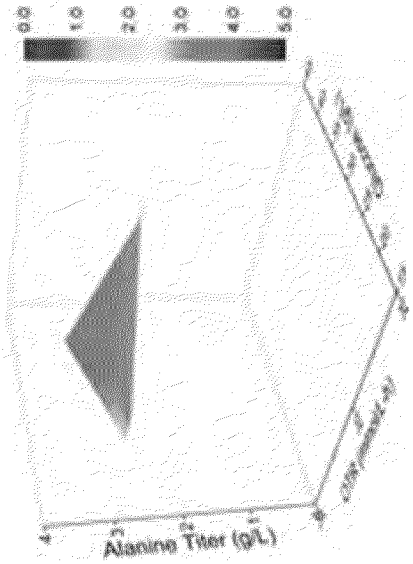
Figure 28D:
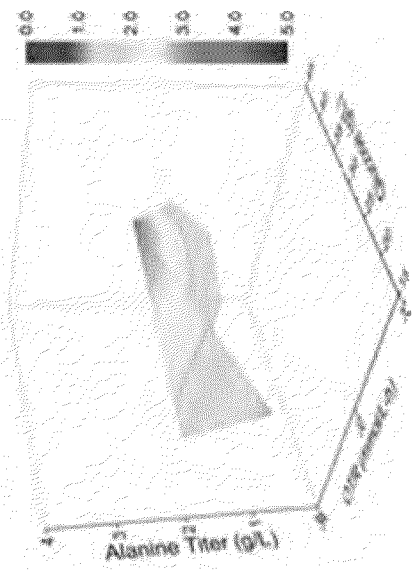
Figure 31A:
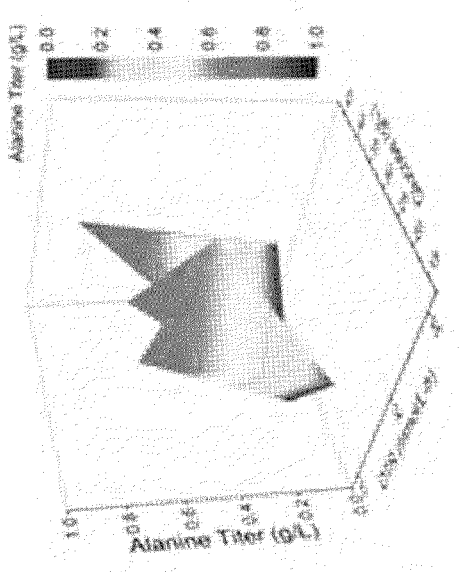
FIGS. 31A-D depict alanine production in response to different OTR and glucose concentration in micro-fermentation for 4 strains evaluated for robustness.
Figure 31B:
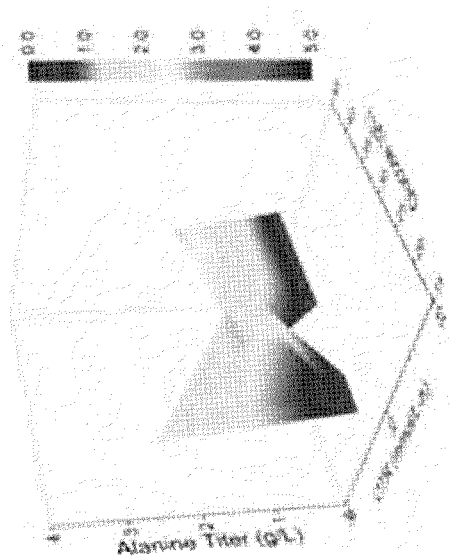
Figure 31C:
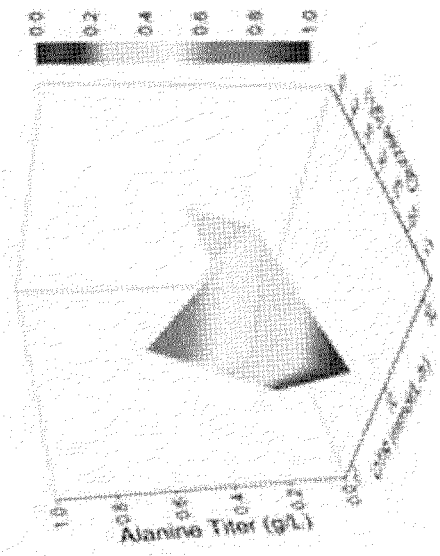
Figure 31D:
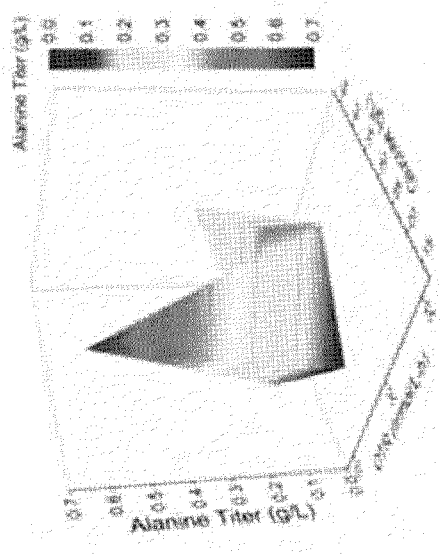

FIG. 18: Heatmap for L-alanine production by gapN/gapA strains.

FIGS. 19A-D: Alanine production in response to different OTR and glucose concentration in micro-fermentation for 4 strains evaluated for robustness.

FIGS. 20A-D: Alanine production in response to different OTR and glucose concentration in micro-fermentation for 4 strains evaluated for robustness.

FIGS. 21A-D: Alanine production in response to different OTR and glucose concentration in micro-fermentation for 4 strains evaluated for robustness.

FIGS. 22A-D: Alanine production in response to different OTR and glucose concentration in micro-fermentation for 4 strains evaluated for robustness.

FIGS. 23A-D: Alanine production in response to different OTR and glucose concentration in micro-fermentation for 4 strains evaluated for robustness.

FIGS. 24A-D: Alanine production in response to different OTR and glucose concentration in micro-fermentation for 4 strains evaluated for robustness.

FIGS. 25A-D: Alanine production in response to different OTR and glucose concentration in micro-fermentation for 4 strains evaluated for robustness.

FIGS. 26A-D: Alanine production in response to different OTR and glucose concentration in micro-fermentation for 4 strains evaluated for robustness.

FIGS. 27A-D: Alanine production in response to different OTR and glucose concentration in micro-fermentation for 4 strains evaluated for robustness.

FIGS. 28A-D: Alanine production in response to different OTR and glucose concentration in micro-fermentation for 4 strains evaluated for robustness.

FIGS. 29A-D: Alanine production in response to different OTR and glucose concentration in micro-fermentation for 4 strains evaluated for robustness.

FIGS. 30A-D: Alanine production in response to different OTR and glucose concentration in micro-fermentation for 4 strains evaluated for robustness.

FIGS. 31A-D: Alanine production in response to different OTR and glucose concentration in micro-fermentation for 4 strains evaluated for robustness.

Figure 32:
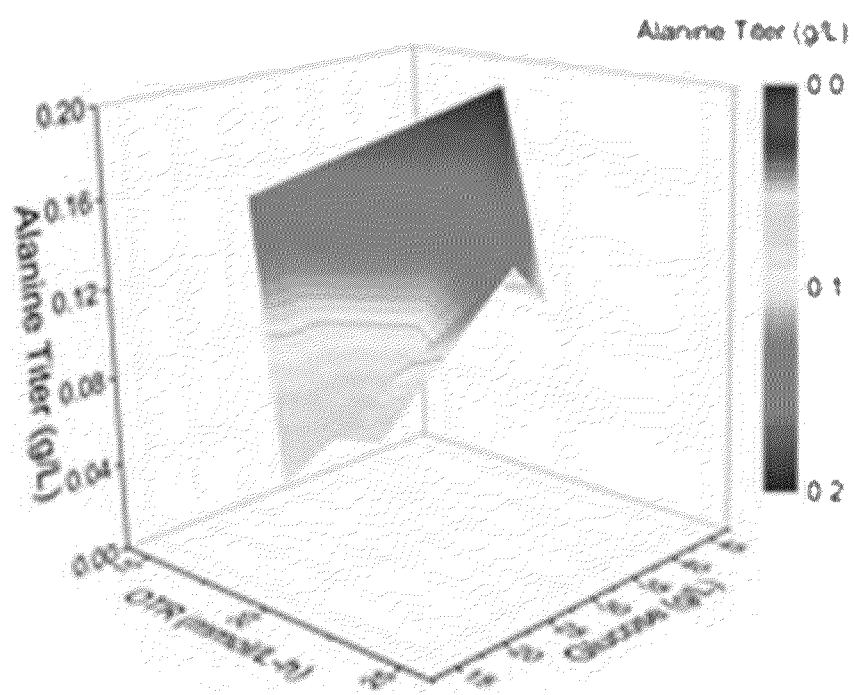
FIG. 32 depicts alanine production in response to different OTR and glucose concentration in micro-fermentation for one strain evaluated for robustness.

FIG. 32: Alanine production in response to different OTR and glucose concentration in micro-fermentation for one strain evaluated for robustness.

FIGS. 33A-B: Growth profile for all (FIG. 33A) valve and (FIG. 33B) growth associated strains at 1 L scale evaluated in this paper. Growth curves were synced to account for any variations in lag time. Valve strains growth curves were synced to the same mid-exponential point. Growth associated strains growth curves were synced to the same take-off point.

Figure 34:
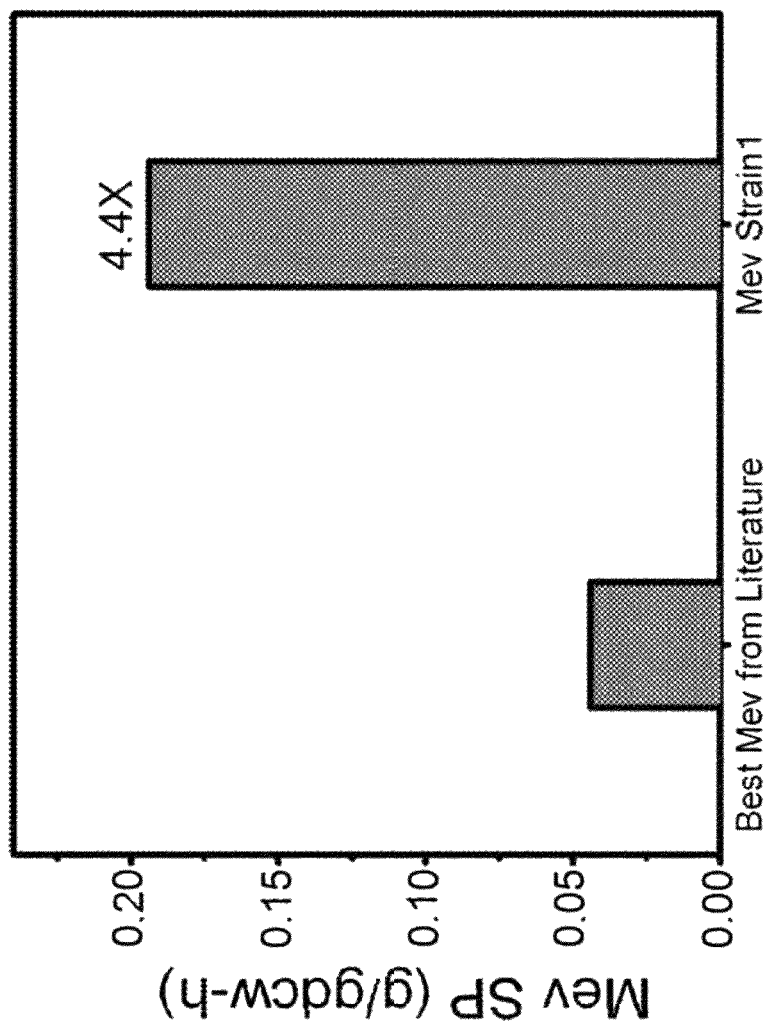
FIG. 34 depicts specific Productivity (SP) comparison for strain with highest mevalonate titer from literature and mevalonate strain 1 evaluated in this work.

FIG. 34: Specific Productivity (SP) comparison for strain with highest mevalonate titer from literature and mevalonate strain 1 evaluated in this work.

Figure 35:
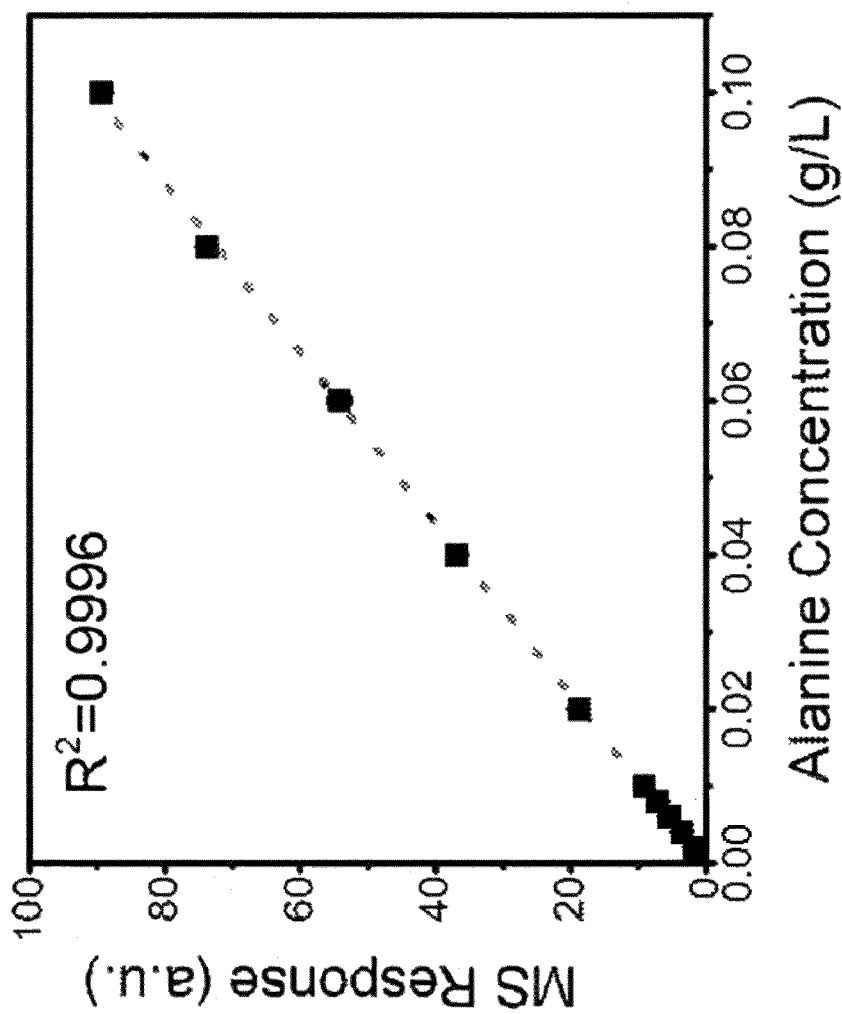
FIG. 35 depicts alanine standard curve from MS measurement. Average and standard deviation for mass spec response from triplicate standard measurement were plotted.

FIG. 35: Alanine standard curve from MS measurement. Average and standard deviation for mass spec response from triplicate standard measurement were plotted.

Figure 36B:
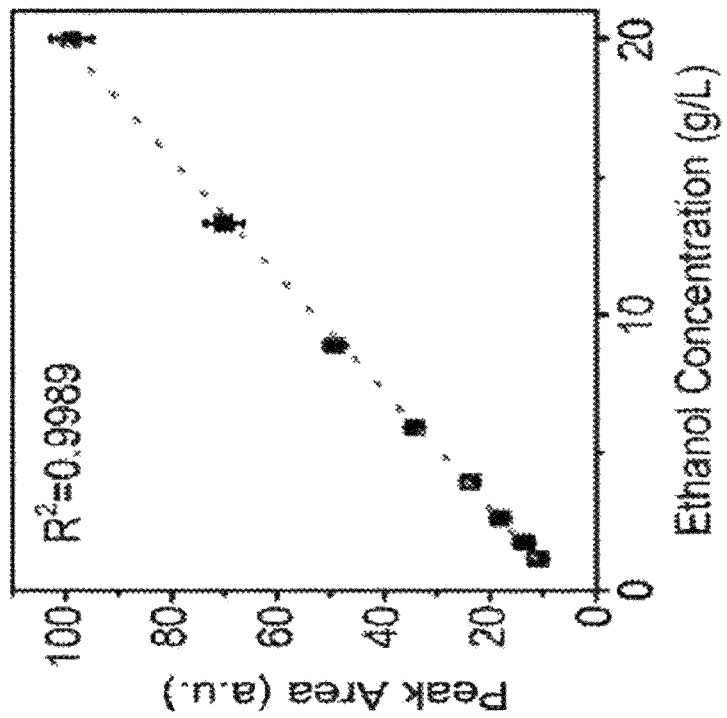
FIGS. 36A-B depict glucose and ethanol standard curves from RI measurement.
Figure 36A:
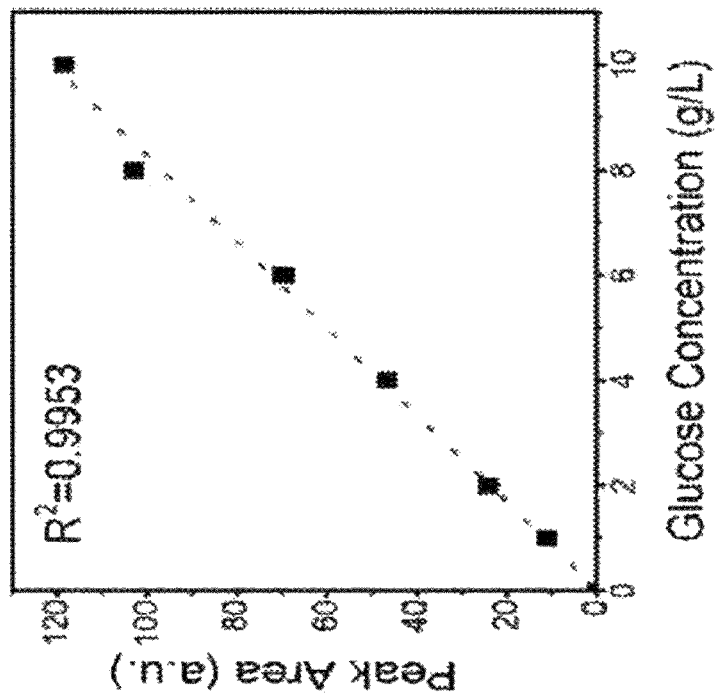

FIGS. 36A-B: Glucose (FIG. 36A) and ethanol (FIG. 36B) standard curves from RI measurement. Average and standard deviation for peak area from triplicate standard measurement were plotted.

Figure 37:
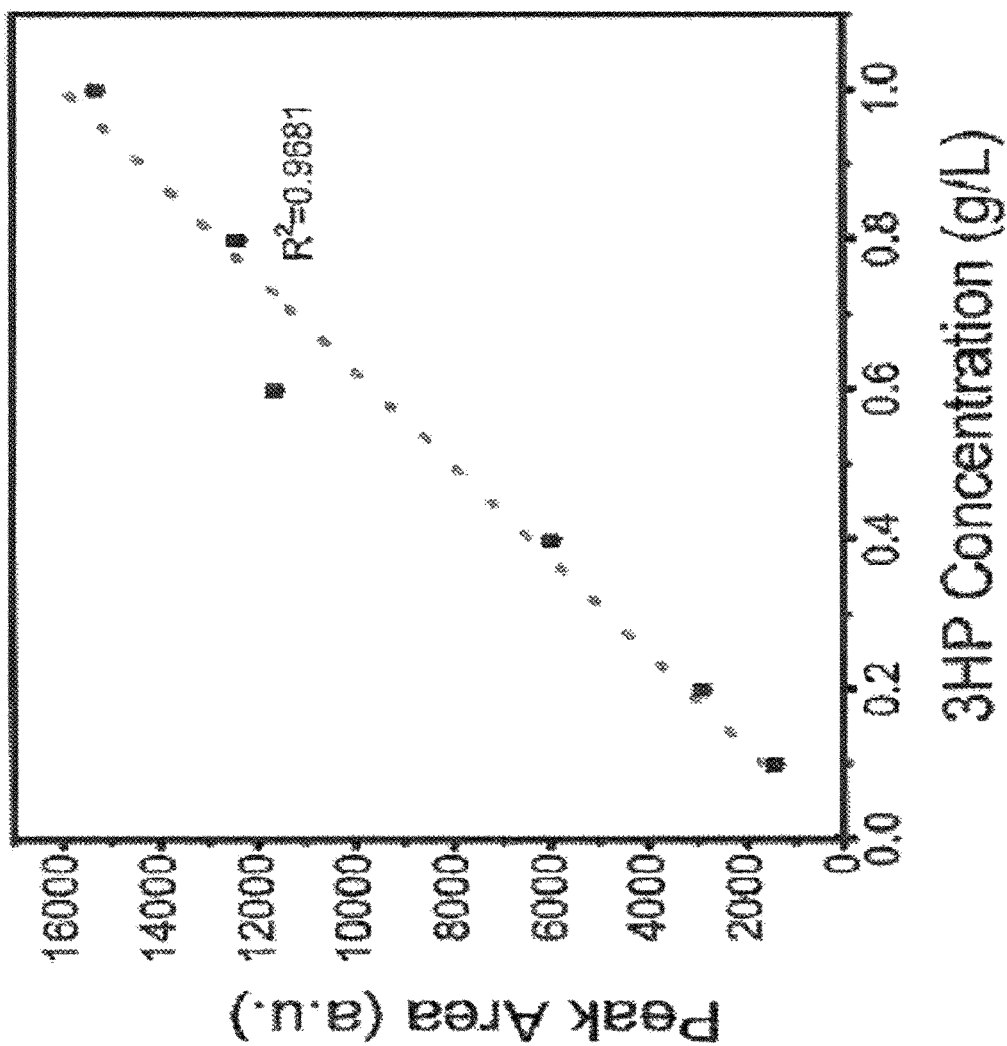
FIG. 37 depicts 3-Hydroxypropionic acid standard curve from TUV measurement.

FIG. 37: 3-Hydroxypropionic acid standard curve from TUV measurement. Average and standard deviation for peak area from duplicate standard measurement were plotted.

FIGS. 38A-D: TUV standard curves for (FIG. 38A) L-alanine, (FIG. 38B) D-alanine, (FIG. 38C) mevalonic acid, and (FIG. 38D) mevalonolactone. Average and standard deviation for peak area from triplicate standard measurement were plotted.

REFERENCES

1. Cameron, D. E.; Bashor, C. J.; Collins, J. J., A brief history of synthetic biology. *Nat Rev Microbiol* 2014, 12 (5), 381-90.
2. Cheong, S.; Clomburg, J. M.; Gonzalez, R., Energy- and carbon-efficient synthesis of functionalized small molecules in bacteria using non-decarboxylative Claisen condensation reactions. *Nature biotechnology* 2016, 34 (5), 556-61.
3. Choi, S. Y.; Park, S. J.; Kim, W. J.; Yang, J. E.; Lee, H.; Shin, J.; Lee, S. Y., One-step fermentative production of poly(lactate-co-glycolate) from carbohydrates in *Escherichia coli*. *Nature biotechnology* 2016, 34 (4), 435-40.
4. Jarboe, L. R.; Zhang, X.; Wang, X.; Moore, J. C.; Shanmugam, K. T.; Ingram, L. O., Metabolic engineering for production of biorenewable fuels and chemicals: contributions of synthetic biology. *Journal of biomedicine & biotechnology* 2010, 761042.
5. Lee, J. W.; Na, D.; Park, J. M.; Lee, J.; Choi, S.; Lee, S. Y., Systems metabolic engineering of microorganisms for natural and non-natural chemicals. *Nat Chem Biol* 2012, 8 (6), 536-46.
6. Dellomonaco, C.; Clomburg, J. M.; Miller, E. N.; Gonzalez, R., Engineered reversal of the beta-oxidation cycle for the synthesis of fuels and chemicals. *Nature* 2011, 476 (7360), 355-9.
7. Kim, S.; Clomburg, J. M.; Gonzalez, R., Synthesis of medium-chain length (C6-C10) fuels and chemicals via beta-oxidation reversal in *Escherichia coli*. *J Ind Microbiol Biotechnol* 2015, 42 (3), 465-75.
8. Meadows, A. L.; Hawkins, K. M.; Tsegaye, Y.; Antipov, E.; Kim, Y.; Raetz, L.; Dahl, R. H.; Tai, A.; Mahatdejkul-Meadows, T.; Xu, L.; Zhao, L.; Dasika, M. S.; Murarka, A.; Lenihan, J.; Eng, D.; Leng, J. S.; Liu, C. L.; Wenger, J. W.; Jiang, H.; Chao, L.; Westfall, P.; Lai, J.; Ganesan, S.; Jackson, P.; Mans, R.; Platt, D.; Reeves, C. D.; Saija, P. R.; Wichmann, G.; Holmes, V. F.; Benjamin, K.; Hill, P. W.; Gardner, T. S.; Tsong, A. E., Rewriting yeast central carbon metabolism for industrial isoprenoid production. *Nature* 2016, 537 (7622), 694-697.
9. Yadav, V. G.; De Mey, M.; Lim, C. G.; Ajikumar, P. K.; Stephanopoulos, G., The future of metabolic engineering and synthetic biology: towards a systematic practice. *Metab Eng* 2012, 14 (3), 233-41.
10. Brophy, J. A.; Voigt, C. A., Principles of genetic circuit design. *Nat Methods* 2014, 11 (5), 508-20.
11. Koutinas, M.; Kiparissides, A.; Pistikopoulos, E. N.; Mantalaris, A., Bioprocess systems engineering: transferring traditional process engineering principles to industrial biotechnology. *Comput Struct Biotechnol J* 2012, 3, e201210022.

12. Rodrigo, G.; Jaramillo, A., AutoBioCAD: full biodesign automation of genetic circuits. *ACS Synth Biol* 2013,2 (5), 230-6.
13. Garst, A. D.; Bassalo, M. C.; Pines, G.; Lynch, S. A.; Halweg-Edwards, A. L.; Liu, R.; Liang, L.; Wang, Z.; Zeitoun, R.; Alexander, W. G.; Gill, R. T., Genome-wide mapping of mutations at single-nucleotide resolution for protein, metabolic and genome engineering. *Nat Biotech* 2017, 35 (1), 48-55.
14. Church, G. M.; Elowitz, M. B.; Smolke, C. D.; Voigt, C. A.; Weiss, R., Realizing the potential of synthetic biology. *Nat Rev Mol Cell Biol* 2014, 15 (4), 289-94.
15. Thomas, S.; Maynard, N. D.; Gill, J., DNA library construction using Gibson Assembly[reg]. *Nat Meth* 2015, 12 (11).
16. Goodwin, S.; McPherson, J. D.; McCombie, W. R., Coming of age: ten years of next-generation sequencing technologies. *Nat Rev Genet* 2016, 17 (6), 333-51.
17. Lynch, M. D.; Warnecke, T.; Gill, R. T., SCALEs: multiscale analysis of library enrichment. *Nat Methods* 2007, 4 (1), 87-93.
18. Zeitoun, R. I.; Garst, A. D.; Degen, G. D.; Pines, G.; Mansell, T. J.; Glebes, T. Y.; Boyle, N. R.; Gill, R. T., Multiplexed tracking of combinatorial genomic mutations in engineered cell populations. *Nat Biotechnol* 2015, 33 (6), 631-7.
19. Crook, N.; Abatemarco, J.; Sun, J.; Wagner, J. M.; Schmitz, A.; Alper, H. S., In vivo continuous evolution of genes and pathways in yeast. *Nat Commun* 2016, 7, 13051.
20. Burg, J. M., Reed, BJ., Ye, Z., Cooper, C. B., Moreb, E. A., and Lynch, M. D, Large-Scale Bioprocess Competitiveness: The Potential of Dynamic Metabolic Control in Two-Stage Fermentations. Current Opinions in Chemical Engineering 2016, (In Review).
21. Zhang, Y. H., Production of biofuels and biochemicals by in vitro synthetic biosystems: Opportunities and challenges. *Biotechnol Adv* 2015, 33 (7), 1467-83.
22. Dietrich, J. A.; McKee, A. E.; Keasling, J. D., High-throughput metabolic engineering: advances in small-molecule screening and selection. *Annu Rev Biochem* 2010, 79, 563-90.
23. Formenti, L. R.; Norregaard, A.; Bolic, A.; Hemandez, D. Q.; Hagemann, T.; Heins, A. L.; Larsson, H.; Mears, L.; Mauricio-Iglesias, M.; Kruhne, U.; Gemaey, K. V., Challenges in industrial fermentation technology research. *Biotechnol J* 2014, 9 (6), 727-38.
24. Levanon, S. S.; San, K. Y.; Bennett, G. N., Effect of oxygen on the *Escherichia coli* ArcA and FNR regulation systems and metabolic responses. *Biotechnol Bioeng* 2005, 89 (5), 556-64.
25. Logue, J. B.; Findlay, S. E.; Comte, J., Editorial: Microbial Responses to Environmental Changes. *Front Microbiol* 2015, 6, 1364.
26. Garcia-Ochoa, F.; Gomez, E., Bioreactor scale-up and oxygen transfer rate in microbial processes: an overview. *Biotechnol Adv* 2009, 27 (2), 153-76.
27. Waegeman, H.; Beauprez, J.; Moens, H.; Maertens, J.; De Mey, M.; Foulquie-Moreno, M. R.; Heijnen, J. J.; Charlier, D.; Soetaert, W., Effect of iclR and arcA knockouts on biomass formation and metabolic fluxes in *Escherichia coli* K12 and its implications on understanding the metabolism of *Escherichia coli* BL21 (DE3). *BMC Microbiol* 2011, 11, 70.
28. Waegeman, H.; Maertens, J.; Beauprez, J.; De Mey, M.; Soetaert, W., Effect of iclR and arcA deletions on physiology and metabolic fluxes in *Escherichia coli* BL21 (DE3). *Biotechnol Lett* 2012, 34 (2), 329-37.
29. Hemmerich, J.; Adelantado, N.; Barrigon, J. M.; Ponte, X.; Hormann, A.; Ferrer, P.; Kensy, F.; Valero, F., Comprehensive clone screening and evaluation of fed-batch strategies in a microbioreactor and lab scale stirred tank bioreactor system: application on *Pichia pastoris* producing *Rhizopus oryzae* lipase. *Microb Cell Fact* 2014, 13 (1), 36.
30. Ramirez-Vargas, R.; Vital-Jacome, M.; Camacho-Perez, E.; Hubbard, L.; Thalasso, F., Characterization of oxygen transfer in a 24-well microbioreactor system and potential respirometric applications. *J Biotechnol* 2014, 186, 58-65.
31. Huber, R.; Roth, S.; Rahmen, N.; Buchs, J., Utilizing high-throughput experimentation to enhance specific productivity of an *E. coli* T7 expression system by phosphate limitation. *BMC biotechnology* 2011, 11, 22.
32. Lynch, M. D., Into new territory: improved microbial synthesis through engineering of the essential metabolic network. *Curr Opin Biotechnol* 2016, 38, 106-11.
33. McGinness, K. E.; Baker, T. A.; Sauer, R. T., Engineering controllable protein degradation. *Mol Cell* 2006, 22 (5), 701-7.
34. Luo, M. L.; Mullis, A. S.; Leenay, R. T.; Beisel, C. L., Repurposing endogenous type I CRISPR-Cas systems for programmable gene repression. *Nucleic acids research* 2015, 43 (1), 674-81.
35. Qi, L. S.; Larson, M. H.; Gilbert, L. A.; Doudna, J. A.; Weissman, J. S.; Arkin, A. P.; Lim, W. A., Repurposing CRISPR as an RNA-guided platform for sequence-specific control of gene expression. *Cell* 2013, 152 (5), 1173-83.
36. Chubukov, V.; Sauer, U., Environmental dependence of stationary-phase metabolism in *Bacillus subtilis* and *Escherichia coli*. *Applied and environmental microbiology* 2014, 80 (9), 2901-9.
37. Santos-Beneit, F., The Pho regulon: a huge regulatory network in bacteria. *Front Microbiol* 2015, 6, 402.
38. Brouns, S. J.; Jore, M. M.; Lundgren, M.; Westra, E. R.; Slijkhuis, R. J.; Snijders, A. P.; Dickman, M. J.; Makarova, K. S.; Koonin, E. V.; van der Oost, J., Small CRISPR RNAs guide antiviral defense in prokaryotes. *Science* 2008, 321 (5891), 960-4.
39. Jian, J.; Zhang, S. Q.; Shi, Z. Y.; Wang, W.; Chen, G. Q.; Wu, Q., Production of polyhydroxyalkanoates by *Escherichia coli* mutants with defected mixed acid fermentation pathways. *Appl Microbiol Biotechnol* 2010, 87 (6), 2247-56.
40. Grunenfelder, B.; Rummel, G.; Vohradsky, J.; Roder, D.; Langen, H.; Jenal, U., Proteomic analysis of the bacterial cell cycle. *Proc Natl Acad Sci USA* 2001, 98 (8), 4681-6.
41. Hintsche, M.; Klumpp, S., Dilution and the theoretical description of growth-rate dependent gene expression. *J Biol Eng* 2013, 7 (1), 22.
42. Lerchner, A.; Jarasch, A.; Skerra, A., Engineering of alanine dehydrogenase from *Bacillus subtilis* for novel cofactor specificity. *Biotechnol Appl Biochem* 2016, 63 (5), 616-624.
43. Hori, H.; Yoneyama, H.; Tobe, R.; Ando, T.; Isogai, E.; Katsumata, R., Inducible L-alanine exporter encoded by the novel gene ygaW (alaE) in *Escherichia coli*. *Applied and environmental microbiology* 2011, 77 (12), 4027-34.
44. Davis, J. H.; Rubin, A. J.; Sauer, R. T., Design, construction and characterization of a set of insulated bacterial promoters. Nucleic acids research 2011, 39 (3), 1131-41.

45. Hedl, M.; Sutherlin, A.; Wilding, E. I.; Mazzulla, M.; McDevitt, D.; Lane, P.; Burgner, J. W., 2nd; Lehnbeuter, K. R.; Stauffacher, C. V.; Gwynn, M. N.; Rodwell, V. W., *Enterococcus faecalis* acetoacetyl-coenzyme A thiolase/3-hydroxy-3-methylglutaryl-coenzyme A reductase, a dual-function protein of isopentenyl diphosphate biosynthesis. *J Bacteriol* 2002, 184 (8), 2116-22.

46. Steussy, C. N.; Robison, A. D.; Tetrick, A. M.; Knight, J. T.; Rodwell, V. W.; Stauffacher, C. V.; Sutherlin, A. L., A structural limitation on enzyme activity: the case of HMG-CoA synthase. Biochemistry 2006, 45 (48), 14407-14.

47. Xiong, M.; Schneiderman, D. K.; Bates, F. S.; Hillmyer, M. A.; Zhang, K., Scalable production of mechanically tunable block polymers from sugar. *Proc Natl Acad Sci USA* 2014, 111 (23), 8357-62.

48. Otterstedt, K.; Larsson, C.; Bill, R. M.; Stahlberg, A.; Boles, E.; Hohmann, S.; Gustafsson, L., Switching the mode of metabolism in the yeast *Saccharomyces cerevisiae*. *EMBO Rep* 2004, 5 (5), 532-7.

49. Hubmann, G.; Guillouet, S.; Nevoigt, E., Gpd1 and Gpd2 fine-tuning for sustainable reduction of glycerol formation in *Saccharomyces cerevisiae*. *Applied and environmental microbiology* 2011, 77 (17), 5857-67.

50. Lascaris, R.; Bussemaker, H. J.; Boorsma, A.; Piper, M.; van der Spek, H.; Grivell, L.; Blom, J., Hap4p overexpression in glucose-grown *Saccharomyces cerevisiae* induces cells to enter a novel metabolic state. *Genome Biol* 2003, 4 (1), R3.

51. Mittal, N.; Babu, M. M.; Roy, N., The efficiency of mitochondrial electron transport chain is increased in the long-lived mrg19 *Saccharomyces cerevisiae*. *Aging Cell* 2009, 8 (6), 643-53.

52. Thomas, M. R.; O'Shea, E. K., An intracellular phosphate buffer filters transient fluctuations in extracellular phosphate levels. *Proc Natl Acad Sci USA* 2005, 102 (27), 9565-70.

53. Gray, J. V.; Petsko, G. A.; Johnston, G. C.; Ringe, D.; Singer, R. A.; Wemer-Washbume, M., "Sleeping beauty": quiescence in *Saccharomyces cerevisiae*. *Microbiol Mol Biol Rev* 2004, 68 (2), 187-206.

54. Grilly, C.; Stricker, J.; Pang, W. L.; Bennett, M. R.; Hasty, J., A synthetic gene network for tuning protein degradation in *Saccharomyces cerevisiae*. *Mol Syst Biol* 2007, 3, 127.

55. Orth, J. D.; Thiele, I.; Palsson, B. O., What is flux balance analysis? *Nat Biotechnol* 2010, 28 (3), 245-8.

56. Yim, H.; Haselbeck, R.; Niu, W.; Pujol-Baxley, C.; Burgard, A.; Boldt, J.; Khandurina, J.; Trawick, J. D.; Osterhout, R. E.; Stephen, R.; Estadilla, J.; Teisan, S.; Schreyer, H. B.; Andrae, S.; Yang, T. H.; Lee, S. Y.; Burk, M. J.; Van Dien, S., Metabolic engineering of *Escherichia coli* for direct production of 1,4-butanediol. *Nat Chem Biol* 2011, 7 (7), 445-52.

57. Gupta, A.; Reizman, I. M.; Reisch, C. R.; Prather, K. L., Dynamic regulation of metabolic flux in engineered bacteria using a pathway-independent quorum-sensing circuit. *Nature biotechnology* 2017, 35 (3), 273-279.

58. Wang, J.; Yu, H. Q., Biosynthesis of polyhydroxybutyrate (PHB) and extracellular polymeric substances (EPS) by *Ralstonia eutropha* ATCC 17699 in batch cultures. *Appl Microbiol Biotechnol* 2007, 75 (4), 871-8.

59. Xu, P.; Qiao, K.; Ahn, W. S.; Stephanopoulos, G., Engineering *Yarrowia lipolytica* as a platform for synthesis of drop-in transportation fuels and oleochemicals. Proc Natl Acad Sci US A 2016, 113 (39), 10848-53.

60. Lynch, M. D.; Warnecke, T.; Gill, R. T. Method for Producing 3-Hydroxypropionic Acid and Other Products. Sep. 8, 2011.

61. Qiao, K.; Wasylenko, T. M.; Zhou, K.; Xu, P.; Stephanopoulos, G., Lipid production in *Yarrowia lipolytica* is maximized by engineering cytosolic redox metabolism. *Nat Biotechnol* 2017.

62. Jian, J.; Zhang, S. Q.; Shi, Z. Y.; Wang, W.; Chen, G. Q.; Wu, Q., Production of polyhydroxyalkanoates by *Escherichia coli* mutants with defected mixed acid fermentation pathways. *Appl Microbiol Biotechnol* 2010, 87 (6), 2247-56.

63. Sharan, S. K.; Thomason, L. C.; Kuznetsov, S. G.; Court, D. L., Recombineering: a homologous recombination-based method of genetic engineering. Nature protocols 2009, 4 (2), 206-23.

64. Li, X. T.; Thomason, L. C.; Sawitzke, J. A.; Costantino, N.; Court, D. L., Positive and negative selection using the tetA-sacB cassette: recombineering and P1 transduction in *Escherichia coli*. *Nucleic acids research* 2013, 41 (22), e204.

65. Baba, T.; Ara, T.; Hasegawa, M.; Takai, Y.; Okumura, Y.; Baba, M.; Datsenko, K. A.; Tomita, M.; Wanner, B. L.; Mori, H., Construction of *Escherichia coli* K-12 in-frame, single-gene knockout mutants: the Keio collection. Molecular systems biology 2006, 2, 2006 0008.

66. van Dijken, J. P.; Bauer, J.; Brambilla, L.; Duboc, P.; Francois, J. M.; Gancedo, C.; Giuseppin, M. L. F.; Heijnen, J. J.; Hoare, M.; Lange, H. C.; Madden, E. A.; Niederberger, P.; Nielsen, J.; Parrou, J. L.; Petit, T.; Porro, D.; Reuss, M.; van Riel, N.; Rizzi, M.; Steensma, H. Y.; Verrips, C. T.; Vindelov, J.; Pronk, J. T., An interlaboratory comparison of physiological and genetic properties of four *Saccharomyces cerevisiae* strains. *Enzyme and Microbial Technology* 2000, 26 (9-10), 706-714.

67. Otterstedt, K.; Larsson, C.; Bill, R. M.; Stahlberg, A.; Boles, E.; Hohmann, S.; Gustafsson, L., Switching the mode of metabolism in the yeast *Saccharomyces cerevisiae*. *EMBO Rep* 2004, 5 (5), 532-7.

68. Wieczorke, R.; Krampe, S.; Weierstall, T.; Freidel, K.; Hollenberg, C. P.; Boles, E., Concurrent knock-out of at least 20 transporter genes is required to block uptake of hexoses in *Saccharomyces cerevisiae*. *FEBS Letters* 1999, 464 (3), 123-128.

69. Gietz, R. D.; Schiestl, R. H., High-efficiency yeast transformation using the LiAc/SS carrier DNA/PEG method. *Nature protocols* 2007, 2 (1), 31-4.

70. Stovicek, V.; Borodina, I.; Forster, J., CRISPR-Cas system enables fast and simple genome editing of industrial *Saccharomyces cerevisiae* strains. *Metabolic Engineering Communications* 2015, 2, 13-22.

71. Labun, K.; Montague, T. G.; Gagnon, J. A.; Thyme, S. B.; Valen, E., CHOPCHOP v2: a web tool for the next generation of CRISPR genome engineering. Nucleic acids research 2016, 44 (W1), W272-6.

72. Hoffman, C. S.; Winston, F., A ten-minute DNA preparation from yeast efficiently releases autonomous plasmids for transformaion of *Escherichia coli*. Gene 1987, 57 (2-3), 267-272.

73. Luo, M. L.; Mullis, A. S.; Leenay, R. T.; Beisel, C. L., Repurposing endogenous type I CRISPR-Cas systems for programmable gene repression. *Nucleic acids research* 2015, 43 (1), 674-81.

74. Davis, J. H.; Rubin, A. J.; Sauer, R. T., Design, construction and characterization of a set of insulated bacterial promoters. *Nucleic acids research* 2011, 39 (3), 1131-41.

75. Smith, J. D.; Suresh, S.; Schlecht, U.; Wu, M.; Wagih, O.; Peltz, G.; Davis, R. W.; Steinmetz, L. M.; Parts, L.; St Onge, R. P., Quantitative CRISPR interference screens in yeast identify chemical-genetic interactions and new rules for guide RNA design. *Genome Biol* 2016, 17, 45.

76. Gilbert, L. A.; Larson, M. H.; Morsut, L.; Liu, Z.; Brar, G. A.; Torres, S. E.; Stern-Ginossar, N.; Brandman, O.; Whitehead, E. H.; Doudna, J. A.; Lim, W. A.; Weissman, J. S.; Qi, L. S., CRISPR-mediated modular RNA-guided regulation of transcription in eukaryotes. *Cell* 2013, 154 (2), 442-51.

77. Sikorski, R. S.; Hieter, P., A system of shuttle vectors and yeast host strains designed for efficient manipulation of DNA in *Saccharomyces cerevisiae*. *Genetics* 1989, 122 (1), 19-27.

78. Duetz, W. A.; Ruedi, L.; Hermann, R.; O'Connor, K.; Buchs, J.; Witholt, B., Methods for intense aeration, growth, storage, and replication of bacterial strains in microtiter plates. *Applied and environmental microbiology* 2000, 66 (6), 2641-6.

79. Duetz, W. A.; Witholt, B., Effectiveness of orbital shaking for the aeration of suspended bacterial cultures in square-deepwell microtiter plates. *Biochem Eng J* 2001, 7 (2), 113-115.

80. Lindemann, C. J.; Singh, M. M.; Ramjit, H. G.; Bell, C.; Ip, D. P., Determination of mevalonolactone in capsules by capillary gas-liquid chromatography. *J Pharm Biomed Anal* 1991, 9 (4), 311-6.

81. Keseler, I. M.; Mackie, A.; Peralta-Gil, M.; Santos-Zavaleta, A.; Gama-Castro, S.; Bonavides-Martinez, C.; Fulcher, C.; Huerta, A. M.; Kothari, A.; Krummenacker, M.; Latendresse, M.; Muniz-Rascado, L.; Ong, Q.; Paley, S.; Schroder, I.; Shearer, A. G.; Subhraveti, P.; Travers, M.; Weerasinghe, D.; Weiss, V.; Collado-Vides, J.; Gunsalus, R. P.; Paulsen, I.; Karp, P. D., EcoCyc: fusing model organism databases with systems biology. *Nucleic acids research* 2013, 41 (Database issue), D605-12.

82. Davis, J. H.; Rubin, A. J.; Sauer, R. T., Design, construction and characterization of a set of insulated bacterial promoters. *Nucleic acids research* 2011, 39 (3), 1131-41.

83. Poo, H.; Song, J. J.; Hong, S.-P.; Choi, Y.-H.; Yun, S. W.; Kim, J.-H.; Lee, S. C.; Lee, S.-G.; Sung, M. H., Novel high-level constitutive expression system, pHCE vector, for a convenient and cost-effective soluble production of human tumor necrosis factor-α. *Biotechnology Letters* 2002, 24 (14), 1185-1189.

84. Baba, T.; Ara, T.; Hasegawa, M.; Takai, Y.; Okumura, Y.; Baba, M.; Datsenko, K. A.; Tomita, M.; Wanner, B. L.; Mori, H., Construction of *Escherichia coli* K-12 in-frame, single-gene knockout mutants: the Keio collection. *Mol Syst Biol* 2006, 2, 2006 0008.

85. Jian, J.; Zhang, S. Q.; Shi, Z. Y.; Wang, W.; Chen, G. Q.; Wu, Q., Production of polyhydroxyalkanoates by *Escherichia coli* mutants with defected mixed acid fermentation pathways. *Appl Microbiol Biotechnol* 2010, 87 (6), 2247-56.

86. van Dijken, J. P.; Bauer, J.; Brambilla, L.; Duboc, P.; Francois, J. M.; Gancedo, C.; Giuseppin, M. L. F.; Heijnen, J. J.; Hoare, M.; Lange, H. C.; Madden, E. A.; Niederberger, P.; Nielsen, J.; Parrou, J. L.; Petit, T.; Porro, D.; Reuss, M.; van Riel, N.; Rizzi, M.; Steensma, H. Y.; Verrips, C. T.; Vindelov, J.; Pronk, J. T., An interlaboratory comparison of physiological and genetic properties of four *Saccharomyces cerevisiae* strains. *Enzyme and Microbial Technology* 2000, 26 (9-10), 706-714.

87. Otterstedt, K.; Larsson, C.; Bill, R. M.; Stahlberg, A.; Boles, E.; Hohmann, S.; Gustafsson, L., Switching the mode of metabolism in the yeast *Saccharomyces cerevisiae*. *EMBO Rep* 2004, 5 (5), 532-7.

88. Luo, M. L.; Mullis, A. S.; Leenay, R. T.; Beisel, C. L., Repurposing endogenous type I CRISPR-Cas systems for programmable gene repression. *Nucleic acids research* 2015, 43 (1), 674-81.

89. Wilde, R. J.; Guest, J. R., Transcript analysis of the citrate synthase and succinate dehydrogenase genes of *Escherichia coli* K12. *J Gen Microbiol* 1986, 132 (12), 3239-51.

90. Charpentier, B.; Branlant, C., The *Escherichia coli* gapA gene is transcribed by the vegetative RNA polymerase holoenzyme E sigma 70 and by the heat shock RNA polymerase E sigma 32. *Journal of Bacteriology* 1994, 176 (3), 830-839.

91. Li, X. T.; Thomason, L. C.; Sawitzke, J. A.; Costantino, N.; Court, D. L., Positive and negative selection using the tetA-sacB cassette: recombineering and P1 transduction in *Escherichia coli*. *Nucleic acids research* 2013, 41 (22), e204.

92. Duetz, W. A.; Ruedi, L.; Hermann, R.; O'Connor, K.; Buchs, J.; Witholt, B., Methods for intense aeration, growth, storage, and replication of bacterial strains in microtiter plates. *Applied and environmental microbiology* 2000, 66 (6), 2641-6.

93. Duetz, W. A.; Witholt, B., Effectiveness of orbital shaking for the aeration of suspended bacterial cultures in square-deepwell microtiter plates. *Biochem Eng J* 2001, 7 (2), 113-115.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A genetically modified microorganism comprising:
   i. a production pathway comprising at least one production enzyme for biosynthesis of a product selected from the group: an amino acid, acetate, acetoin, acetone, acrylic, malate, fatty acid ethyl esters, isoprenoids, glycerol, ethylene glycol, ethylene, propylene, butylene, isobutylene, ethyl acetate, vinyl acetate, 1,4-butanediol, 2,3-butanediol, butanol, isobutanol, sec-butanol, butyrate, isobutyrate, 2-OH-isobutryate, 3-OH-butyrate, ethanol, isopropanol, D-lactate, L-lactate, pyruvate, itaconate, levulinate, glucarate, glutarate, caprolactam, adipic acid, propanol, isopropanol, fused alcohols, 1,2-propanediol, 1,3-propanediol, formate, fumaric acid, propionic acid, succinic acid, valeric acid, maleic acid, or poly-hydroxybutyrate; and
   ii. one or more synthetic metabolic valves for reducing or eliminating flux through multiple metabolic pathways within the genetically modified microorganism when the synthetic metabolic valves are induced, the one or more synthetic metabolic valves comprising:
      a) at least one silencing synthetic metabolic valve that silences gene expression of a gene selected from: fabI, gltA, lpd, zwf, and udhA, or
      b) at least one proteolytic synthetic metabolic valve that controls proteolysis of a proteolyzable enzyme selected from: fabI, gltA, lpd, zwf, and udhA; and
   wherein growth of the genetically modified microorganism is slowed or stopped and product production is enhanced, as compared to a microorganism lacking the production pathway or synthetic metabolic valve, by inducing the synthetic metabolic valve, and
   wherein growth of the genetically modified microorganism is slowed or stopped by depletion of a limiting nutrient thereby inducing a stationary phase, and product production is enhanced, as compared to a microorganism lacking the production pathway or synthetic metabolic valve, by inducing the synthetic metabolic valve in the stationary phase,
   wherein the synthetic metabolic valve combination produces a genetically modified microorganism that is robust to changes in environmental conditions as evidenced by a robustness score greater than 0.6.

2. A genetically modified *E. coli*, comprising:
   i. a production pathway comprising at least one production enzyme for biosynthesis of a product selected from the group: an amino acid, acetate, acetoin, acetone, acrylic, malate, fatty acid ethyl esters, isoprenoids, glycerol, ethylene glycol, ethylene, propylene, butylene, isobutylene, ethyl acetate, vinyl acetate, 1,4-butanediol, 2,3-butanediol, butanol, isobutanol, sec-butanol, butyrate, isobutyrate, 2-OH-isobutryate, 3-OH-butyrate, ethanol, isopropanol, D-lactate, L-lactate, pyruvate, itaconate, levulinate, glucarate, glutarate, caprolactam, adipic acid, propanol, isopropanol, fused alcohols, 1,2-propanediol, 1,3-propanediol, formate, fumaric acid, propionic acid, succinic acid, valeric acid, maleic acid, or poly-hydroxybutyrate; and
   ii. one or more synthetic metabolic valves for reducing or eliminating flux through multiple metabolic pathways within the genetically modified *E. coli* when the one or more synthetic metabolic valves are induced, the one or more synthetic metabolic valves comprising:
      a) at least one silencing synthetic metabolic valve that silences gene expression of a gene encoding at least one silenceable enzyme, or
      b) at least one proteolytic synthetic metabolic valve that controls proteolysis of a proteolyzable enzyme; and
   wherein growth of the genetically modified *E. coli* is slowed or stopped and product production is enhanced, as compared to *E. coli* lacking the production pathway or synthetic metabolic valve, by inducing the synthetic metabolic valve, and
   wherein growth of the genetically modified microorganism is slowed or stopped by depletion of a limiting nutrient thereby inducing a stationary phase, and product production is enhanced, as compared to a microorganism lacking the production pathway or synthetic metabolic valve, by inducing the synthetic metabolic valve in the stationary phase,
   wherein the synthetic metabolic valve combination produces a genetically modified microorganism that is robust to changes in environmental conditions as evidenced by a robustness score greater than 0.6.

3. The microorganism of claim 2, wherein the silencing synthetic metabolic valve that silences gene expression of a gene is a gene selected from the group: fabI, gltA, ldp, zwf, or udhA; or the proteolytic synthetic metabolic valve that controls proteolysis of a proteolyzable enzyme is an enzyme selected from the group: fabI, gltA, ldp, zwf, or udhA.

* * * * *